(12) United States Patent
Koberstein et al.

(10) Patent No.: US 11,331,392 B2
(45) Date of Patent: May 17, 2022

(54) BIODEGRADABLE THERMO-RESPONSIVE POLYMERS AND USES THEREOF

(71) Applicant: The Trustees of Columbia University in the City of New York, New York, NY (US)

(72) Inventors: Jeffrey T. Koberstein, Cataumet, MA (US); Sanjoy Samanta, Selmabad (IN); Chathuranga De Silva, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 152 days.

(21) Appl. No.: 15/532,405

(22) PCT Filed: Dec. 3, 2015

(86) PCT No.: PCT/US2015/063669
§ 371 (c)(1),
(2) Date: Jan. 11, 2018

(87) PCT Pub. No.: WO2016/090103
PCT Pub. Date: Jun. 9, 2016

(65) Prior Publication Data
US 2018/0133333 A1    May 17, 2018

Related U.S. Application Data

(60) Provisional application No. 62/192,822, filed on Jul. 15, 2015, provisional application No. 62/087,409, filed on Dec. 4, 2014, provisional application No. 62/087,407, filed on Dec. 4, 2014, provisional application No. 62/087,404, filed on Dec. 4, 2014.

(51) Int. Cl.
| | |
|---|---|
| *A61K 47/60* | (2017.01) |
| *C08F 220/18* | (2006.01) |
| *A61K 47/59* | (2017.01) |
| *A61K 47/69* | (2017.01) |
| *A61P 35/02* | (2006.01) |
| *A61P 35/00* | (2006.01) |
| *A01N 25/04* | (2006.01) |
| *A01N 25/10* | (2006.01) |
| *A61K 9/06* | (2006.01) |
| *A61K 9/107* | (2006.01) |
| *A61K 31/7068* | (2006.01) |
| *C08G 65/333* | (2006.01) |
| *C08G 65/48* | (2006.01) |
| *C08G 81/00* | (2006.01) |
| *C08J 3/075* | (2006.01) |
| *C08J 3/24* | (2006.01) |
| *C08L 33/06* | (2006.01) |

(52) U.S. Cl.
CPC .............. *A61K 47/60* (2017.08); *A01N 25/04* (2013.01); *A01N 25/10* (2013.01); *A61K 9/06* (2013.01); *A61K 9/1075* (2013.01); *A61K 31/7068* (2013.01); *A61K 47/59* (2017.08); *A61K 47/6907* (2017.08); *A61P 35/00* (2018.01); *A61P 35/02* (2018.01); *C08F 220/18* (2013.01); *C08G 65/33396* (2013.01); *C08G 65/48* (2013.01); *C08G 81/00* (2013.01); *C08J 3/075* (2013.01); *C08J 3/24* (2013.01); *C08G 2230/00* (2013.01); *C08G 2650/04* (2013.01); *C08G 2650/30* (2013.01); *C08G 2650/44* (2013.01); *C08J 2371/08* (2013.01); *C08L 33/06* (2013.01)

(58) Field of Classification Search
CPC .... A01N 25/10; A61K 31/7068; A61K 47/59; A61K 47/60; A61K 47/6907; A61P 35/00; A61P 35/02; C08F 220/18; C08G 2650/04; C08G 2650/30; C08G 2650/44; C08G 65/33396; C08G 65/48; C08G 81/00; C08J 3/075; C08J 3/24
See application file for complete search history.

(56) References Cited

U.S. PATENT DOCUMENTS

| | | |
|---|---|---|
| 6,043,331 A | 3/2000 | Herzig |
| 6,338,843 B1 | 1/2002 | Duncan et al. |
| 6,414,101 B1 | 7/2002 | Watanabe et al. |
| 7,220,414 B2 | 5/2007 | Brocchini et al. |

(Continued)

FOREIGN PATENT DOCUMENTS

| | | |
|---|---|---|
| CA | 2818583 | 11/2011 |
| EP | 2042538 | 4/2009 |

(Continued)

OTHER PUBLICATIONS

International Search Report and Written Opinion dated Apr. 14, 2016 in International Application No. PCT/US2015/063669; 11 pages.

(Continued)

*Primary Examiner* — Robert A Wax
*Assistant Examiner* — Olga V. Tcherkasskaya
(74) *Attorney, Agent, or Firm* — Leason Ellis LLP

(57) ABSTRACT

The invention provides for novel thermo-responsive polymers and compositions comprising the same. In some embodiments, the polymers are water soluble, pH-degradable and have tunable lower critical solution temperatures. Other aspects of the invention include micelles and gels comprising the thermo-responsive polymers and derivatives thereof, as well as methods of delivering therapeutic agents comprising administering a biodegradable gel or micelle comprising a polyacetal compound cross-linked with a linker.

14 Claims, 71 Drawing Sheets

(56) References Cited

U.S. PATENT DOCUMENTS

| | | | |
|---|---|---|---|
| 7,951,846 | B2 | 5/2011 | Bae et al. |
| 8,962,577 | B2 | 2/2015 | Hanes et al. |
| 2004/0116348 | A1 | 6/2004 | Chau et al. |
| 2008/0003422 | A1 | 1/2008 | Ueda |
| 2011/0275732 | A1 | 11/2011 | Bruchmann et al. |
| 2013/0295052 | A1 | 11/2013 | Chaudhary |

FOREIGN PATENT DOCUMENTS

| | | |
|---|---|---|
| WO | 1999064484 | 12/1999 |
| WO | 2006105123 | 10/2006 |
| WO | 2008127532 | 10/2008 |

OTHER PUBLICATIONS

Singh, Biocompatible and Boidegradable Nanogels and Hydrogels for Protein/Peptide Delivery, Ph.D. Dissertation, RWTH Aachen University, pp. iv, v, and 26-55(2013). [retrieved on Mar. 3, 2016]. Retrieved from the internet. <URL: http://publications.rwth-aachen.de/record/44867/files/5095.pdf>.

Trofimov et al. Synthesis of Cross-Linked Polyethylane Oxide-Acetal Macrocycles for Solid Superbase Catalysts. Journal of Applied Polymer Science 120(6); 3363-3369 (2011) [retrieved on Mar. 3, 2016]. Retrieved from the internet. <URL: https://www.researchgate.net/publication/230487120_Synthesis_of_Cross-Linked_Polyethylene_Oxide-Acetal_Macrocycles_for_Solid_Superbase_Catalysts>.

Tomlinson R et al, "Polyacetal-Doxorubicin Conjugates Designed for PH-Dependent Degradation", Bioconjugate Chemistry, American Chemical Society, US, vol. 14, No. 6, 2003, pp. 1096-1106.

Meyer et al, "Drug targeting using thermally responsive polymers and local hyperthermia", J. Control. Rel., (2001) vol. 74: 213-224.

Putnam, "Drug delivery: The heart of the matter", Nat. Mater., (2008) vol. 7, 11: 836-837.

Larson et al, "Polymeric Conjugates for Drug Delivery", Chem. Mater., (2012) vol. 24, Issue 5, pp. 840-853.

Kokardekar et al, "pNIPAM Poly (N-isopropylacrylamide): A thermoresponsive "smart" polymer in novel drug delivery systems", Internet J. Med. Update, (2012) vol. 7, Issue 2, pp. 60-63.

Vicent et al, "Polymer therapeutics: Clinical applications and challenges for development", Adv. Drug Deliv. Rev., (2009) vol. 61, Issue 13, pp. 1117-1120.

Bae et al, "Targeted drug delivery to tumors: Myths, reality and possibility", J Control Release, (2011) 153(3), pp. 198-205.

Schmaljohann, "Thermo- and pH-responsive polymers in drug delivery", Adv Drug Delivery Reviews, (2006) 58(15), pp. 1655-1670.

Li et al, "Antitumor activity of poly(L-glutamic acid)-paclitaxel on syngeneic and xenografted tumors", Clin Cancer Res, (1999) vol. 5, Issue 4, pp. 891-897.

Fu et al, "Thermo-responsive triblock copolymer micelles containing PEG6000 for either water-soluble or water-insoluble drug sustained release and treatment" RSC Advances, (2015) vol. 5, Issue 47, pp. 37451-37461.

Kim et al, "Thermoresponsive nanostructured polycarbonate block copolymers as biodegradable therapeutic delivery carriers" Biomaterials, (2011) vol. 32, Issue 23, pp. 5505-5514.

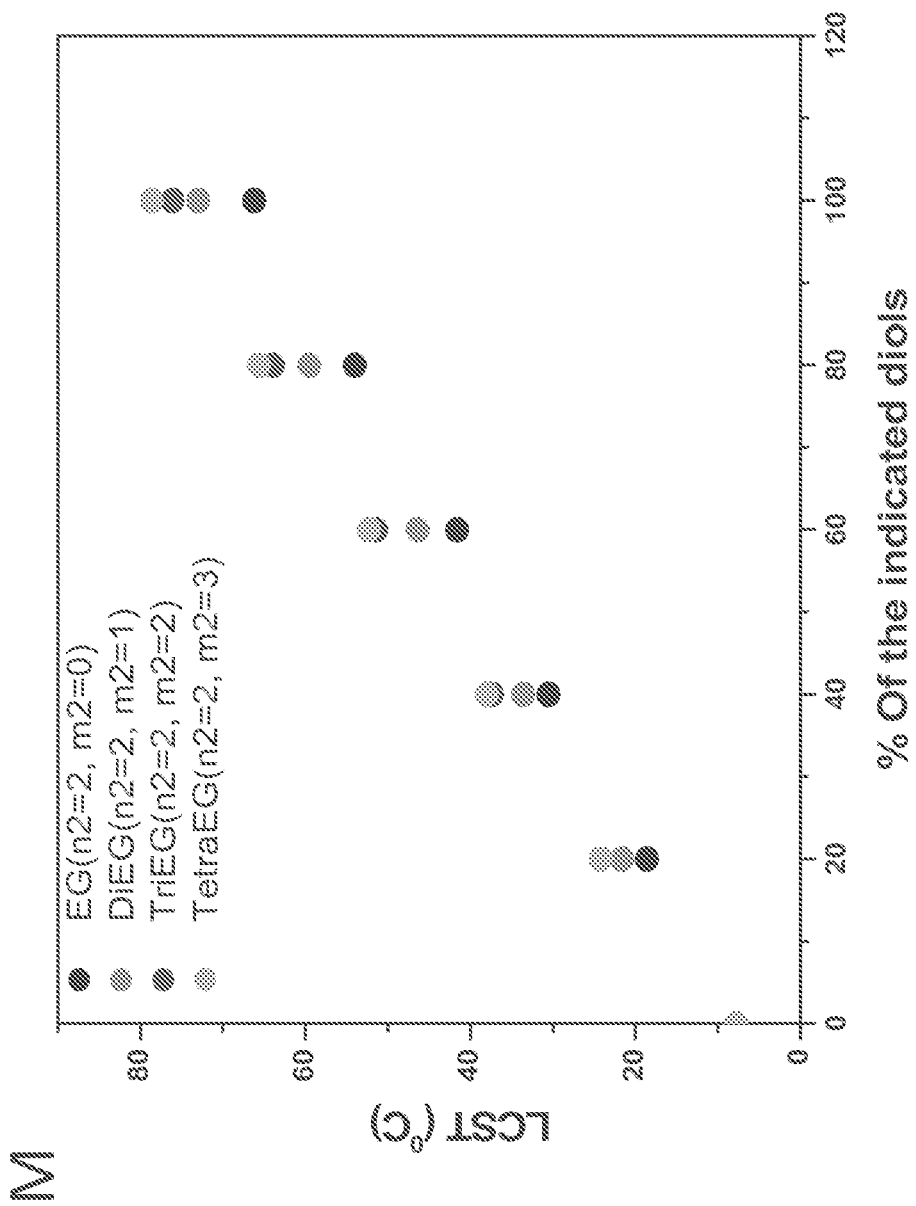

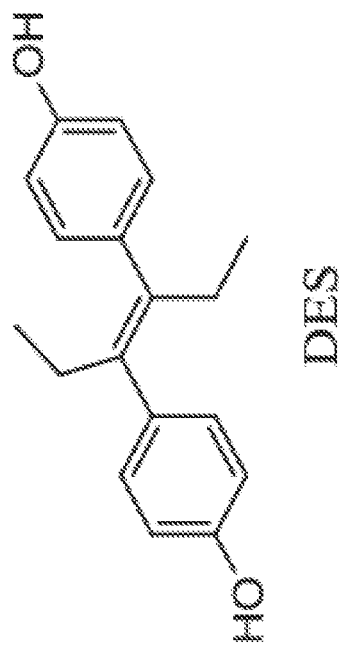
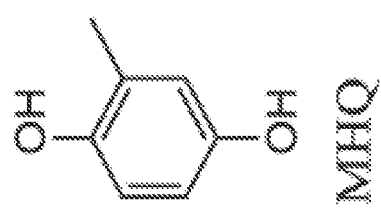
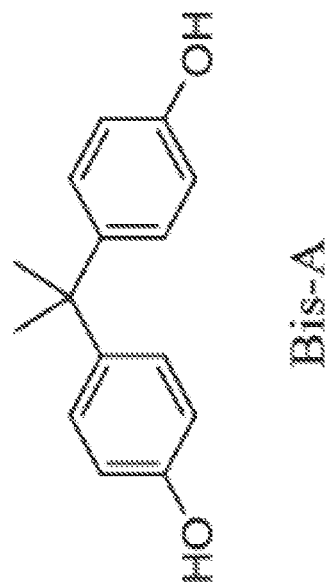
FIG. 30

BIODEGRADABLE THERMO-RESPONSIVE POLYMERS AND USES THEREOF

This application claims the benefit of and priority to U.S. Provisional Application No. 62/087,404, filed on Dec. 4, 2014; U.S. Provisional Application No. 62/087,407, filed on Dec. 4, 2014; U.S. Provisional Application No. 62/087,409, filed on Dec. 4, 2014; and U.S. Provisional Application No. 62/192,822, filed on Jul. 15, 2015; each of which is incorporated herein by reference.

GOVERNMENT SUPPORT

This invention was made with government support under Army Research Office Grant Nos. W911NF-11-1-0372 and W911NF-10-1-0184, awarded by the Department of Army Research, and National Science Foundation Grant No. DMR1206191, awarded by the Division of Materials Research Polymers Program at the National Science Foundation. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Water-soluble polymers have received much attention as novel therapeutic agent delivery systems. The conjugation of therapeutic agents to water-soluble polymers yields soluble polymeric therapeutic agent carriers, which have been studied as therapeutics for the treatment of cancer. The macromolecular nature (high molecular weight) of soluble polymeric therapeutic agent carriers reduces renal clearance and exploits the enhanced permeability and retention (EPR) effect of tumor tissue to improve therapeutic agent accumulation within the tumor. However, this can lead to lysosomal storage disease syndrome if the polymer is not bio-degradable. Consequently, there has been much focus on the design of soluble polymeric therapeutic agent carriers that are also bio-degradable and, in particular, bio-degradable polymers that are sensitive to the acidic pH conditions of lysosomes and endosomes.

Soluble polymeric therapeutic agent carriers that can deliver therapeutic agents to a specific site via a targeting mechanism are highly advantageous. One such approach is "thermal targeting" wherein temperature-sensitive polymers are triggered by local hyperthermia to undergo a reversible lower critical solution temperature (LCST) phase transition to expel its liquid content and enable cellular uptake. The effectiveness of the "thermal targeting" technique has been demonstrated by the enhanced uptake of poly(N-isopropylacrylamide) (or pNIPAM) in mice with hyperthermic tumor tissue. However, pNIPAM is not a bio-degradable polymer. In addition, pNIPAM gels have a slow rate of volume change and the thermal transition is broad, showing strong hysteresis. Thus, there is a need for thermoresponsive compounds.

There is also a need for developing soluble polymeric therapeutic agent carriers that are both temperature-sensitive and bio-degradable.

SUMMARY OF THE INVENTION

In one aspect, the invention is directed to a class of compounds of formula (I)

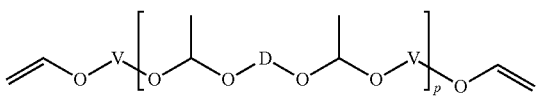

wherein V is

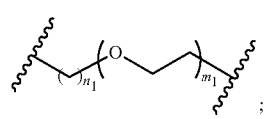

each D may be the same or different and is

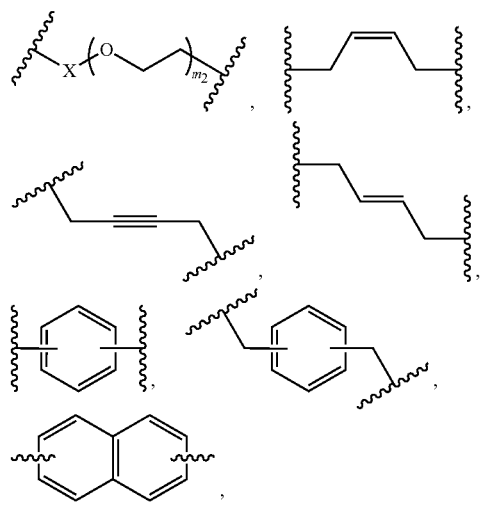

or a therapeutic agent core; each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20; and
p is an integer between 3 and 200.

In another aspect, the invention is directed to a biodegradable gel comprising a compound of formula (I) cross-linked with a linker at a terminus of the compound of formula (I), and wherein the linker is bonded to a plurality of compounds of formula (I).

In another aspect, the invention is directed to a method of making a gel, comprising cross-linking a compound of formula (I) with a trifunctional linker.

In another aspect, the invention is directed to a method of delivering a therapeutic agent to a tumor cell comprising, administering a biodegradable gel comprising a compound of formula (I) cross-linked with a linker at a terminus of the compound of formula (I), and wherein the linker is bonded to a plurality of compounds of formula (I); and a therapeutic agent, wherein said gel degrades at pH from about 5 to about 6.5 to release said therapeutic agent.

In one aspect, the invention is directed to a class of compounds of formula (II)

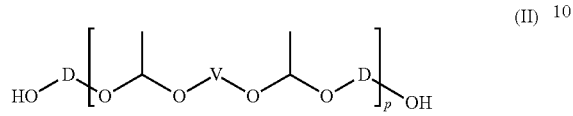

wherein, V is

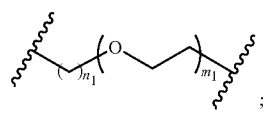

each D may be the same or different and is

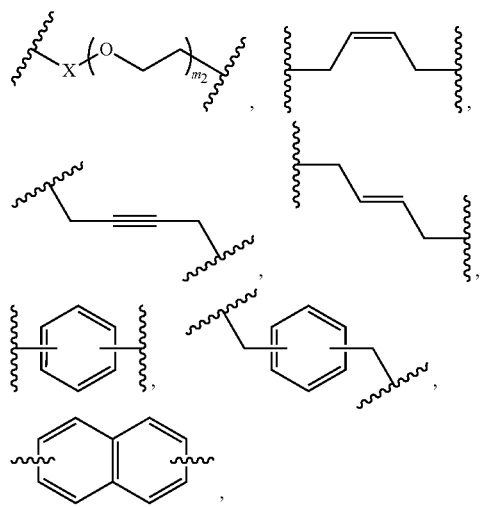

or a therapeutic agent core;
each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20; and
p is an integer between 3 and 200.

In another aspect, the invention is directed to a biodegradable gel comprising a compound of formula (II) cross-linked with a linker at a terminus of the compound of formula (II), and wherein the linker is bonded to a plurality of compounds of formula (II).

In another aspect, the invention is directed to a method of making a gel, comprising cross-linking a compound of formula (II) with a trifunctional linker. In some embodiments, the trifunctional linker comprises a triisocyanate.

In another aspect, the invention is directed to a method of delivering a therapeutic agent to a tumor cell comprising, administering a biodegradable gel comprising a compound of formula (II) cross-linked with a linker at a terminus of the compound of formula (II), and wherein the linker is bonded to a plurality of compounds of formula (II); and a therapeutic agent, wherein said gel degrades at pH from about 5 to about 6.5 to release said therapeutic agent.

In another aspect, the invention is directed to compositions comprising a compound of formula (I) wherein each D may be the same or different and is

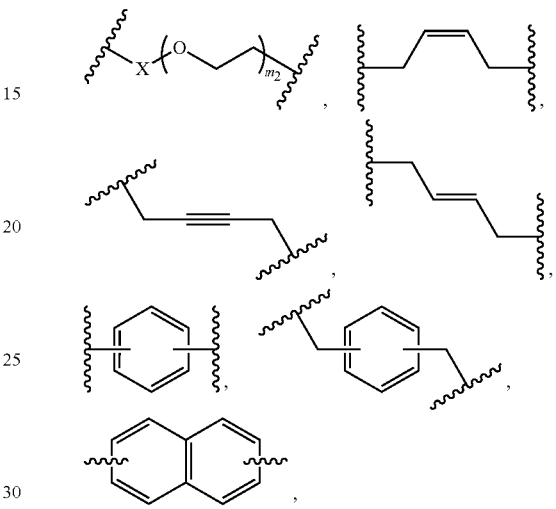

or a therapeutic agent core; and a pharmaceutically acceptable carrier.

In another aspect, the invention is directed to a method for treating cancer in a subject, the method comprising administering to a subject a therapeutic amount of a compound of formula (I), wherein each D may be the same or different and is

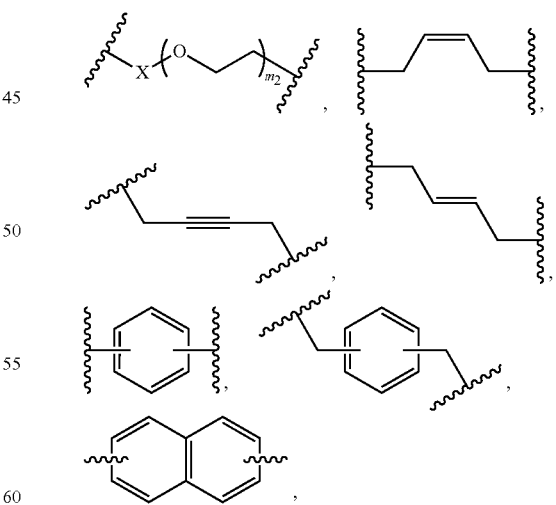

therapeutic agent core; or a pharmaceutical composition thereof.

In another aspect, the invention is directed to compositions comprising a compound of formula (I), wherein each D may be the same or different and is

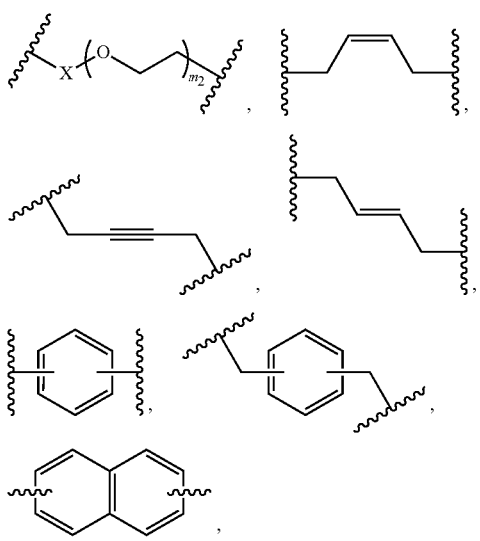

or a therapeutic agent core; and water or a liquid chemical carrier.

In another aspect, the invention is directed to a method for delivering a therapeutic agent to crops, plants or seeds, the method comprising administering to crops, plants, or seeds a compound of formula (I), wherein each D may be the same or different and is

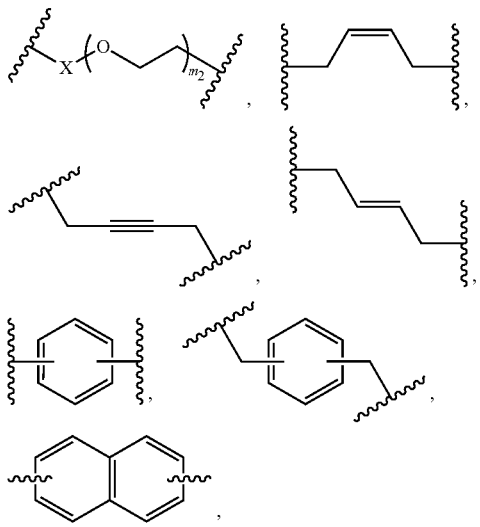

or a therapeutic agent core; or a chemical composition thereof.

In another aspect, the invention is directed to compositions comprising a compound of formula (II) wherein each D may be the same or different and is

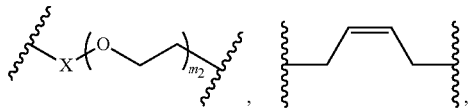

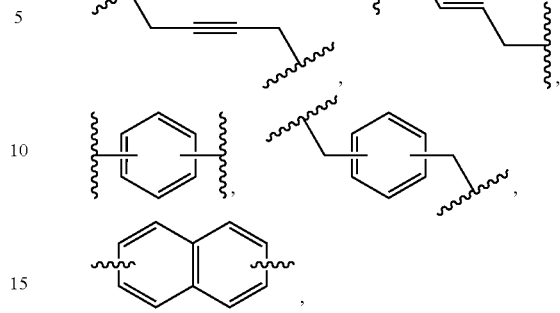

or a therapeutic agent core; and a pharmaceutically acceptable carrier.

In another aspect, the invention is directed to a method for treating cancer in a subject, the method comprising administering to a subject a therapeutic amount of a compound of formula (II), wherein each D may be the same or different and is

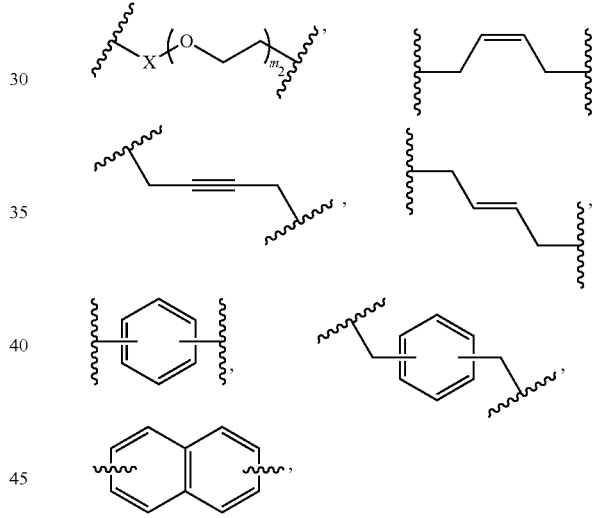

or a therapeutic agent core; or a pharmaceutical composition thereof.

In another aspect, the invention is directed to compositions comprising a compound of formula (II), wherein each D may be the same or different and is

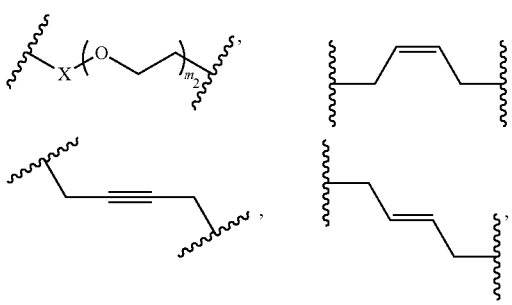

-continued

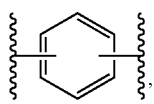 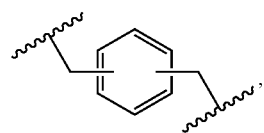

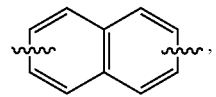

or a therapeutic agent core; and water or a liquid chemical carrier.

In another aspect, the invention is directed to a method for delivering a therapeutic agent to crops, plants or seeds, the method comprising administering to crops, plants, or seed a compound of formula (II), wherein each D may be the same or different and is

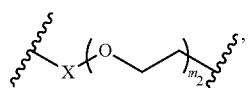 

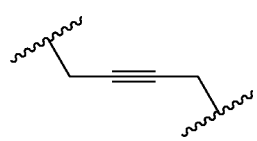 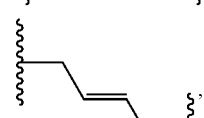

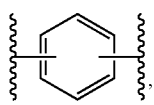 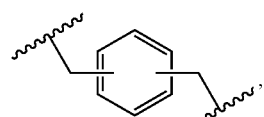

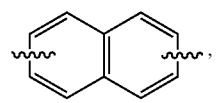

or a therapeutic agent core; or a chemical composition thereof.

In another aspect, the invention is directed to a class of compounds of formula (III)

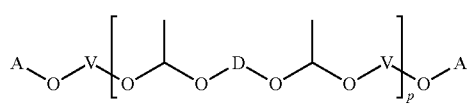

(III)

wherein,

A is

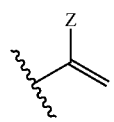 or 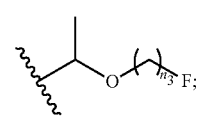

F is

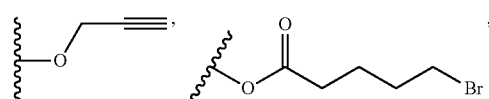

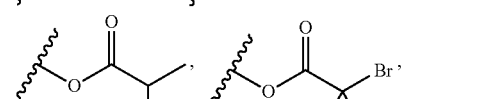

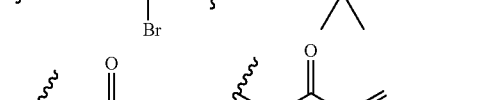

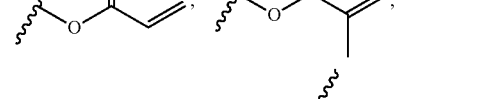

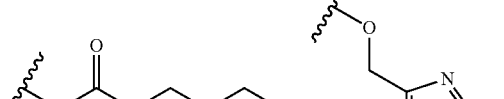

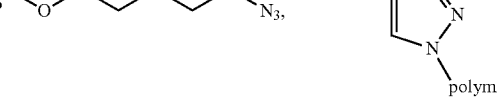

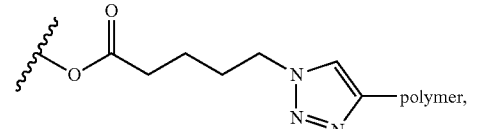

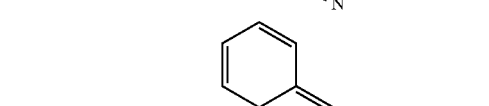

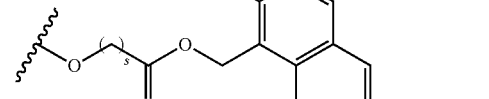

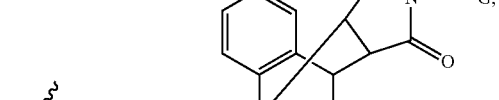

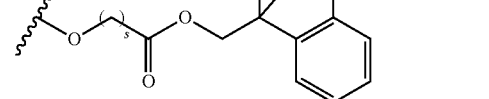

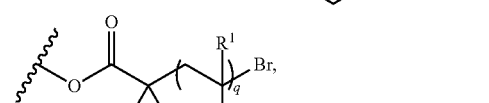

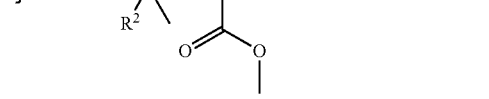

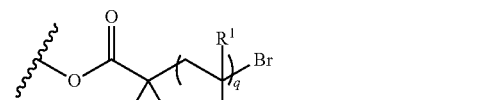

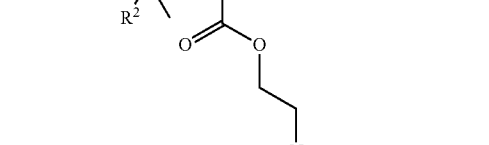

-continued

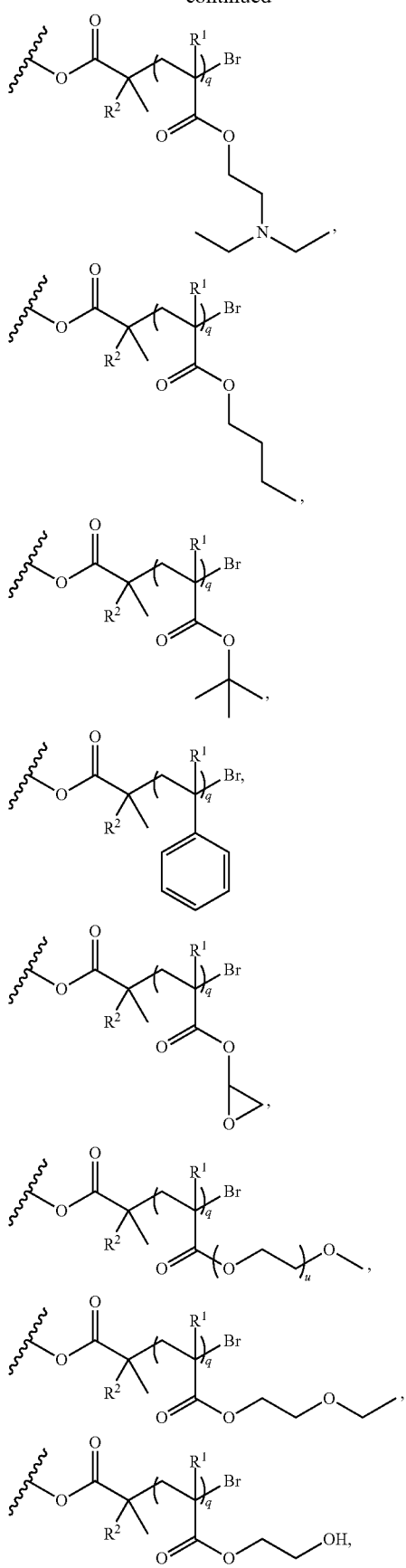

-continued

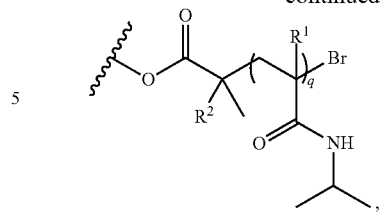

or a polymer;
Z is a polymer, aryl, hetero-aryl, or vinyl;
V is

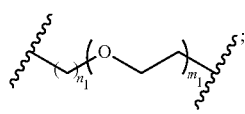

each D may be the same or different and is

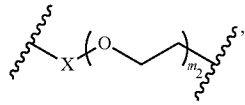

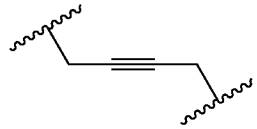

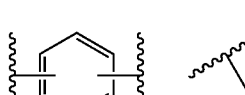

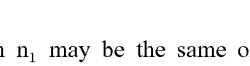

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
p is an integer between 3 and 200;
q is an integer between 1 and 100;
s is an integer between 1 and 10;
t is an integer between 1 and 10;
u is an integer between 1 and 100;
G is a polymer, aryl, or alkyl;
$R^1$ is H or $CH_3$; and
$R^2$ is H or $CH_3$.

In another aspect, the invention is directed to a class of compounds of formula (III)

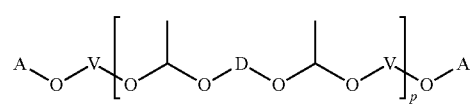
(III)
wherein,
A is
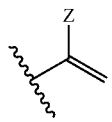 or 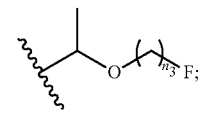;
F is
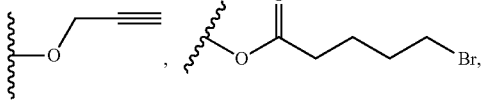
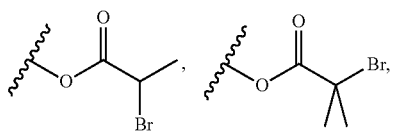
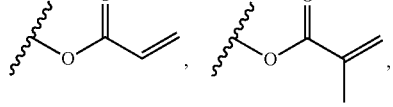
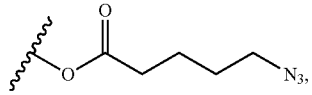
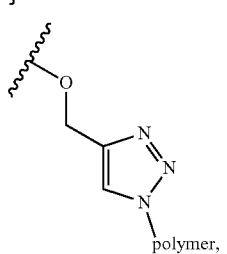
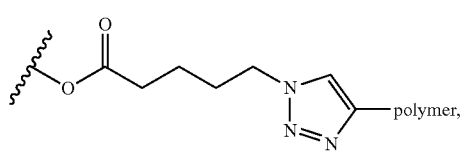
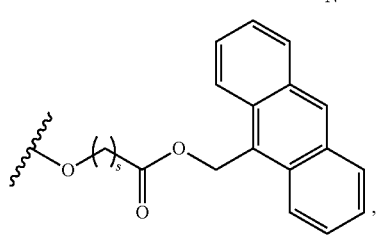
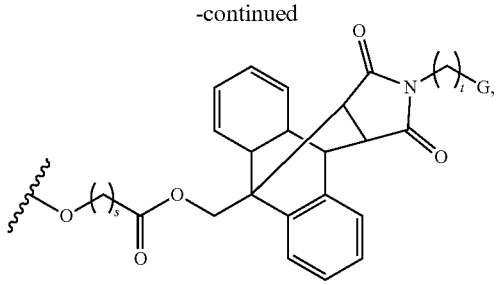
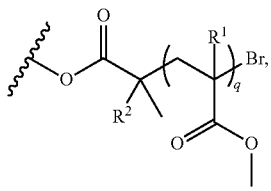
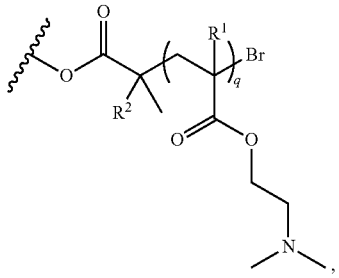
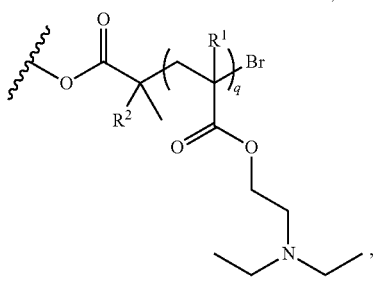
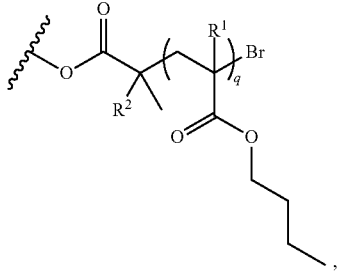
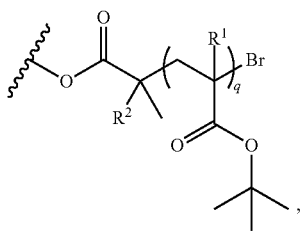
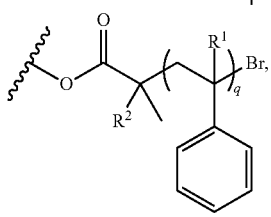

-continued

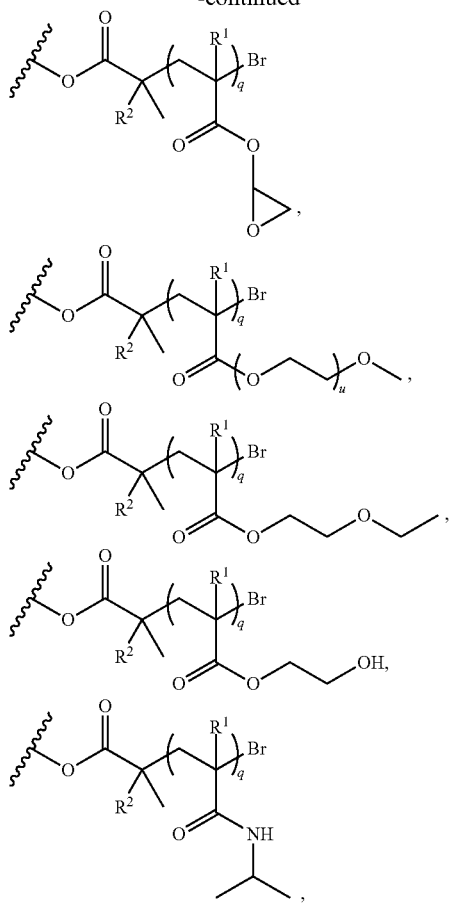

or a polymer;
Z is a polymer, aryl, hetero-aryl, or vinyl;
V is

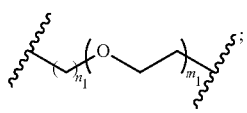

each D may be the same or different and is

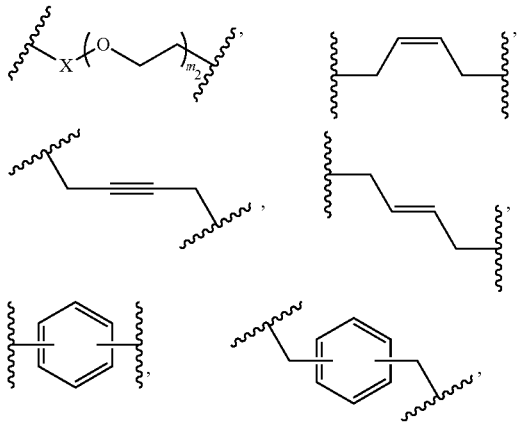

-continued

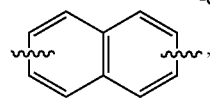

or a therapeutic agent core;
each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
p is an integer between 3 and 200;
q is an integer between 1 and 100;
s is an integer between 1 and 10;
t is an integer between 1 and 10;
u is an integer between 1 and 100;
G is a polymer, aryl, or alkyl;
$R^1$ is H or $CH_3$; and
$R^2$ is H or $CH_3$.

In another aspect, the invention is directed to a biodegradable gel comprising a compound of formula (III) cross-linked with a linker at an alkyne or azide terminus of the compound.

In another aspect, the invention is directed to a method of making a gel, comprising crosslinking a compound of formula (III) with a trifunctional linker.

In another aspect, the invention is directed to a method of delivering a therapeutic agent to a tumor cell comprising, administering a biodegradable gel comprising a compound of formula (III) cross-linked with a linker at an alkyne or azide terminus of the compound, and a therapeutic agent, wherein said gel degrades at pH from about 5 to about 6.5 to release said therapeutic agent.

In another aspect, the invention is directed to a class of compounds of formula (IV)

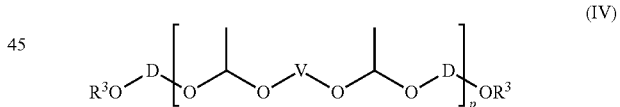

(IV)

wherein,
R is

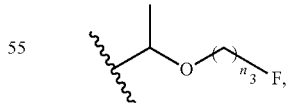

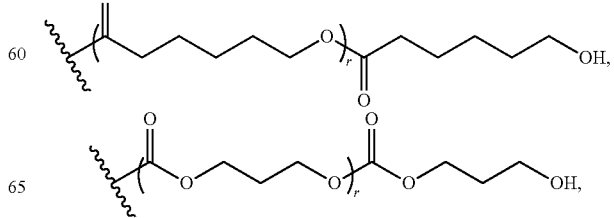

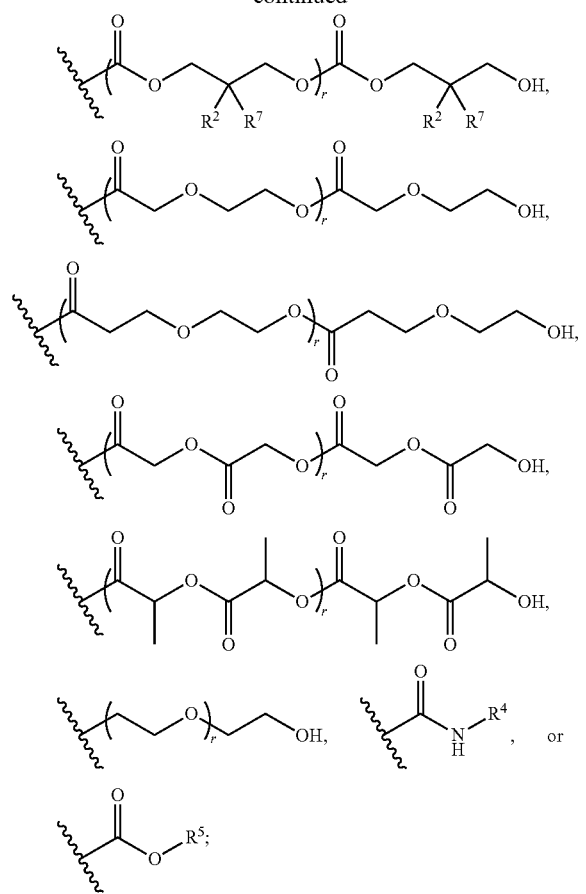
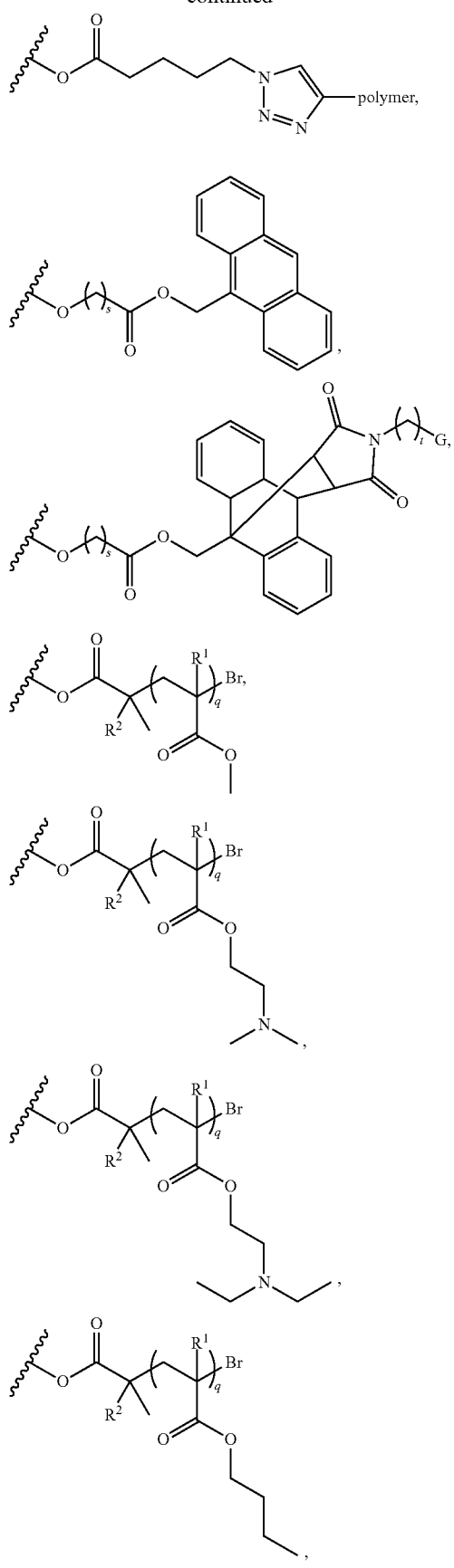
F is
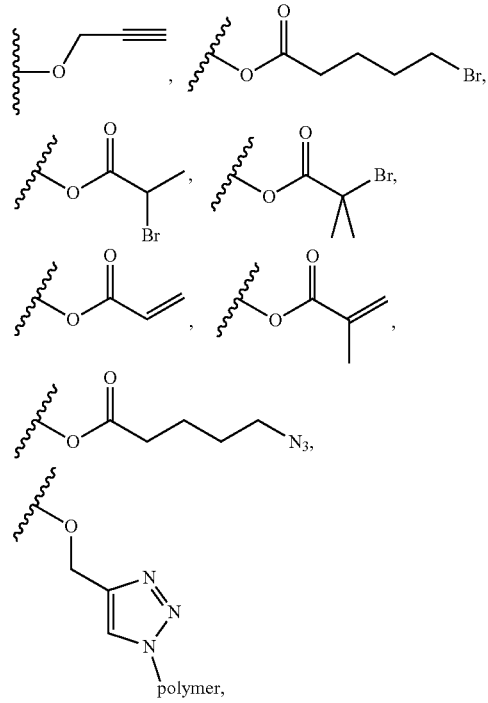

-continued

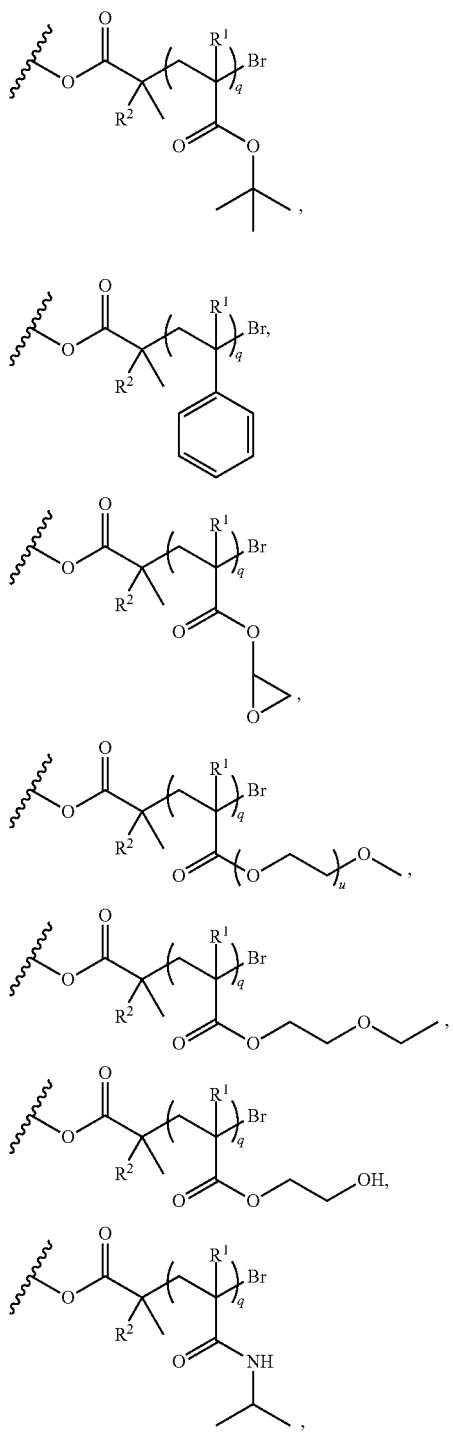

or a polymer;
V is

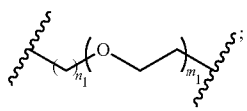

each D may be the same or different and is

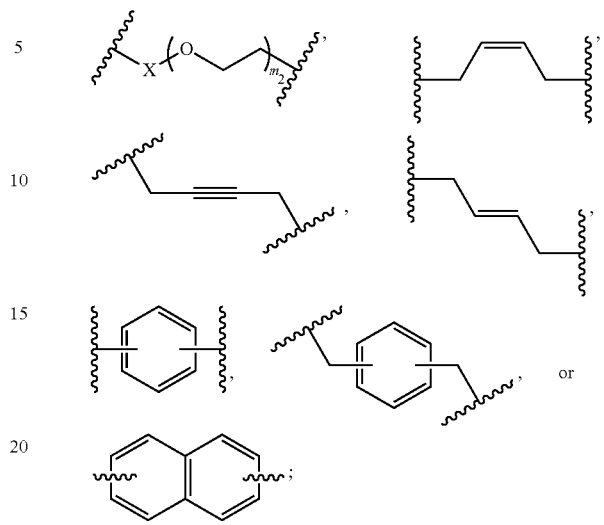

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
$R^1$ is H or $CH_3$;
$R^2$ is H or $CH_3$;
$R^4$ is aryl, alkyl, or a polymer;
$R^5$ is aryl, alkyl, or a polymer;
$R^7$ is H or halogen;
p is an integer between 3 and 200;
q is an integer between 1 and 100;
r is an integer between 0 and 100;
s is an integer between 1 and 10;
t is an integer between 1 and 10;
u is an integer between 1 and 100; and
G is a polymer, aryl, or alkyl.

In another aspect, the invention is directed to a class of compounds of formula (IV)

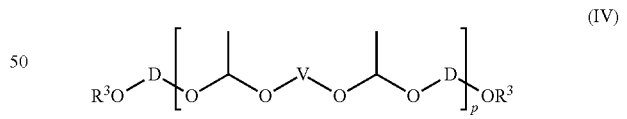

wherein,
$R^3$ is

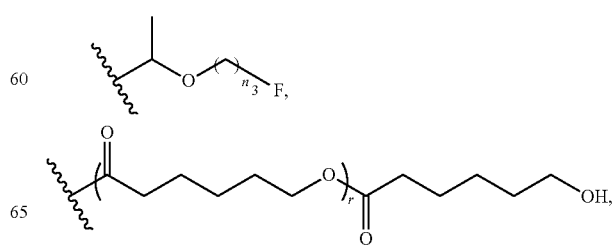

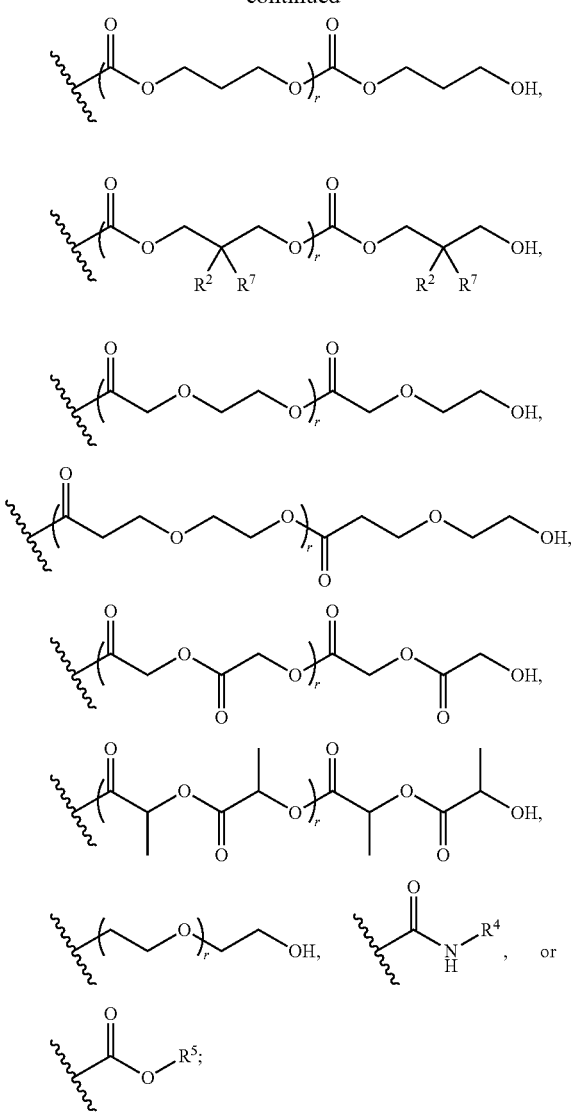
F is
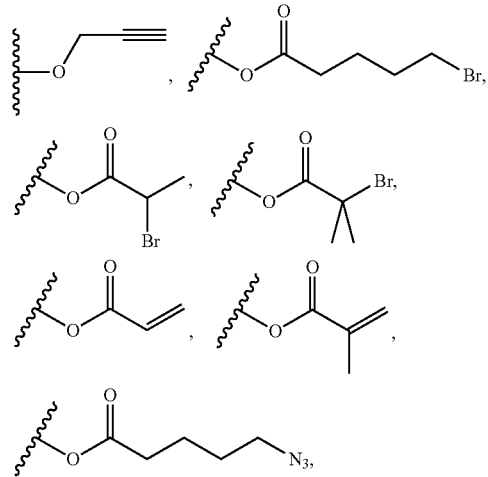
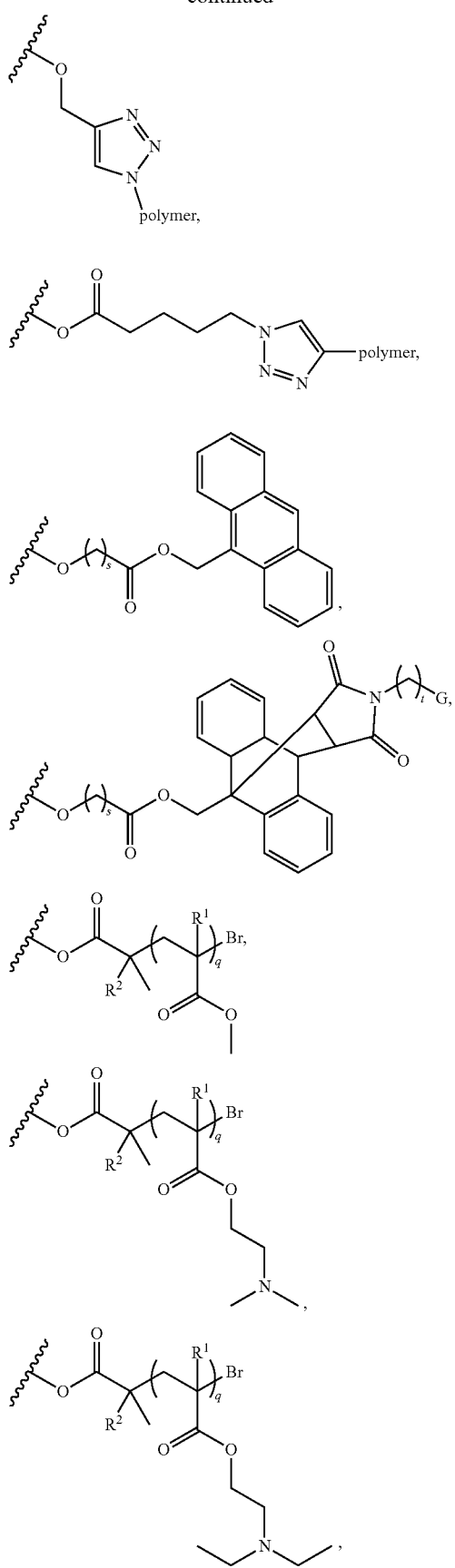

-continued

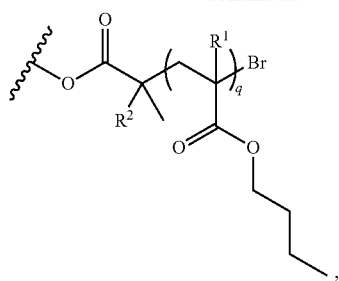

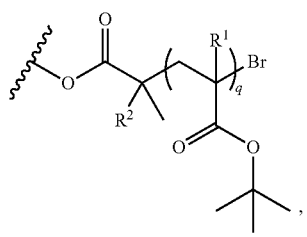

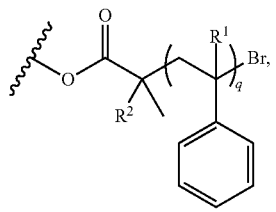

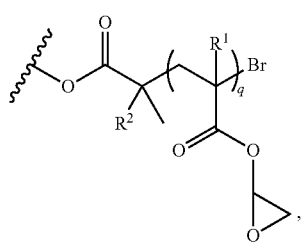

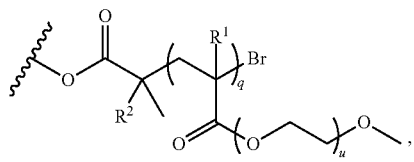

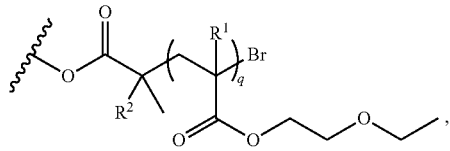

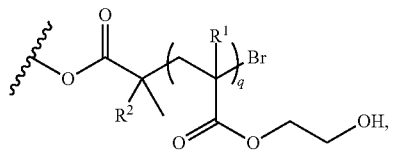

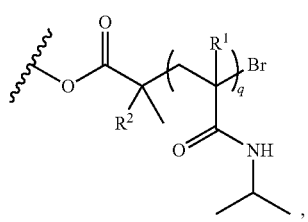

or a polymer;

V is

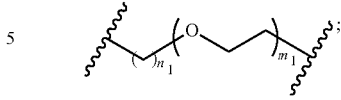

each D may be the same or different and is

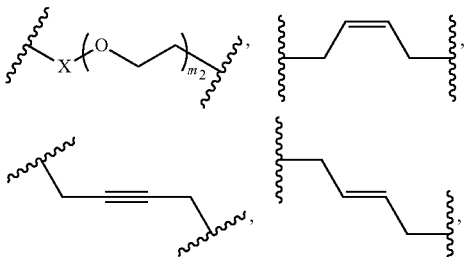

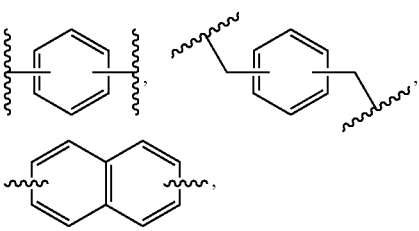

or a therapeutic agent core;
each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
$R^1$ is H or $CH_3$;
$R^2$ is H or $CH_3$;
$R^4$ is aryl, alkyl, or a polymer;
$R^5$ is aryl, alkyl, or a polymer;
$R^7$ is H or halogen;
p is an integer between 3 and 200;
q is an integer between 1 and 100;
r is an integer between 0 and 100;
s is an integer between 1 and 10;
t is an integer between 1 and 10;
u is an integer between 1 and 100; and
G is a polymer, aryl, or alkyl.

In another aspect, the invention is directed to a biodegradable gel comprising a compound of formula (IV) cross-linked with a linker, wherein the compound is cross-linked with a linker at a hydroxyl, alkyne or azide terminus.

In another aspect, the invention is directed to a method of making a gel, comprising crosslinking a compound of formula (IV) with a trifunctional linker.

In another aspect, the invention is directed to a method of delivering a therapeutic agent to a tumor cell comprising, administering a biodegradable gel comprising a compound of formula (IV) cross-linked with a linker, wherein the compound is cross-linked with a linker at a hydroxyl, alkyne or azide terminus, and a therapeutic agent, wherein said gel degrades at pH from about 5 to about 6.5 to release said therapeutic agent.

In another aspect, the invention is directed to micelle comprising a compound of formula (III)
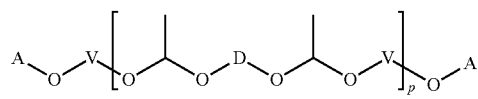
(III)
wherein,
A is
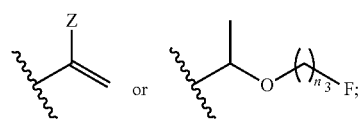
F is
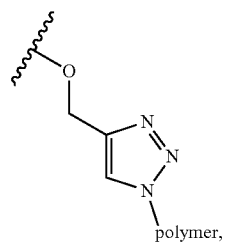
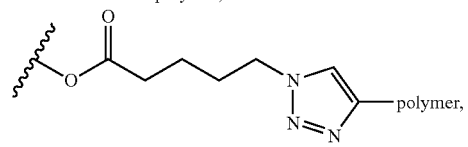
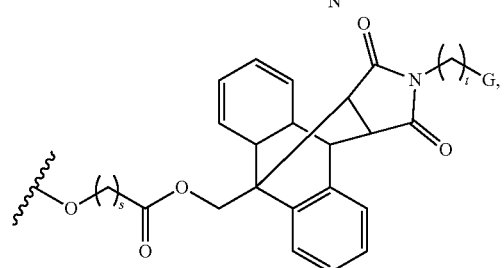
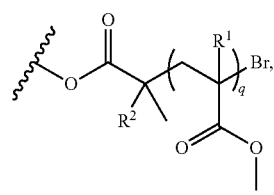
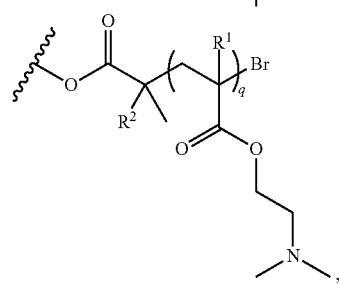
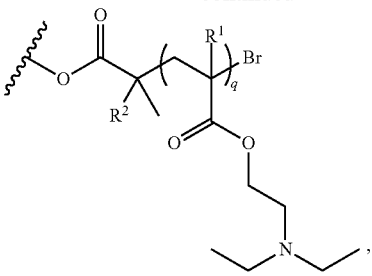
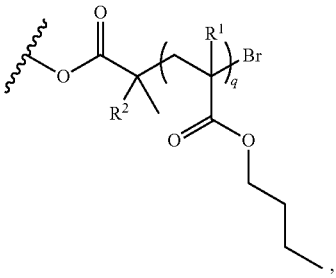
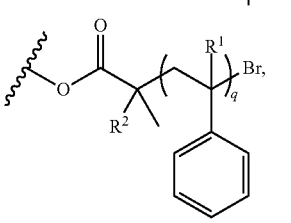
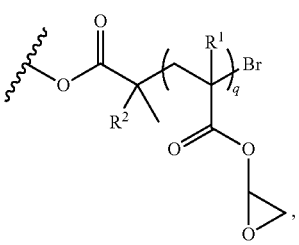
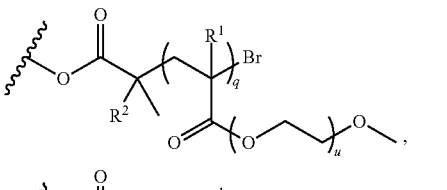
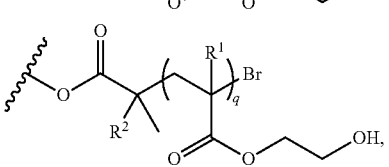

-continued

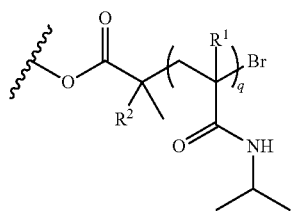

or a polymer;

V is

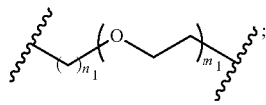

each D may be the same or different and is

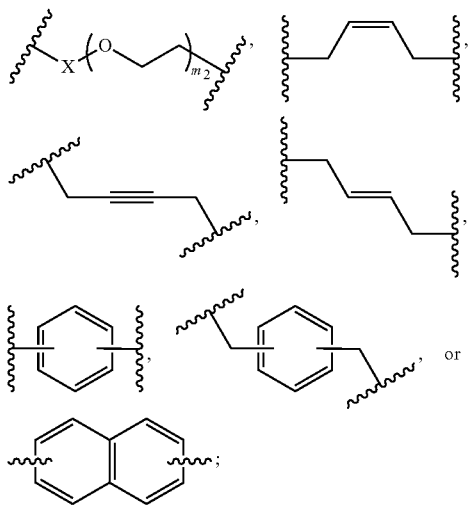

each $n_1$ may be the same or different and is an integer between 2 and 10;

each $m_1$ may be the same or different and is an integer between 0 and 20;

each X may be the same or different and is $C_2$-$C_{10}$ alkyl;

each $m_2$ may be the same or different and is an integer between 0 and 20;

$n_3$ is an integer between 2 and 10;

G is a polymer;

Z is a polymer;

$R^1$ is H or $CH_3$;

$R^2$ is H or $CH_3$;

p is an integer between 3 and 200;

q is an integer between 1 and 100;

s is an integer between 1 and 10;

t is an integer between 1 and 10;

u is an integer between 1 and 100; or, a compound of formula (IV)

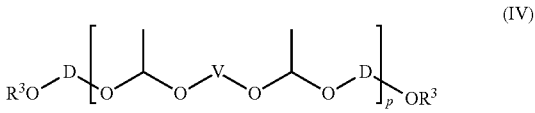

wherein, $R^3$ is

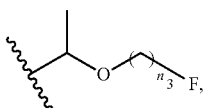

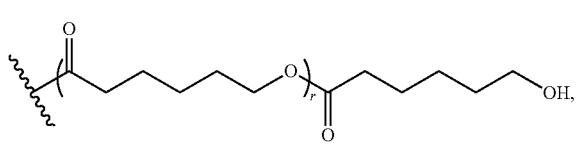

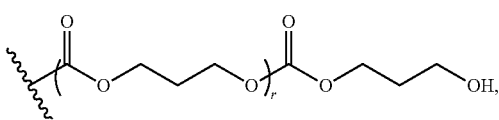

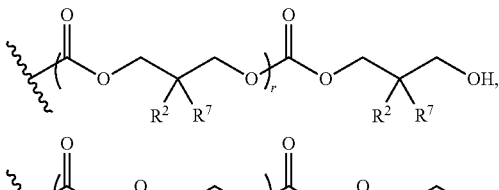

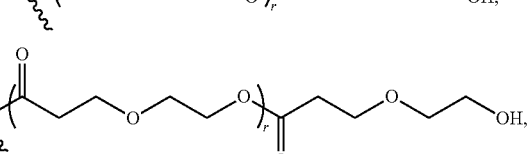

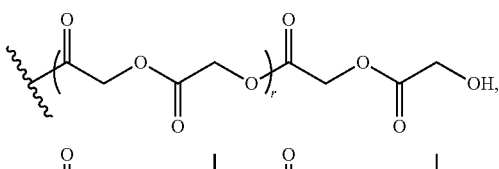

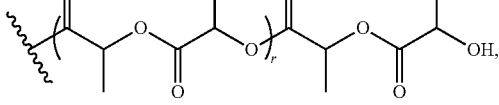

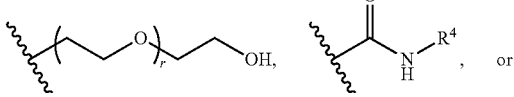

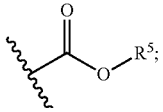

F is
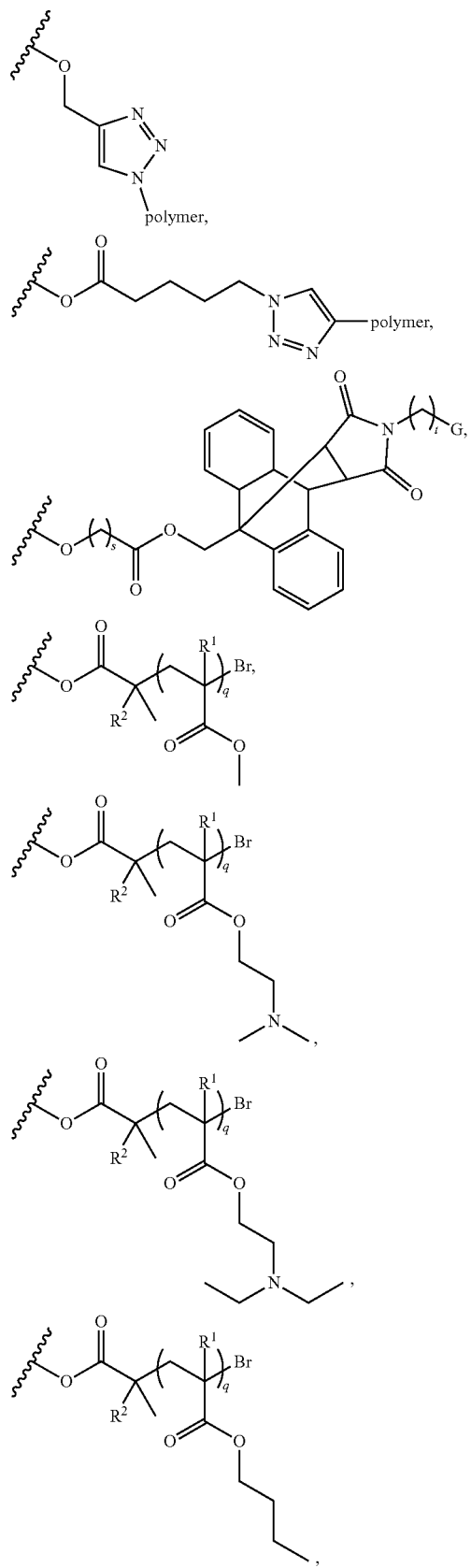
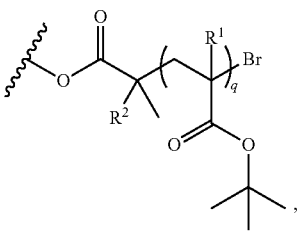
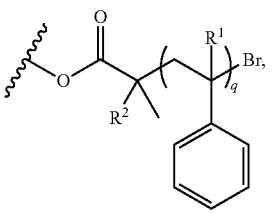
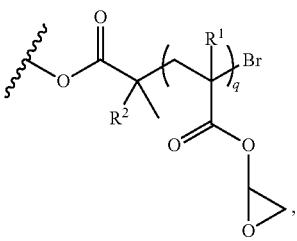
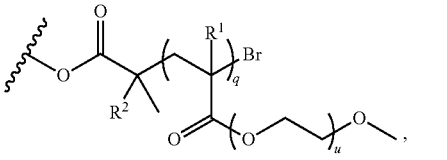
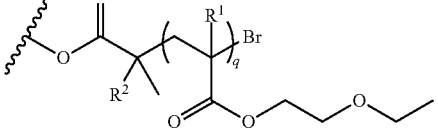
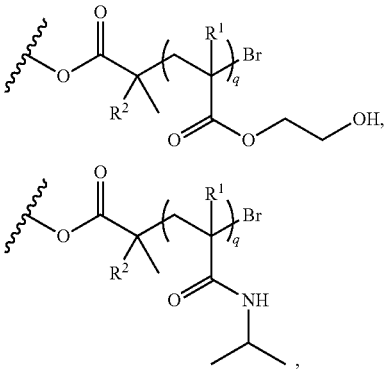
or a polymer;
V is
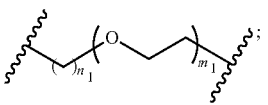

each D may be the same or different and is

[chemical structures shown]

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
G is a polymer;
$R^1$ is H or $CH_3$;
$R^2$ is H or $CH_3$;
$R^4$ is a polymer;
$R^5$ is a polymer;
$R^7$ is H or halogen;
p is an integer between 3 and 200;
q is an integer between 1 and 100;
r is an integer between 0 and 100;
s is an integer between 1 and 10;
t is an integer between 1 and 10; and
u is an integer between 1 and 100.

In another aspect, the invention is directed to a pharmaceutical composition comprising a micelle comprising a compound of formula (III) or (IV).

In another aspect, the invention is directed to a method of delivering a therapeutic agent to a tumor cell comprising, administering a micelle comprising a compound of formula (III) or (IV), or a pharmaceutical composition comprising a micelle comprising a compound of formula (III) or (IV), wherein said micelle further comprises a therapeutic agent, and wherein said micelle degrades at pH from about 5 to about 6.5 to release said therapeutic agent.

In another aspect, the invention is directed to a class of compounds of formula (V)

[chemical structure (V)]

wherein,
V is

[chemical structure]

each D may be the same or different and is

[chemical structures shown]

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
p is an integer between 3 and 200;
Y is a polymer or therapeutic agent; and
$R^6$ is alkyl, aryl, or a polymer.

In another aspect, the invention is directed to a biodegradable gel comprising a compound of formula (V) cross-linked with a linker at a terminus of the compound, wherein the cross-linker is bonded to a plurality of compounds of formula (V).

In another aspect, the invention is directed to a method of making a gel, comprising crosslinking a compound of formula (V) with a trifunctional linker.

In another aspect, the invention is directed to a method of delivering a therapeutic agent to a tumor cell comprising, administering a biodegradable gel comprising a compound of formula (V) cross-linked with a linker at a terminus of the compound, wherein the cross-linker is bonded to a plurality of compounds of formula (V), and a therapeutic agent, wherein said gel degrades at pH from about 5 to about 6.5 to release said therapeutic agent.

In another aspect, the invention is directed to a class of compounds of formula (VI)

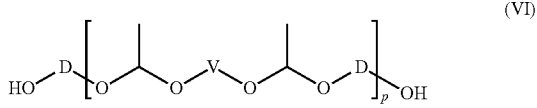

wherein,
V is

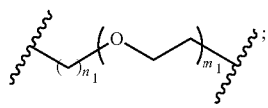

each D may be the same or different and is

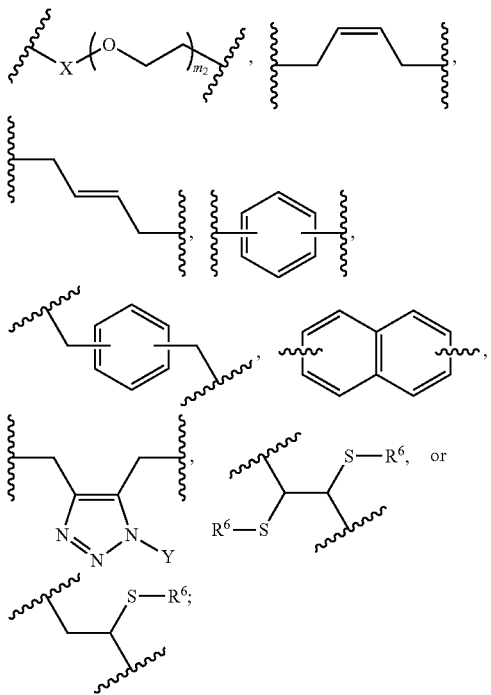

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
p is an integer between 3 and 200;
Y is a polymer or therapeutic agent; and
$R^6$ is alkyl, aryl, or a polymer.

In another aspect, the invention is directed to a biodegradable gel comprising a compound of formula (VI), wherein the compound is cross-linked with a linker at a terminus of the compound; and wherein the cross-linker is bonded to a plurality of compounds of formula (VI).

In another aspect, the invention is directed to a method of making a gel, comprising crosslinking a compound of formula (VI) with a trifunctional linker.

In another aspect, the invention is directed to a method of delivering a therapeutic agent to a tumor cell comprising, administering a biodegradable gel comprising a compound of formula (VI), wherein the compound is cross-linked with a linker at a terminus of the compound; and wherein the cross-linker is bonded to a plurality of compounds of formula (VI), and a therapeutic agent, wherein said gel degrades at pH from about 5 to about 6.5 to release said therapeutic agent.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

BRIEF DESCRIPTION OF THE FIGURES

To conform to the requirements for PCT patent applications, many of the figures presented herein are black and white representations of images originally created in color. In the below descriptions and the examples, the colored images are described in terms of their appearance in black and white.

The following figures are provided for the purpose of illustration only and are not intended to be limiting.

(FIG. 2B) the shifting of GPC traces in a kinetic study by GPC (Gel Permeation Chromatography) for the preparation of the polyacetal from FIG. 2A; (FIG. 2C) the increment of degree of polymerization (DP) with polymerization time.

(FIG. 6B) heating and cooling cycle for P2a (marked area represents phase transition region); and (FIG. 6C) plot of experimental LCSTs as a function of the average number of ethylene oxide unit(s) per repeating unit of polyacetals.

(FIG. 7B) particle size distribution of polymer P2a by volume; and (FIG. 7C) variation of hydrodynamic radius ($R_h$) of polymer P2a as a function of temperature, recorded by DLS.

(FIG. 8B) variation of LCST of polymer P2a as a function of salt (NaCl) concentration.

(FIG. 9A) Variation of LCSTs with degree of polymerization (DP) for vinyl ether terminated polyacetals (bottom, from right to left, P2a, P2b, P2c, and P2d) and hydroxyl terminated polyacetals (top, from right to left, P'2a, P'2b, P'2c, and P'2d); (FIG. 9B) Scaling of LCSTs of above polyacetals (P2a, P2b, P2c, P2d, P'2a, P'2b, P'2c, and P'2d) with their respective $M_n^{-1}$ to achieve the exact LCST of P2 or P'2-category polyacetals.

(FIG. 10A) Synthetic scheme for polyacetal formation from a linear diol (ethylene glycol, diethylene glycol, triethylene glycol, or tetraethylene glycol) and 1,4-butanediol divinyl ether, wherein the molar feed ratio of the divinyl ether to the diol is 1.04 to 1. (FIG. 10B) Plot of temperature induced phase transition (heating and cooling) for polyacetal formed from ethylene glycol and 1,4-butanediol divinyl ether. (FIG. 10C) Plot of temperature induced phase transition (heating and cooling) for polyacetal formed from diethylene glycol and 1,4-butanediol divinyl ether. (FIG. 10D) Plot of temperature induced phase transition (heating and cooling) for polyacetal formed from triethylene glycol and 1,4-butanediol divinyl ether. (FIG. 10E) Plot of temperature induced phase transition (heating and cooling) for polyacetal formed from tetraethylene glycol and 1,4-butanediol divinyl ether.

(FIG. 11A) Plot of temperature induced phase transition (heating and cooling) for polyacetal with an average of 0.5 ethylene oxide units in the repeating unit, formed from ethylene glycol, diethylene glycol, and 1,4-butanediol divinyl ether. (FIG. 11B) Plot of temperature induced phase transition (heating and cooling) for polyacetal with an average of 1.5 ethylene oxide units in the repeating unit, formed from diethylene glycol, triethylene glycol, and 1,4-butanediol divinyl ether. (FIG. 11C) Plot of temperature induced phase transition (heating and cooling) for polyacetal with an average of 2.5 ethylene oxide units in the repeating unit, formed from triethylene glycol, tetraethylene glycol, and 1,4-butanediol divinyl ether.

(FIG. 12A) Synthetic scheme for polyacetal formation from divinyl ether (di(ethylene glycol) divinyl ether or tri(ethylene glycol) divinyl ether) and linear diol (ethylene glycol, diethylene glycol, triethylene glycol, or tetraethylene glycol), wherein the molar feed ratio of the divinyl ether to the diol is 1.05 to 1. (FIG. 12B) Plot of temperature induced phase transition (heating and cooling) for polyacetal formed from di(ethylene glycol) divinyl ether and ethylene glycol. (FIG. 12C) Plot of temperature induced phase transition (heating and cooling) for polyacetal formed from di(ethylene glycol) divinyl ether and diethylene glycol. (FIG. 12D) Plot of temperature induced phase transition (heating and cooling) for polyacetal formed from di(ethylene glycol) divinyl ether and triethylene glycol. (FIG. 12E) Plot of temperature induced phase transition (heating and cooling) for polyacetal formed from di(ethylene glycol) divinyl ether and tetraethylene glycol. (FIG. 12F) Plot of temperature induced phase transition (heating and cooling) for polyacetal formed from tri(ethylene glycol) divinyl ether and ethylene glycol. (FIG. 12G) Plot of temperature induced phase transition (heating and cooling) for polyacetal formed from tri(ethylene glycol) divinyl ether and diethylene glycol. (FIG. 12H) Plot of temperature induced phase transition (heating and cooling) for polyacetal formed from tri(ethylene glycol) divinyl ether and triethylene glycol. (FIG. 12I) Plot of temperature induced phase transition (heating and cooling) for polyacetal formed from tri(ethylene glycol) divinyl ether and tetraethylene glycol.

(FIG. 13B) the combined plots of % transmittance versus temperature for polyacetals formed from tri (ethylene glycol) divinyl ether and diols that vary in the number of ethylene oxide units (heating shown in solid circle and solid line, cooling shown in empty circle and dotted line); (FIG. 13C) non-linearity in the plot of experimental LCSTs versus m2 (the number of ethylene oxide units in the diol portion of the polyacetal) for polyacetals prepared from di(ethylene glycol) divinyl ether and tri (ethylene glycol) divinyl ether.

(FIG. 14A) Synthetic scheme for polyacetal formation from divinyl ether (di (ethylene glycol) divinyl ether or tri(ethylene glycol) divinyl ether) and diol (ethylene glycol, 1,3-propanediol, 1,4-butanediol, or 1,5-pentanediol), wherein the molar feed ratio of the divinyl ether to the diol is 1.05 to 1. (FIG. 14B) The combined plots of % transmittance versus temperature for polyacetals formed from di(ethylene glycol) divinyl ether and diols that vary in the number of carbon atoms (heating shown in solid circle and solid line, cooling shown in empty circle and dotted line). (FIG. 14C) The combined plots of % transmittance versus temperature for polyacetals formed from tri(ethylene glycol) divinyl ether and diols that vary in the number of carbon atoms (heating shown in solid circle and solid line, cooling shown in empty circle and dotted line). (FIG. 14D) Plot of the experimental LCSTs versus number of $CH_2$ groups in the diol part of the polyacetal.

(FIG. 15A) GPC trace for degradation of P3a at pH 7.4. (FIG. 15B) GPC trace for degradation of P3a at pH 6.5. (FIG. 15C) GPC trace for degradation of P3a at pH 5.5. (FIG. 15D) GPC trace for degradation of P3a at pH 3. (FIG. 15E) Plot of no. average molecular weight versus time (h) for the degradation study of P3a at different pH values.

(FIG. 17B) GPC traces of end-functional polyacetal, PEG-N3, and PEG-polyacetal-PEG tri-block copolymer.

FIGS. 20A-M show the preparation of main-chain clickable polyacetal with higher LCST and related data. (FIG. 20A) Synthetic scheme for polyacetal formation from tri (ethylene glycol) divinyl ether, 1,4-butyne diol, and tetraethylene glycol, wherein the molar feed ratio of the divinyl ether to the diols is 1.05 to 1 and the molar feed ratio of diols is varied. (FIG. 20B) Combined plots of % transmittance versus temperature for polyacetals from FIG. 20A (heating shown in solid circle and solid line, cooling shown in empty circle and dotted line). (FIG. 20C) Plot of the experimental LCSTs versus different percentages of tetraethylene glycol for polyacetals from FIG. 20A. (FIG. 20D) Synthetic scheme for polyacetal formation from tri(ethylene glycol) divinyl ether, 1,4-butyne diol, and triethylene glycol, wherein the molar feed ratio of the divinyl ether to the diols is 1.05 to 1 and the molar feed ratio of diols is varied. (FIG. 20E) Combined plots of % transmittance versus temperature for polyacetals from FIG. 20D (heating shown in solid circle and solid line, cooling shown in empty circle and dotted line). (FIG. 20F) Plot of the experimental LCSTs versus different percentages of triethylene glycol for polyacetals from FIG. 20D. (FIG. 20G) Synthetic scheme for polyacetal formation from tri(ethylene glycol) divinyl ether, 1,4-butyne diol, and diethylene glycol, wherein the molar feed ratio of the divinyl ether to the diols is 1.05 to 1 and the molar feed ratio of diols is varied. (FIG. 20H) Combined plots of % transmittance versus temperature for polyacetals from FIG. 20G (heating shown in solid circle and solid line, cooling shown in empty circle and dotted line). (FIG. 20I) Plot of the experimental LCSTs versus different percentages of diethylene glycol for polyacetals from FIG. 20G. (FIG. 20J) Synthetic scheme for polyacetal formation from tri(ethylene glycol) divinyl ether, 1,4-butyne diol, and ethylene glycol, wherein the molar feed ratio of the divinyl ether to the diols is 1.05 to 1 and the molar feed ratio of diols is varied. (FIG. 20K) Combined plots of % transmittance versus temperature for polyacetals from FIG. 20J (heating shown in solid circle and solid line, cooling shown in empty circle and dotted line). (FIG. 20L) Plot of the experimental LCSTs versus different percentages of ethylene glycol for polyacetals from FIG. 20J. (FIG. 20M) Plot of the experimental LCSTs versus different percentages of diols ($n_2=2$; $m_2=0$ to $n_2=2$; $m_2=3$) for the polyacetals prepared from 1,4-butyne diol and tri-ethylene glycol divinyl ether ($n_1=2$; $m_1=2$) (diol/divinyl ether-1/1.05 (mol/mol)).

(FIG. 25B) gel aggregate forms in tumor upon temperature release; and (FIG. 25C) micelles degrading in acidic tumor.

FIG. 30 shows exemplary therapeutic agents that comprise at least two hydroxyl groups.

DETAILED DESCRIPTION OF THE INVENTION

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Figure 1:
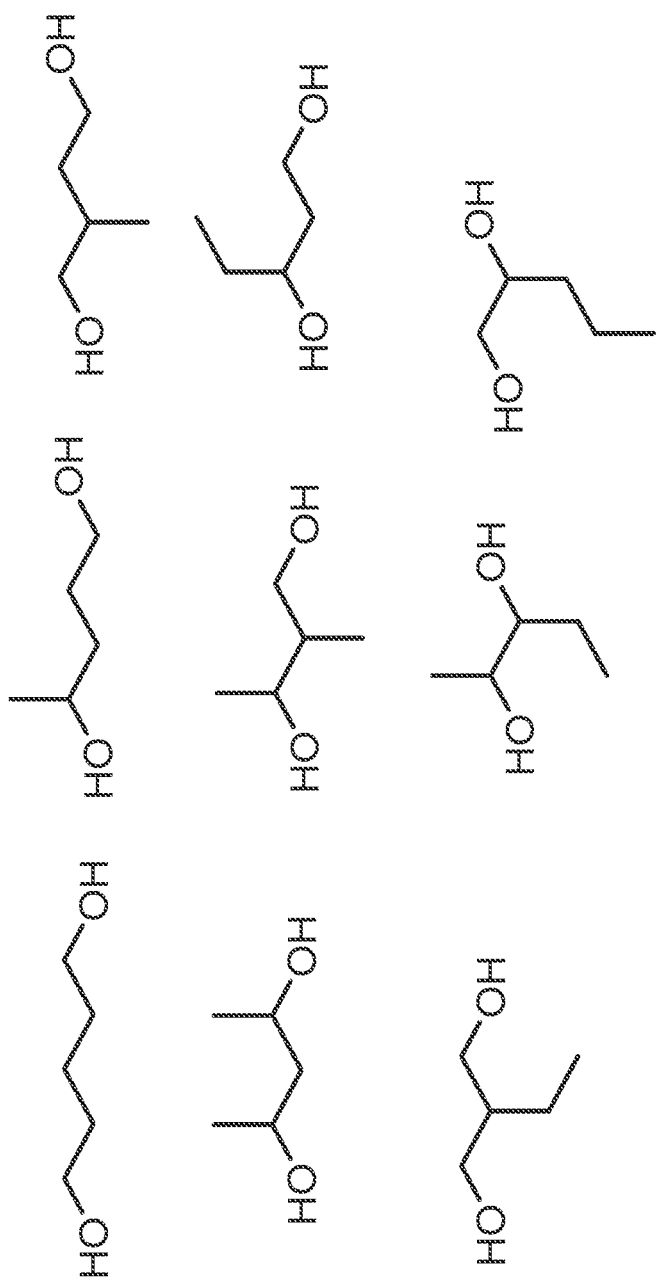
FIG. 1 shows exemplary $C_5$ alkyl diols.

As used herein the term "alkyl" denotes a branched, unbranched, or cyclic saturated hydrocarbon having from one to the number of carbon atoms designated (e.g., $C_1$-$C_{10}$ alkyl). Examples of alkyl include, but are not limited to, methyl, ethyl, n-propyl, isopropyl, n-butyl, t-butyl, n-hexyl, n-octyl, and the like. It will also be appreciated that the prefix "n" denotes an unbranched, acyclic group. For example, "$C_3$ n-alkyl" denotes an unbranched propyl group, which can also be referred to as "n-propyl". For a diol comprising a $C_n$ alkyl group, the $C_n$ alkyl group can be arranged in any number of ways known to a person of ordinary skill in the art (e.g., branched, unbranched, cyclic). For example, a $C_5$ alkyl diol includes the exemplary alcohols shown in FIG. 1.

As used herein the term "diol" denotes a compound that comprises at least two hydroxyl groups. Representative diols include, but are not limited to, therapeutic agents that comprise at least two hydroxyl groups. A therapeutic agent that contains a diol comprises at least two hydroxyl groups and a "therapeutic agent core". As used herein the term "therapeutic agent core" denotes a therapeutic agent without (in the absence of) two of the at least two hydroxyl groups in the therapeutic agent.

Therapeutic agents include, but are not limited to, drugs, agricultural agents, proteins, small molecule therapeutics, carbohydrate and peptides. Drugs include, but are not limited to, anticancer agents, agents to treat bone damage caused by breast cancer, and agents to treat hypercalcemia. Exemplary drugs include bisphenol A, methylhydroquinone, diethylstilbestrol, paclitaxel, doxorubicin, everolimus, pamidronate disodium, nelarabine, azacitidine, bleomycin, bortezomib, capecitabine, cytarabine, daunorubicin hydrochloride, decitabine, docetaxel, epirubicin, etoposide, raloxifene, fulvestrant, fludarabine, goserelin, topotecan, idarubicin, azaepothilone B, lanreotide, leuprolide, mitoxantrone, predinisone, temsirolimus, vinblastine, vincristine, or zoledronic acid.

Agricultural agents include, but are not limited to, pesticides, herbicides, fungicides, insecticides, nematode control agents, antihelminthics, and nutrients.

A drug that contains a diol comprises at least two hydroxyl groups and a "drug core". As used herein the term "drug core" denotes a drug without (in the absence of) two of the at least two hydroxyl groups in the drug.

An agricultural agent that contains a diol comprises at least two hydroxyl groups and an "agricultural agent core". As used herein the term "agricultural agent core" denotes an agricultural agent without (in the absence of) two of the at least two hydroxyl groups in the agricultural agent.

In one aspect, the invention is directed to a class of compounds of formula (I)

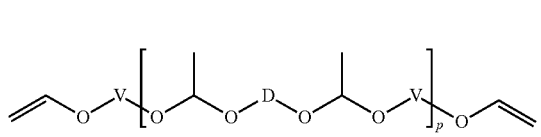 (I)

wherein V is

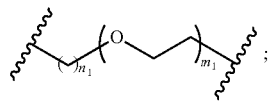

each D may be the same or different and is

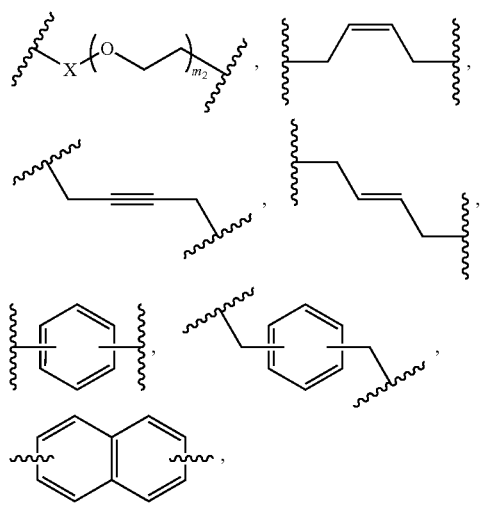

or a therapeutic agent core; each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20; and
p is an integer between 3 and 200.

In another aspect, the invention is directed to a biodegradable gel comprising a compound of formula (I) cross-linked with a linker at a terminus of the compound of formula (I), and wherein the linker is bonded to a plurality of compounds of formula (I).

In another aspect, the invention is directed to a method of making a gel, comprising cross-linking a compound of formula (I) with a trifunctional linker.

In another aspect, the invention is directed to a method of delivering a therapeutic agent to a tumor cell comprising, administering a biodegradable gel comprising a compound of formula (I) cross-linked with a linker at a terminus of the compound of formula (I), and wherein the linker is bonded to a plurality of compounds of formula (I); and a therapeutic agent, wherein said gel degrades at pH from about 5 to about 6.5 to release said therapeutic agent.

In another aspect, the invention is directed to a class of compounds of formula (II)

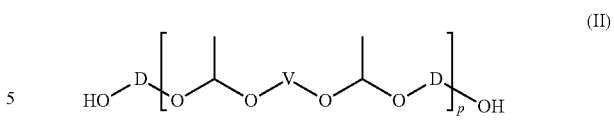 (II)

wherein,
V is

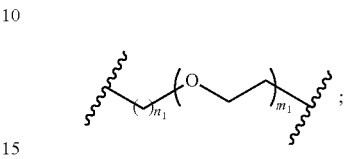

each D may be the same or different and is

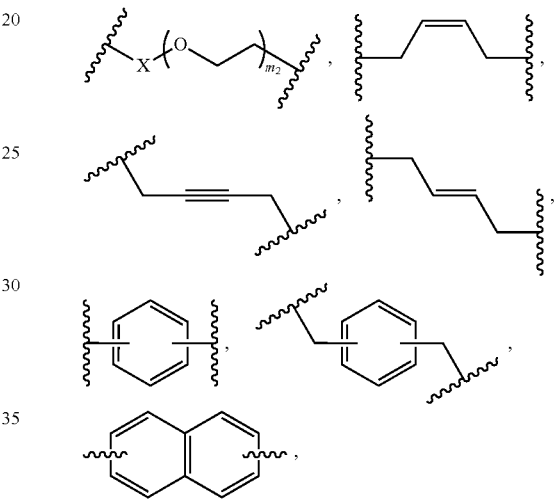

or a therapeutic agent core;
each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20; and
p is an integer between 3 and 200.

In another aspect, the invention is directed to a biodegradable gel comprising a compound of formula (II) cross-linked with a linker at a terminus of the compound of formula (II), and wherein the linker is bonded to a plurality of compounds of formula (II).

In another aspect, the invention is directed to a method of making a gel, comprising cross-linking a compound of formula (II) with a trifunctional linker. In some embodiments, the trifunctional linker comprises a triisocyanate.

In another aspect, the invention is directed to a method of delivering a therapeutic agent to a tumor cell comprising, administering a biodegradable gel comprising a compound of formula (II) cross-linked with a linker at a terminus of the compound of formula (II), and wherein the linker is bonded to a plurality of compounds of formula (II); and a therapeutic agent, wherein said gel degrades at pH from about 5 to about 6.5 to release said therapeutic agent.

In some embodiments, the compound of formula (I) comprises a therapeutic agent core and is used to treat a cancer in a subject in need thereof. In some embodiments, the compound of formula (II) comprises a therapeutic agent core and is used to treat a cancer in a subject in need thereof. Non-limiting examples of cancers treated by the therapeutic agent which comprises the therapeutic agent core include breast cancer, non-small cell lung cancer, pancreatic cancer, acute lymphoblastic leukemia (ALL), acute myeloid leukemia (AML), gastric cancer, Hodgkin lymphoma, neuroblastoma, Non-Hodgkin lymphoma, ovarian cancer, small cell lung cancer, soft tissue and bone sarcomas, thyroid cancer, transitional cell bladder cancer, Wilms tumor, adjuvant therapy for breast cancer that has spread to the lymph nodes after surgery, renal cell carcinoma, subependymal giant cell astrocytoma, Multiple myeloma, T-cell acute lymphoblastic leukemia, T-cell lymphoblastic lymphoma, Myelodysplastic syndromes (MDS), Chronic myelomonocytic leukemia (CMML), penile cancer, squamous cell carcinoma of the cervix, of the head and neck, and of the vulva, testicular cancer, mantle cell lymphoma, colorectal cancer, gastric cancer, esophageal cancer, Chronic myelogenous leukemia, meningeal leukemia, Myelodysplastic syndromes (MDS), adenocarcinoma, prostate cancer, squamous cell carcinoma of the head and neck, Chronic lymphocytic leukemia, cervical cancer, gastroenteropancreatic neuroendocrine tumors, AIDS related Kaposi sarcoma, bladder cancer, melanoma, esophageal cancer, mycosis fungoides, thymoma, thymic carcinoma, choriocarcinoma, Kaposi sarcoma, Mycosis fungoides, acute leukemia, and rhabdomyosarcoma.

In some embodiments, the compound of formula (I) comprises a therapeutic agent core and is used to treat bone damage caused by breast cancer in a subject in need thereof. In some embodiments, the compound of formula (I) comprises a therapeutic agent core and is used to treat hypercalcemia in a subject in need thereof. In some embodiments, the compound of formula (II) comprises a therapeutic agent core and is used to treat bone damage caused by breast cancer in a subject in need thereof. In some embodiments, the compound of formula (II) comprises a therapeutic agent core and is used to treat hypercalcemia in a subject in need thereof. In some embodiments, the therapeutic agent which comprises the therapeutic agent core is used to treat hypercalcemia or bone damage caused by breast cancer.

In some embodiments, the compound of formula (I) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, the compound of formula (II) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, a composition comprising the compound of formula (I) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, a composition comprising the compound of formula (II) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, therapeutic agents are compounds that are pharmaceutically active. In some embodiments, the compound of formula (I) comprises a "drug core". In some embodiments, the compound of formula (II) comprises a "drug core". In some embodiments, the compound of formula (I) comprises an "agricultural agent core". In some embodiments, the compound of formula (II) comprises an "agricultural agent core".

Polymeric materials, including thermoresponsive polymers, are attractive candidates in biomedical field and are often used as therapeutic agent carriers in different forms (Larcon, C. et al., *Chem. Soc. Rev.* 2005, 34, 276-285; Ward, M. A.; Georgiou, T. K. Polymers 2011, 3, 1215-1242; Galaev, I. Y.; Mattiasson, B. *Trends Biotechnol.* 1999, 17, 335-340; Samanta, S.; Das, S.; Layek, R. K.; Chatterjee, D. P.; Nandi, A. K. *Soft Matter* 2012, 8, 6066-6072; Das, S.; Samanta, S.; Chatterjee, D. P.; Nandi, A. K. *J. Polym. Sci., Part A: Polym. Chem.* 2013, 51, 1417-1427). Both biocompatibility and degradation capability are particularly advantageous for the development of therapeutic agent carriers. One approach that could improve the biocompatibility is the preparation of degradable polymers from materials that are easily metabolized by the body (Putnam, D. *Nat. Mater.* 2008, 7, 836-837). However, this approach is not always borne out. For example, polyesters are well-known hydrolytically degradable materials and are often modified with a smart material to prepare degradable thermoresponsive polymers for therapeutic agent delivery (Hales, M.; Barner-Kowollik, C.; Davis, T. P.; Stenzel, M. H. *Langmuir* 2004, 20, 10809-10817; Kim, I. S.; Jeong, Y. I.; Cho, C. S.; Kim, S. H. *Int. J. Pharm.* 2000, 211, 1-8; Jiang, X.; Smith, M. R.; Baker, G. L. *Macromolecules* 2008, 41, 318-324; Zhang, L. J.; Dong, B. T.; Du, F. S.; Li, Z. C. *Macromolecules* 2012, 45, 8580-8587). Although their degradation products can be metabolized, they are acidic in nature and can cause significant local inflammation (Putnam, D. *Nat. Mater.* 2008, 7, 836-837). This effect might not be troublesome for some sites of injection (for example, intramuscular), but an undesired inflammatory response in the myocardium can diminish cardiac function (Putnam, D. *Nat. Mater.* 2008, 7, 836-837). The problem of inflammation is directly addressed by Davis et al. (Sy, J. C.; Seshadri, G.; Yang, S. C.; Brown, M.; Oh, T.; Dikalov, S.; Murthy, N.; Davis, M. E. *Nature Mater.* 2008, 7, 863-869), who have prepared therapeutic agent delivery vehicles by using polyketals, which degrade into neutral degradation products and therefore, the local inflammatory response to the polymer is minimal. Thus, during the preparation of therapeutic agent carriers, it is particularly advantageous to have sufficient knowledge about their degradation products, which are advantageously neutral, non-toxic, and well metabolized by the body. Additionally, the degradation products are advantageously water-soluble small molecules so as to be fully cleared from the body. This is more particularly advantageous, particularly from cancer cells that have reduced renal clearance due to their defective (or absent) lymphatic drainage (Fox, M. E.; Szoka, F. C.; Frechet, J. M. *J. Acc. Chem. Res.* 2009, 42, 1141-1151).

Thermoresponsive polymers have been considered as smart materials that undergo a reversible lower critical solution temperature (LCST) phase separation (coil to globule transition) that is driven by the expulsion of water molecules associated with the polymer chain. The reversible (or 'smart') behavior has been exploited mainly in biotechnology and the medical field for therapeutic agent delivery, tissue engineering, bioseparation, biocatalysts, biomimetic actuators, sensors and so forth (Alarcon, C. d. l. H.; Pennadam, S.; Alexander, C. Chem. Soc. Rev. 2005, 34, 276-285; Ward, M. A.; Georgiou, T. K. Polymers 2011, 3, 1215-1242; Galaev, I. Y.; Mattiasson, B. Trends Biotechnol. 1999, 17, 335-340; Samanta, S.; Das, S.; Layek, R. K.; Chatterjee, D. P.; Nandi, A. K. Soft Matter 2012, 8, 6066-6072; Das, S.; Samanta, S.; Chatterjee, D. P.; Nandi, A. K. J. Polym. Sci., Part A: Polym. Chem. 2013, 51, 1417-1427). In particular, in the context of therapeutic agent delivery, thermoresponsive polymers have been studied to develop new cancer treatments as an alternative to traditional cancer chemotherapy. Chemotherapy is also harmful to cells that divide rapidly under normal circumstances, including cells in bone marrow, the digestive tract, and hair follicles, and leads to a decrease in blood cells, inflammation of the digestive tract, and hair loss. Such adverse side effects restrict the frequency with which the chemotherapeutic agents can be applied in proper dosage. Consequently, there is a need for developing alternative techniques for targeted therapeutic agent delivery to solid tumors.

Hyperthermia in cancer research is currently under preclinical evaluation (Wust, P.; Hildebrandt, B.; Sreenivasa, G.; Rau, B.; Gellermann, J.; Riess, H.; Felix, R.; Schlag, P. M. The LANCET Oncology 2002, 3, 487-497). However, the application of hyperthermia alone for cancer treatment is not as productive as the combination of hyperthermia with chemotherapy (Fotopoulou, C.; Cho, C. H.; Kraetschell, R.; Gellermann, J.; Wust, P.; Lichtenegger, W.; Sehouli, J. Int. J. Hyperthermia 2010, 26, 118-126).

The application of 'soluble polymeric therapeutic agent carriers' (Water-soluble polymer conjugated with therapeutic agent) (Fox, M. E.; Szoka, F. C.; Frechet, J. M. J. Acc. Chem. Res. 2009, 42, 1141-1151; Larson, N.; Ghandehari, H. Chem. Mater. 2012, 24, 840-853; Langer, R. Nature 1998, 392, 5-10) is under investigation in current chemotherapy methods. The soluble polymeric carriers offer improved therapeutic agent pharmacokinetics by reducing renal clearance and exploiting the enhanced permeability and retention (EPR) effect of fast-growing tumors to enhance therapeutic agent accumulation within the tumor tissue (Fox, M. E.; Szoka, F. C.; Frechet, J. M. J. Acc. Chem. Res. 2009, 42, 1141-1151). Preclinical evaluation has focused mainly on polyethylene glycol (PEG) or N-(2-hydroxypropyl)methacrylamide (HPMA) based conjugates, which are non-degradable and well tolerated in the body (Larson, N.; Ghandehari, H. Chem. Mater. 2012, 24, 840-853; Langer, R. Nature 1998, 392, 5-10). However, in order to exploit the valuable EPR effect, only high molecular weight carriers (>40,000 g·mol$^{-1}$) are acceptable, which might lead to lysosomal storage disease syndrome.

Furthermore, the polymeric carriers do not provide any intrinsic active targeting property to enable site specific delivery of therapeutic agents. For site specificity, much attention is given to the modern 'thermal targeting' technique (Meyer, D. E.; Shin, B. C.; Kong, G. A.; Dewhirst, M. W.; Chilkoti, A. J. Control. Rel. 2001, 74, 213-224). In thermal targeting, thermosensitive polymers are used as soluble polymeric carriers and are triggered by local hyperthermia to undergo an entropically favorable phase separation to expel their water content and enable selective cellular uptake of the therapeutic load. For this technique, the LCSTs of the polymeric carriers should be higher than physiological body temperature (37° C.) but less than the temperature in a region of local hyperthermia (42° C.) such that the polymeric carriers are soluble when injected into the body (37° C.), but become insoluble upon phase transition in locally heated regions to enhance tumor (hyperthermic region) accumulation over time. The effectiveness of 'thermal targeting' technique has been demonstrated by the enhanced uptake of poly(N-isopropylacrylamide), (pNIPAM), in mice with hyperthermic tumor tissue (Meyer, D. E.; Shin, B. C.; Kong, G. A.; Dewhirst, M. W.; Chilkoti, A. J. Control. Rel. 2001, 74, 213-224).

However, effective therapeutic agent delivery involves a balance between the concentration of the polymeric therapeutic agent carrier in the bloodstream and in the tumor. To drive the accumulation-equilibrium most favorably toward hyperthermic regions and also to reduce the toxicity level associated with indefinite accumulation of foreign bodies in tissues, a degradation mechanism within the polymer backbone is important (Phillips, D. J.; Gibson, M. I. Chem. Commun. 2012, 48, 1054-1056). A degradable backbone allows the polymeric carrier to be degraded into small molecules that can return to the blood compartment through the defective lymphatic systems of tumor cells before finally being removed by the kidneys.

Polymers that would be particularly advantageous as polymeric carriers for thermally targeted therapeutic agent delivery are those that have (i) appropriate functional group(s) for therapeutic agent conjugation, (ii) a thermoresponsive property with tunable LCST, and (iii) a degradation capability with neutral, nontoxic, and water soluble small molecular degradation products. Hydrolytic or biodegradable thermoresponsive polymers (mainly based on polyesters or polyamides) (Hales, M.; Barner-Kowollik, C.; Davis, T. P.; Stenzel, M. H. Langmuir 2004, 20, 10809-10817; Kim, I. S.; Jeong, Y. I.; Cho, C. S.; Kim, S. H. Int. J. Pharm. 2000, 211, 1-8; Jiang, X.; Smith, M. R.; Baker, G. L. Macromolecules 2008, 41, 318-324; Zhang, L. J.; Dong, B. T.; Du, F. S.; Li, Z. C. Macromolecules 2012, 45, 8580-8587; Bi, Y.; Yan, C.; Shao, L.; Wang, Y.; Ma, Y.; Tang, G. J. Polym. Sci., Part A: Polym. Chem. 2013, 51, 3240-3250; Moon, J. R.; Kim, J. H. Bull. Korean Chem. Soc. 2006, 27, 1981-1984) are known to be degraded in a non-specific pathway to generate acidic degradation products that lead to certain drops in pH and cause significant local inflammation (Putnam, D. Nat. Mater. 2008, 7, 836-837). The degradation of poly(propylene sulfide), via a non-specific oxidative pathway (Rehor, A.; Hubbell, J. A.; Tirelli, N. Langmuir 2005, 21, 411-417), and self-immolating polymers, via a series of cascade reactions (Sagi, A.; Weinstain, R.; Karton N.; Shabat, D. J. Am. Chem. Soc. 2008, 130, 5434-5435), has also been demonstrated; however, these polymers are not temperature sensitive.

If soluble, degradable polymeric carriers are to be used in cancer therapy, acid degradable polyacetals would be particularly advantageous candidates because of their degradation capability under mildly acidic conditions, which is similar to that of cancer cells (pH 5-6.5) (Paramonov, S. E.; Bachelder, E. M.; Beaudette, T. T.; Standley, S. M.; Lee, C. C.; Dashe, J.; Frechet, J. M. J. Bioconjugate Chem. 2008, 19, 911-919; Tomlinson, R.; Heller, J.; Brocchini, S.; Duncan, R. Bioconjugate Chem. 2003, 14, 1096-1106; Tomlinson, R.; Klee, M.; Garrett, S.; Heller, J.; Duncan, R.; Brocchini, S. Macromolecules 2002, 35, 473-480; Rickerby, J.; Prabhakar, R.; Ali, M.; Knowles, J.; Brocchini, S. J. Mater. Chem. 2005, 15, 1849-1856; Wang, Y.; Morinaga, H.; Sudo, A.; Endo, T. *J. Polym. Sci., Part A: Polym. Chem.* 2011, 49, 596-602). Moreover, polyacetals can be prepared smoothly under mild conditions from diols and divinyl ethers through condensation polymerization to generate free end groups that would be beneficial for drug conjugation. The previously reported polyacetals did not demonstrate any thermoresponsive property. In contrast, the polyacetals described herein are thermoresponsive due in part to the hydrophobic/hydrophilic balance of the polymer. An aspect of the invention described herein relates to the design and synthesis of a new family of acid degradable thermoresponsive polyacetals. In some embodiments, the polyacetals can be used as soluble polymeric therapeutic agent carriers for "thermally targeted" therapeutic agent delivery to solid tumors. Water soluble thermoresponsive polyacetals would open a new door in the biomedical field by providing an alternative to chemotherapy. The local hyperthermia of a solid tumor region can trigger an entropically favorable phase transition of a polyacetal carrier to expel water content and enable selective cellular uptake of the therapeutic load within the tumor. The acidic nature (pH 5-6.5) of cancer cells can help to degrade a polyacetal carrier into small molecules over time, which ultimately would be removed from the body through the kidneys. Thus, the accumulation-equilibrium is driven toward a hyperthermic region (hence, more therapeutic agent accumulation) and any cytotoxicity associated with insoluble (above LCST) polymers inside the tumor cells is reduced or avoided. In some embodiments, the above requirements are fulfilled by polyacetals that degrade into different linear diols and acetaldehyde. Acetaldehyde occurs naturally in coffee, bread, and ripe fruit, and is produced by plants. In the liver, the enzyme alcohol dehydrogenase oxidizes ethanol into acetaldehyde, which is then further oxidized into harmless acetic acid by acetaldehyde dehydrogenase (http://en.wikipedia.org/wiki/Acetaldehyde). These two oxidation reactions are coupled with the reduction of $NAD^+$ to NADH. Since the degradation products of polyacetals are neutral, nontoxic and water soluble small molecules, they would be suitable candidates for soluble polymeric therapeutic agent carriers.

The availability of thermoresponsive, pH-degradable polyacetals would revolutionize the field of thermoresponsive polymers and the biomedical field. First of all, many of the initial monomers (diols and divinyl ethers) are commercially available and the polymerization reactions are very fast. In contrast to the previously reported polyacetals, which are not temperature sensitive, the polyacetals described herein are thermoresponsive, with LCSTs that can be varied systematically from about 6° C. to about 80° C. and that can be adjusted. This is not possible for pNIPAM. Additionally, these polyacetals could be considered "macromonomers" due to the availability of chain-end functionalities that could be used for a variety of purposes including, but not limited to, further chain extension, preparation of ABA-type block copolymers, and therapeutic agent attachment. The hydroxyl terminated polyacetals (P'-category polyacetals, Table 1, entries 21-24), which are also thermoresponsive, could be considered "diol macromonomers" and could be used for the preparation of thermoresponsive and pH degradable polyurethane. Moreover, unlike pNIPAM, which is not degradable, the polyacetals described herein degrade. In some embodiments, degradation products comprise neutral, nontoxic, water soluble small molecules that result from degradation under the same mildly acidic conditions that prevail for fast-growing tumors (cancer cells). In one aspect, the polyacetals described herein are suitable candidates for soluble polymeric therapeutic agent carriers for "thermally targeted" therapeutic agent delivery in solid tumors in presence of local hyperthermia.

Figure 2A:
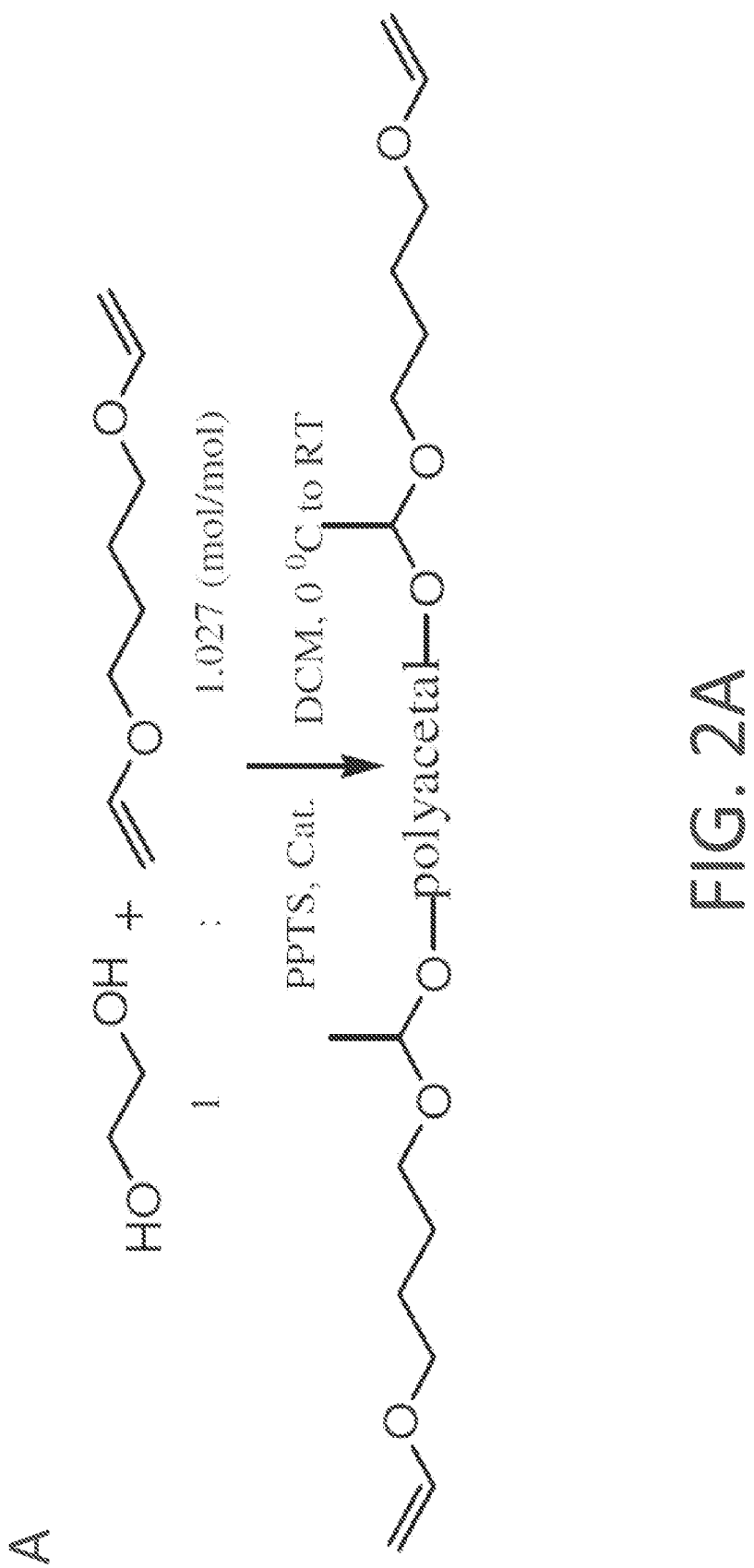
FIGS. 2A-C show (FIG. 2A) polyacetal formation from ethylene glycol and 1,4-butanediol divinyl ether, wherein the molar feed ratio of the divinyl ether to the diol is 1.027 to 1.

A hydrophobic polyacetal was constructed using 1,4-butanediol divinyl ether ($M_{DVE}$) and ethylene glycol ($M_0$) as the two initial monomers. The term "$M_{DVE}$" represents the divinyl ether monomer, wherein there are zero ethylene oxide units, and the term "$M_0$" represents the diol monomer wherein there are zero ethylene oxide units. The ratio of $M_{DVE}$ to $M_0$ represents the molar feed ratio, which is the ratio of mmol of $M_{DVE}$ to mmol of $M_0$. 1,4-butanediol divinyl ether is a commercially available hydrophobic divinyl ether. Ethylene glycol represents the smallest possible linear diol and is also the repeating unit of PEG. The overall scheme is presented in FIG. 2A. Initially, $M_0$ and $M_{DVE}$ (in excess) are reacted in anhydrous dichloromethane (DCM) to yield a telechelic polymer that is periodically segmented by pH degradable acetal moieties and contains free vinyl ether groups at the terminal ends, since $M_{DVE}$ is used in excess. The resulting thermoresponsive polyacetal is soluble in many common organic solvents and in water (at low temperature), in contrast to previously reported polyacetals that were also prepared from PEG and hydrophilic divinyl ethers but did not demonstrate thermoresponsive behavior. Polymers that are linear, acid-degradable and thermoresponsive are not previously reported in literature.

The selective delivery of anticancer agents to tumors has been identified as an alternative to chemotherapy, with the goal of minimizing detrimental side effects. One approach for the selective delivery of anticancer agents to tumors is to use thermoresponsive polymers. Thermoresponsive polymers that are initially water soluble at normal body temperature can be carried throughout the body by the circulatory system. At elevated temperatures, the thermoresponsive polymers become insoluble and can then diffuse out of the solution to be absorbed by the surrounding tissue. Areas of localized heating, such as tumors, can thus be targeted by thermoresponsive polymers. While anticancer agents alone do not exhibit the desired thermoresponsive behavior and thus cannot target areas of localized heating, the infusion/incorporation of anticancer agents into a suitable polymer to yield a polymer-anticancer agent conjugate could enable their delivery to such areas. Furthermore, once the polymer-anticancer agent conjugate has been delivered, it can degrade to yield the anticancer agent and other degradation products, which will be removed by the kidneys. Thus, the polymer-anticancer agent conjugates are biodegradable and thermoresponsive polymers for the targeted delivery of anticancer agents wherein the harmful side effects experienced by patients undergoing conventional cancer treatment is reduced. As of yet, suitable polymer-anticancer agent conjugates have not been identified that demonstrate the aforementioned properties.

In one aspect, the polyacetals described herein are polymer-therapeutic agent conjugates. By using a therapeutic agent comprising a divinyl ether or a therapeutic agent comprising a diol as monomers in the construction of the polyacetals, therapeutic agents can be incorporated into the backbone of the polyacetal to yield polymer-therapeutic agent conjugates that are water soluble, thermoresponsive, and pH-degradable. In some embodiments, the polymer-therapeutic agent conjugates can be used in hyperthermia-triggered therapeutic agent delivery in solid tumors because the inherent acidic environment of the cancer cells will degrade the polymer-therapeutic agent conjugate to generate the intact therapeutic agent as a degradation product. The process for constructing or preparing the polymer-therapeutic agent conjugates is versatile as various therapeutic agents that comprise a divinyl ether or a diol can be used as monomers without requiring the process to be modified.

In some embodiments, therapeutic agents that target hypoxia-inducible factor-1 (HIF-1), such as bisphenol A (BIS-A) and diethylstilbestrol (DES), can be used to prepare polymer-therapeutic agent conjugates that have improved pharmacological properties relative to the therapeutic agent alone.

HIF-1 is a heterodimer formed by the association of an 02-regulated HIF-1α subunit with a constitutively expressed HIF-1β subunit. It plays an important role in mediating cellular response to hypoxia, a condition in which the body or a region of the body is deprived of adequate oxygen supply. Solid tumors with regions of reduced oxygen concentration undergo "intratumoral hypoxia" (Vaupel, P. and Mayer, A. Hypoxia in cancer: significance and impact on clinical outcome. Cancer Metastasis Rev. 2007, 26, 225-339). Intratumoral hypoxia is observed when cells are located too far from a functional blood vessel for diffusion of adequate amounts of 02, a result of the formation of structurally and functionally abnormal blood vessels (Semenza, G. L. Drug Discovery Today 2007, 12, 853-859) which leads to cell death. In response, cancer cells can select to inactivate apoptotic pathways, activate anti-apoptotic pathways, or activate invasion/metastasis pathways that promote escape from the hypoxic microenvironment. The best-characterized hypoxia response pathway is mediated by HIF-1.

HIF-1 regulates the transcription of many genes involved in cancer biology, including immortalization, maintenance of stem cell pools, cellular dedifferentiation, genetic instability, vascularization, metabolic reprogramming, autocrine growth factor signaling, invasion/metastasis, and treatment failure. Under normoxia, HIF-1α is located in the cytosol and is subject to 02-dependent prolyl hydroxylation, allowing their recognition and ubiquitination by the von Hippel-Lindau tumor suppressor protein (VHL), which labels them for rapid degradation by the proteasome. Under hypoxic conditions, the rate of prolyl hydroxylation and ubiquitination is inhibited or declined, since it utilizes oxygen as a cosubstrate, allowing HIF-1α to subsequently transfer to the nucleus and, in concert with HIF-10, bind to hypoxia-responsive element (HRE) sequences in the DNA and activate the transcription of at least 150 hypoxia-related genes (Semenza, G. L. Drug Discovery Today 2007, 12, 853-859). In animal models, HIF-1 overexpression is associated with increased tumor growth, vascularization, and metastasis, which also lead to increased patient mortality in many human cancers. In contrast, the loss of HIF-1 function has the opposite effect. Consequently, HIF-1 is considered an important therapeutic target (Semenza, G. L. Drug Discovery Today 2007, 12, 853-859).

A library of novel anticancer agents (FIG. 30 and drugs that contain a diol, as explained above) have been identified as potential candidates for the inhibition of HIF-1 in the treatment of solid tumors. The anticancer agents inhibit HIF-1 through a variety of molecular mechanisms. For example, bisphenol A (BIS-A) plays a role in the dissociation of heat shock protein 90 (Hsp90) from HIF-1α, which causes HIF-1α destabilization. The degradation of HIF-1 usually occurs first by ubiquitination and then by the proteasome pathway (Kubo, T.; Maezawa, N.; Osada, M.; Katsumura, S.; Funae, Y.; Imaoka, S. Biochem. Biophys. Res. Commun. 2004, 318, 1006-1011). Diethylstilbestrol (DES) is a HIF inhibitor that binds and inhibits estrogen-related receptors (ERRs), which serve as essential cofactors of HIF in mediating the hypoxic response. Thus, diethylstilbestrol functions by blocking the HIF-dependent hypoxic response (Ao, A.; Wang, H.; Kamarajugadda, S.; Lu, J. Proc. Natl. Acad. Sci. U.S.A 2008, 105, 7821-7826). Similarly, methylhydroquinone (MHQ) inhibits the growth of endothelial and tumor cells in culture in the micromolar range and is a promising therapeutic candidate in the treatment of cancer and other angiogenesis-related pathologies (García-Caballero, M.; Mari-Beffa, M.; Cañedo, L.; Medina, M. A.; Quesada, A. R. Biochemical Pharmacology, 2013, 85, 1727-1740). However, these molecules often present limitations, such as poor stability in plasma, low aqueous solubility, or even capacity to trigger other molecular actions that indirectly induce the decrease of HIF protein levels. Consequently, the reported HIF inhibitors have yet to meet the pharmacological requirements for human therapeutic use (Giaccia, A.; Siim, B. G.; Johnson, R. S. Nat. Rev. Drug Discov. 2003, 2, 803-811).

As discussed above, soluble polymeric therapeutic agent carriers have been used successfully as novel polymer therapeutics for the treatment of cancer. They offer improved therapeutic agent pharmacokinetics by reducing renal clearance and exploiting the enhanced permeability and retention (EPR) effect of fast-growing tumors to enhance therapeutic agent accumulation within the tumor tissue (Fox, M. E.; Szoka, F. C.; Frechet, J. M. J. Acc. Chem. Res. 2009, 42, 1141-1151). Although 16 polymer-therapeutic agent conjugates are currently in advanced clinical trials, most of them as anticancer therapeutics, progress has been slow due to clinical failures arising from (a) poor rational design of polymeric carriers and (b) trouble in targeted therapeutic agent delivery.

Anticancer agents, for example, can be incorporated into the backbone of the polyacetals to prepare water soluble, thermoresponsive and pH degradable polyacetal-based polymer therapeutics with tunable LCSTs. Such polyacetal-based polymer therapeutics can be used in the "thermally targeted" delivery and release of, for example, anticancer agents for the inhibition of HIF-1 in the treatment of solid tumors. The availability of such polymer therapeutics would be beneficial to cancer research as an alternative to chemotherapy: the local hyperthermia of solid tumors would facilitate polymer accumulation within the tumor while the acidic nature (pH 5-6.5) of cancer cells would facilitate the degradation of the polymer therapeutic to release the intact anticancer agent. In some embodiments, the hydrophobic nature of the anticancer agent enables the agent to be retained in the cancer region while the other degradation products, which are water soluble small molecules, will be removed from the body.

Figure 31A:
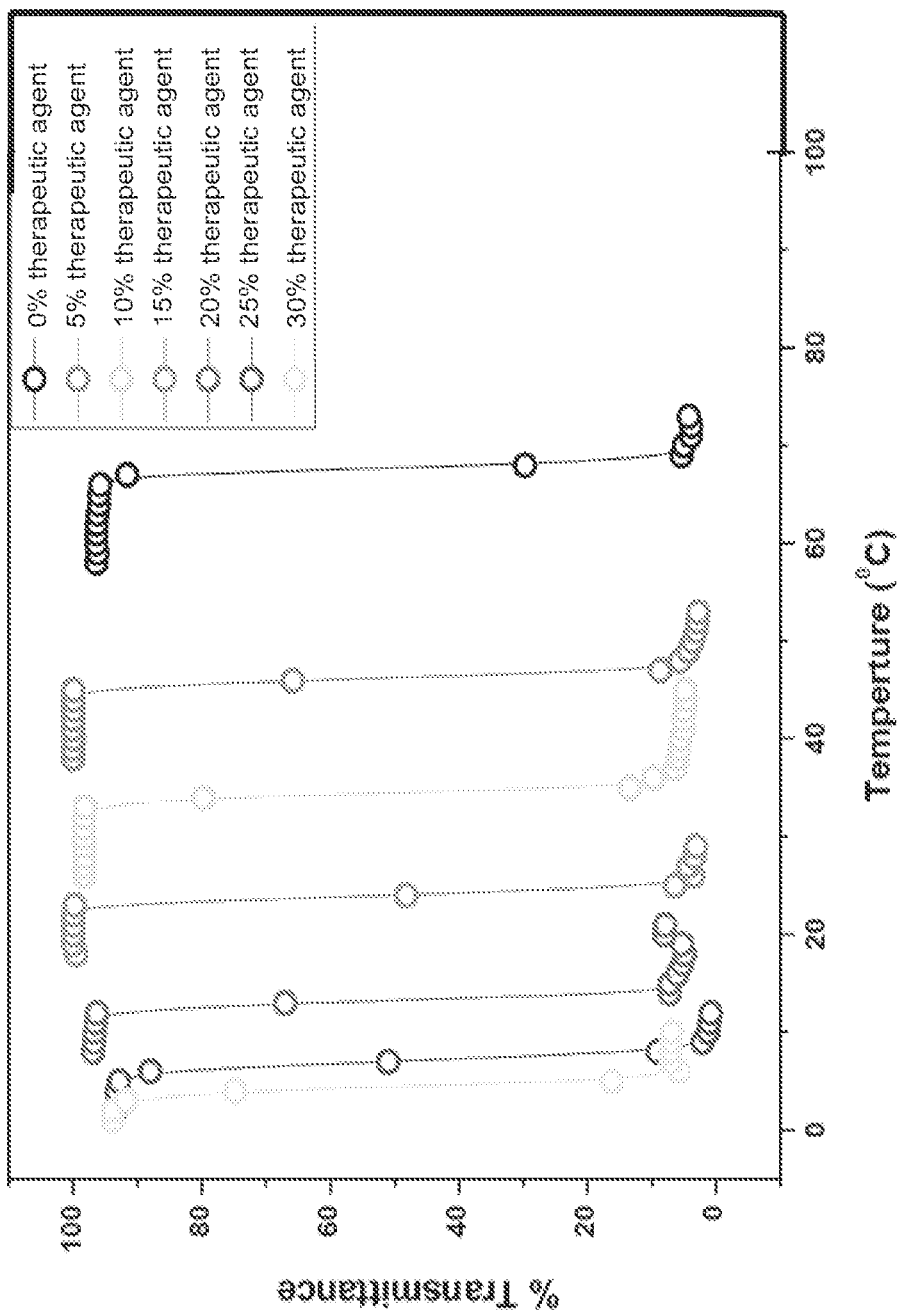
FIGS. 31A-B show temperature induced phase transition for several polyacetal-based polymer therapeutics prepared from bisphenol A (FIG. 31A) and variation of LCST as a function of percent bisphenol A in the polyacetal (FIG. 31B).
Figure 31B:
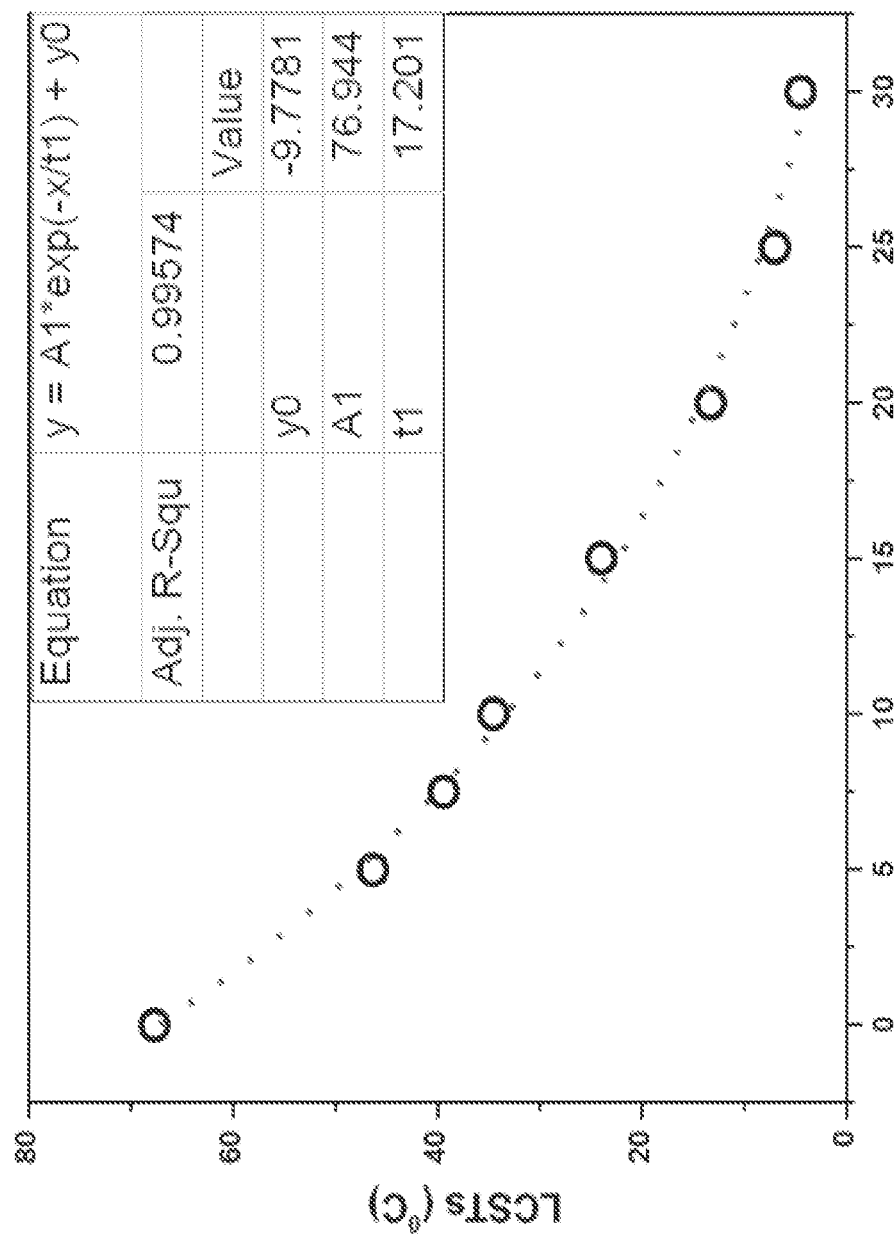
Figure 32A:
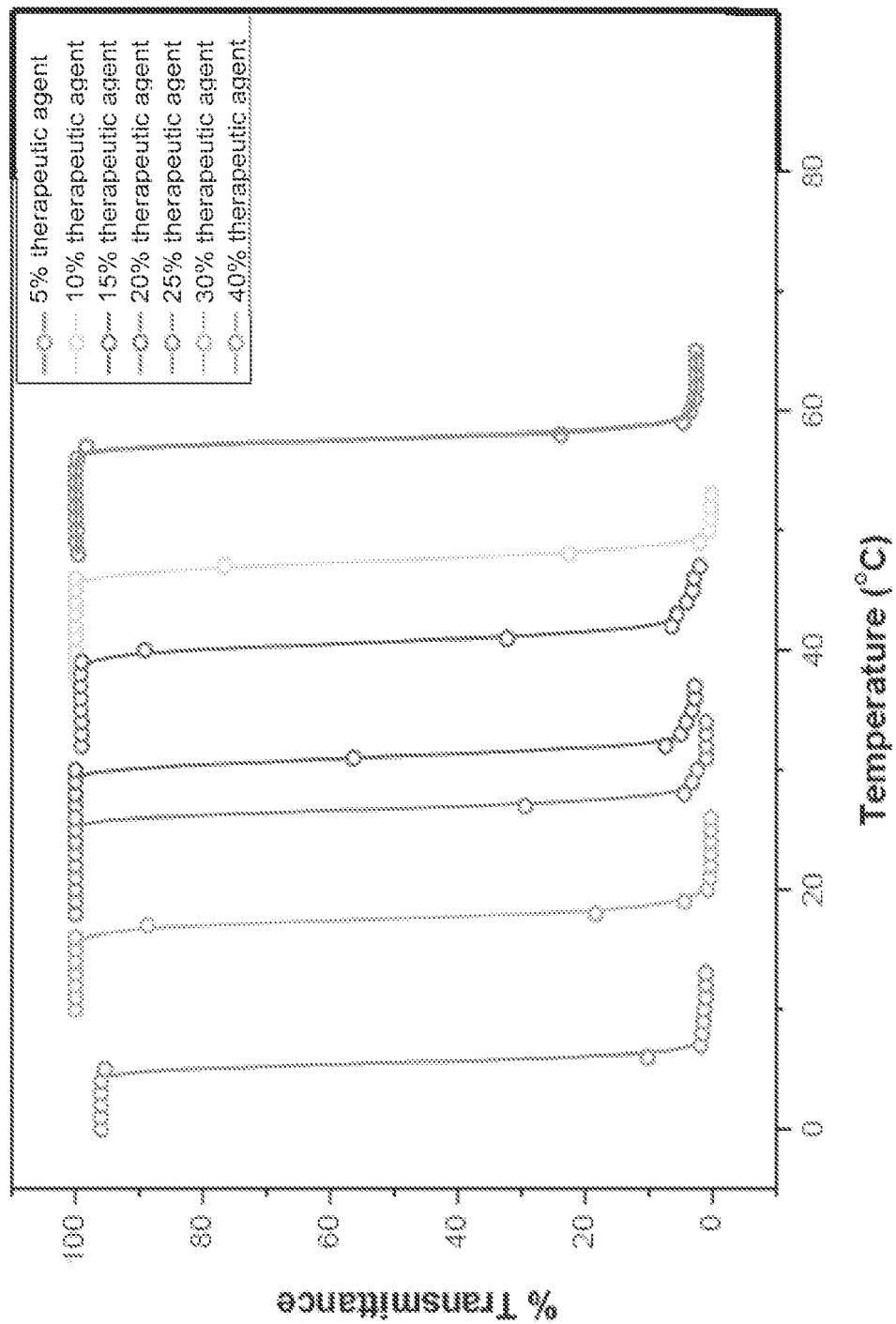
FIGS. 32A-B show temperature induced phase transition for several polyacetal-based polymer therapeutics prepared from MHQ (FIG. 32A) and variation of LCST as a function of percent MHQ in the polyacetal (FIG. 32B).
Figure 32B:
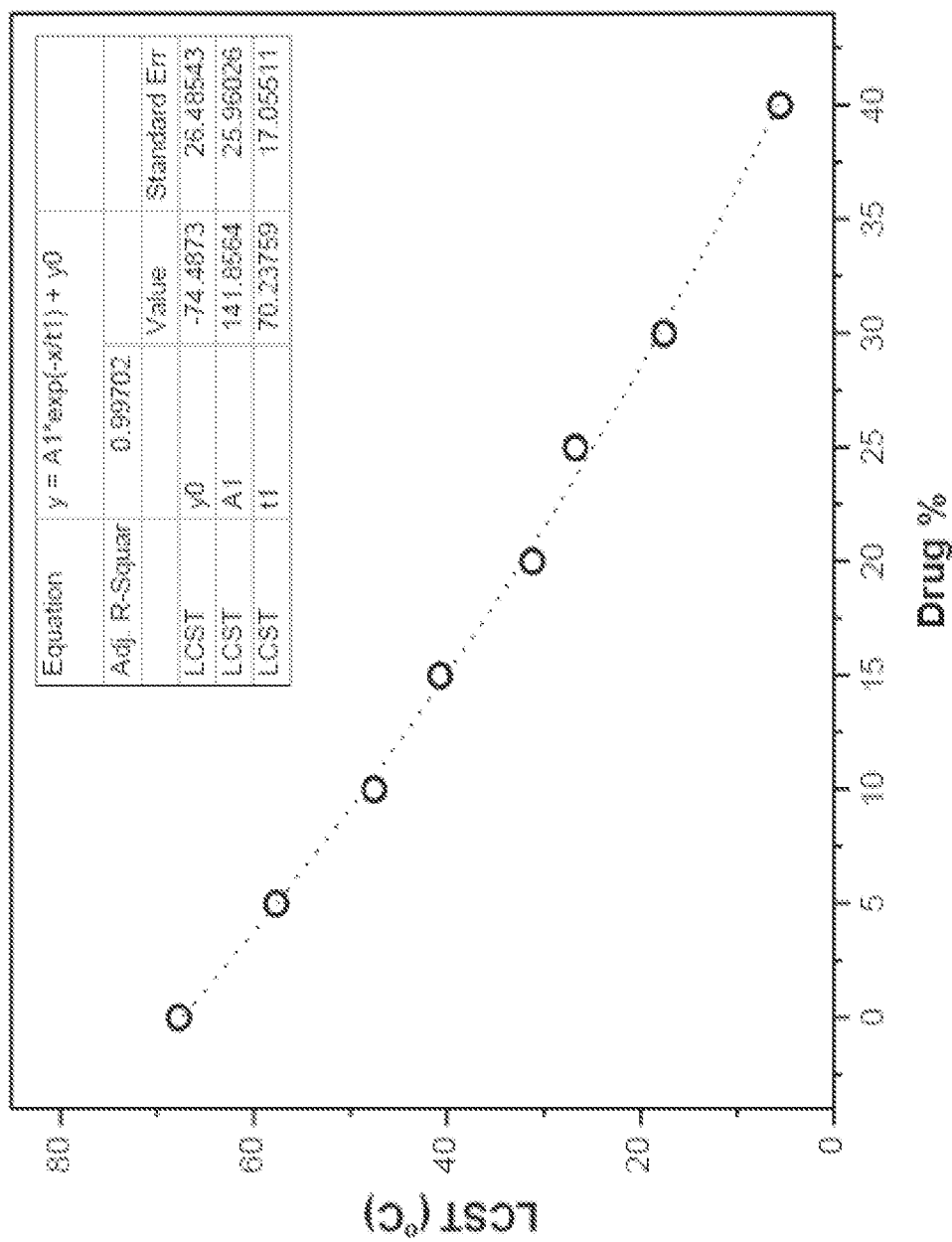

The ability to tune the LCST of the polyacetal-based polymer therapeutics is particularly advantageous if the polymers are to be used in hyperthermia-triggered therapeutic agent delivery in solid tumors, where a LCST is between about 37-42° C. FIG. 31B shows the variation of LCST as a function of the percent of bisphenol A in the polyacetal. FIG. 32B shows the variation of LCST as a function of the percent of MHQ in the polyacetal. The data fit well with first order exponential decay, indicating that the LCST of polyacetals can be tuned by adjusting the percentage of therapeutic agent present in the polyacetal. Thus, it is possible to predict the LCST of polymer therapeutics based on the percent of therapeutic agent present in the polymer and to design polymer therapeutics that have LCSTs that make the polymers suitable therapeutic candidates for hyperthermia-triggered delivery and release of anticancer agents. In contrast, the reported polyacetal-based therapeutic agent conjugates, which are prepared from PEG, do not demonstrate thermoresponsive behavior and thus cannot be used for hyperthermia-triggered delivery and release of therapeutic agents (Tomlinson, R.; Heller, J.; Brocchini, S.; Duncan, R. *Bioconjugate Chem.* 2003, 14, 1096-1106; England, R. M.; Masiá, E.; Giménez, V.; Lucas, R.; Vicent, M. J. Journal of Controlled Release 2012, 164, 314-322). Other polyacetal-based therapeutic agent conjugates that have been reported also do not demonstrate thermoresponsive behavior (U.S. Pat. No. 7,220,414

The polyacetal-based polymer therapeutics are intrinsically biodegradable, with a degradation mechanism that releases the original, intact therapeutic agent. This is in contrast to the majority of reported polyacetal-based therapeutic agent conjugates, which degrade to generate derivatives of therapeutic agents rather than the intact therapeutic agent (Tomlinson, R.; Heller, J.; Brocchini, S.; Duncan, R. Bioconjugate Chem. 2003, 14, 1096-1106), a difference that could affect the therapeutic activity of the released agent.

In some embodiments, the polyacetal-based polymer therapeutics comprises triethyleneglycol divinyl ether, tetraethylene glycol, and an anticancer agent, wherein the anticancer agent comprises at least two hydroxyl groups. In some embodiments, the LCST of the polyacetal-based polymer therapeutics is adjusted by changing the amount of anticancer agent that is incorporated into the polyacetal-based polymer therapeutic. Thus, in some embodiments, the temperature at which the polyacetal-based polymer therapeutic becomes insoluble can be adjusted by changing the amount of anticancer agent that is incorporated into the polyacetal-based polymer therapeutic.

Polyacetal-based polymer therapeutics can be prepared from anticancer agents comprising at least two hydroxyl groups. These polymer therapeutics are intrinsically thermoresponsive and pH degradable with tunable LCSTs that depend on the amount of therapeutic agent present within the polymer. The polymers degrade under mildly acidic conditions, which is similar to that of cancer cells (pH 5-6.5), to release the intact anticancer agent. Thus, the polyacetal-based polymer therapeutics are potential candidates for hyperthermia-triggered delivery and release of anticancer agents for the inhibition of HIF-1 in the treatment of solid tumors.

In another aspect, the polyacetals described herein are polymer-agricultural agent conjugates. By using an agricultural agent comprising a divinyl ether or an agricultural agent comprising a diol as monomers in the construction of the polyacetals, agricultural agents can be incorporated into the backbone of the polyacetal to yield polymer-agricultural agent conjugates that are water soluble, thermoresponsive, and pH-degradable. As the optimum soil pH range for most plants is between 5.5 and 7.0, the polymer-agricultural agent conjugates can be used to deliver agricultural agents to many soil-based plants, where the inherent acidic environment of the soil will degrade the polymer-agricultural agent conjugate to release the intact agricultural agent as a degradation product. Depending on the nature of the agricultural agent, delivery of the polymer-agricultural agent conjugate can be accomplished by seed treatment, spraying of pre-emergent crops, or spraying of post-emergent crops. Seed treatment allows an agricultural agent or agents to be applied to the seed prior to planting to protect against soil-borne risks or to provide additional nutrients to promote growth. After planting, the inherent acidic environment of the soil will degrade the polymer-agricultural agent conjugate to release the intact agricultural agent as a degradation product. Depending on the nature of the agricultural agent, spraying of pre-emergent crops with an appropriate formulation of the polymer-agricultural agent conjugate can reduce competitive pressure on newly germinated plants by removing unwanted or harmful organisms or maximize the amount of nutrients available for the crop. The spraying of pre-emergent crops with an appropriate formulation of the polymer-agricultural agent conjugate delivers the polymer-agricultural agent conjugate to the soil, where the polymer-agricultural agent conjugate can be degraded to release into the soil the intact agricultural agent as a degradation product. Alternatively, the spraying of post-emergent crops with an appropriate formulation of the polymer-agricultural delivers the polymer-agricultural agent conjugate to the plant surface, where it can form a coating. The coating, which is water soluble, can subsequently be washed with water to deliver the polymer-agricultural agent conjugate to the soil, where it can be degraded to release the intact agricultural agent.

In some embodiments of formula (I), the sum of $(m_1+m_2)$ is greater than or equal to zero. In some embodiments of formula (I), the sum of $(m_1+m_2)$ is greater than zero.

In some embodiments of formula (I), each D may be the same or different and is

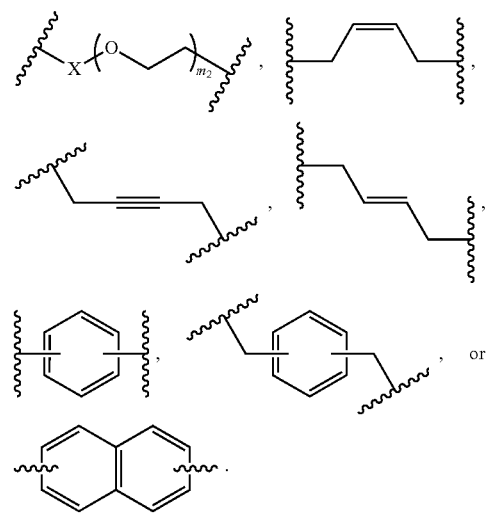

In some embodiments of formula (I), each D may be the same or different and is

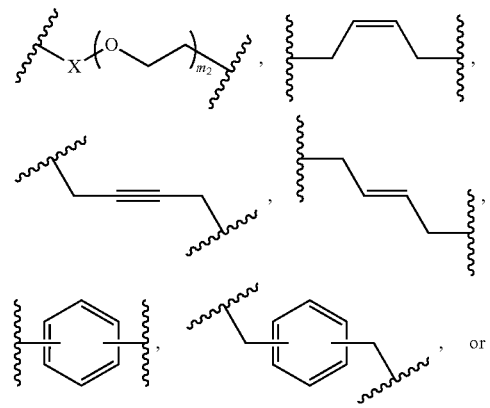

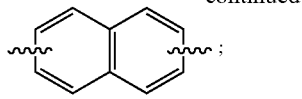

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), D is

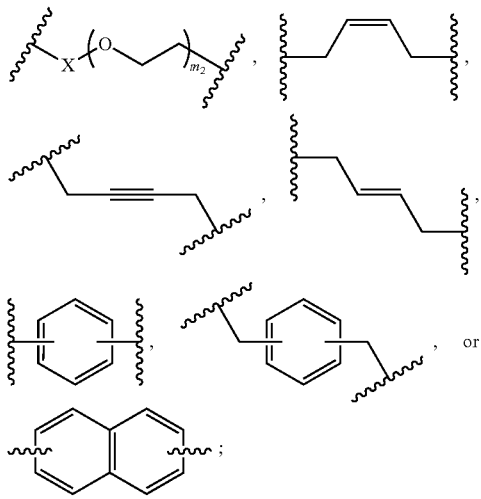

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (I), each D may be the same or different and is

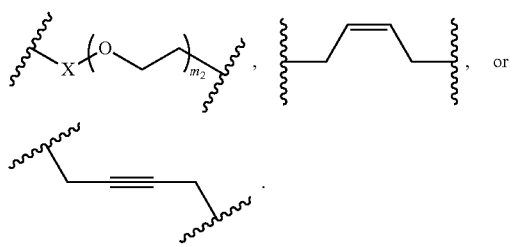

In some embodiments of formula (I), each D may be the same or different and is

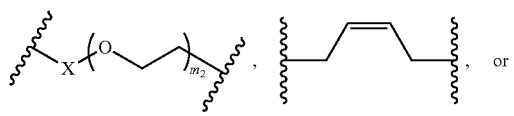

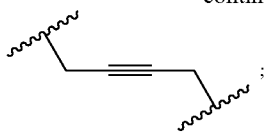

each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (I), each $n_1$ may be the same or different and is an integer between 2 and 4; each $m_1$ may be the same or different and is an integer between 0 and 2; each X may be the same or different and is $C_2$-$C_5$ n-alkyl; each $m_2$ may be the same or different and is an integer between 0 and 3; and p is an integer between 3 and 100.

In some embodiments of formula (I), each $n_1$ may be the same or different and is an integer between 2 and 4; each $m_1$ may be the same or different and is an integer between 0 and 2; each X may be the same or different and is $C_2$-$C_5$ n-alkyl; each $m_2$ may be the same or different and is an integer between 0 and 3; and p is an integer between 3 and 50.

In some embodiments of formula (I), X is $C_2$-$C_5$ n-alkyl.

In some embodiments of formula (I), each $m_2$ may be the same or different and is 2 or 3.

In some embodiments of formula (I), each D may be the same or different and is

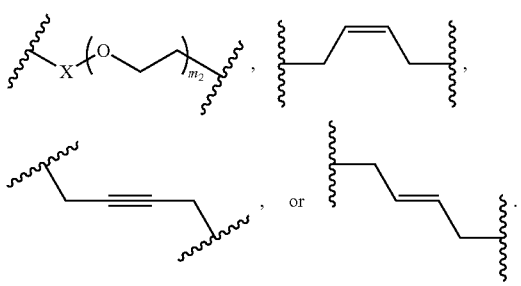

In some embodiments of formula (I), $n_1$ is an integer between 2 and 4; $m_1$ is an integer between 0 and 2; X is $C_2$-$C_5$ alkyl; $m_2$ is an integer between 0 and 3; and p is an integer between 3 and 100.

In some embodiments of formula (I), $n_1$ is an integer between 2 and 4; $m_1$ is an integer between 0 and 2; X is $C_2$-$C_5$ n-alkyl; $m_2$ is an integer between 0 and 3; and p is an integer between 3 and 100.

In some embodiments of formula (I), D is

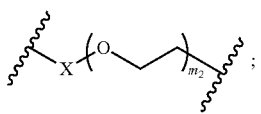

$n_1$ is 4; $m_1$ is 0; X is $C_2$ alkyl; each $m_2$ may be the same or different and is an integer between 0 and 3; and p is an integer between 3 and 100.

In some embodiments of formula (I), D is

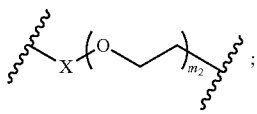

$n_1$ is 4; $m_1$ is 0; X is $C_2$ alkyl; each $m_2$ may be the same or different and is 2 or 3; and p is an integer between 3 and 100.

In some embodiments of formula (I), D is

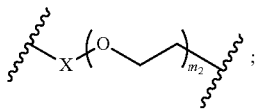

$n_1$ is 2; each $m_1$ may be the same or different and is 1 or 2; X is $C_2$ alkyl; $m_2$ may be the same or different and is an integer between 0 and 3; and p is an integer between 3 and 100.

In some embodiments of formula (I), D is

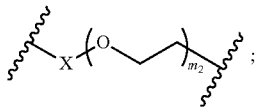

$n_1$ is 2; each $m_1$ may be the same or different and is 1 or 2; X is $C_2$-$C_5$ alkyl; $m_2$ is 0; and p is an integer between 3 and 100.

In some embodiments of formula (I), D is

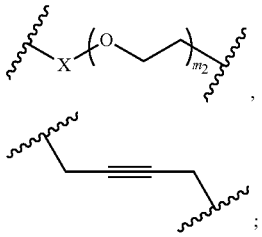

$n_1$ is 2; $m_1$ is 2; X is $C_4$ alkyl; $m_2$ is 0; and p is an integer between 3 and 100.

In some embodiments of formula (I), each D may be the same or different and is

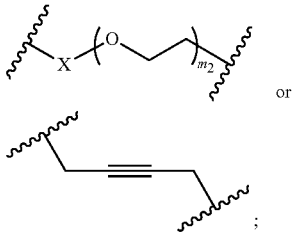

$n_1$ is 2; $m_1$ is 2; X is $C_2$ alkyl; $m_2$ is 2; and p is an integer between 3 and 100.

In some embodiments of formula (I), p is an integer between 3 and 50.

In one aspect, the invention is directed to compositions comprising a compound of formula (I) wherein each D may be the same or different and is

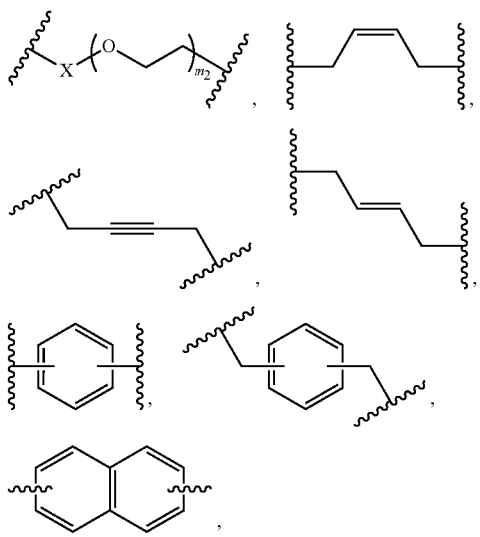

or a therapeutic agent core; and a pharmaceutically acceptable carrier.

In another aspect, the invention is directed to a method for treating cancer in a subject, the method comprising administering to a subject a therapeutic amount of a compound of formula (I), wherein each D may be the same or different and is

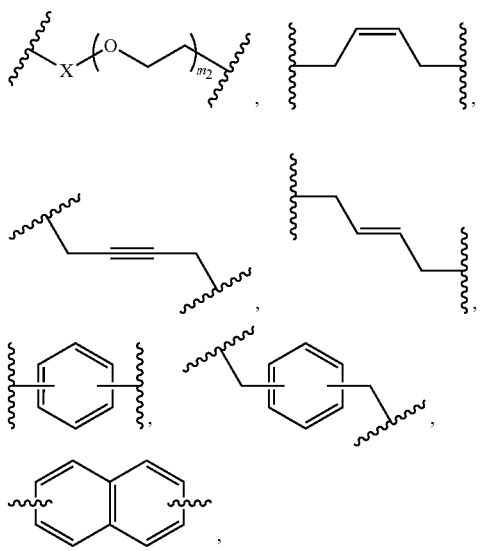

or a therapeutic agent core; or a pharmaceutical composition thereof.

In another aspect, the invention is directed to compositions comprising a compound of formula (I), wherein each D may be the same or different and is

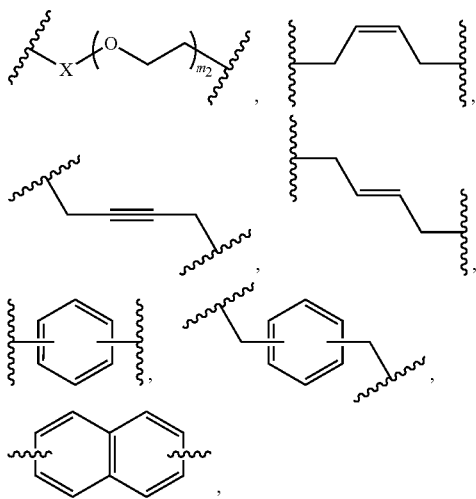

or a therapeutic agent core; and water or a liquid chemical carrier.

In another aspect, the invention is directed to a method for delivering a therapeutic agent to crops, plants or seeds, the method comprising administering to crops, plants, or seeds a compound of formula (I), wherein each D may be the same or different and is

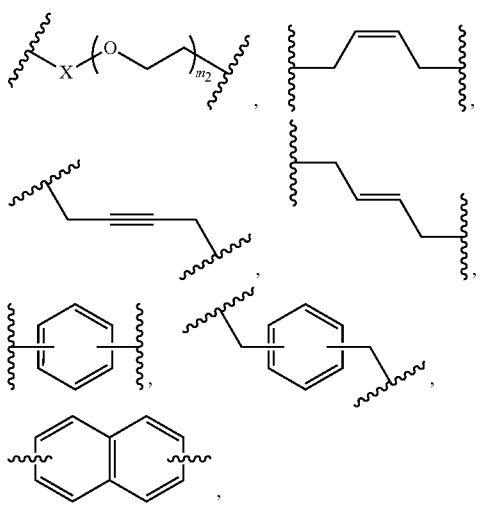

or a therapeutic agent core; or a chemical composition thereof.

In some embodiments of formula (I), each D may be the same or different and is

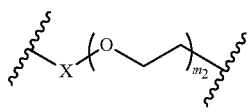

or a therapeutic agent core.

In some embodiments of formula (I), each D may be the same or different and is

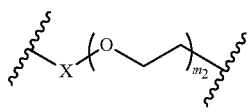

or a therapeutic agent core; $n_1$ is an integer between 2 and 10; $m_1$ is an integer between 0 and 20; X is $C_2$-$C_{10}$ alkyl; and $m_2$ is an integer between 0 and 20.

In some embodiments of formula (I), the therapeutic agent core is

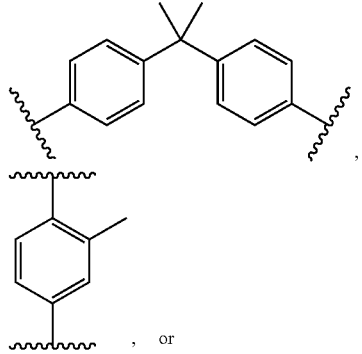

, or

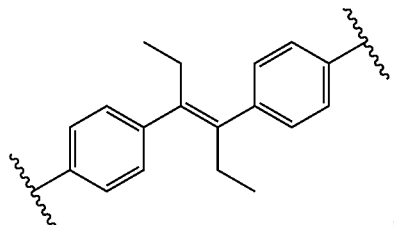

;

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), the therapeutic agent core is

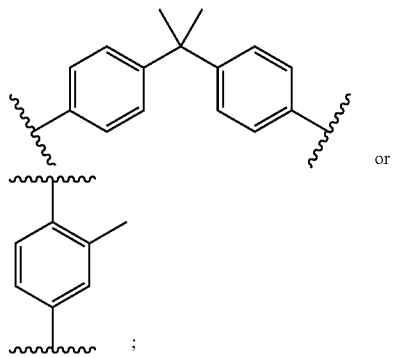 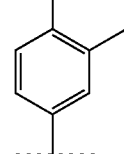

or

;

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), the therapeutic agent core is

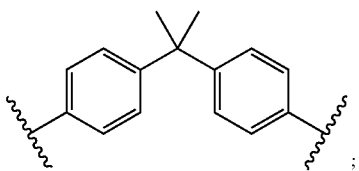 [SMILES: *c1ccc(C(C)(C)c2ccc(*)cc2)cc1]

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), the therapeutic agent core is

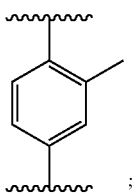 [SMILES: *c1ccc(*)c(C)c1]

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), the therapeutic agent core is

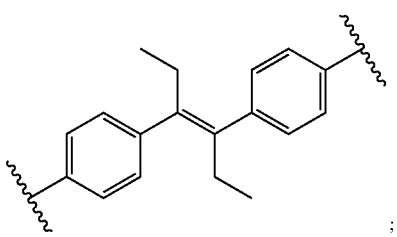 [SMILES: *c1ccc(/C(CC)=C(\CC)c2ccc(*)cc2)cc1]

$n_1$ is an integer between 2 and 10; $m_1$ is an integer between 0 and 20; X is $C_2$-$C_{10}$ alkyl; and $m_2$ is an integer between 0 and 20.

In some embodiments of formula (I), each D may be the same or different and is

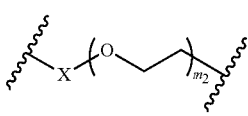

or a therapeutic agent core; $n_1$ is 2; $m_1$ is 2; X is $C_2$ alkyl; and $m_2$ is 3.

In some embodiments of formula (I), the therapeutic agent core is

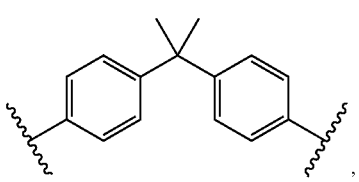

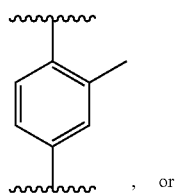, or

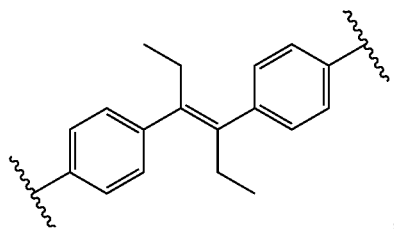

$n_1$ is 2; $m_1$ is 2; X is $C_2$ alkyl; and $m_2$ is 3.

In some embodiments of formula (I), the therapeutic agent core is

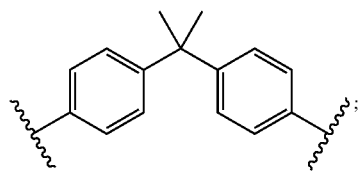 [SMILES: *c1ccc(C(C)(C)c2ccc(*)cc2)cc1]

$n_1$ is 2; $m_1$ is 2; X is $C_2$ alkyl; and $m_2$ is 3.

In some embodiments of formula (I), the therapeutic agent core is

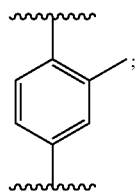 [SMILES: *c1ccc(*)c(C)c1]

$n_1$ is 2; $m_1$ is 2; X is $C_2$ alkyl; and $m_2$ is 3.

In some embodiments of formula (I), the therapeutic agent core is

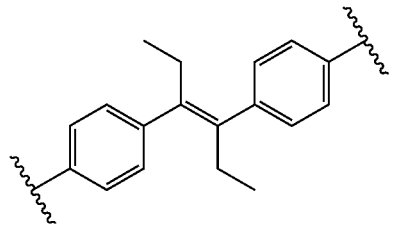

$n_1$ is 2; $m_1$ is 2; X is $C_2$ alkyl; and $m_2$ is 3.

In some embodiments of formula (I), the therapeutic agent core is a core of bisphenol A, methylhydroquinone, diethylstilbestrol, paclitaxel, doxorubicin, everolimus, pamidronate disodium, nelarabine, Azacitidine, bleomycin, bortezomib, capecitabine, Cytarabine, daunorubicin hydrochloride, Decitabine, Docetaxel, Epirubicin, etoposide, Raloxifene, fulvestrant, fludarabine, Gemcitabine, Goserelin, Topotecan, Idarubicin, azaepothilone B, Lanreotide, Leuprolide, Mitoxantrone, Prednisone, Temsirolimus, Vinblastine, vincristine, or zoledronic acid.

In some embodiments of formula (II), the sum of $(m_1+m_2)$ is greater than zero.

In some embodiments of formula (II), each D maybe the same or different and is

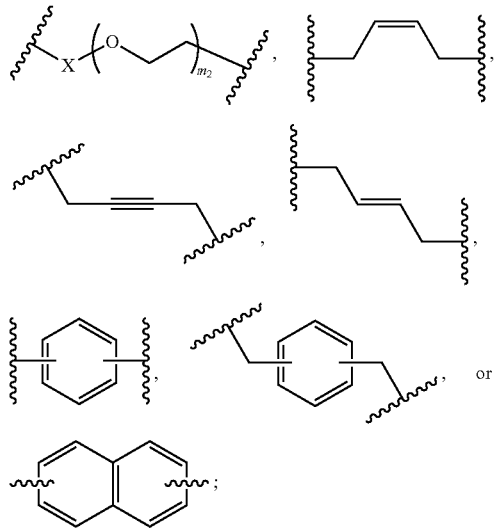

$n_1$ is an integer between 2 and 10; $m_1$ is an integer between 0 and 20; X is $C_2$-$C_{10}$ alkyl; and $m_2$ is an integer between 0 and 20.

In some embodiments of formula (II), D is

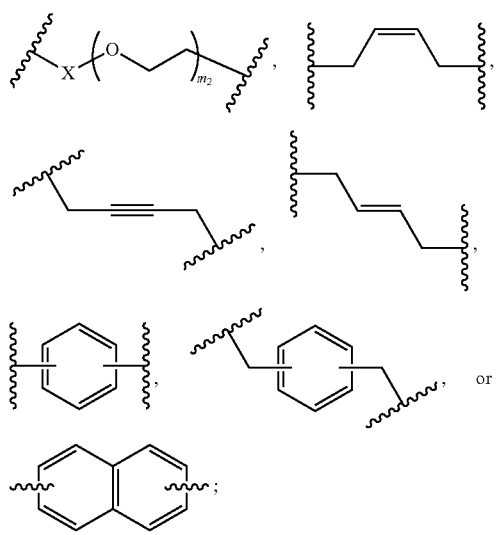

$n_1$ is an integer between 2 and 10; $m_1$ is an integer between 0 and 20; X is $C_2$-$C_{10}$ alkyl; and $m_2$ is an integer between 0 and 20.

In some embodiments of formula (II), each D may be the same or different and is

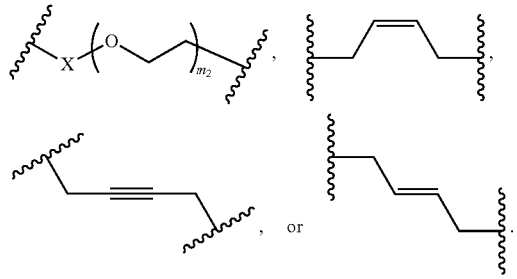

In some embodiments of formula (II), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (II), each $n_1$ may be the same or different and is an integer between 2 and 4; each $m_1$ may be the same or different and is an integer between 0 and 2; X is $C_2$-$C_5$ alkyl; each $m_2$ may be the same or different and is an integer between 0 and 3; and p is an integer between 3 and 100.

In some embodiments of formula (II), each $n_1$ may be the same or different and is an integer between 2 and 4; each $m_1$ may be the same or different and is an integer between 0 and 2; X is $C_2$-$C_5$ n-alkyl; each $m_2$ may be the same or different and is an integer between 0 and 3; and p is an integer between 3 and 100.

In some embodiments of formula (II), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 50.

In some embodiments of formula (II), each D may be the same or different and is

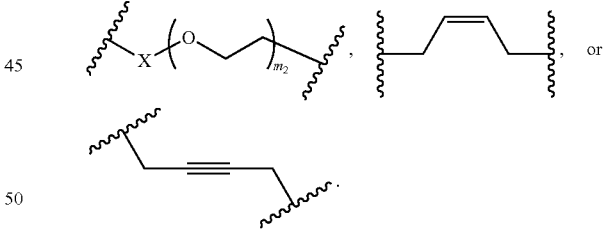

In some embodiments of formula (II), each D may be the same or different and is

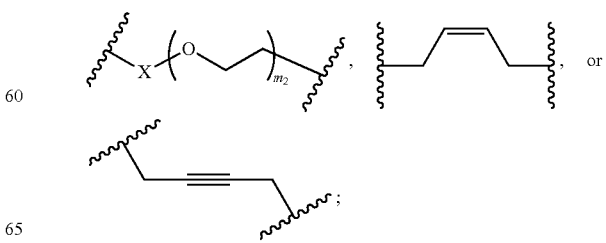

each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (II), $n_1$ is an integer between 2 and 4; $m_1$ is an integer between 0 and 2; X is $C_2$-$C_5$ alkyl; $m_2$ is an integer between 0 and 3; and p is an integer between 3 and 100.

In some embodiments of formula (II), $n_1$ is an integer between 2 and 4; $m_1$ is an integer between 0 and 2; X is $C_2$-$C_5$ n-alkyl; $m_2$ is an integer between 0 and 3; and p is an integer between 3 and 100.

In some embodiments of formula (II), D is

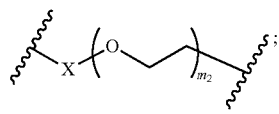

$n_1$ is 4; $m_1$ is 0; X is $C_2$ alkyl; and $m_2$ is 2.

In some embodiments of formula (II), D is

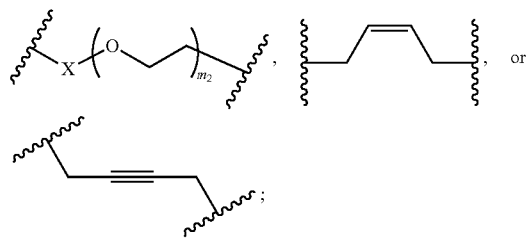

$n_1$ is 2; $m_1$ is 2; X is $C_4$ alkyl; and $m_2$ is 0.

In another aspect, the invention is directed to compositions comprising a compound of formula (II) wherein each D may be the same or different and is

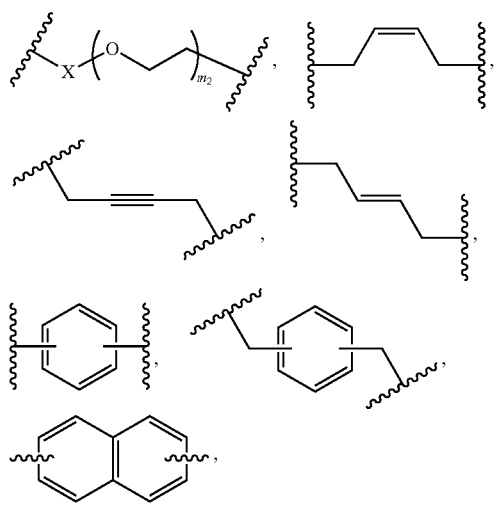

or a therapeutic agent core; and a pharmaceutically acceptable carrier.

In another aspect, the invention is directed to a method for treating cancer in a subject, the method comprising administering to a subject a therapeutic amount of a compound of formula (II), wherein each D may be the same or different and is

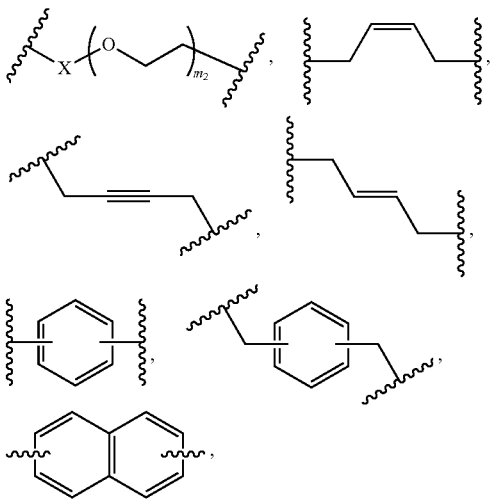

or a therapeutic agent core; or a pharmaceutical composition thereof.

In another aspect, the invention is directed to compositions comprising a compound of formula (II), wherein each D may be the same or different and is

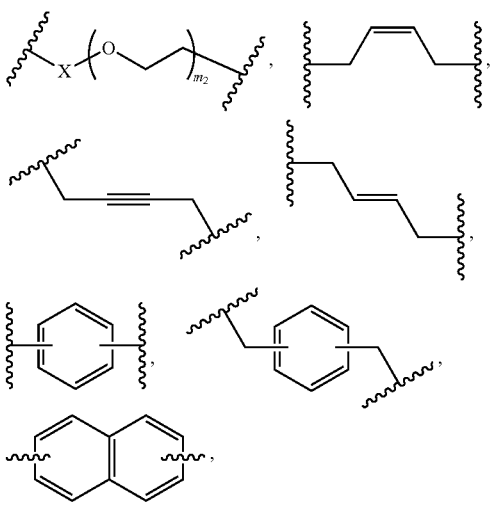

or a therapeutic agent core; and water or a liquid chemical carrier.

In another aspect, the invention is directed to a method for delivering a therapeutic agent to crops, plants or seeds, the method comprising administering to crops, plants, or seeds a compound of formula (II), wherein each D may be the same or different and is

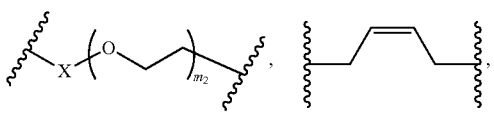

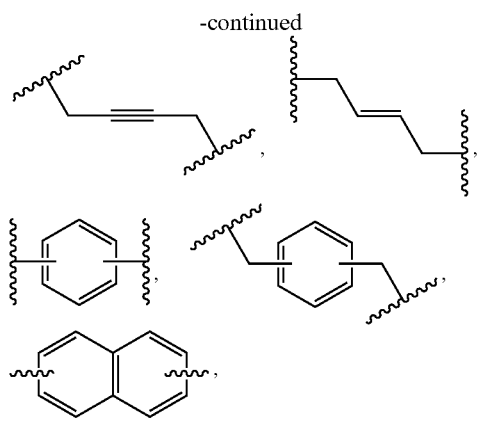

or a therapeutic agent core; or a chemical composition thereof.

In some embodiments of formula (II), each D maybe the same or different and is

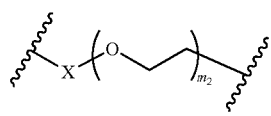

or a therapeutic agent core.

In some embodiments of formula (II), each $n_1$ may be the same or different and is an integer between 2 and 4; each $m_1$ may be the same or different and is an integer between 0 and 2; each X may be the same or different and is $C_2$-$C_5$ alkyl; and each $m_2$ may be the same or different and is an integer between 0 and 3; and p is an integer between 3 and 100.

In some embodiments of formula (II), each D maybe the same or different and is

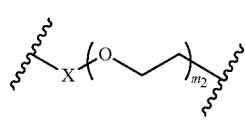

or a therapeutic agent core; $n_1$ is an integer between 2 and 10; $m_1$ is an integer between 0 and 20; X is $C_2$-$C_{10}$ alkyl; and $m_2$ is an integer between 0 and 20.

In some embodiments of formula (II), X is $C_2$-$C_5$ n-alkyl.

In some embodiments of formula (II), p is an integer between 3 and 50.

In some embodiments of formula (II), each D maybe the same or different and is

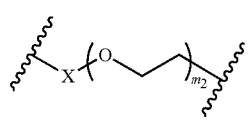

or a therapeutic agent core; $n_1$ is 2; $m_1$ is 2; X is $C_2$ alkyl; and $m_2$ is 3.

In some embodiments of formula (II), the therapeutic agent core is

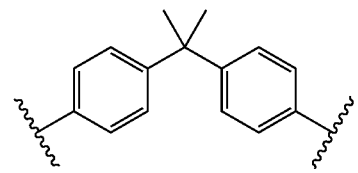

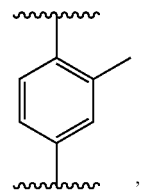 [SMILES: *c1ccc(*)c(C)c1]

, or

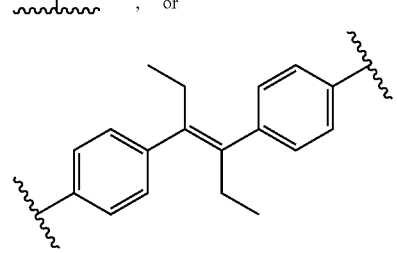

In some embodiments of formula (II), the therapeutic agent core is

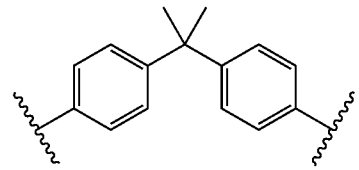

In some embodiments of formula (II), the therapeutic agent core is

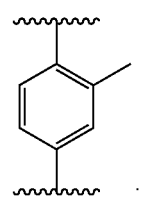

In some embodiments of formula (II), the therapeutic agent core is

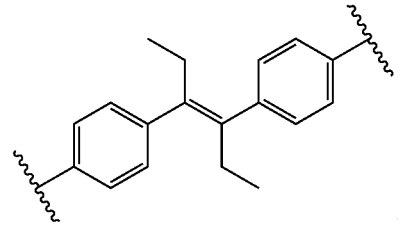

In some embodiments of formula (II), the therapeutic agent core is

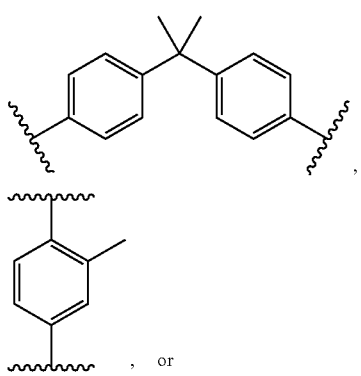

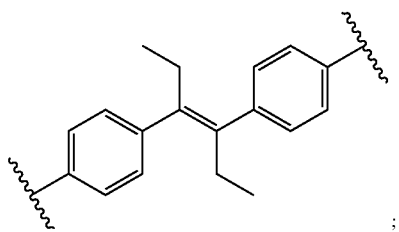 [SMILES: *c1ccc(/C(CC)=C(\CC)c2ccc(*)cc2)cc1], or

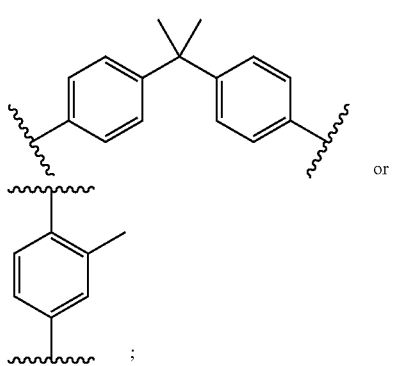;

$n_1$ is an integer between 2 and 10; $m_1$ is an integer between 0 and 20; X is $C_2$-$C_{10}$ alkyl; and $m_2$ is an integer between 0 and 20.

In some embodiments of formula (II), the therapeutic agent core is

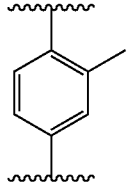 or

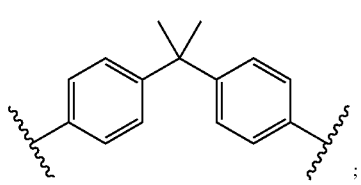;

$n_1$ is an integer between 2 and 10; $m_1$ is an integer between 0 and 20; X is $C_2$-$C_{10}$ alkyl; and $m_2$ is an integer between 0 and 20.

In some embodiments of formula (II), the therapeutic agent core is

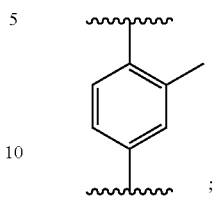;

$n_1$ is an integer between 2 and 10; $m_1$ is an integer between 0 and 20; X is $C_2$-$C_{10}$ alkyl; and $m_2$ is an integer between 0 and 20.

In some embodiments of formula (II), the therapeutic agent core is

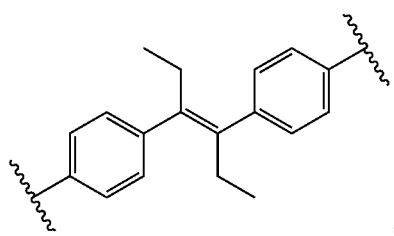;

$n_1$ is an integer between 2 and 10; $m_1$ is an integer between 0 and 20; X is $C_2$-$C_{10}$ alkyl; and $m_2$ is an integer between 0 and 20.

In some embodiments of formula (II), each D may be the same or different and is

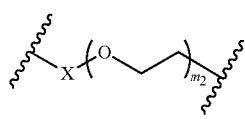

or a therapeutic agent core; $n_1$ is 2; $m_1$ is 2; X is $C_2$ alkyl; and $m_2$ is 3.

In some embodiments of formula (II), the therapeutic agent core is

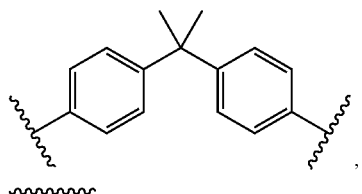,

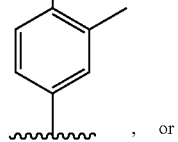, or

[structure: diethylstilbestrol-like core]

$n_1$ is 2; $m_1$ is 2; X is $C_2$ alkyl; and $m_2$ is 3.

In some embodiments of formula (II), the therapeutic agent core is

[structure: bisphenol A core]

$n_1$ is 2; $m_1$ is 2; X is $C_2$ alkyl; and $m_2$ is 3.

In some embodiments of formula (II), the therapeutic agent core is

[structure: methylhydroquinone core]

$n_1$ is 2; $m_1$ is 2; X is $C_2$ alkyl; and $m_2$ is 3.

In some embodiments of formula (II), the therapeutic agent core is

[structure: diethylstilbestrol-like core]

$n_1$ is 2; $m_1$ is 2; X is $C_2$ alkyl; and $m_2$ is 3.

In some embodiments of formula (II), the therapeutic agent core is a core of bisphenol A, methylhydroquinone, diethylstilbestrol, paclitaxel, doxorubicin, everolimus, pamidronate disodium, nelarabine, Azacitidine, bleomycin, bortezomib, capecitabine, Cytarabine, daunorubicin hydrochloride, Decitabine, Docetaxel, Epirubicin, etoposide, Raloxifene, fulvestrant, fludarabine, Gemcitabine, Goserelin, Topotecan, Idarubicin, azaepothilone B, Lanreotide, Leuprolide, Mitoxantrone, Prednisone, Temsirolimus, Vinblastine, vincristine, or zoledronic acid.

In another aspect, the invention is directed to a class of compounds of formula (III)

$$A-O-V-[O-\overset{|}{C}H-O-D-O-\overset{|}{C}H-O-V]_p-O-A \quad (III)$$

wherein,

A is

[structures: vinyl with Z substituent; or CH(CH$_3$)O(CH$_2$)$_{n_3}$F];

F is

[structures: propargyl ether; ester-(CH$_2$)$_3$Br;

ester-CH(Br)CH$_3$; ester-C(CH$_3$)$_2$Br;

acrylate; methacrylate;

ester-(CH$_2$)$_3$-N$_3$;

triazole-CH$_2$O- linked to polymer;

ester-(CH$_2$)$_3$-triazole-polymer;

anthracenylmethyl ester-O-(CH$_2$)$_s$-].

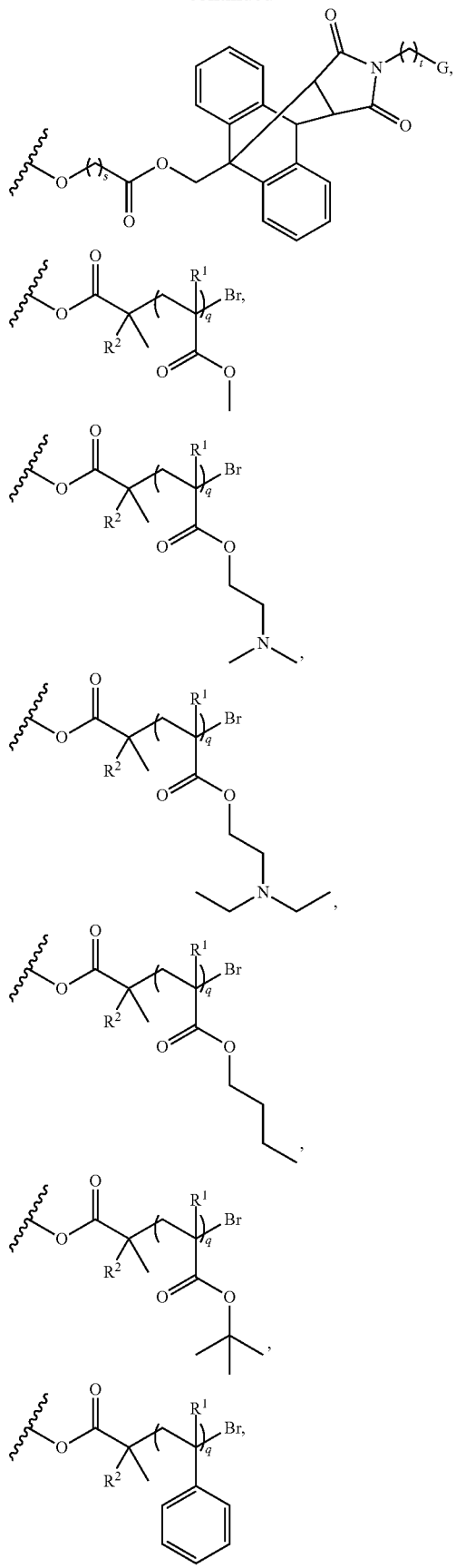
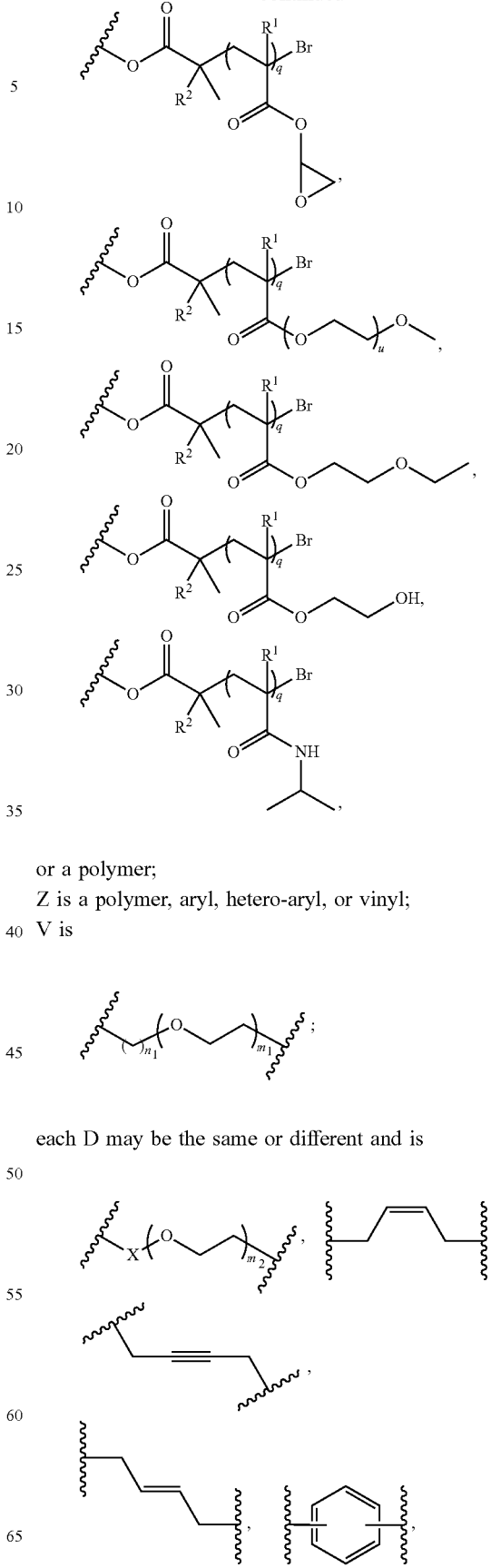
or a polymer;
Z is a polymer, aryl, hetero-aryl, or vinyl;
V is
each D may be the same or different and is each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
p is an integer between 3 and 200;
q is an integer between 1 and 100;
s is an integer between 1 and 10;
t is an integer between 1 and 10;
u is an integer between 1 and 100;
G is a polymer, aryl, or alkyl;
$R^1$ is H or $CH_3$; and
$R^2$ is H or $CH_3$.

In another aspect, the invention is directed to a class of compounds of formula (III)

wherein,
A is

F is

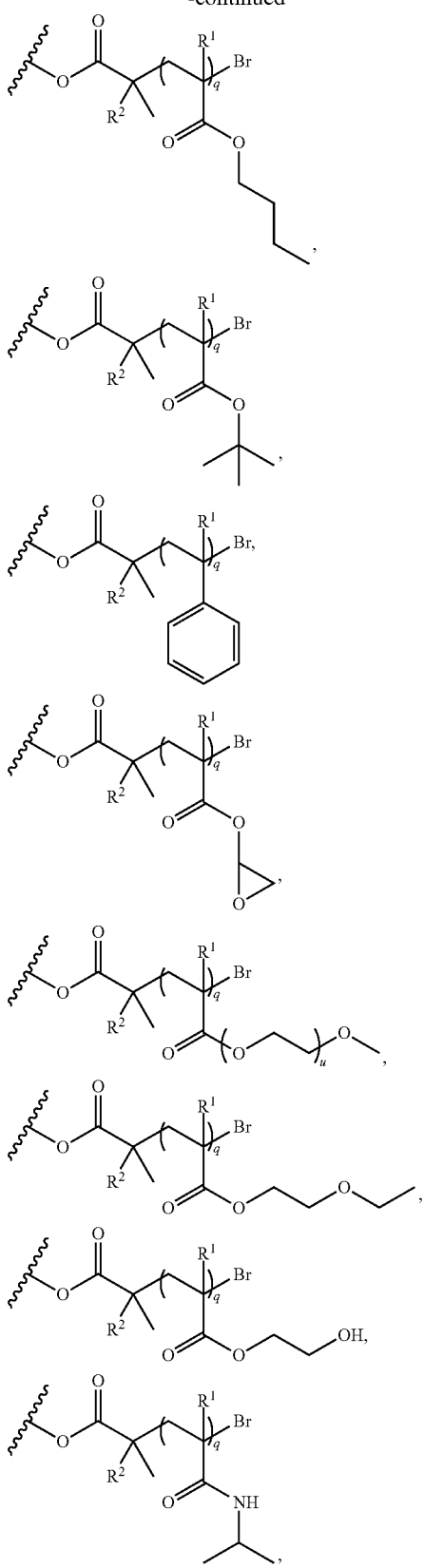

or a polymer;

Z is a polymer, aryl, hetero-aryl, or vinyl;

V is

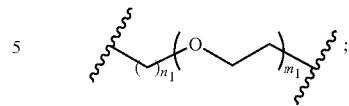

each D may be the same or different and is

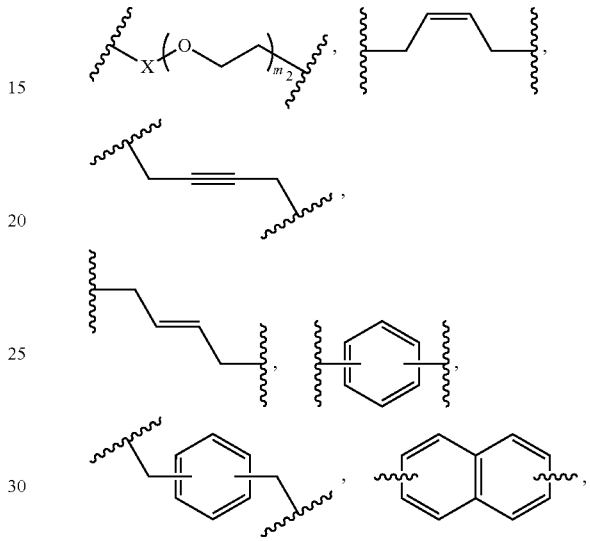

or a therapeutic agent core;

each $n_1$ may be the same or different and is an integer between 2 and 10;

each $m_1$ may be the same or different and is an integer between 0 and 20;

each X may be the same or different and is $C_2$-$C_{10}$ alkyl;

each $m_2$ may be the same or different and is an integer between 0 and 20;

$n_3$ is an integer between 2 and 10;

p is an integer between 3 and 200;

q is an integer between 1 and 100;

s is an integer between 1 and 10;

t is an integer between 1 and 10;

u is an integer between 1 and 100;

G is a polymer, aryl, or alkyl;

$R^1$ is H or $CH_3$; and $R^2$ is H or $CH_3$.

In another aspect, the invention is directed to a biodegradable gel comprising a compound of formula (III) cross-linked with a linker at an alkyne or azide terminus of the compound.

In another aspect, the invention is directed to a method of making a gel, comprising crosslinking a compound of formula (III) with a trifunctional linker.

In another aspect, the invention is directed to a method of delivering a therapeutic agent to a tumor cell comprising, administering a biodegradable gel comprising a compound of formula (III) cross-linked with a linker at an alkyne or azide terminus of the compound, and a therapeutic agent, wherein said gel degrades at pH from about 5 to about 6.5 to release said therapeutic agent.

In another aspect, the invention is directed to micelle comprising a compound of formula (III)

(III)

wherein,

A is or ;

F is

-continued

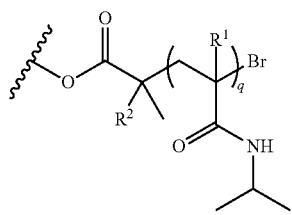

V is

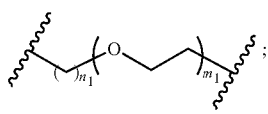

each D may be the same or different and is

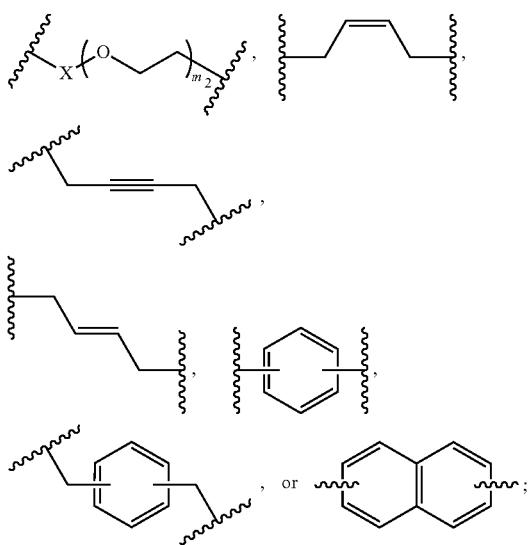

each $n_1$ may be the same or different and is an integer between 2 and 10;

each $m_1$ may be the same or different and is an integer between 0 and 20;

each X may be the same or different and is $C_2$-$C_{10}$ alkyl;

each $m_2$ may be the same or different and is an integer between 0 and 20;

$n_3$ is an integer between 2 and 10;

G is a polymer;

Z is a polymer;

$R^1$ is H or $CH_3$;

$R^2$ is H or $CH_3$;

p is an integer between 3 and 200;

q is an integer between 1 and 100;

s is an integer between 1 and 10;

t is an integer between 1 and 10;

u is an integer between 1 and 100; or, a compound of formula (IV)

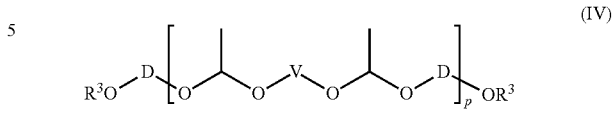 (IV)

wherein, $R^3$ is

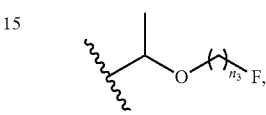

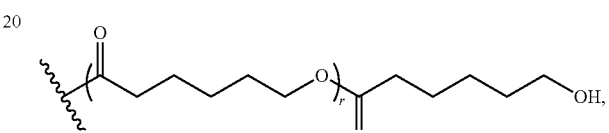

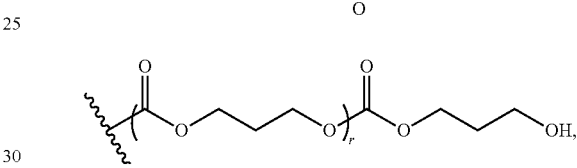

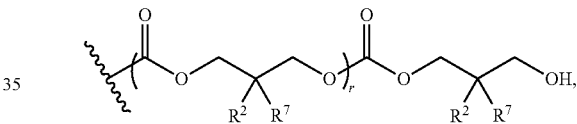

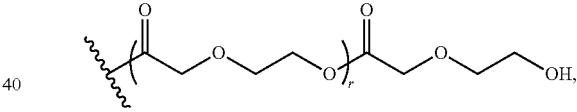

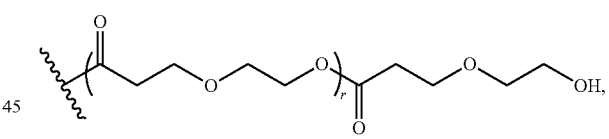

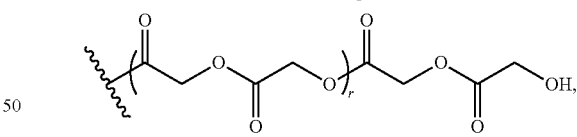

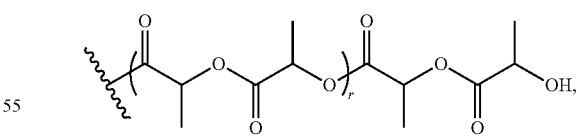

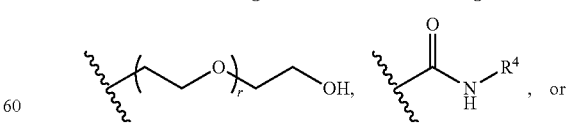

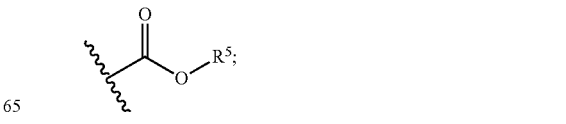

F is
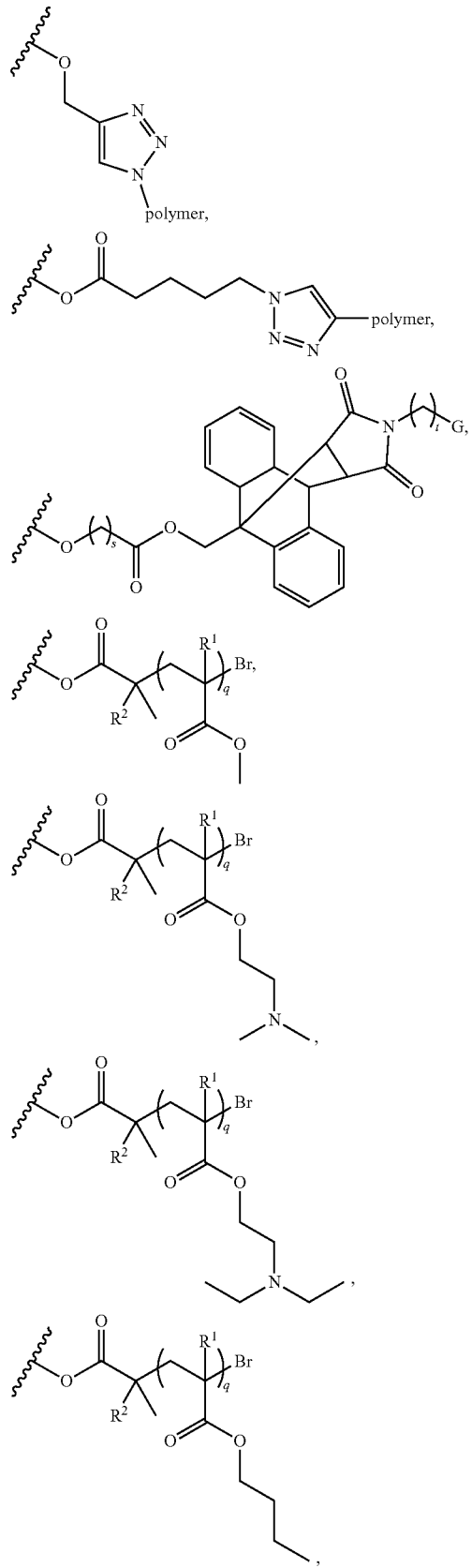
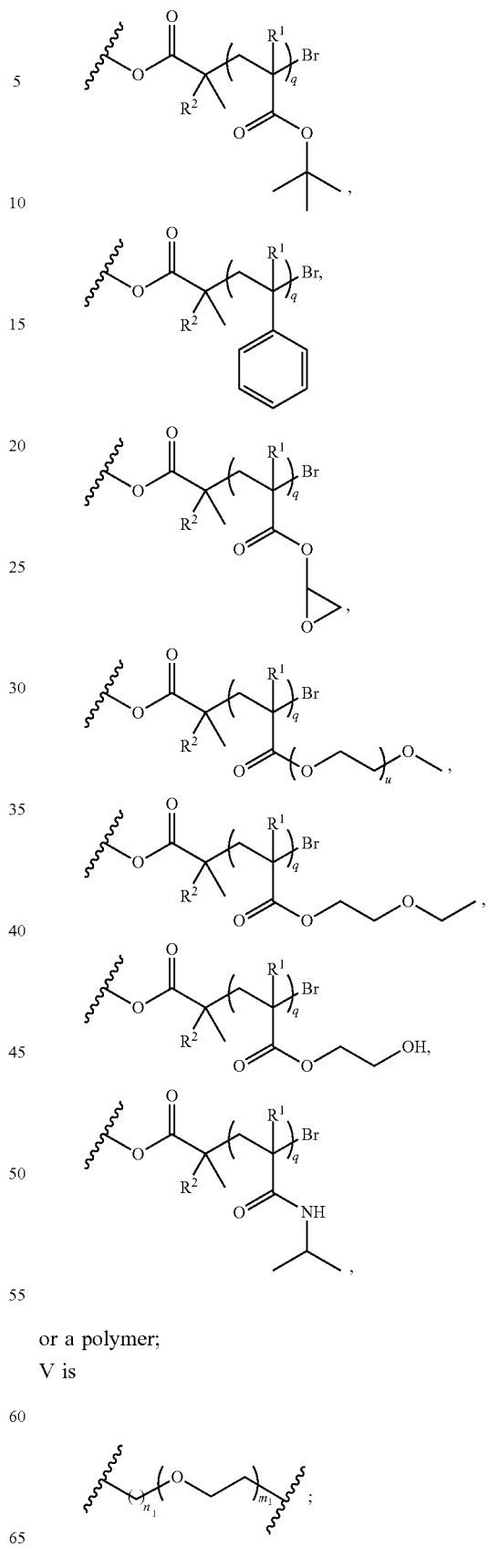
or a polymer;
V is each D may be the same or different and is

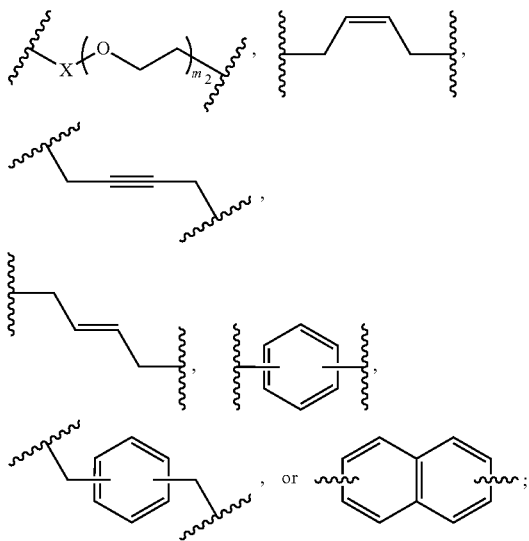

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
G is a polymer;
$R^1$ is H or $CH_3$;
$R^2$ is H or $CH_3$;
$R^4$ is a polymer;
$R^5$ is a polymer;
$R^7$ is H or halogen;
p is an integer between 3 and 200;
q is an integer between 1 and 100;
r is an integer between 0 and 100;
s is an integer between 1 and 10;
t is an integer between 1 and 10; and
u is an integer between 1 and 100.

In another aspect, the invention is directed to a pharmaceutical composition comprising a micelle comprising a compound of formula (III) or (IV).

In another aspect, the invention is directed to a method of delivering a therapeutic agent to a tumor cell comprising, administering a micelle comprising a compound of formula (III) or (IV), or a pharmaceutical composition comprising a micelle comprising a compound of formula (III) or (IV), wherein said micelle further comprises a therapeutic agent, and wherein said micelle degrades at pH from about 5 to about 6.5 to release said therapeutic agent.

In some embodiments of formula (III), the sum of ($m_1$+$m_2$) is greater than zero.

In some embodiments of formula (III), A is

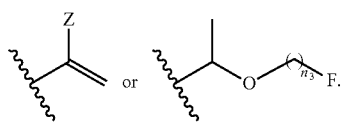

In some embodiments of formula (III), A is

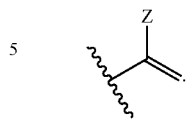

In some embodiments of formula (III), A is

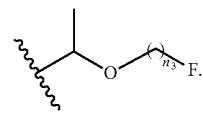 [SMILES: *C(C)OCF]

In some embodiments of formula (III), D is

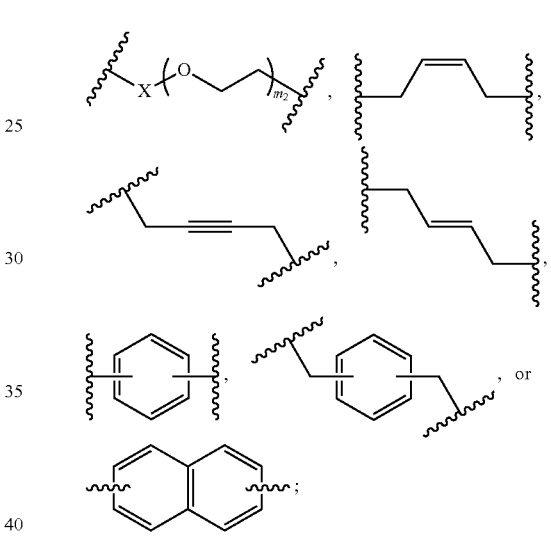

$n_1$ is an integer between 2 and 10; $m_1$ is an integer between 0 and 20; X is $C_2$-$C_{10}$ alkyl; $m_2$ is an integer between 0 and 20; and p is an integer between 3 and 200.

In some embodiments of formula (III), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (III), each $n_1$ may be the same or different and is an integer between 2 and 4; each $m_1$ may be the same or different and is an integer between 0 and 2; each X may be the same or different and is $C_2$-$C_5$ n-alkyl; each $m_2$ may be the same or different and is an integer between 0 and 3; and p is an integer between 3 and 100.

In some embodiments of formula (III), X is $C_2$-$C_5$ n-alkyl.

In some embodiments of formula (III), p is an integer between 3 and 50.

In some embodiments of formula (III), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 50.

In some embodiments of formula (III), A is

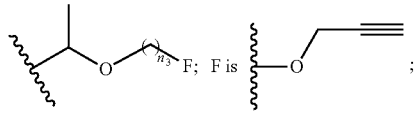 F is 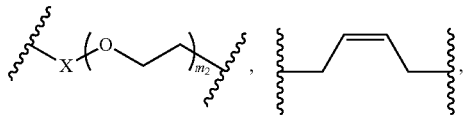 ;

each D may be the same or different and is

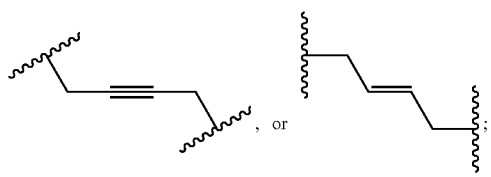, or ;

each $n_1$ may be the same or different and is an integer between 2 and 4; $n_3$ is 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (III), the polymer is polystyrene, poly-t-butyl acrylate, polymethyl methacrylate, or polyethylene glycol.

In some embodiments of formula (III), A is

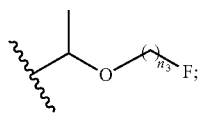

F is

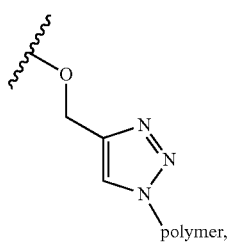

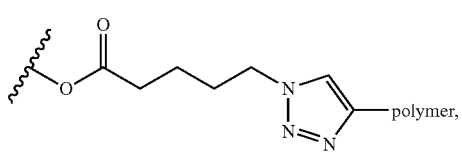

-continued

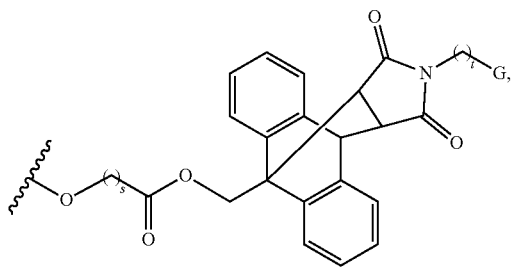

or a polymer; wherein G is a polymer; wherein the polymer is polystyrene, poly-t-butyl acrylate, or polymethyl methacrylate; and D is

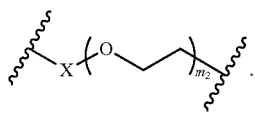.

In some embodiments of formula (III), A is

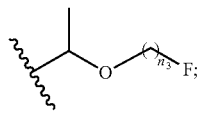 [SMILES: *C(C)OCF]

F is

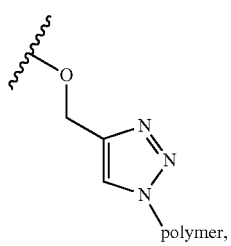

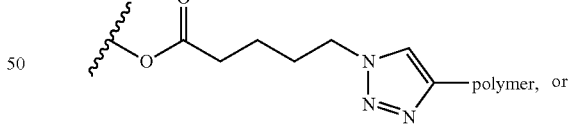

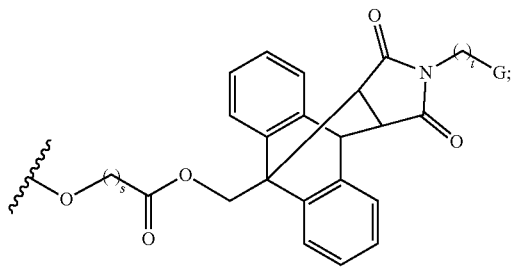

wherein G is a polymer; wherein the polymer is polyethylene glycol; and D is

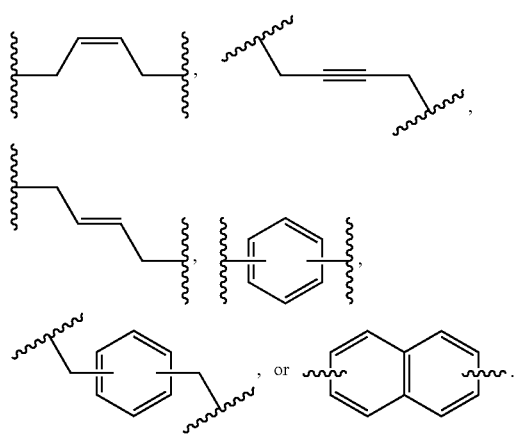
In some embodiments of formula (III), A is
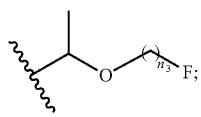
F is
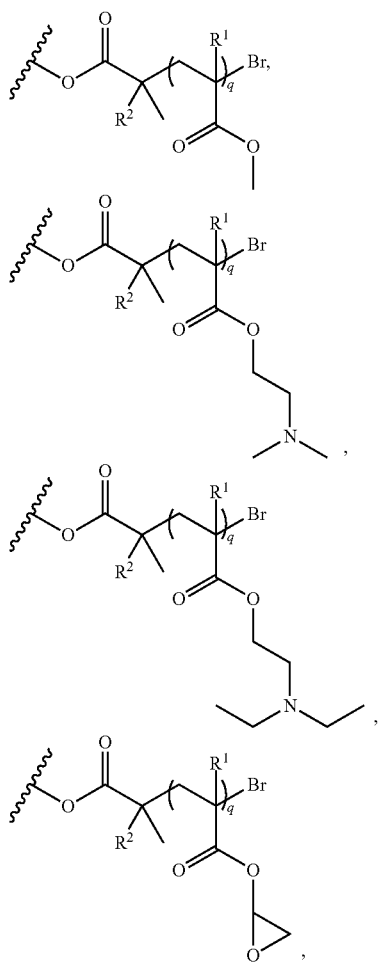
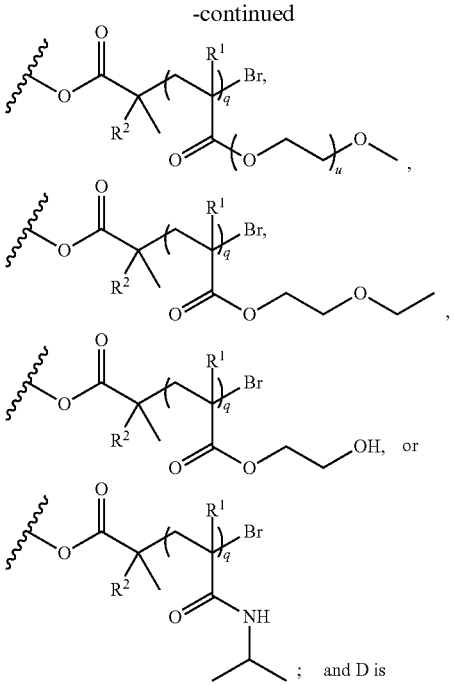
In some embodiments of formula (III), A is
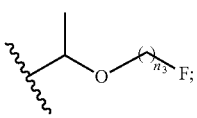 [SMILES: *C(C)OCF]
F is
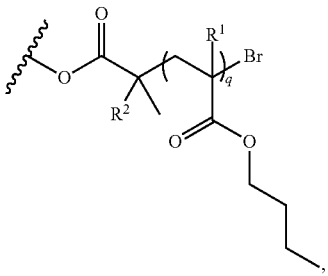

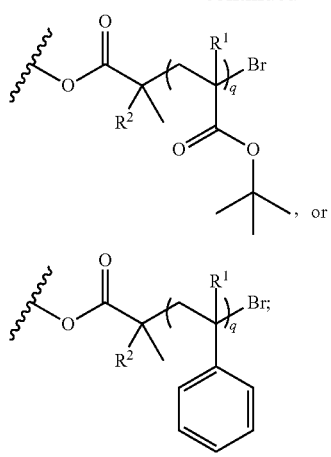

, or and D is

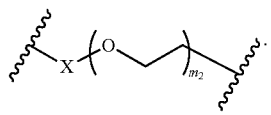

In some embodiments of formula (III), A is

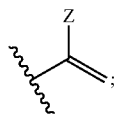

Z is a polymer wherein the polymer is polystyrene, poly-t-butyl acrylate, or polymethyl methacrylate; and D is

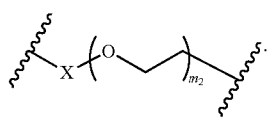

In some embodiments of formula (III), A is

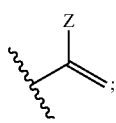

Z is a polymer wherein the polymer is polyethylene glycol; and D is

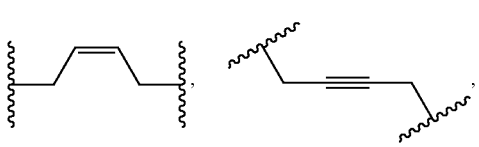

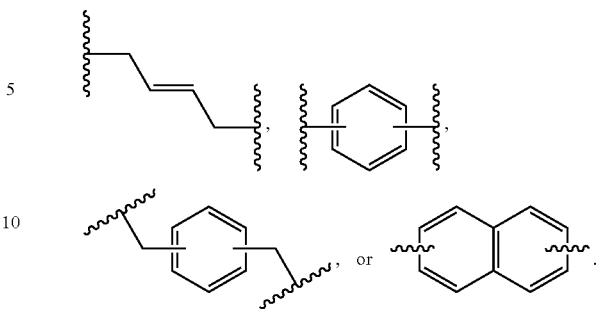

In some embodiments of formula (III), D is

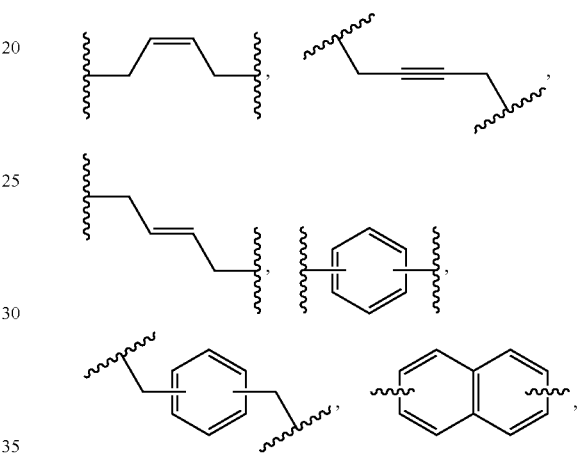

or a therapeutic agent core.

In another aspect, the invention is directed to a class of compounds of formula (IV)

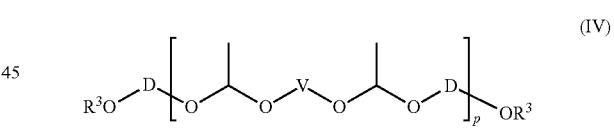

wherein,
$R^3$ is

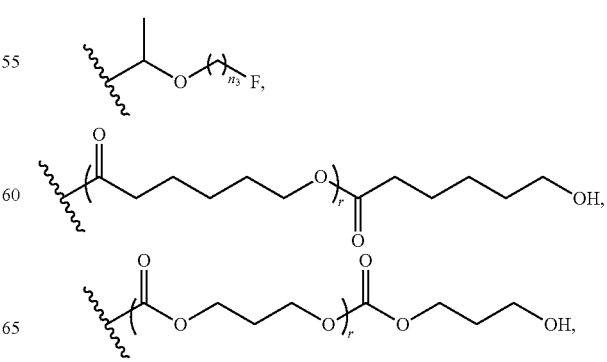

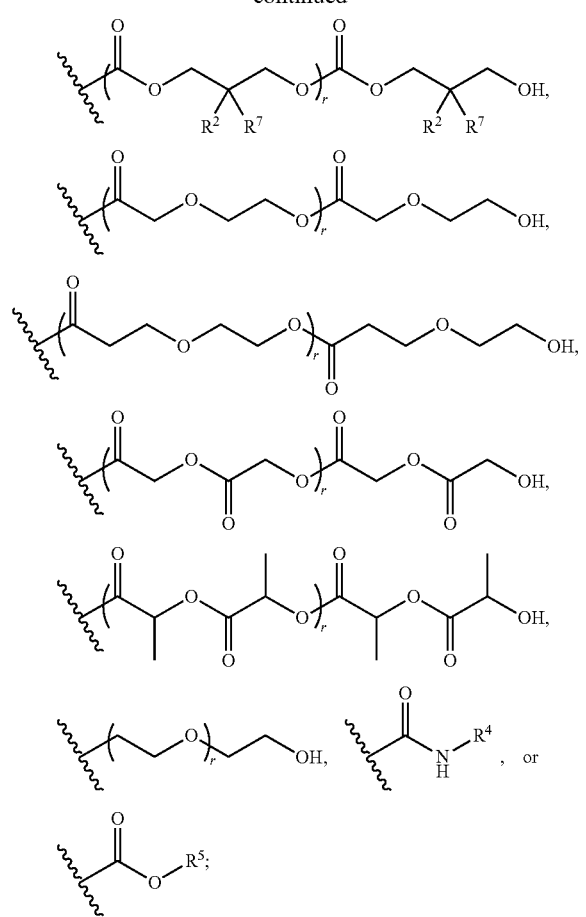
F is
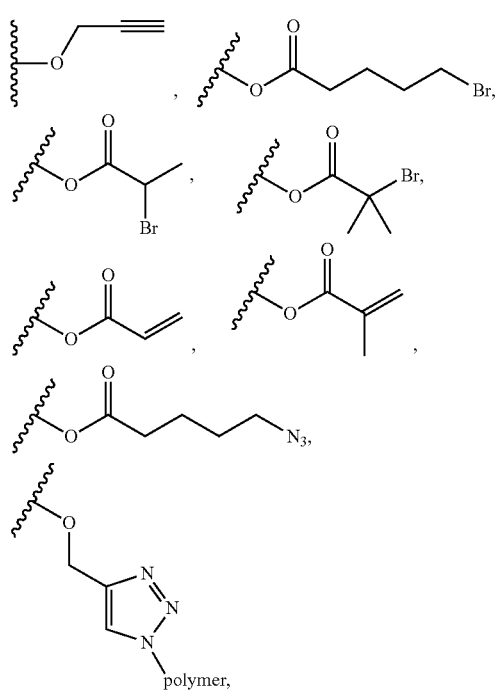
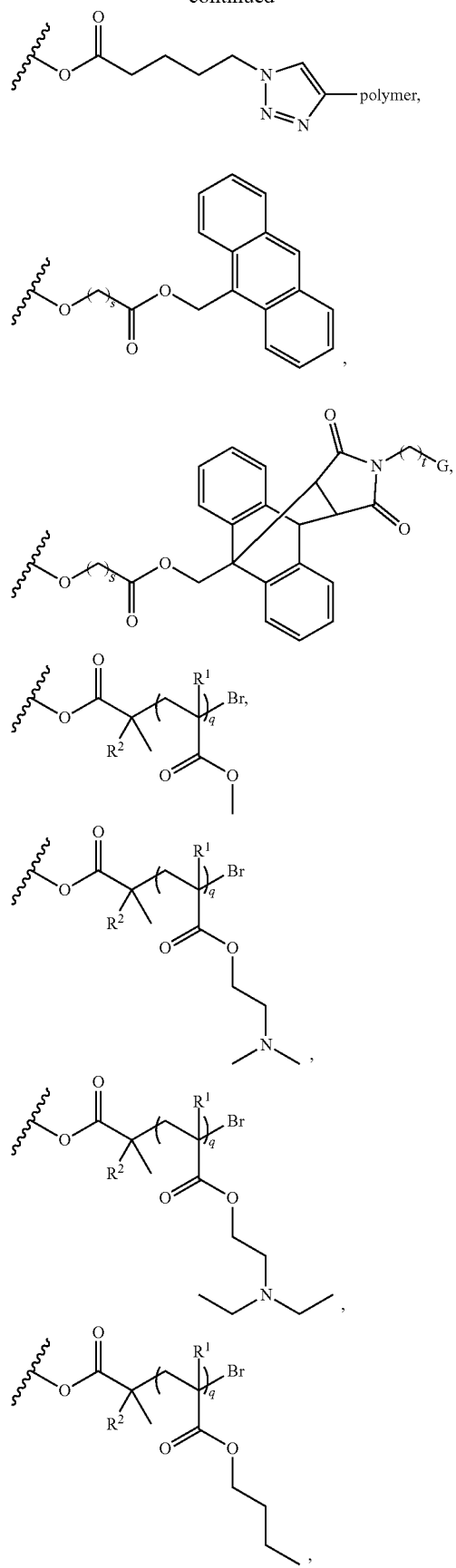

-continued

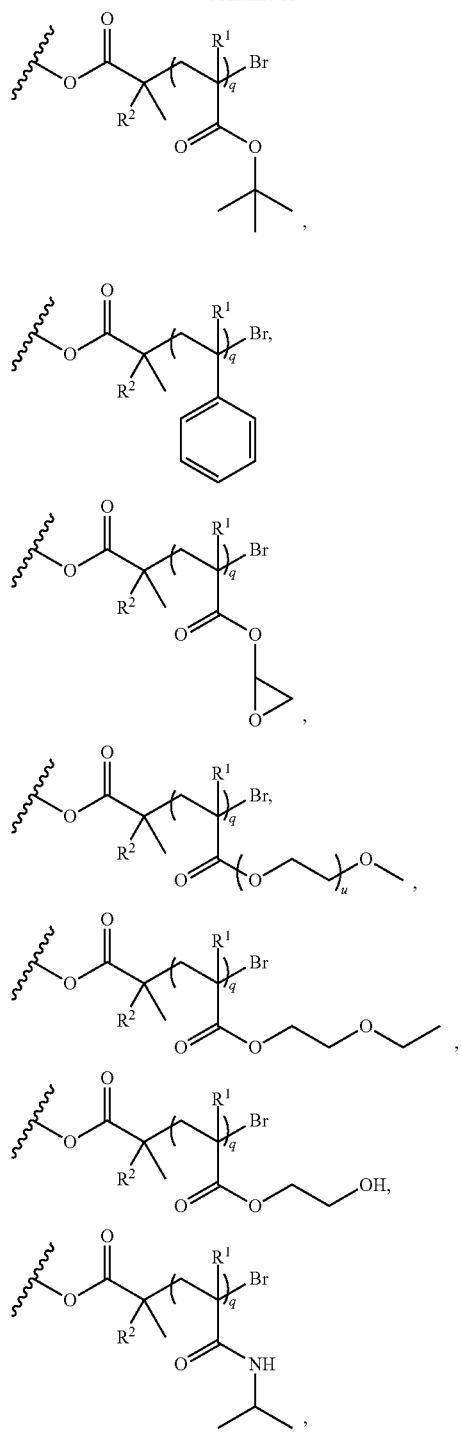

or a polymer;
V is

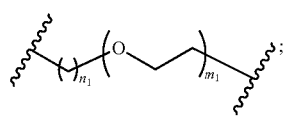

each D may be the same or different and is

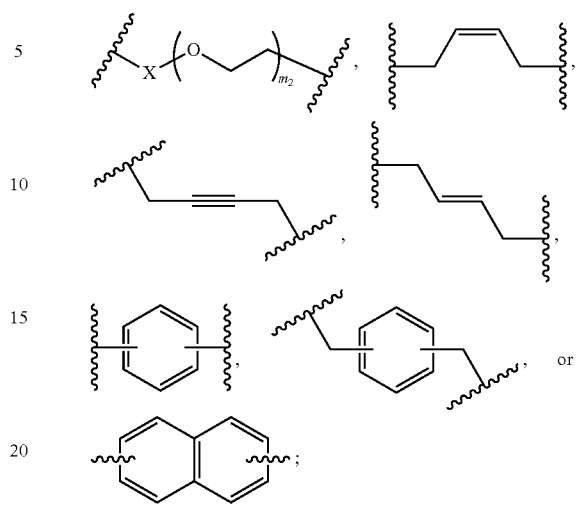

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
$R^1$ is H or $CH_3$;
$R^2$ is H or $CH_3$;
$R^4$ is aryl, alkyl, or a polymer;
$R^5$ is aryl, alkyl, or a polymer;
$R^7$ is H or halogen;
p is an integer between 3 and 200;
q is an integer between 1 and 100;
r is an integer between 0 and 100;
s is an integer between 1 and 10;
t is an integer between 1 and 10;
u is an integer between 1 and 100; and
G is a polymer, aryl, or alkyl.

In another aspect, the invention is directed to a class of compounds of formula (IV)

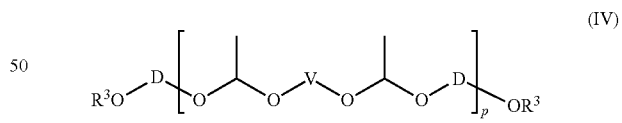

wherein,
$R^3$ is

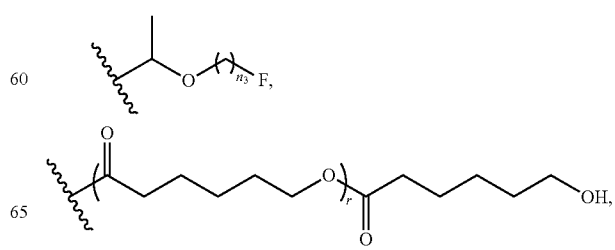

91
-continued
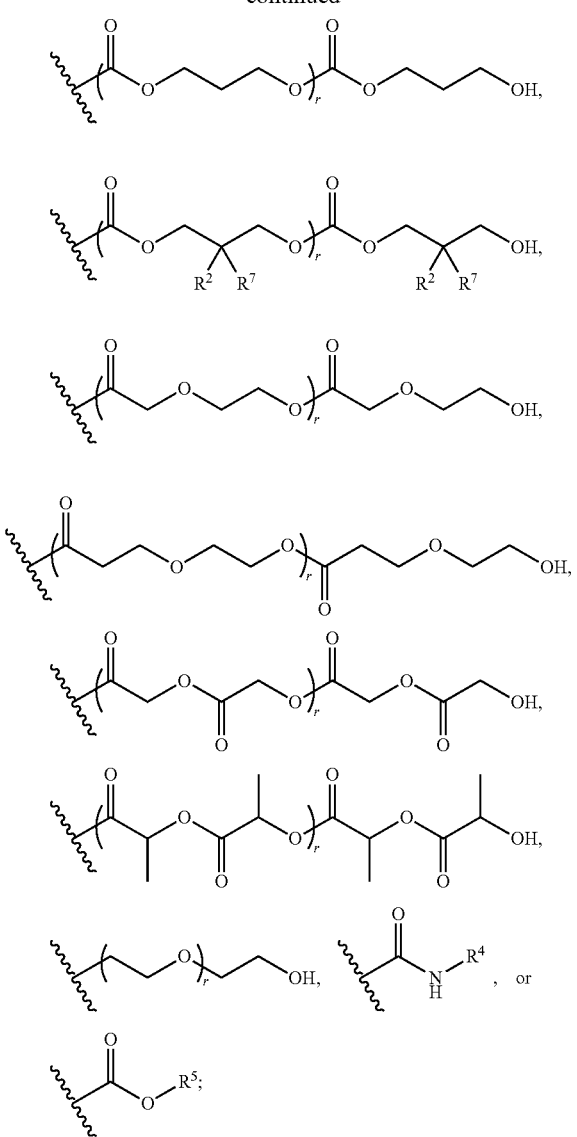
F is
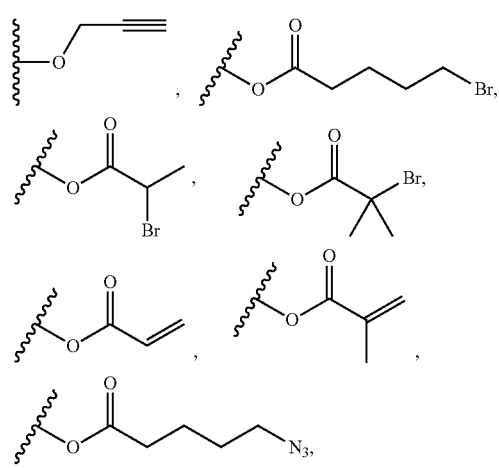
92
-continued
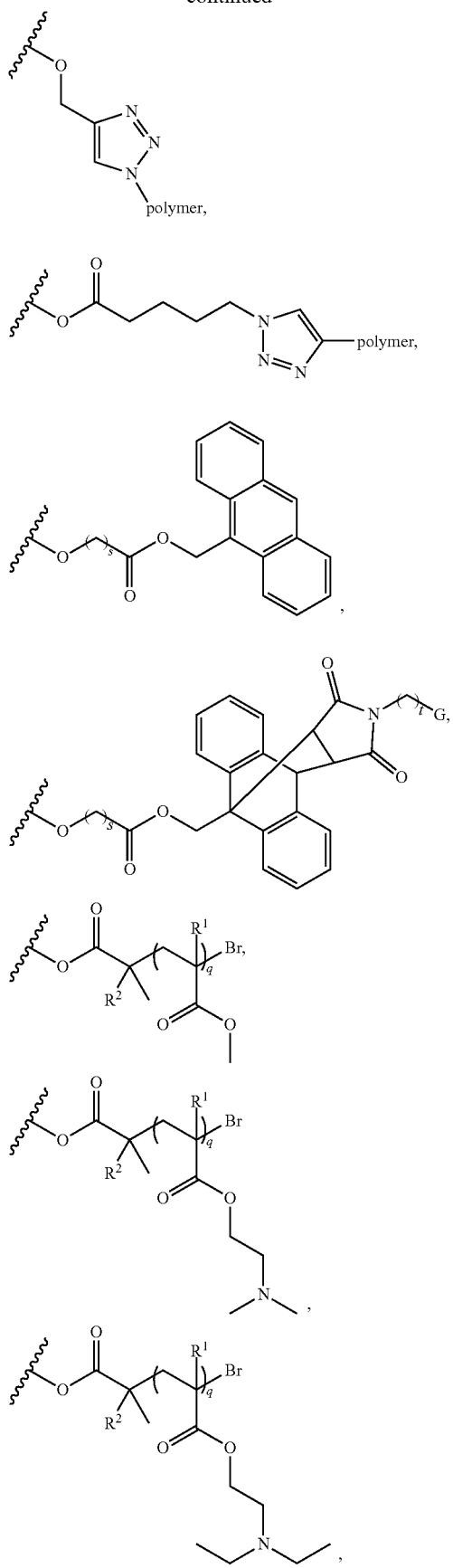

93

-continued

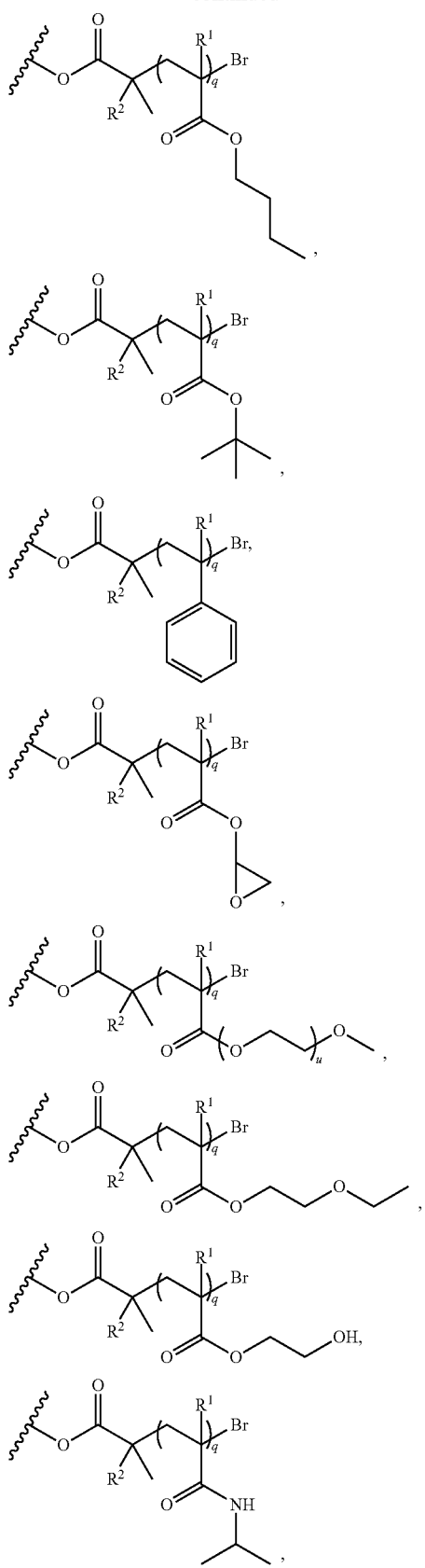

or a polymer;

V is

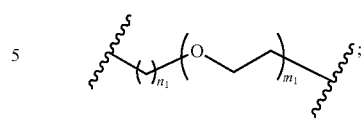

each D may be the same or different and is

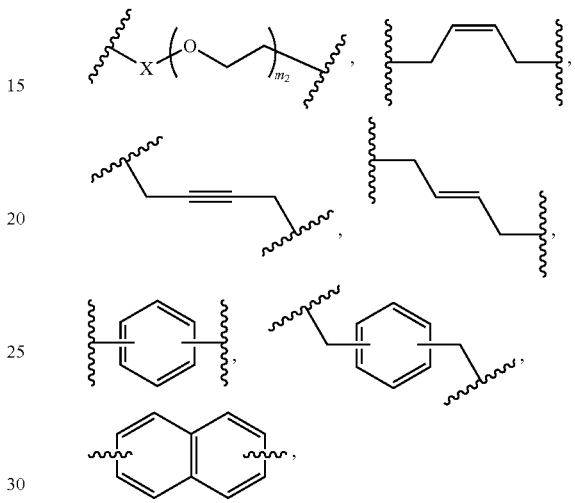

or a therapeutic agent core;
each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
$n_3$ is an integer between 2 and 10;
$R^1$ is H or $CH_3$;
$R^2$ is H or $CH_3$;
$R^4$ is aryl, alkyl, or a polymer;
$R^5$ is aryl, alkyl, or a polymer;
$R^7$ is H or halogen;
p is an integer between 3 and 200;
q is an integer between 1 and 100;
r is an integer between 0 and 100;
s is an integer between 1 and 10;
t is an integer between 1 and 10;
u is an integer between 1 and 100; and
G is a polymer, aryl, or alkyl.

In another aspect, the invention is directed to a biodegradable gel comprising a compound of formula (IV) cross-linked with a linker, wherein the compound is cross-linked with a linker at a hydroxyl, alkyne or azide terminus.

In another aspect, the invention is directed to a method of making a gel, comprising crosslinking a compound of formula (IV) with a trifunctional linker.

In another aspect, the invention is directed to a method of delivering a therapeutic agent to a tumor cell comprising, administering a biodegradable gel comprising a compound of formula (IV) cross-linked with a linker, wherein the compound is cross-linked with a linker at a hydroxyl, alkyne or azide terminus, and a therapeutic agent, wherein said gel degrades at pH from about 5 to about 6.5 to release said therapeutic agent.

In some embodiments of formula (IV), the sum of ($m_1+m_2$) is greater than zero.

In some embodiments of formula (IV), D is

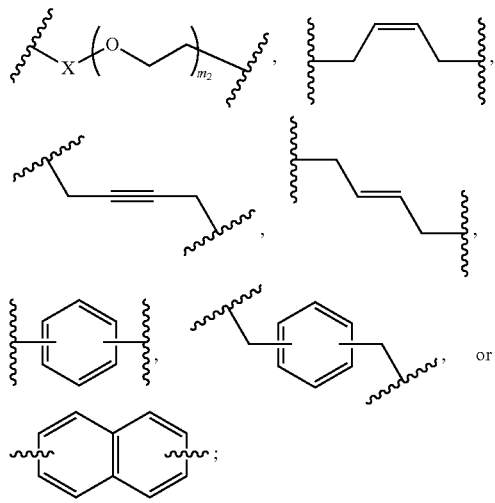

$n_1$ is an integer between 2 and 10; $m_1$ is an integer between 0 and 20; X is $C_2$-$C_{10}$ alkyl; and $m_2$ is an integer between 0 and 20.

In some embodiments of formula (IV), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (IV), each $n_1$ may be the same or different and is an integer between 2 and 4; each $m_1$ may be the same or different and is an integer between 0 and 2; each X may be the same or different and is $C_2$-$C_5$ n-alkyl; each $m_2$ may be the same or different and is an integer between 0 and 3; and p is an integer between 3 and 100.

In some embodiments of formula (IV), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 50.

In some embodiments of formula (IV), X is $C_2$-$C_5$ n-alkyl.

In some embodiments of formula (IV), p is an integer between 3 and 50.

In some embodiments of formula (IV), $R^3$ is

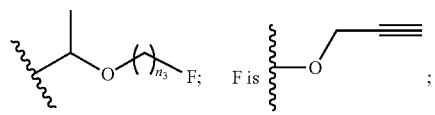

each D may be the same or different and is

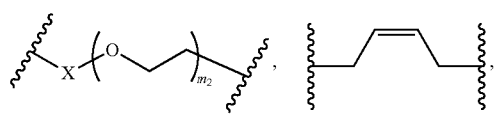

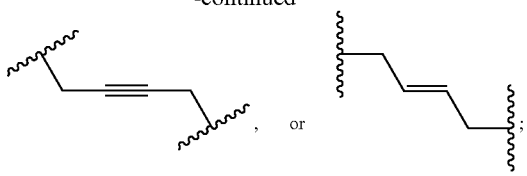

and $n_3$ is 4.

In some embodiments of formula (IV), the polymer is polystyrene, poly-t-butyl acrylate, polymethyl methacrylate, or polyethylene glycol.

In some embodiments of formula (IV), $R^3$ is

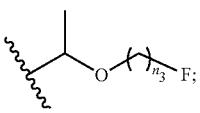

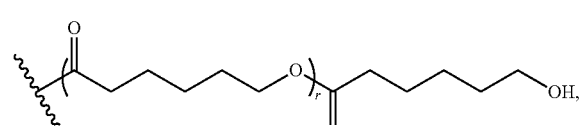

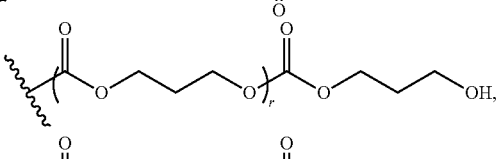

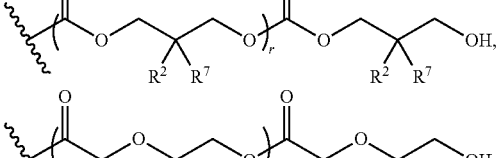

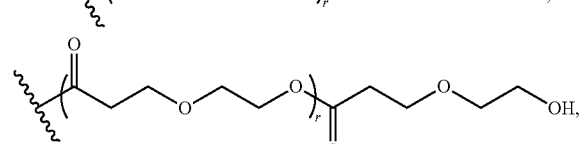

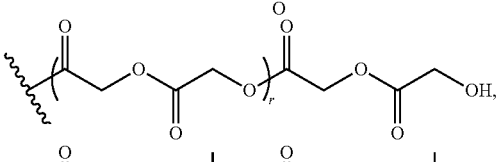

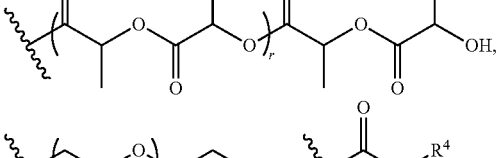

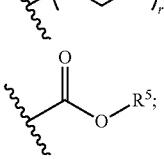

F is

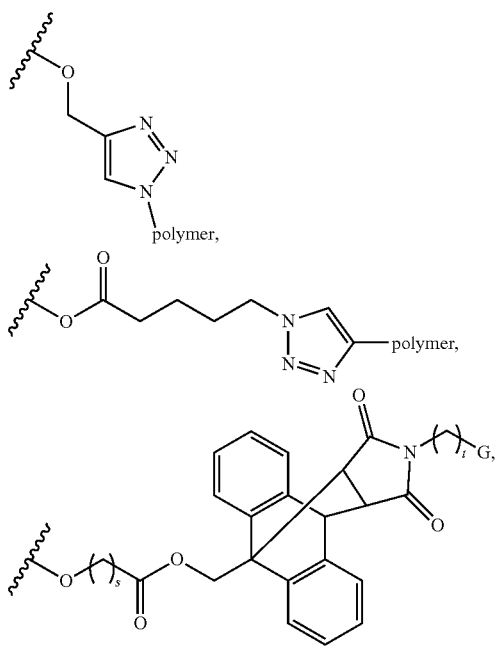

or a polymer; D is

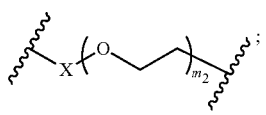

G is a polymer; $R^4$ is a polymer; $R^5$ is a polymer; and wherein the polymer is polystyrene, poly-t-butyl acrylate, or polymethyl methacrylate.

In some embodiments of formula (IV), $R^3$ is

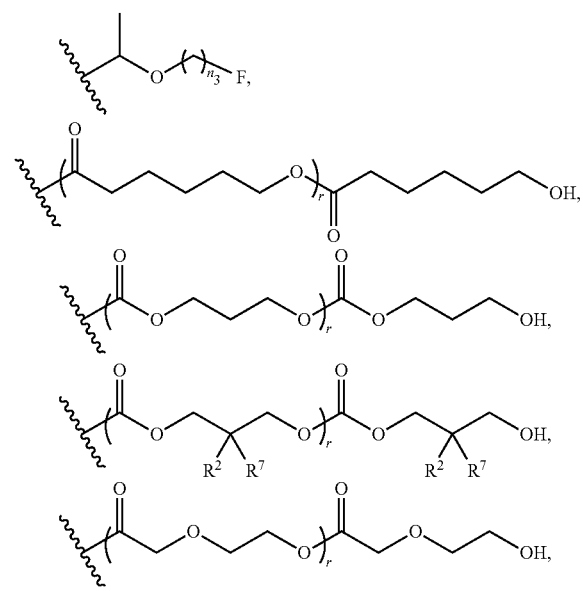

-continued

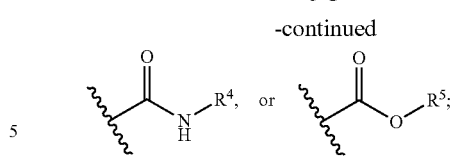

F is

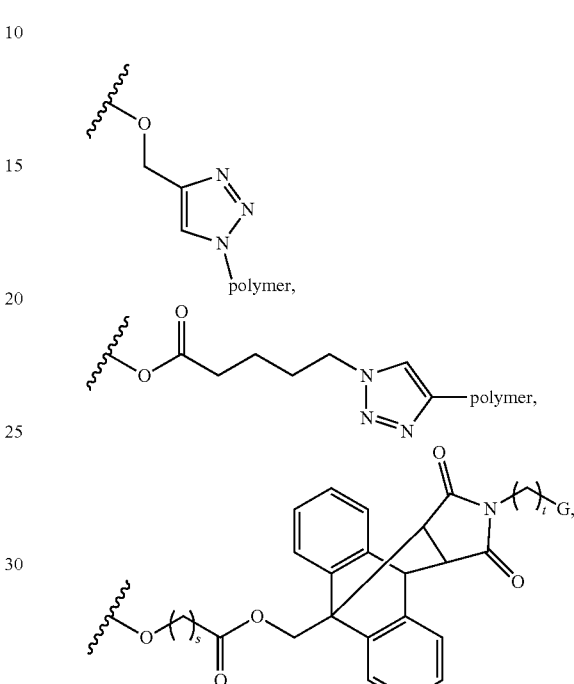

or a polymer; D is

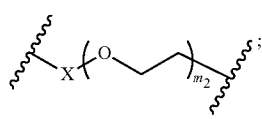

G is a polymer; $R^4$ is a polymer; $R^5$ is a polymer; and wherein the polymer is polystyrene, poly-t-butyl acrylate, or polymethyl methacrylate.

In some embodiments of formula (IV), $R^3$ is

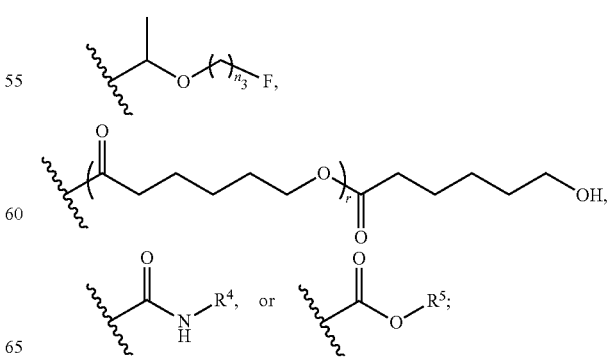

F is
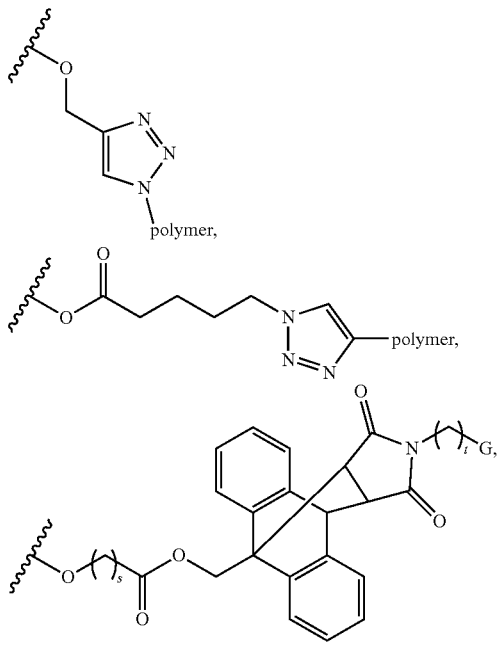
or a polymer; D is
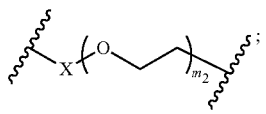
G is a polymer; $R^4$ is a polymer; $R^5$ is a polymer; and wherein the polymer is polystyrene, poly-t-butyl acrylate, or polymethyl methacrylate.
In some embodiments of formula (IV), $R^3$ is
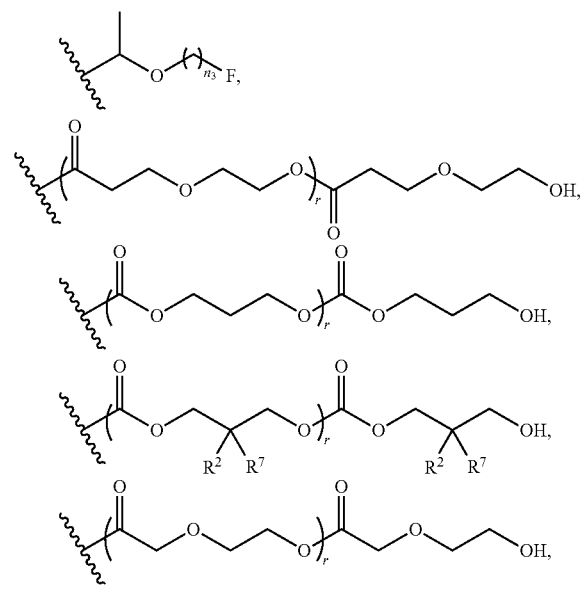
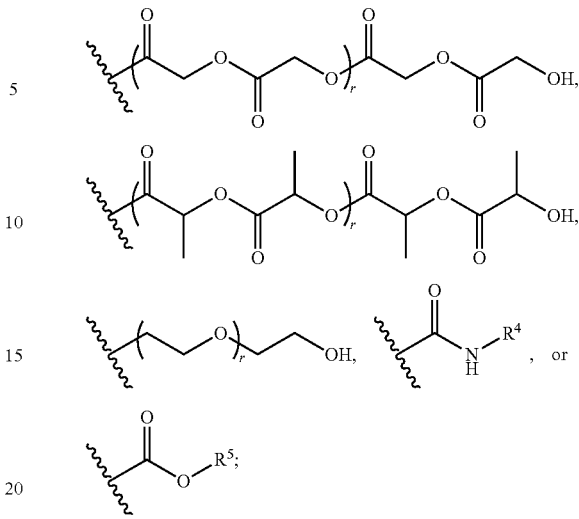
F is
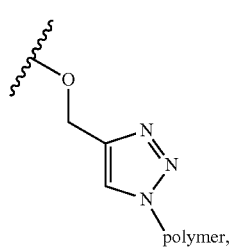
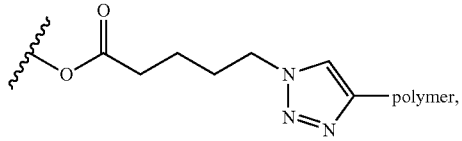
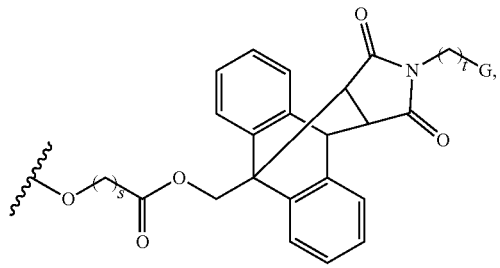
or a polymer; D is
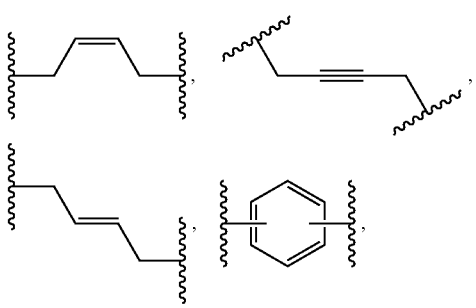

101
-continued
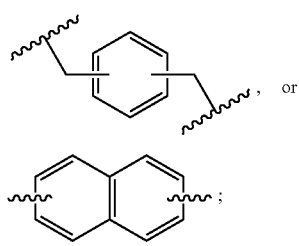
G is a polymer; R⁴ is a polymer; R⁵ is a polymer; and the polymer is polyethylene glycol.
In some embodiments of formula (IV), R³ is
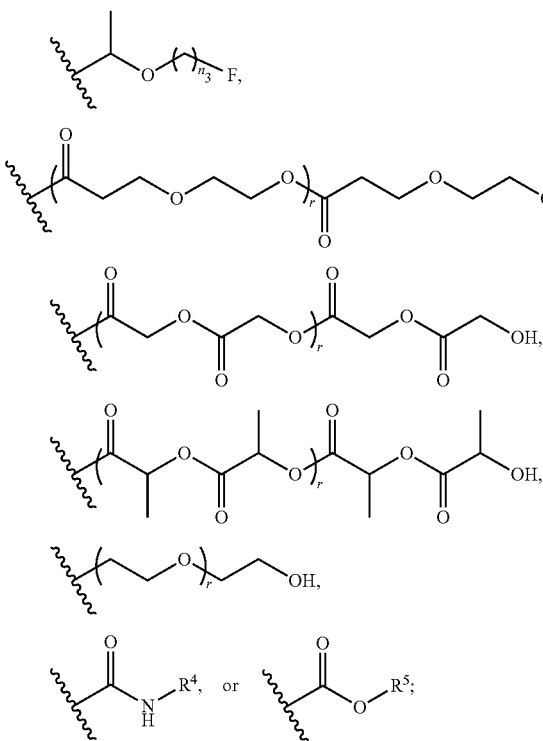
F is
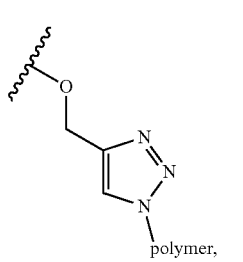
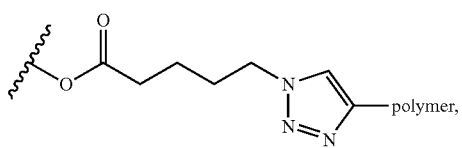
102
-continued
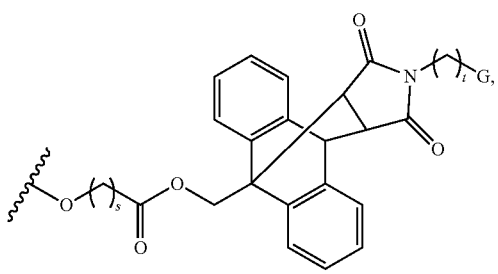
or a polymer; D is
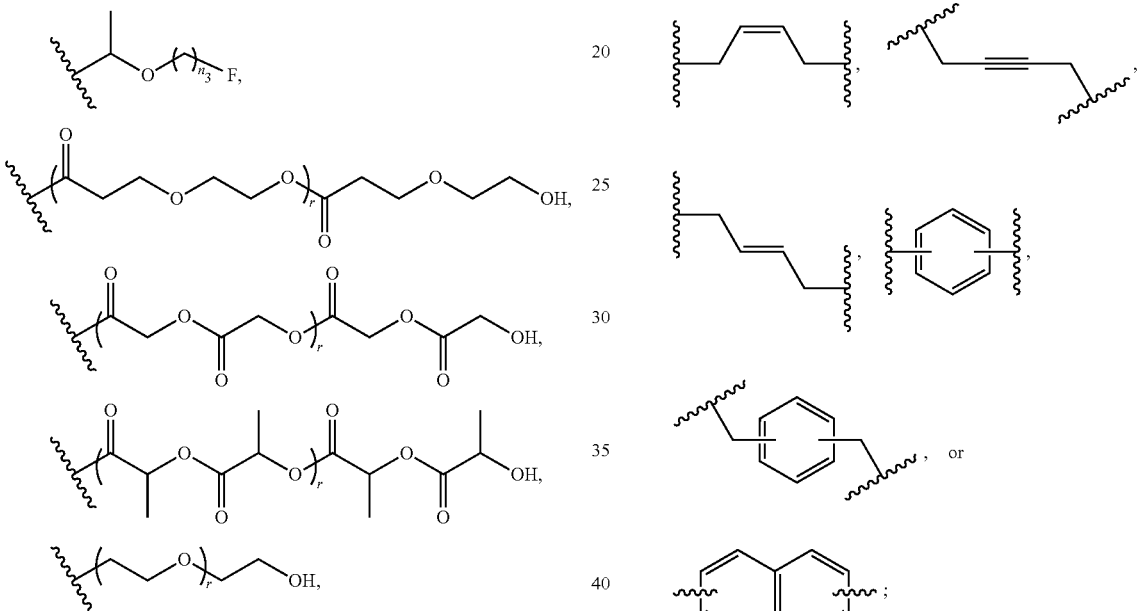
G is a polymer; R⁴ is a polymer; R⁵ is a polymer; and the polymer is polyethylene glycol.
In some embodiments of formula (IV), R³ is
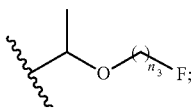 [SMILES: *C(C)OCF]
F is
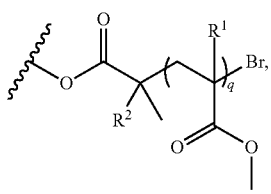

103
-continued
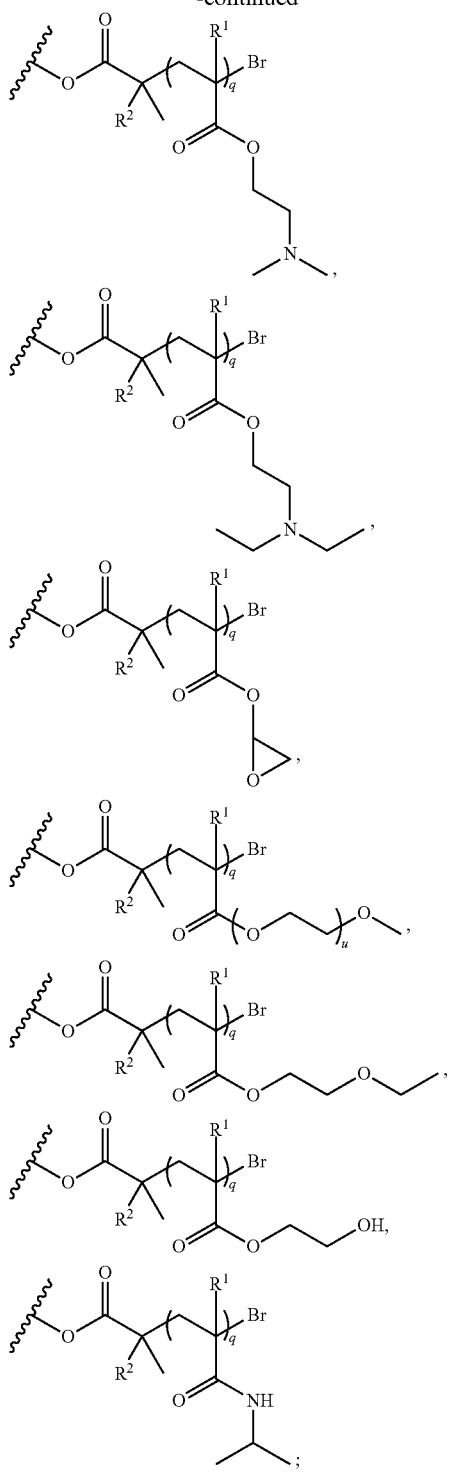
and D is
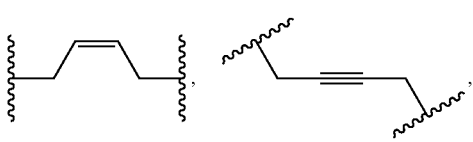
104
-continued
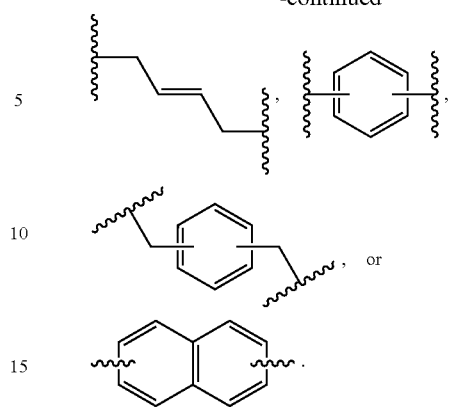
In some embodiments of formula (IV), $R^3$ is
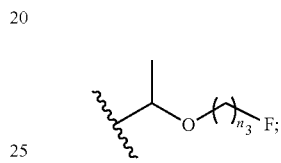
F is
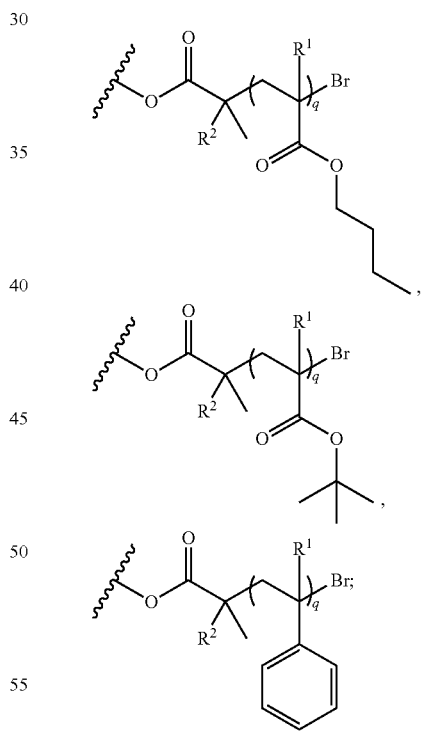
and D is
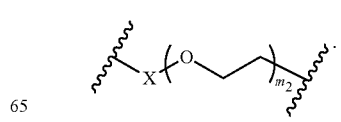

In some embodiments of formula (IV), $R^3$ is

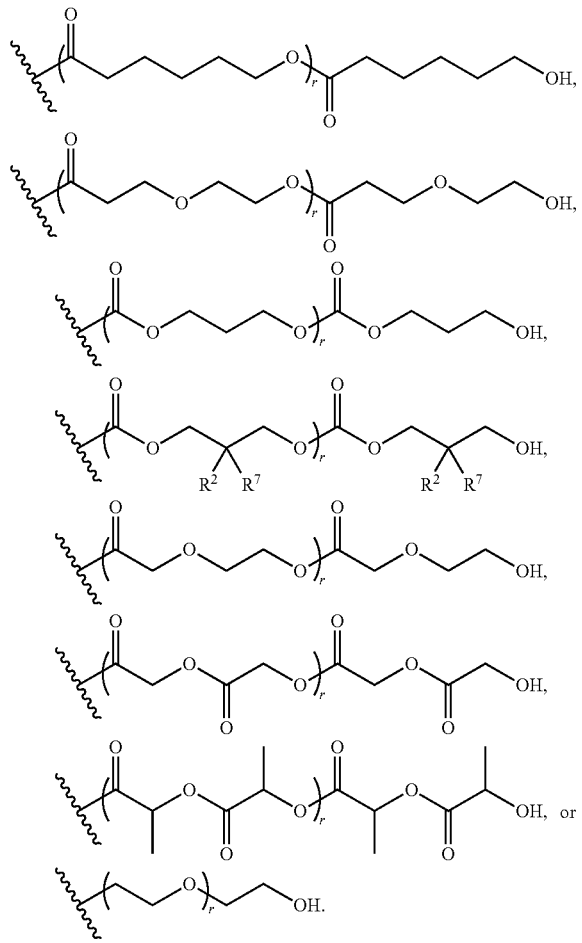

In some embodiments of formula (IV), $R^3$ is

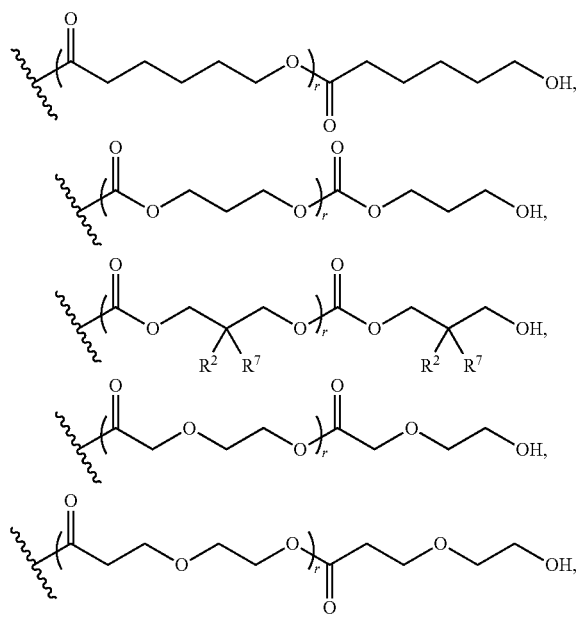

In some embodiments of formula (IV), $R^3$ is

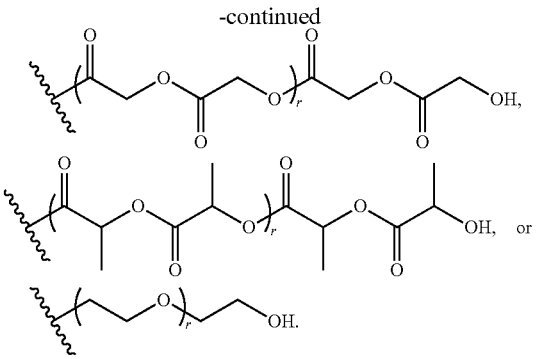

In some embodiments of formula (IV), $R^3$ is

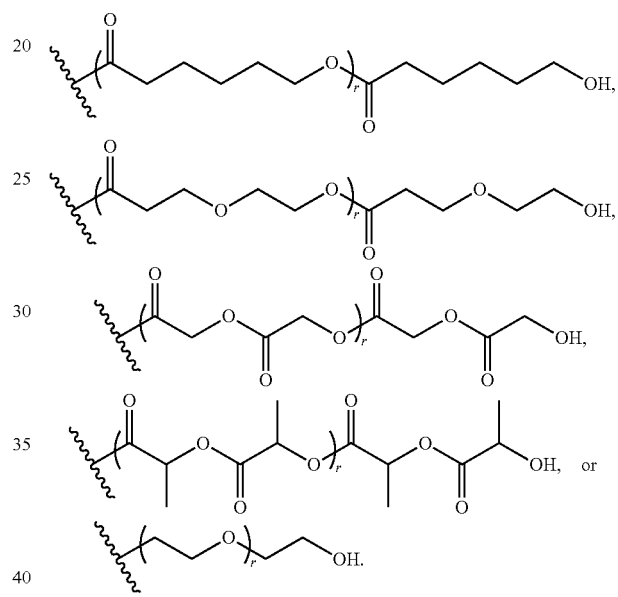

In some embodiments, the compound of formula (III) comprises a therapeutic agent core and is used to treat a cancer in a subject in need thereof. In some embodiments, the compound of formula (IV) comprises a therapeutic agent core and is used to treat a cancer in a subject in need thereof. Non-limiting examples of cancers treated by the therapeutic agent which comprises the therapeutic agent core include breast cancer, non-small cell lung cancer, pancreatic cancer, acute lymphoblastic leukemia (ALL), acute myeloid leukemia (AML), gastric cancer, Hodgkin lymphoma, neuroblastoma, Non-Hodgkin lymphoma, ovarian cancer, small cell lung cancer, soft tissue and bone sarcomas, thyroid cancer, transitional cell bladder cancer, Wilms tumor, adjuvant therapy for breast cancer that has spread to the lymph nodes after surgery, renal cell carcinoma, subependymal giant cell astrocytoma, Multiple myeloma, T-cell acute lymphoblastic leukemia, T-cell lymphoblastic lymphoma, Myelodysplastic syndromes (MDS), Chronic myelomonocytic leukemia (CMML), penile cancer, squamous cell carcinoma of the cervix, of the head and neck, and of the vulva, testicular cancer, mantle cell lymphoma, colorectal cancer, gastric cancer, esophageal cancer, Chronic myelogenous leukemia, meningeal leukemia, Myelodysplastic syndromes (MDS), adenocarcinoma, prostate cancer, squamous cell carcinoma of the head and neck, Chronic lymphocytic leukemia, cervical cancer, gastroenteropancreatic neuroendocrine tumors, AIDS related Kaposi sarcoma, bladder cancer, melanoma, esophageal cancer, mycosis fungoides, thymoma, thymic carcinoma, choriocarcinoma, Kaposi sarcoma, Mycosis fungoides, acute leukemia, and rhabdomyosarcoma.

In some embodiments, the compound of formula (III) comprises a therapeutic agent core and is used to treat bone damage caused by breast cancer in a subject in need thereof. In some embodiments, the compound of formula (III) comprises a therapeutic agent core and is used to treat hypercalcemia in a subject in need thereof. In some embodiments, the compound of formula (IV) comprises a therapeutic agent core and is used to treat bone damage caused by breast cancer in a subject in need thereof. In some embodiments, the compound of formula (IV) comprises a therapeutic agent core and is used to treat hypercalcemia in a subject in need thereof. In some embodiments, the therapeutic agent which comprises the therapeutic agent core is used to treat hypercalcemia or bone damage caused by breast cancer.

In some embodiments, the compound of formula (III) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, the compound of formula (IV) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, a composition comprising the compound of formula (III) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, a composition comprising the compound of formula (IV) is administered to a subject in need thereof. For example, administration may occur to a subject having a tumor cell. Subjects include, but are not limited to, rodents, dogs, monkeys, and humans. In some embodiments, the subject is a rodent, dog, monkey or human. In some embodiments, the subject is a rodent. In some embodiments, the subject is a human.

In some embodiments, therapeutic agents are compounds that are pharmaceutically active. In some embodiments, the compound of formula (III) comprises a "drug core". In some embodiments, the compound of formula (IV) comprises a "drug core". In some embodiments, the compound of formula (III) comprises an "agricultural agent core". In some embodiments, the compound of formula (IV) comprises an "agricultural agent core".

In some embodiments of formula (IV), D is

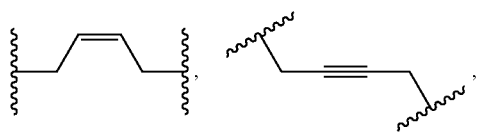

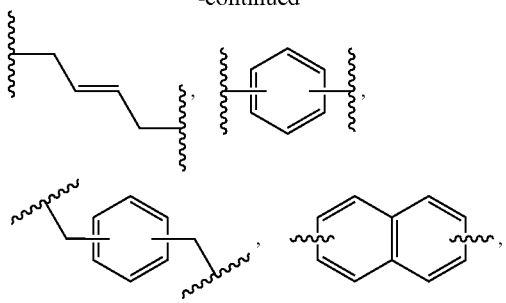

or a therapeutic agent core.

In another aspect, the invention is directed to a class of compounds of formula (V)

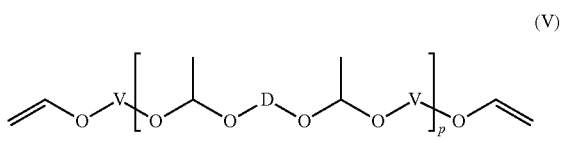

wherein,
V is

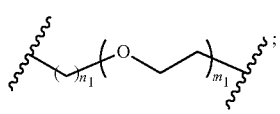

each D may be the same or different and is

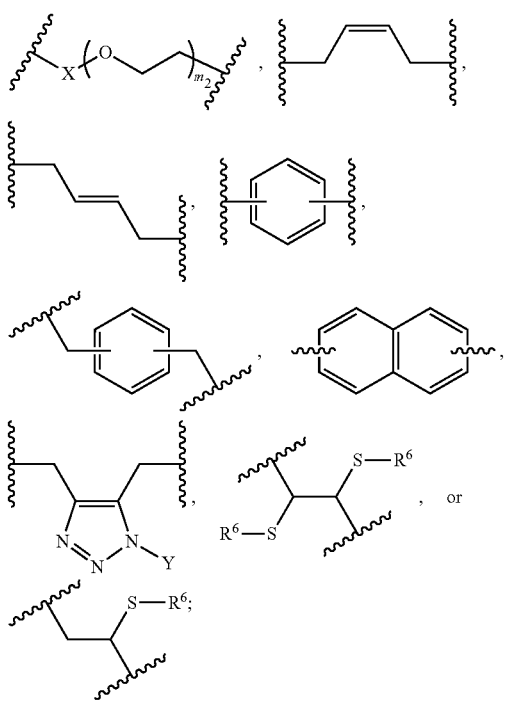

each $n_1$ may be the same or different and is an integer between 2 and 10;

each $m_1$ may be the same or different and is an integer between 0 and 20;
each X may be the same or different and is $C_2$-$C_{10}$ alkyl;
each $m_2$ may be the same or different and is an integer between 0 and 20;
p is an integer between 3 and 200;
Y is a polymer or therapeutic agent; and
$R^6$ is alkyl, aryl, or a polymer.

In another aspect, the invention is directed to a biodegradable gel comprising a compound of formula (V) cross-linked with a linker at a terminus of the compound, wherein the cross-linker is bonded to a plurality of compounds of formula (V).

In another aspect, the invention is directed to a method of making a gel, comprising crosslinking a compound of formula (V) with a trifunctional linker.

In another aspect, the invention is directed to a method of delivering a therapeutic agent to a tumor cell comprising, administering a biodegradable gel comprising a compound of formula (V) cross-linked with a linker at a terminus of the compound, wherein the cross-linker is bonded to a plurality of compounds of formula (V), and a therapeutic agent, wherein said gel degrades at pH from about 5 to about 6.5 to release said therapeutic agent.

In some embodiments of formula (V), the sum of ($m_1$+$m_2$) is greater than zero.

In some embodiments of formula (V), D is

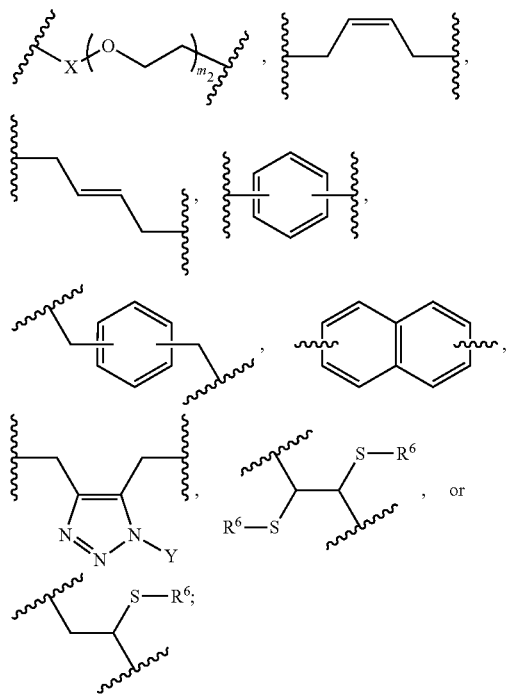

$n_1$ is an integer between 2 and 10; $m_1$ is an integer between 0 and 20; X is $C_2$-$C_{10}$ alkyl; and $m_2$ is an integer between 0 and 20.

In some embodiments of formula (V), D is

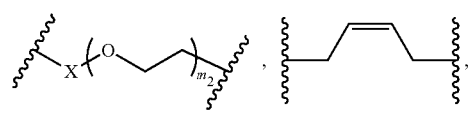

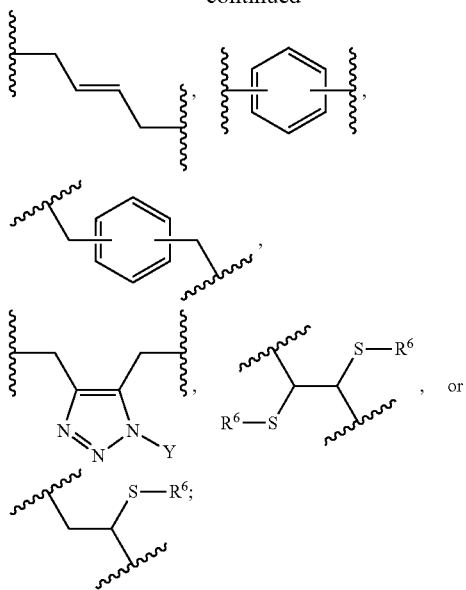

$n_1$ is an integer between 2 and 10; $m_1$ is an integer between 0 and 20; X is $C_2$-$C_{10}$ alkyl; and $m_2$ is an integer between 0 and 20.

In some embodiments of formula (V), each D may be the same or different and is

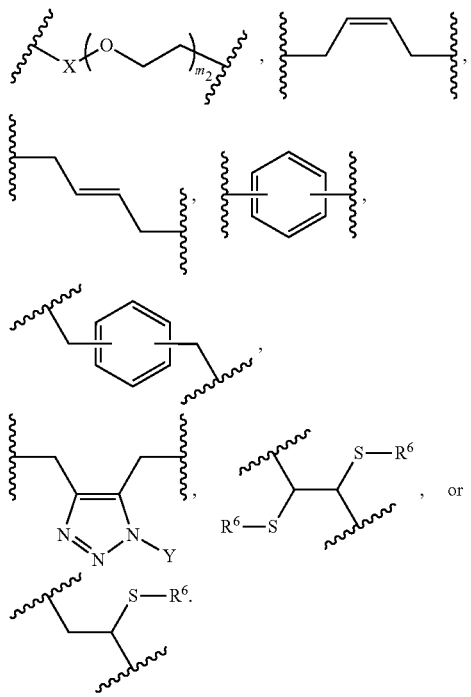

In some embodiments of formula (V), Y is a polymer.
In some embodiments of formula (V), $R^6$ is a polymer.
In some embodiments of formula (V), X is $C_2$-$C_5$ n-alkyl.
In some embodiments of formula (V), each $n_1$ may be the same or different and is an integer between 2 and 4; each $m_1$ may be the same or different and is an integer between 0 and 2; each X may be the same or different and is $C_2$-$C_5$ alkyl;

each $m_2$ may be the same or different and is an integer between 0 and 3; and p is an integer between 3 and 100.

In some embodiments of formula (V), each $n_1$ may be the same or different and is an integer between 2 and 4; each $m_1$ may be the same or different and is an integer between 0 and 2; each X may be the same or different and is $C_2$-$C_5$ n-alkyl; each $m_2$ may be the same or different and is an integer between 0 and 3; and p is an integer between 3 and 100.

In some embodiments of formula (V), each D may be the same or different and is

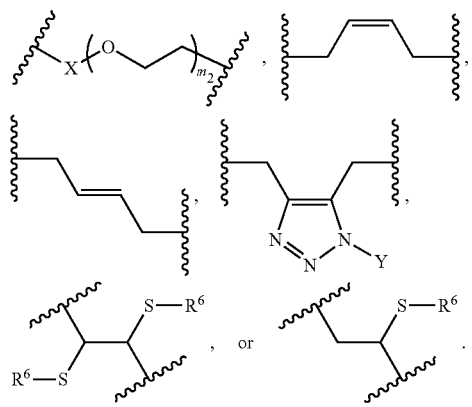

In some embodiments of formula (V), each D may be the same or different and is

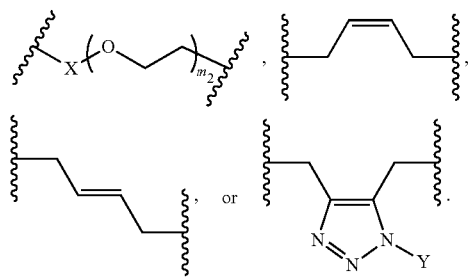

In some embodiments of formula (V), $n_1$ is an integer between 2 and 4; $m_1$ is an integer between 0 and 2; X is $C_2$-$C_5$ alkyl; $m_2$ is an integer between 0 and 3; and p is an integer between 3 and 100.

In some embodiments of formula (V), $n_1$ is an integer between 2 and 4; $m_1$ is an integer between 0 and 2; X is $C_2$-$C_5$ n-alkyl; $m_2$ is an integer between 0 and 3; and p is an integer between 3 and 100.

In some embodiments of formula (V), D is

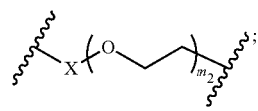

$n_1$ is 4; $m_1$ is 0; X is $C_2$ alkyl.

In another aspect, the invention is directed to a class of compounds of formula (VI)

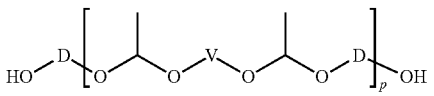

wherein,
V is

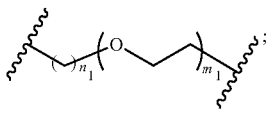

each D may be the same or different and is

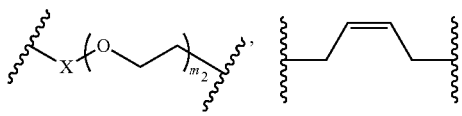

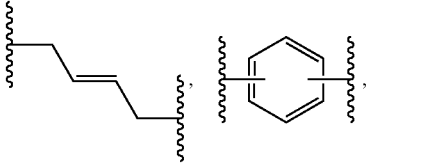

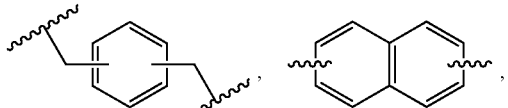

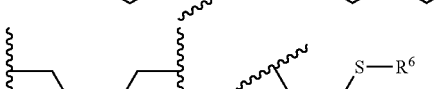

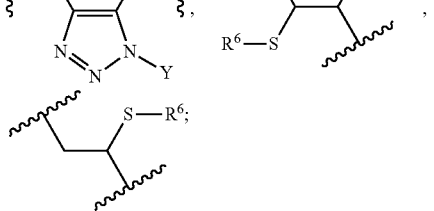

each $n_1$ may be the same or different and is an integer between 2 and 10;
each $m_1$ may be the same or different and is an integer between 0 and 20;
each X may be the same or different and is $C_2$-$C_{10}$ alkyl;
each $m_2$ may be the same or different and is an integer between 0 and 20;
p is an integer between 3 and 200;
Y is a polymer or therapeutic agent; and
$R^6$ is alkyl, aryl, or a polymer.

In another aspect, the invention is directed to a biodegradable gel comprising a compound of formula (VI), wherein the compound is cross-linked with a linker at a terminus of the compound; and wherein the cross-linker is bonded to a plurality of compounds of formula (VI).

In another aspect, the invention is directed to a method of making a gel, comprising crosslinking a compound of formula (VI) with a trifunctional linker.

In another aspect, the invention is directed to a method of delivering a therapeutic agent to a tumor cell comprising, administering a biodegradable gel comprising a compound of formula (VI), wherein the compound is cross-linked with a linker at a terminus of the compound; and wherein the cross-linker is bonded to a plurality of compounds of formula (VI), and a therapeutic agent, wherein said gel degrades at pH from about 5 to about 6.5 to release said therapeutic agent.

In some embodiments of formula (VI), the sum of ($m_1$+$m_2$) is greater than zero.

In some embodiments of formula (VI), D is

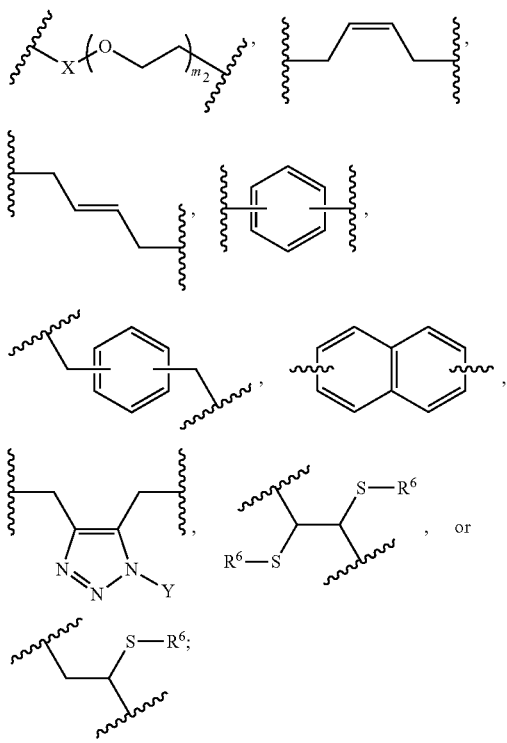

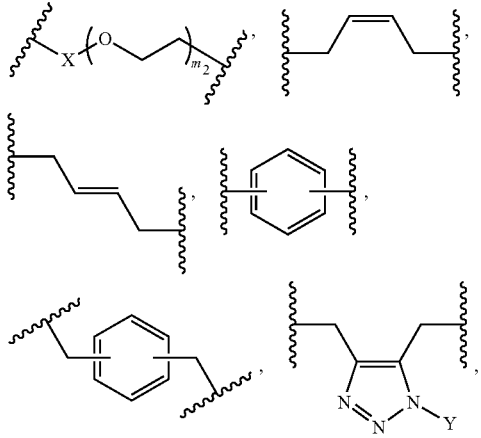

$n_1$ is an integer between 2 and 10; $m_1$ is an integer between 0 and 20; X is $C_2$-$C_{10}$ alkyl; and $m_2$ is an integer between 0 and 20.

In some embodiments of formula (VI), D is

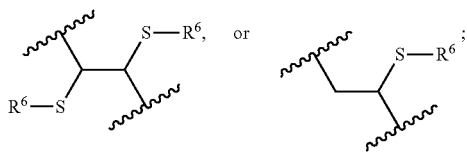

$n_1$ is an integer between 2 and 10; $m_1$ is an integer between 0 and 20; X is $C_2$-$C_{10}$ alkyl; and $m_2$ is an integer between 0 and 20.

In some embodiments of formula (VI), each D may be the same or different and is

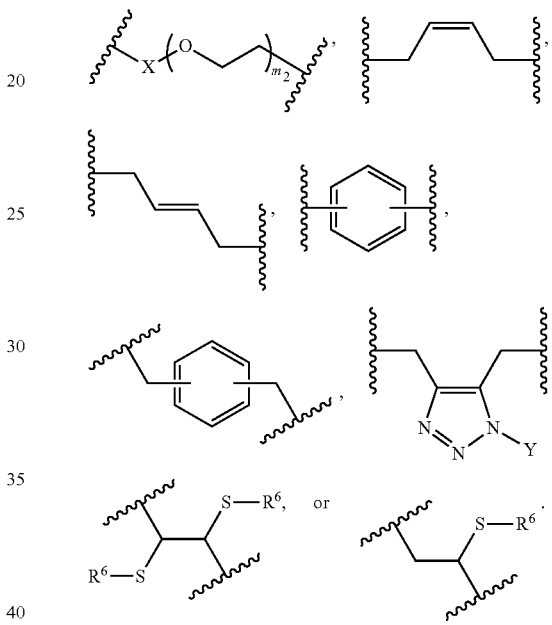

In some embodiments of formula (VI), Y is a polymer.

In some embodiments of formula (VI), $R^6$ is a polymer.

In some embodiments of formula (VI), each $n_1$ may be the same or different and is an integer between 2 and 4; each $m_1$ may be the same or different and is an integer between 0 and 2; each X may be the same or different and is $C_2$-$C_5$ alkyl; each $m_2$ may be the same or different and is an integer between 0 and 3; and p is an integer between 3 and 100.

In some embodiments of formula (VI), each $n_1$ may be the same or different and is an integer between 2 and 4; each $m_1$ may be the same or different and is an integer between 0 and 2; each X may be the same or different and is $C_2$-$C_5$ n-alkyl; each $m_2$ may be the same or different and is an integer between 0 and 3; and p is an integer between 3 and 100.

In some embodiments of formula (VI), each D may be the same or different and is

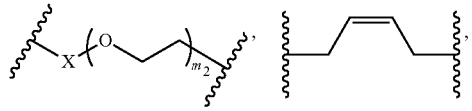

-continued

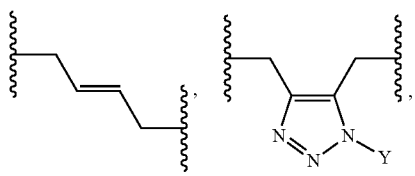

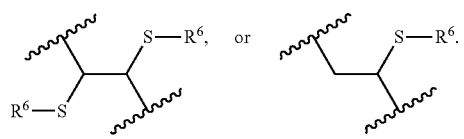

In some embodiments of formula (VI), each D may be the same or different and is

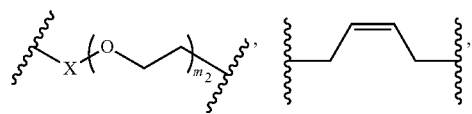

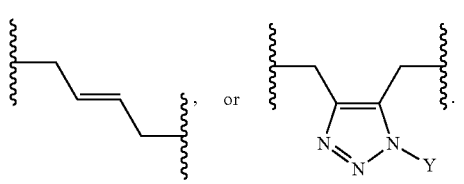

In some embodiments of formula (VI), $n_1$ is an integer between 2 and 4; $m_1$ is an integer between 0 and 2; X is $C_2$-$C_5$ alkyl; $m_2$ is an integer between 0 and 3; and p is an integer between 3 and 100.

In some embodiments of formula (VI), $n_1$ is an integer between 2 and 4; $m_1$ is an integer between 0 and 2; X is $C_2$-$C_5$ n-alkyl; $m_2$ is an integer between 0 and 3; and p is an integer between 3 and 100.

In some embodiments of formula (VI), X is $C_2$-$C_5$ n-alkyl.

In some embodiments of formula (VI), D is

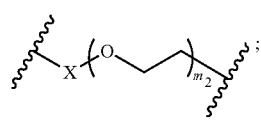

$n_1$ is 4; $m_1$ is 0; X is $C_2$ alkyl; and $m_2$ is 2.

In another aspect, the invention is directed to compositions comprising a compound of any of formulas (I)-(VI) and a pharmaceutically acceptable carrier.

In some embodiments, A is

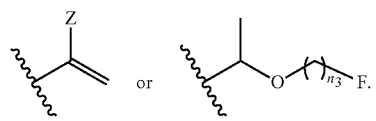

In some embodiments, A is

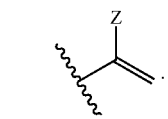

In some embodiments, A is

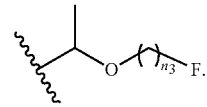

In some embodiments, D is

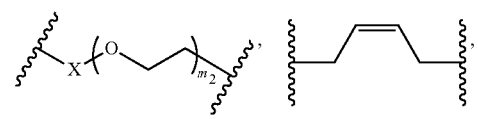

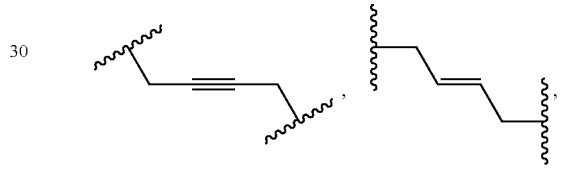

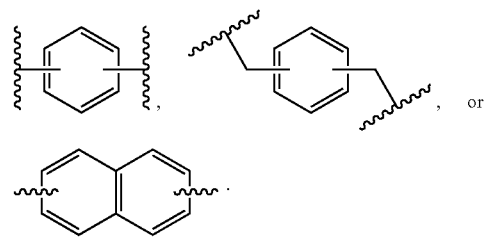

In some embodiments, D is

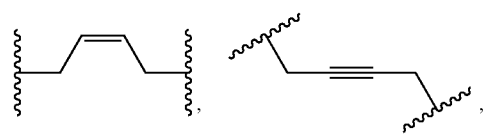

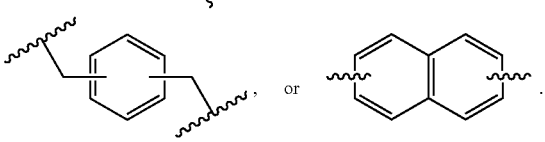

In some embodiments, D is

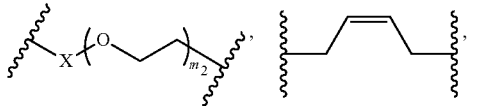

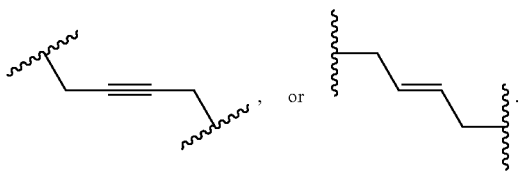

In some embodiments, D is

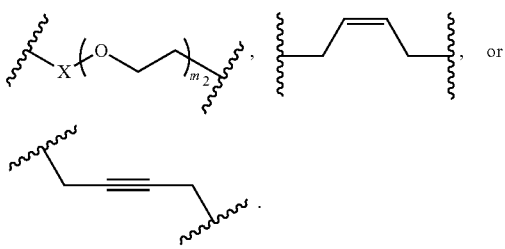

In some embodiments, D is

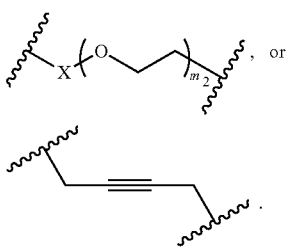

In some embodiments, D is

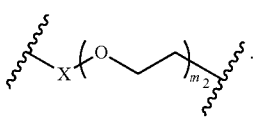

In some embodiments, D is

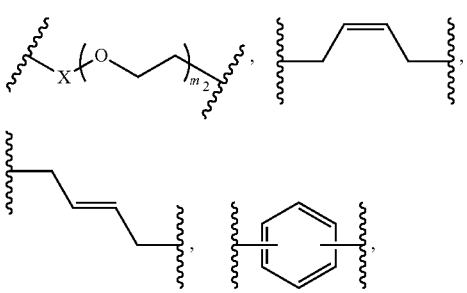

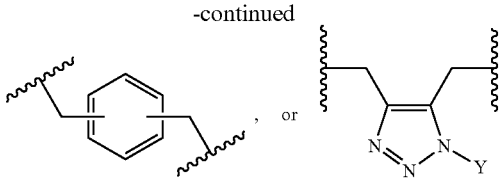

In some embodiments, D is

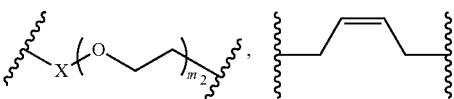

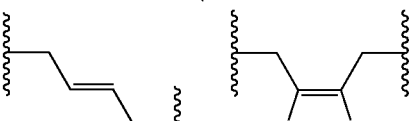

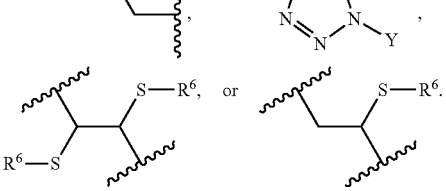

In some embodiments, D is

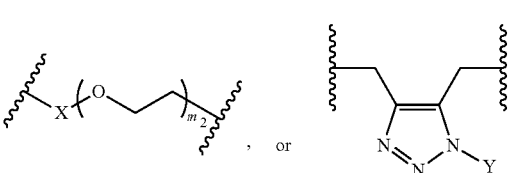

In some embodiments, D is

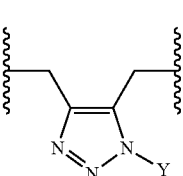

In some embodiments, D is

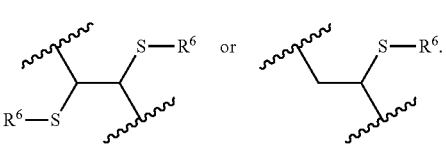

In some embodiments, each $n_1$ may be the same or different and is an integer between 2 and 10. In some embodiments, $n_1$ is an integer between 2 and 10. In some embodiments, each $n_1$ may be the same or different and is an integer between 2 and 4. In some embodiments, $n_1$ is an integer between 2 and 4. In some embodiments, $n_1$ is 4. In some embodiments, $n_1$ is 2.

In some embodiments, each $m_1$ may be the same or different and is an integer between 0 and 20. In some embodiments, $m_1$ is an integer between 0 and 20. In some embodiments, each $m_1$ may be the same or different and is an integer between 0 and 2. In some embodiments, each $m_1$ may be the same or different and is 1 or 2. In some embodiments, $m_1$ is an integer between 0 and 2. In some embodiments, $m_1$ is 0. In some embodiments, $m_1$ is 2.

In some embodiments, each X may be the same or different and is $C_2$-$C_{10}$ alkyl. In some embodiments, each X may be the same or different and is $C_2$-$C_5$ alkyl. In some embodiments, each X may be the same or different and is $C_2$-$C_5$ n-alkyl. In some embodiments, X is $C_2$-$C_{10}$ alkyl. In some embodiments, X is $C_2$-$C_5$ alkyl. In some embodiments, X is $C_2$-$C_5$ n-alkyl. In some embodiments, X is $C_4$ alkyl. In some embodiments, X is $C_4$ n-alkyl. In some embodiments, X is $C_2$ alkyl.

In some embodiments, each $m_2$ may be the same or different and is an integer between 0 and 20. In some embodiments, each $m_2$ may be the same or different and is an integer between 0 and 3. In some embodiments, each $m_2$ may be the same or different and is 2 or 3.

In some embodiments, $m_2$ is an integer between 0 and 20. In some embodiments, $m_2$ is an integer between 0 and 3. In some embodiments, $m_2$ is 2 or 3. In some embodiments, $m_2$ is 0 or 2. In some embodiments, $m_2$ is 2. In some embodiments, $m_2$ is 0.

In some embodiments, p is an integer between 3 and 200. In some embodiments, p is an integer between 3 and 100. In some embodiments, p is an integer between 3 and 50. In some embodiments, p is an integer between 10 and 200. In some embodiments, p is an integer between 10 and 100. In some embodiments, p is an integer between 10 and 50.

In some embodiments, F is

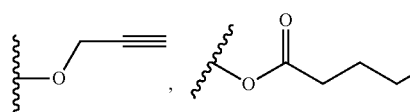

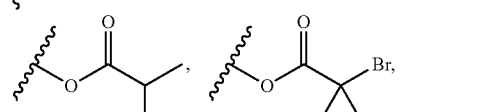

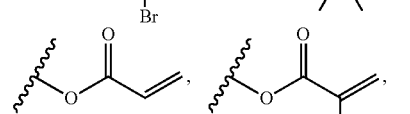

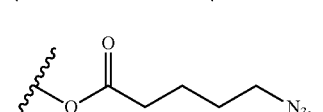

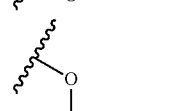

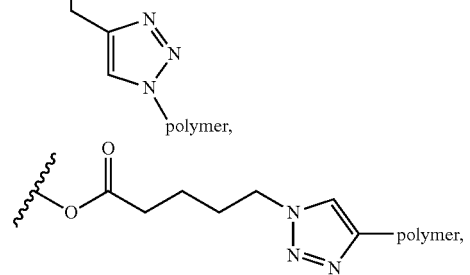

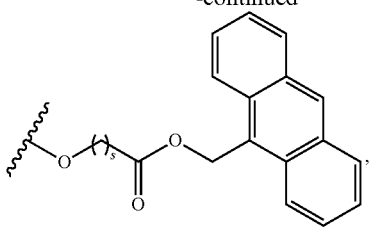

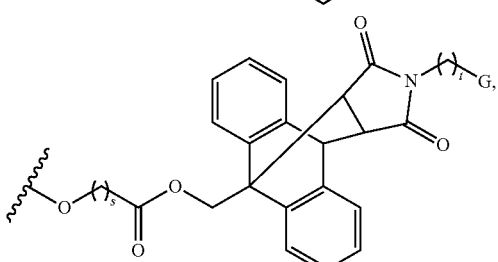

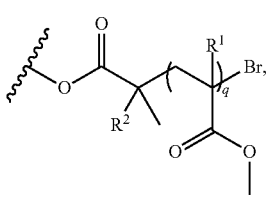

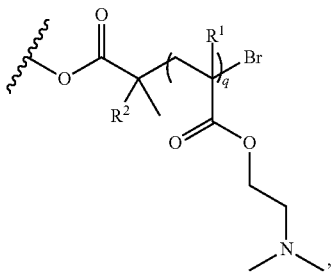

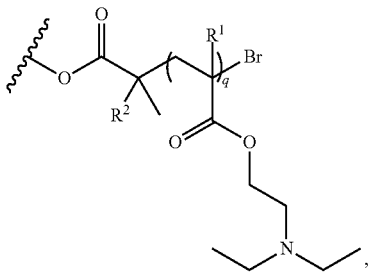

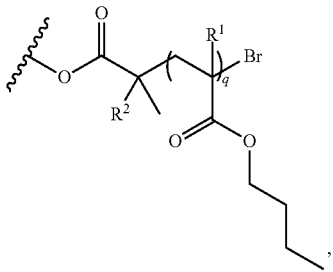

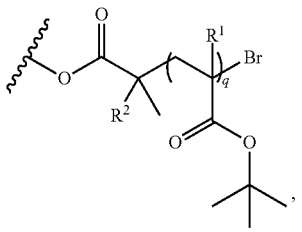

121
-continued
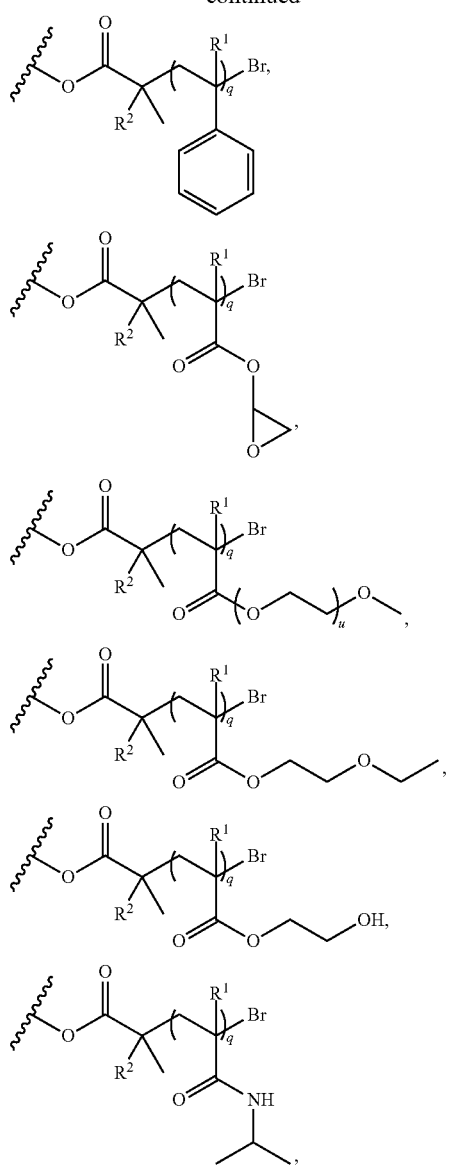
or a polymer.
In some embodiments, F is
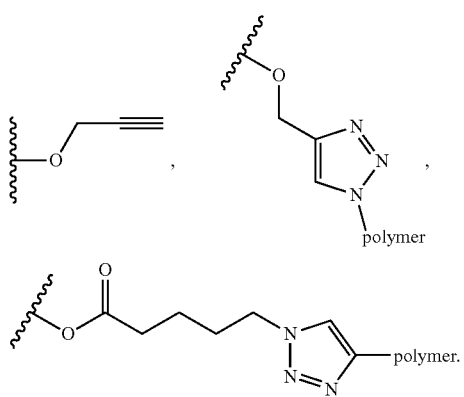
122
-continued
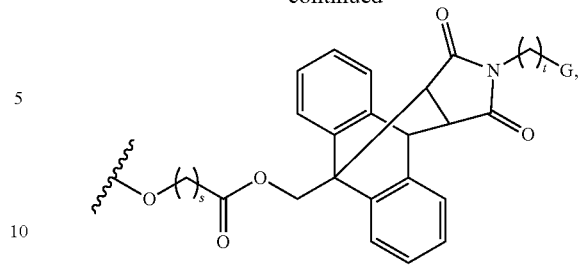
or a polymer; wherein G is a polymer. In some embodiments, F is
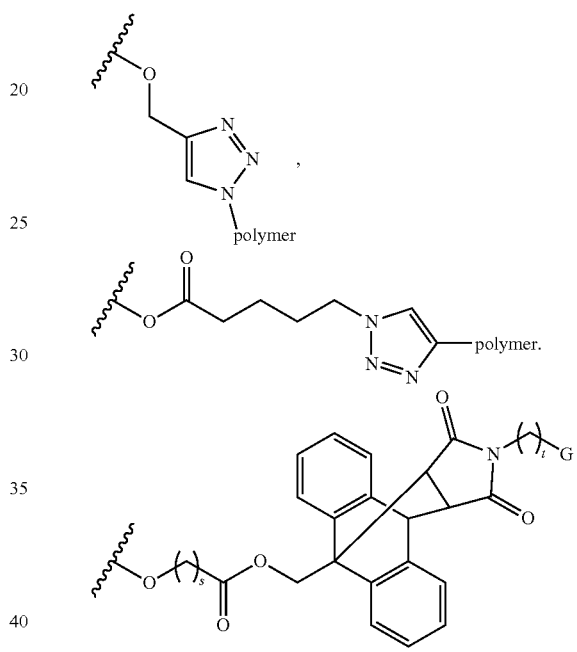
or a polymer; wherein G is a polymer. In some embodiments, F is
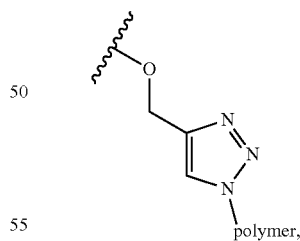
or a polymer. In some embodiments, F is
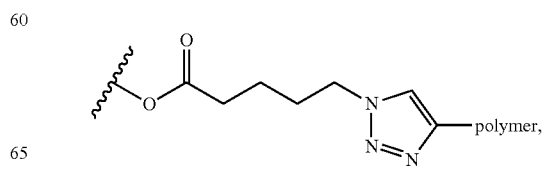

or a polymer. In some embodiments, F is

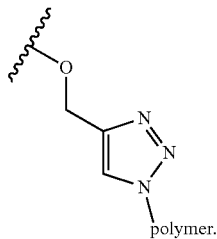

In some embodiments, F is

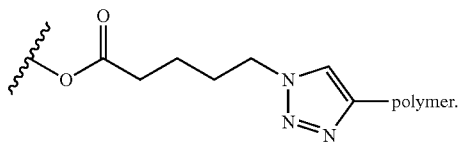

In some embodiments, F is

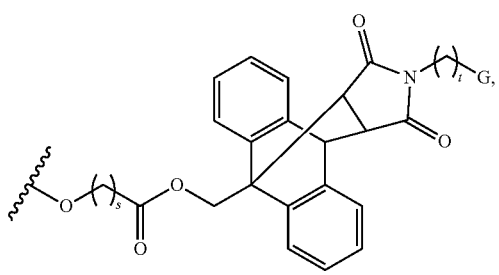

wherein G is a polymer. In some F embodiments, F is a polymer.

In some embodiments, F is

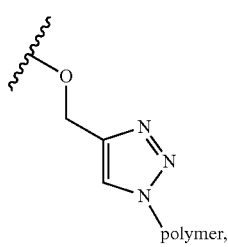

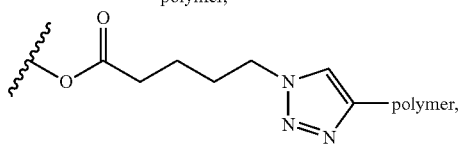

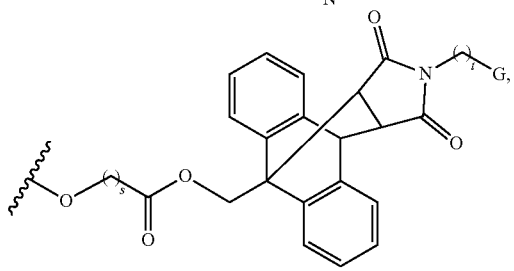

or a polymer; wherein G is a polymer; wherein the polymer is polystyrene, poly-t-butyl acrylate, or polymethyl methacrylate.

In some embodiments, F is

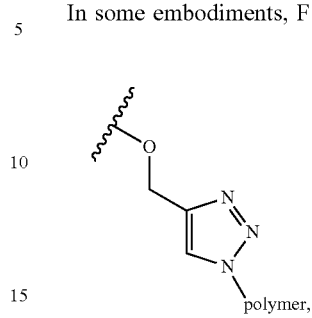

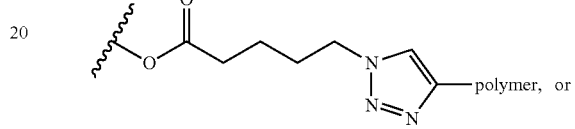

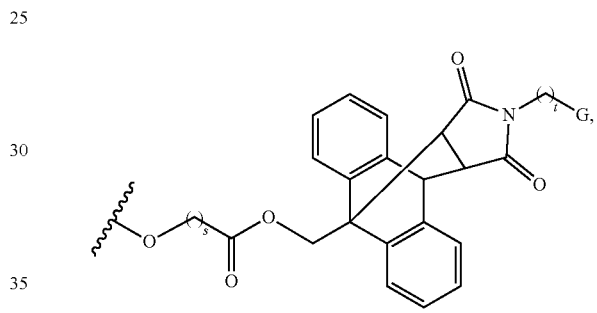

wherein G is a polymer; wherein the polymer is polyethylene glycol.

In some embodiments, polymer is polystyrene, poly-t-butyl acrylate, polymethyl methacrylate, or polyethylene glycol.

In some embodiments, F is

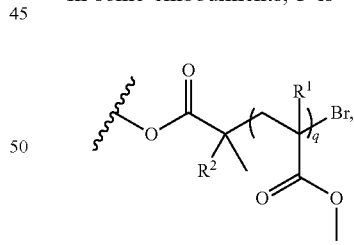

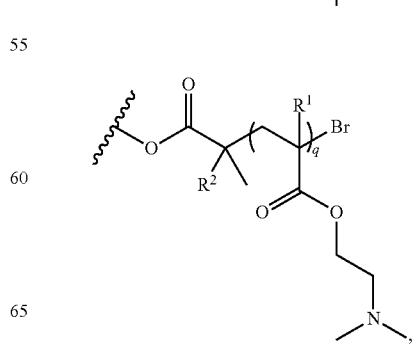

-continued

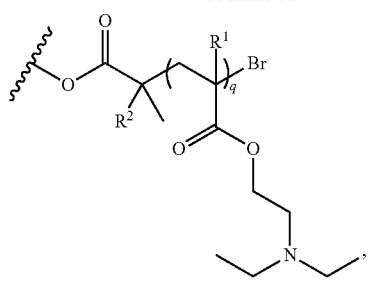

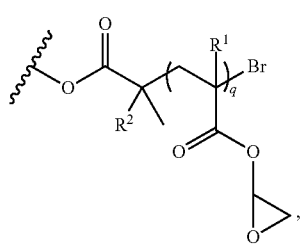

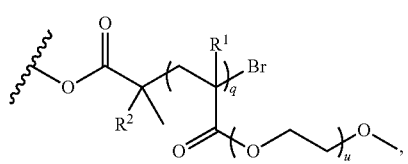

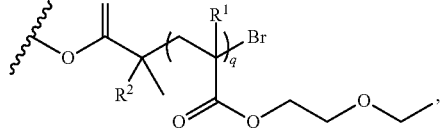

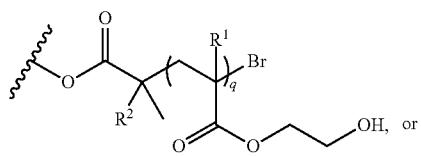

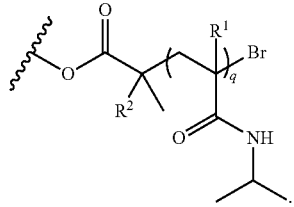

In some embodiments, F is

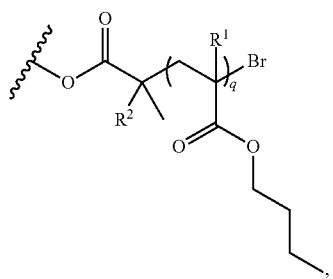

-continued

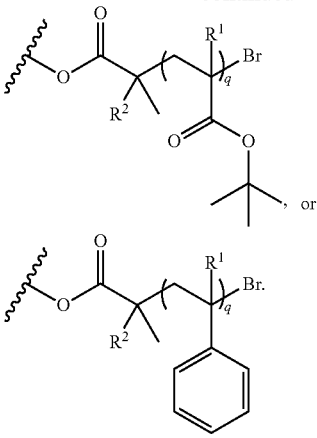

In some embodiments, G is a polymer, aryl, or alkyl. In some embodiments, G is aryl or alkyl. In some embodiments, G is a polymer. In some embodiments, G is aryl. In some embodiments, G is alkyl.

In some embodiments, Z is a polymer, aryl, hetero-aryl, or vinyl. In some embodiments, Z is a aryl, hetero-aryl, or vinyl. In some embodiments, Z is a polymer, aryl, or hetero-aryl. In some embodiments, Z is a aryl or hetero-aryl. In some embodiments, Z is aryl or vinyl. In some embodiments, Z is a polymer. In some embodiments, Z is aryl. In some embodiments, Z is hetero-aryl. In some embodiments, Z is vinyl.

In some embodiments, q is an integer between 1 and 1000. In some embodiments, q is an integer between 1 and 500. In some embodiments, q is an integer between 1 and 100. In some embodiments, q is an integer between 100 and 1000. In some embodiments, q is an integer between 100 and 500. In some embodiments, q is an integer between 10 and 1000. In some embodiments, q is an integer between 10 and 500. In some embodiments, q is an integer between 10 and 100.

In some embodiments, r is an integer between 1 and 1000. In some embodiments, r is an integer between 1 and 500. In some embodiments, r is an integer between 1 and 100. In some embodiments, r is an integer between 100 and 1000. In some embodiments, r is an integer between 100 and 500. In some embodiments, r is an integer between 10 and 1000. In some embodiments, r is an integer between 10 and 500. In some embodiments, r is an integer between 10 and 100.

In some embodiments, s is an integer between 1 and 10. In some embodiments, s is an integer between 1 and 8. In some embodiments, s is an integer between 1 and 5. In some embodiments, s is an integer between 1 and 3. In some embodiments, s is 2. In some embodiments, s is 1.

In some embodiments, t is an integer between 1 and 10. In some embodiments, t is an integer between 1 and 8. In some embodiments, t is an integer between 1 and 5. In some embodiments, t is an integer between 1 and 3. In some embodiments, t is 2. In some embodiments, t is 1.

In some embodiments, u is an integer between 1 and 1000. In some embodiments, u is an integer between 1 and 500. In some embodiments, u is an integer between 1 and 100. In some embodiments, u is an integer between 100 and 1000. In some embodiments, u is an integer between 100 and 500. In some embodiments, u is an integer between 10 and 1000. In some embodiments, u is an integer between 10 and 500. In some embodiments, u is an integer between 10 and 100.

In some embodiments, $R^1$ is H or $CH_3$. In some embodiments, $R^1$ is H. In some embodiments, $R^1$ is $CH_3$.

In some embodiments, $R^2$ is H or $CH_3$. In some embodiments, $R^2$ is H. In some embodiments, $R^2$ is $CH_3$.
In some embodiments, $R^3$ is
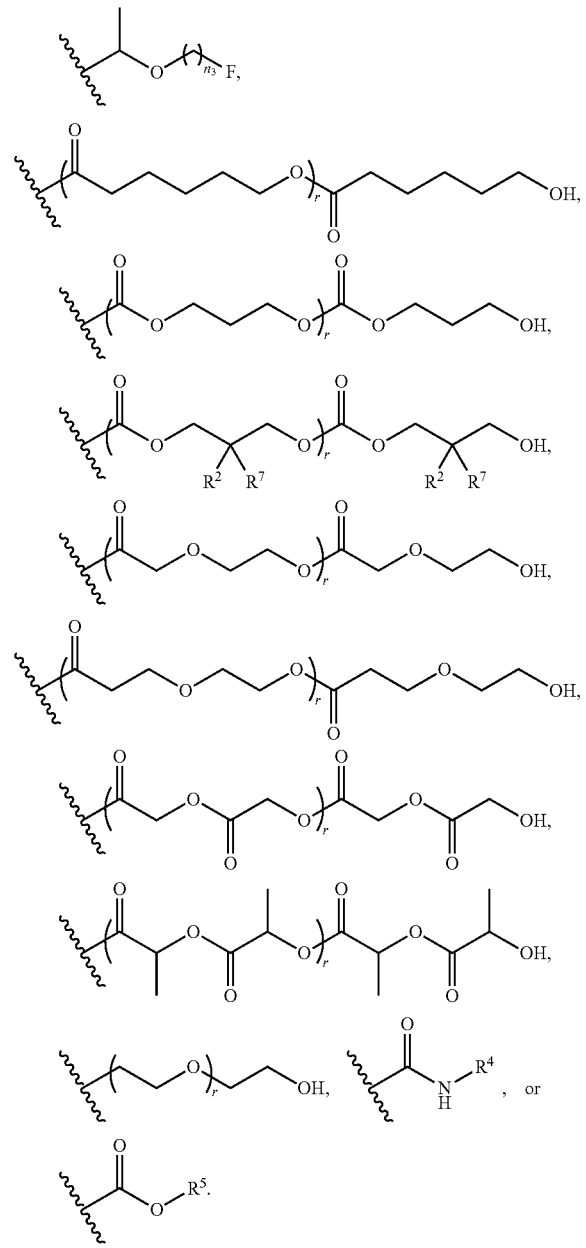
In some embodiments, $R^3$ is
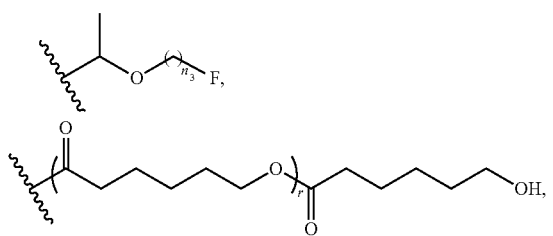
-continued
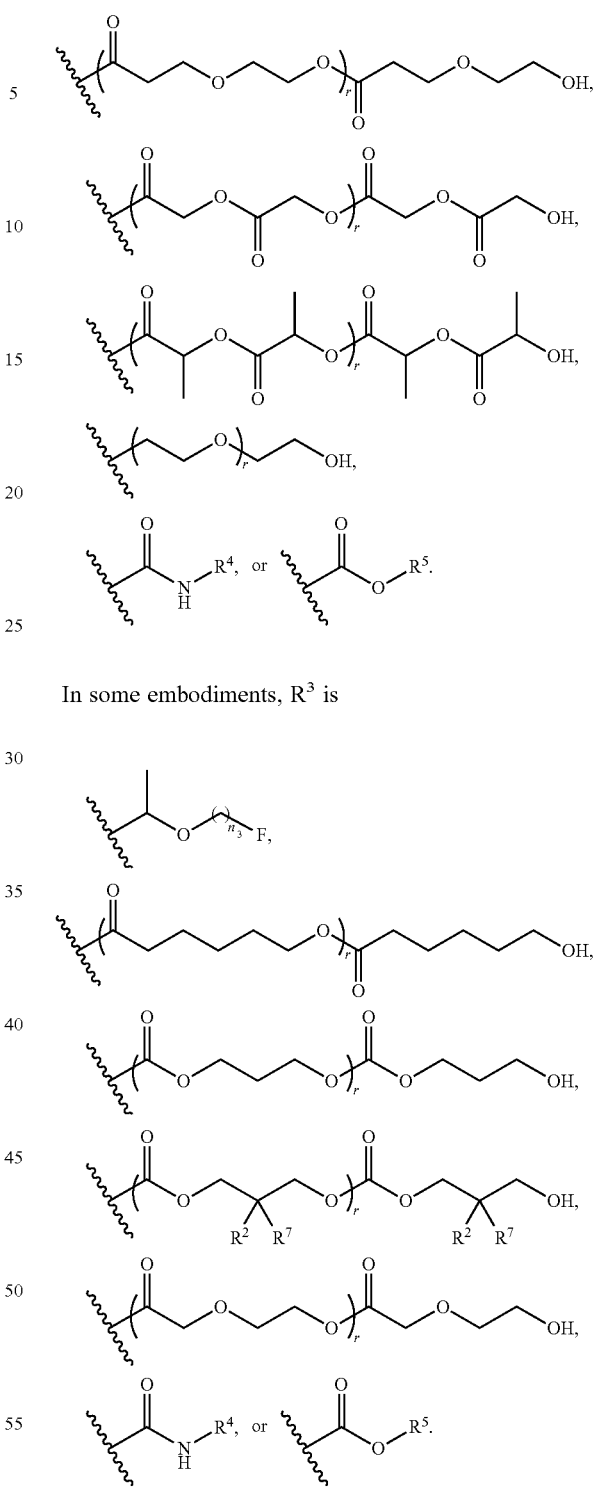
In some embodiments, $R^3$ is
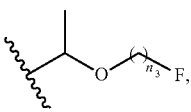 [SMILES: *C(C)OCF]

-continued

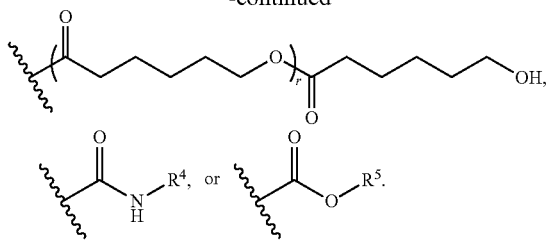

In some embodiments, $R^3$ is

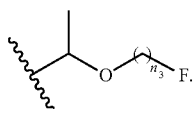

In some embodiments, $R^4$ is aryl, alkyl, or a polymer. In some embodiments, $R^4$ is aryl or alkyl. In some embodiments, $R^4$ is aryl. In some embodiments, $R^4$ is alkyl. In some embodiments, $R^4$ is a polymer.

In some embodiments, $R^5$ is aryl, alkyl, or a polymer. In some embodiments, $R^5$ is aryl or alkyl. In some embodiments, $R^5$ is aryl. In some embodiments, $R^5$ is alkyl. In some embodiments, $R^5$ is a polymer.

In some embodiments, $R^6$ is aryl, alkyl, or a polymer. In some embodiments, $R^6$ is aryl or alkyl. In some embodiments, $R^6$ is aryl. In some embodiments, $R^6$ is alkyl. In some embodiments, $R^6$ is a polymer.

In some embodiments, alkyl is $C_1$-$C_{10}$ alkyl. In some embodiments, alkyl is $C_2$-$C_{10}$ alkyl. In some embodiments, alkyl is $C_1$-$C_6$ alkyl. In some embodiments, alkyl is $C_2$-$C_6$ alkyl. In some embodiments, alkyl is $C_1$-$C_6$ alkyl. In some embodiments, alkyl is $C_1$-$C_3$ alkyl. In some embodiments, alkyl is methyl or ethyl. In some embodiments, alkyl is ethyl. In some embodiments, alkyl is methyl.

In some embodiments, $R^7$ is H or halogen. In some embodiments, $R^7$ is H, F, Cl, or Br. In some embodiments, $R^7$ is H. In some embodiments, $R^7$ is halogen. In some embodiments, $R^7$ is F, Cl, or Br. In some embodiments, $R^7$ is H, Cl or Br. In some embodiments, $R^7$ is Cl or Br.

In some embodiments, the value of $[(m_1+m_2)/p]$ is a number between 0 and 8. In some embodiments, the value of $[(m_1+m_2)/p]$ is a number between 1 and 8. In some embodiments, the value of $[(m_1+m_2)/p]$ is a number between 0 and 6. In some embodiments, the value of $[(m_1+m_2)/p]$ is a number between 1 and 6. In some embodiments, the value of $[(m_1+m_2)/p]$ is a number between 0 and 4. In some embodiments, the value of $[(m_1+m_2)/p]$ is a number between 1 and 4.

In some embodiments, the trifunctional linker comprises a plurality of alkynes, alcohols or isocyanates. In some embodiments, the trifunctional linker comprises a plurality of alkynes. In some embodiments, the trifunctional linker comprises a plurality of alcohols. In some embodiments, the trifunctional linker comprises a plurality of isocyanates. In some embodiments, the trifunctional linker comprises three alkynes, three alcohols or three isocyanates. In some embodiments, the trifunctional linker comprises three alkynes. In some embodiments, the trifunctional linker comprises a triol. In some embodiments, the trifunctional linker is a triol. In some embodiments, the triol is glycerol or trimethylolpropane. In some embodiments, the triol is glycerol. In some embodiments, the triol is trimethylolpropane. In some embodiments, the trifunctional linker comprises three isocyanates.

In some embodiments, the trifunctional linker comprises a plurality of isocyanates, azides or alkynes. In some embodiments, the trifunctional linker comprises a plurality of isocyanates. In some embodiments, the trifunctional linker comprises a plurality of azides. In some embodiments, the trifunctional linker comprises a plurality of alkynes.

In some embodiments, the trifunctional linker comprises an isocyanate, azide or alkyne. In some embodiments, the trifunctional linker comprises an azide or alkyne. In some embodiments, the trifunctional linker comprises an isocyanate. In some embodiments, the trifunctional linker comprises an azide. In some embodiments, the trifunctional linker comprises an alkyne.

In some embodiments, the trifunctional linker is an isocyanate, azide or alkyne. In some embodiments, the trifunctional linker is an azide or alkyne. In some embodiments, the trifunctional linker is an isocyanate. In some embodiments, the trifunctional linker is an azide. In some embodiments, the trifunctional linker is an alkyne.

In some embodiments, the cross-link comprises a urethane, triazole, or an ester. In some embodiments, the cross-link comprises a urethane or an ester. In some embodiments, the cross-link comprises a urethane. In some embodiments, the cross-link comprises a triazole. In some embodiments, the cross-link comprises an ester.

In some embodiments, the cross-link comprises three urethane linkages. In some embodiments, the cross-link comprises three ester linkages. In some embodiments, the cross-link comprises three triazole linkages.

In some embodiments, the linker is linked to three compounds of formula (II).

In some embodiments, the linker is linked to three compounds of formula (VI).

In some embodiments, the trifunctional linker comprises a tri-isocyante. In some embodiments, the trifunctional linker is a tri-isocyante. In some embodiments, the tri-isocyante is triphenylmethane-4,4',4"-triisocyanate, 1,3,5-cyclohexane triisocyanate, or 1,3,5-benzene triisocyanate.

In some embodiments, the cross-linker is linked to three polyacetals.

In some embodiments, the cross-link comprises an acetal. In some embodiments, the cross-link comprises three acetal linkages. In some embodiments, the cross-link forms acetal linkages to a plurality of compounds of formula (V).

In some embodiments, the linker forms acetal linkages to a plurality of compounds of formula (I). In some embodiments, the linker comprises a triol. In some embodiments, the linker is a triol.

In some embodiments, the cross-link comprises a triazole. In some embodiments, the cross-link comprises three triazoles.

In some embodiments, the compounds exhibit a hydrodynamic radius of about 4.5 nm to about 75 nm. In some embodiments, the hydrodynamic radius is about 4.4 nm. In some embodiments, the hydrodynamic radius is about 75 nm.

In some embodiments, the compound has a lower critical solution temperature (LCST) from about 6° C. to about 80° C. In some embodiments, the LCST is from about 6° C. to about 70° C. In some embodiments, the LCST is from about 12° C. to about 70° C. In some embodiments, the LCST is from about 12° C. to about 38° C. In some embodiments, the LCST is from about 25° C. to about 50° C. In some embodiments, the LCST is from about 25° C. to about 45° C. In some embodiments, the LCST is from about 26° C. to about 43° C. In some embodiments, the LCST is from about 31° C. to about 43° C. In some embodiments, the LCST is from about 37° C. to about 43° C.

In some embodiments, the $m_{(av)}$ is from about 0.5 to about 2.5. In some embodiments, the $m_{(av)}$ is from about 1.5 to about 2.5.

In some embodiments, the lower critical solution temperature transition occurs over a range of about 3-9° C. In some embodiments, the lower critical solution temperature transition occurs over a range of about 3-5° C. In some embodiments, the lower critical solution temperature transition occurs over a range of about 3-4° C. In some embodiments, the lower critical solution temperature transition occurs over a range of about 3° C. In some embodiments, the lower critical solution temperature transition occurs over a range of about 4° C. In some embodiments, the lower critical solution temperature transition occurs over a range of about 5° C.

In some embodiments, the transition temperature occurs over a range of about 3-9° C. In some embodiments, the transition temperature occurs over a range of about 3-5° C. In some embodiments, the transition temperature occurs over a range of about 3-4° C. In some embodiments, the transition temperature occurs over a range of about 3° C. In some embodiments, the transition temperature occurs over a range of about 4° C. In some embodiments, the transition temperature occurs over a range of about 5° C.

In some embodiments, the click functional macromonomers are poly-azide or poly-alkyne macromonomers. Poly-azide macromonomers can include any azide-terminated polymer. Exemplary poly-azide macromonomers include PEG-$N_3$, PMMA-$N_3$, NIPAM-$N_3$, PDMAEDA-$N_3$, PS-$N_3$, PEO-$N_3$, and PtBA-$N_3$. Other poly-azide macromonomers are disclosed, for example, in WO 10/053993. Poly-alkyne macromonomers can include any alkyne-terminated polymer. Exemplary alkyne-terminated macromonomers include PEG-alkyne, PMMA-alkyne, NIPAM-alkyne, PDMAEDA-alkyne, PS-alkyne, PEO-alkyne, and PtBA-alkyne.

Triblock copolymers may include any ABA-type polymer wherein the B-block is a polyacetal. Exemplary triblock copolymers include PEG-polyacetal-PEG, PMMA-polyacetal-PMMA, PEO-polyacetal-PEO, NIPAM-polyacetal-NIPAM, PDMAEDA-polyacetal-PDMAEDA.

In some embodiments, the polymer is PEG, PMMA, PEO, NIPAM, PDMAEDA, PS, or PtBA. In some embodiments, the polymer is PEG, PMMA, PEO, NIPAM, or PDMAEDA. In some embodiments, the polymer is PEG, PMMA, PEO, PDMAEDA, PS, or PtBA. In some embodiments, the polymer is PEG, PS, or PtBA.

In some embodiments, the therapeutic agent is a protein, peptide, drug, agricultural agent, small molecule therapeutic, or carbohydrate. In some embodiments, the therapeutic agent is a protein, peptide, drug, or carbohydrate. In some embodiments, the therapeutic agent is a protein. In some embodiments, the therapeutic agent is a peptide. In some embodiments, the therapeutic agent is a carbohydrate. In some embodiments, the therapeutic agent is a small molecule therapeutic. In some embodiments, the therapeutic agent is a drug. In some embodiments, the drug is an antitumor agent. In some embodiments, the drug is gemcitabine. In some embodiments, the drug is bisphenol A. In some embodiments, the drug is methylhydroquinone. In some embodiments, the drug is diethylstilbestrol. In some embodiments, the drug is paclitaxel. In some embodiments, the drug is doxorubicin. In some embodiments, the drug is everolimus. In some embodiments, the drug is pamidronate disodium. In some embodiments, the drug is nelarabine. In some embodiments, the drug is azacitidine. In some embodiments, the drug is bleomycin. In some embodiments, the drug is bortezomib. In some embodiments, the drug is capecitabine. In some embodiments, the drug is cytarabine. In some embodiments, the drug is daunorubicin hydrochloride. In some embodiments, the drug is decitabine. In some embodiments, the drug is docetaxel. In some embodiments, the drug is epirubicin. In some embodiments, the drug is etoposide. In some embodiments, the drug is raloxifene. In some embodiments, the drug is fulvestrant. In some embodiments, the drug is fludarabine. In some embodiments, the drug is goserelin. In some embodiments, the drug is topotecan. In some embodiments, the drug is idarubicin. In some embodiments, the drug is azaepothilone B. In some embodiments, the drug is lanreotide. In some embodiments, the drug is leuprolide. In some embodiments, the drug is mitoxantrone. In some embodiments, the drug is prednisone. In some embodiments, the drug is temsirolimus. In some embodiments, the drug is vinblastine. In some embodiments, the drug is vincristine. In some embodiments, the drug is zoledronic acid. In some embodiments, the therapeutic agent is an agricultural agent. In some embodiments, the agricultural agent is a pesticide. In some embodiments, the agricultural agent is a herbicide. In some embodiments, the agricultural agent is a fungicide. In some embodiments, the agricultural agent is an insecticide. In some embodiments, the agricultural agent is a nematode control agent. In some embodiments, the agricultural agent is a antihelminthic. In some embodiments, the agricultural agent is a nutrient. In some embodiments, the therapeutic agent is gemcitabine.

In some embodiments of formula (I), the therapeutic agent is a protein, peptide, drug, or carbohydrate. In some embodiments of formula (II), the therapeutic agent is a protein, peptide, drug, or carbohydrate. In some embodiments of formula (III), the therapeutic agent is a protein, peptide, drug, or carbohydrate. In some embodiments of formula (IV), the therapeutic agent is a protein, peptide, drug, or carbohydrate. In some embodiments of formula (V), the therapeutic agent is a protein, peptide, drug, or carbohydrate. In some embodiments of formula (VI), the therapeutic agent is a protein, peptide, drug, or carbohydrate. In some embodiments of formula (I), the therapeutic agent is gemcitabine. In some embodiments of formula (II), the therapeutic agent is gemcitabine. In some embodiments of formula (III), the therapeutic agent is gemcitabine. In some embodiments of formula (IV), the therapeutic agent is gemcitabine. In some embodiments of formula (V), the therapeutic agent is gemcitabine. In some embodiments of formula (VI), the therapeutic agent is gemcitabine.

In some embodiments, the polyacetal compounds (PAs) herein show a number of advantageous and unique properties and behaviors that distinguish them from existing temperature responsive or pH-degradable polymers. For example, polyacetals are produced by reactions complete within about 2 hours. The polyacetal compounds are also the first water-soluble polymers that are intrinsically both pH-degradable and temperature responsive, with LCSTs bracketing body temperature. LCST transitions are sharp; copolymers need not be prepared to introduce degradation sites. PAs studied herein show no hysteresis in their LCST behavior. LCSTs do not depend strongly on either salt or polymer concentration. LCSTs can be controlled and predicted over essentially all practical temperatures for aqueous solutions (e.g., 6-80° C.), by using a mixture of two different diol monomers. PAs have a degradation mechanism that produces neutral products, whereas many polymers degrade to produce acidic products that can cause inflammation. In addition, aqueous PA solutions are biocompatible.

Compounds of formula (I) are synthesized by methods within the purview of the ordinarily skilled artisan. Exemplary methods by which such derivatives can be synthesized are as follows, in addition to those described in, for example, Heller et al., U.S. Pat. No. 5,968,543; *J. Applied Polymer Sci.* 2011, 120, 3363. Additional exemplary methods of preparation for compounds of formula (I) are shown in Scheme A and the Examples.

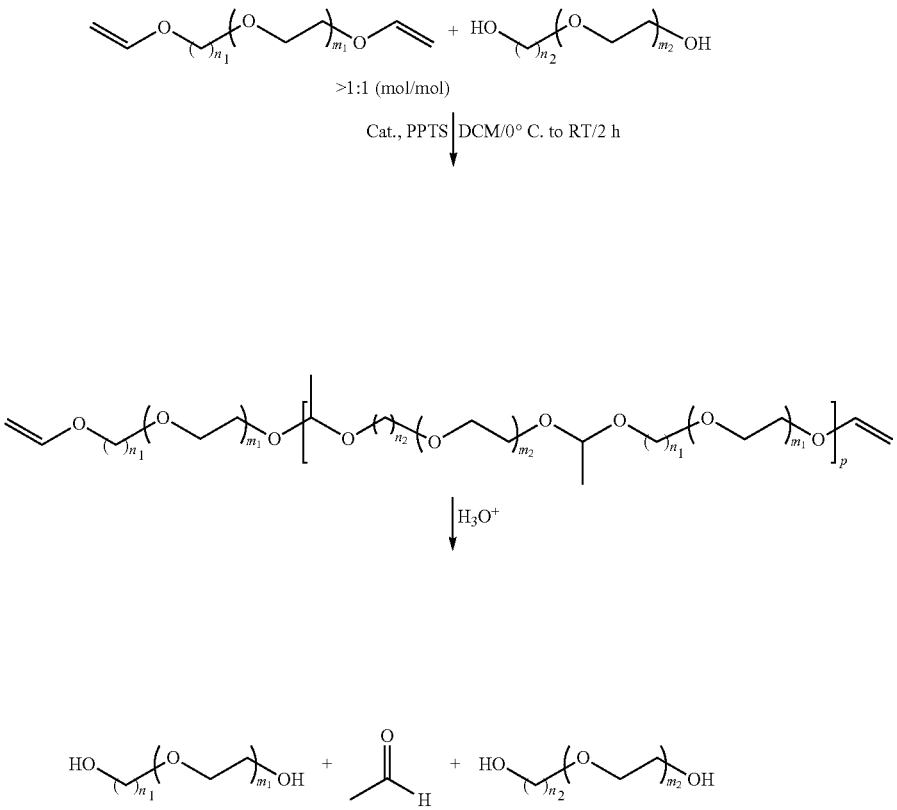

Scheme A. Exemplary Synthesis of Compounds of Formula I.

Initially, the diol and divinyl ether, which is in excess, are allowed to react for about 2 to 24 hours in the presence of an acid such as, for example, pyridinium p-toluenesulfonate in anhydrous dichloromethane. The reaction temperature is initially maintained by using an ice/water mixture for about 25 minutes and then at about room temperature for the remainder of the reaction.

Compounds of formula (II) are synthesized by methods within the purview of the ordinarily skilled artisan. Exemplary methods by which such derivatives can be synthesized are as follows, in addition to those described in, for example, Heller et al., U.S. Pat. No. 5,968,543; *J. Applied Polymer Sci.* 2011, 120, 3363. Additional exemplary methods of preparation for compounds of formula (II) are shown in Scheme B and the Examples.

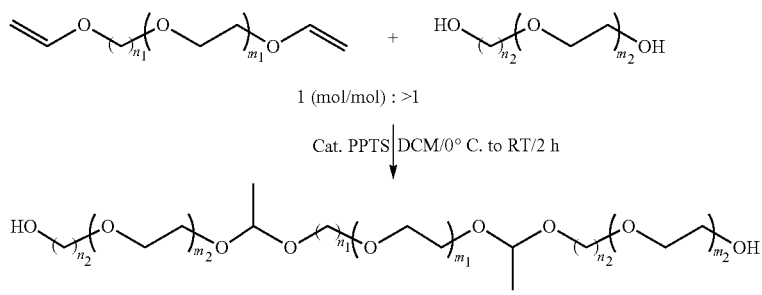

Initially, the divinyl ether and diol, which is in excess, are allowed to react for about 2 to 24 hours in the presence of an acid such as, for example, pyridinium p-toluenesulfonate in anhydrous dichloromethane. The reaction temperature is initially maintained by using an ice/water mixture for about 25 minutes and then at about room temperature for the remainder of the reaction.

Exemplary methods of preparation and degradation of polyacetals of Formula I and II are shown in Scheme C.

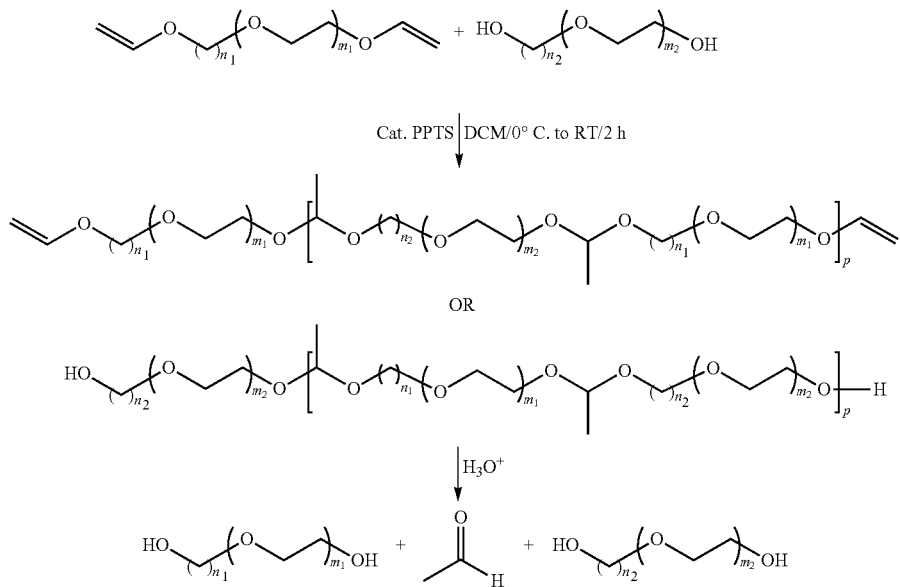

The polyacetal is formed by treatment of a diol and divinyl ether with an acid such as, for example, PPTs, in a solvent such as dichloromethane to provide a polyacetal. Treatment of the polyacetal with aqueous acid degrades the acetal to generate an aldehyde and the diol products as shown in Scheme C.

Additional exemplary methods of preparation for polyacetal compounds are shown in Scheme D and the Examples.

Scheme D. Exemplary Synthesis of Polyacetal Compounds.

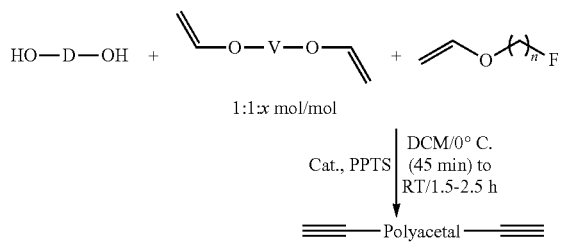

Initially, 1:1 (mol/mol) divinyl ether, diol, and different amount of monovinyl ether are allowed to react for about 2 to 3.5 hours in the presence of an acid catalyst such as, for example, pyridinium p-toluenesulfonate in anhydrous dichloromethane. The reaction temperature is initially maintained by using an ice/water mixture for about 45 minutes and then at about room temperature for the remainder of the reaction.

Additional exemplary methods of preparation and degradation for polyacetal compounds are shown in Scheme E and the Examples.

degrades the acetal to generate an aldehyde and the diol products as shown in Scheme E.

Homopolymers and Macromonomers. One extension is to provide main chain functionality in the polyacetals, that is, reactive sites in the polymer backbone for attachment of, e.g., therapeutic agents or any other functional moiety of interest. An exemplary base functional group for this purpose can be an alkyne, which permits grafting to the polymer backbone through azide-alkyne or thiol-ene click reactions. Alkyne main chain functionality can be incorporated by using an alkyne diol monomer. An azide modified moiety can be grafted onto the main chain by a click reaction to form a triazole. The triazole linkage is biocompatible and peptidomimetic, and an advantageous choice for biomedical applications. In addition, the incorporation of azide end groups onto a host of biologically relevant molecules and therapeutic agents is facile, permitting the grafting of a variety of molecules with disparate function. The alkyne-functional polyacetals exhibit temperature responsive behavior with appropriate LCSTs. Alkyne groups also permit grafting to the polymer backbone through thiol-ene click reactions. A thiol modified moiety can be grafted onto the main chain by a click reaction to form a thioether. Another exemplary base functional group that introduces a reactive site in the polymer backbone can be an alkene, which permits grafting to the polymer backbone through thiol-ene click reactions. Alkene main chain functionality can be incorporated by using an alkene diol monomer. A thiol modified moiety can be grafted onto the main chain by a click reaction to form a thioether.

Another extension is to prepare macromonomers with functional chain ends. The hydroxyl-terminated and vinyl ether-terminated macromonomers are described herein.

Scheme E. Exemplary Synthesis and Degradation of Polyacetal Compounds.

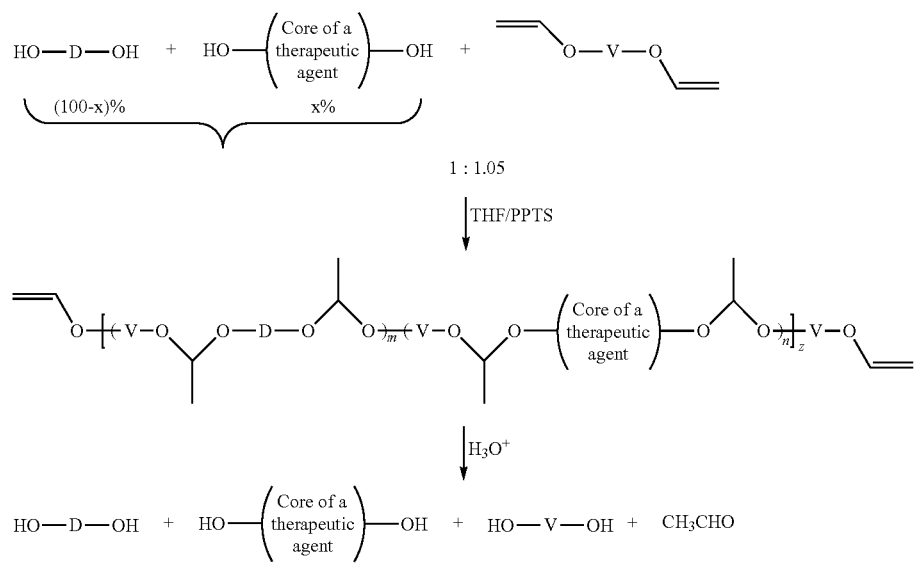

The polyacetal is formed by treatment of a 1:1.05 (mol/mol) total diol and divinyl ether mixture, using different amounts of two diol monomers, with an acid such as, for example, PPTs, in a solvent such as tetrahydrofuran to provide a polyacetal-based polymer conjugate. Treatment of the polyacetal-based polymer conjugate with aqueous acid While these macromonomers can serve as useful building blocks, it is not advantageous to end-link them by acetal linkages because the resultant structures will be compositionally scrambled due to trans-acetalization under the required reaction conditions.

End-functional Polyacetal Macromonomers. Chain end modification with alkyne and azide functionalities can produce versatile click-functional macromonomers. Such macromonomers can be used to produce block copolymers or gels via end-linking reactions with other click functional macromonomers or click functional crosslinkers, respectively.

Figure 3:
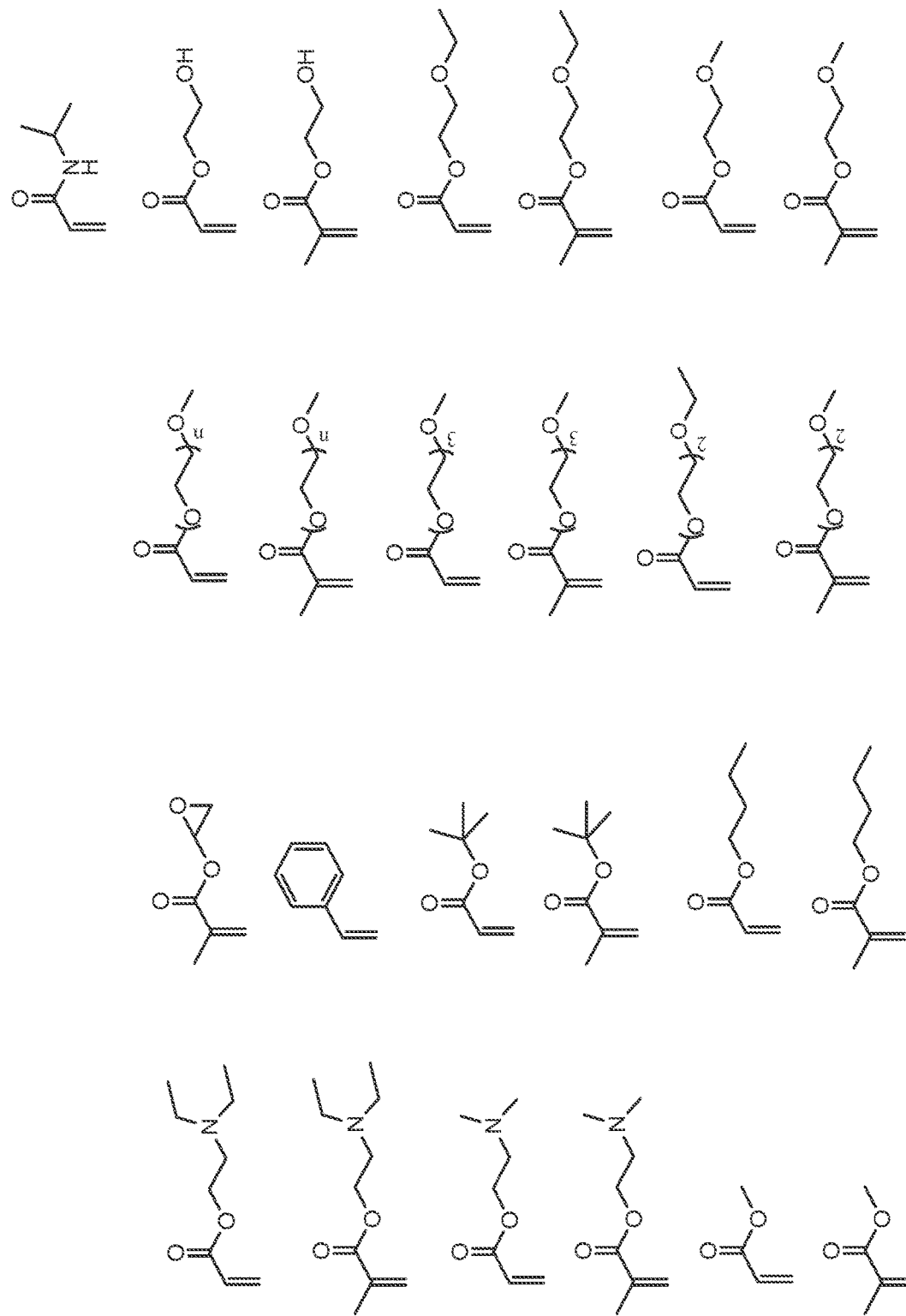
FIG. 3 shows exemplary atom transfer radical polymerization (ATRP) substrates.

Polyacetals as macroinitiators for the preparation of block copolymers by atom transfer radical polymerization (ATRP) (Matyjaszewski, K.; Xia, J. Fundamentals of Atom Transfer Radical Polymerization. In Handbook of Radical Polymerization, Matyjaszewski, K. T.; Davis, T. P., Eds. Wiley-Interscience: New York, 2002; pp 523-628). The chain ends are modified with, e.g., tertiary bromine chain ends that are initiators for ATRP. Since the number of monomers that can be polymerized by ATRP is vast, both in number and in nature, a diverse number of triblock copolymers with a central PA block can be prepared in this fashion. Representative exemplary substrates for ATRP are shown in FIG. 3.

Figure 4:
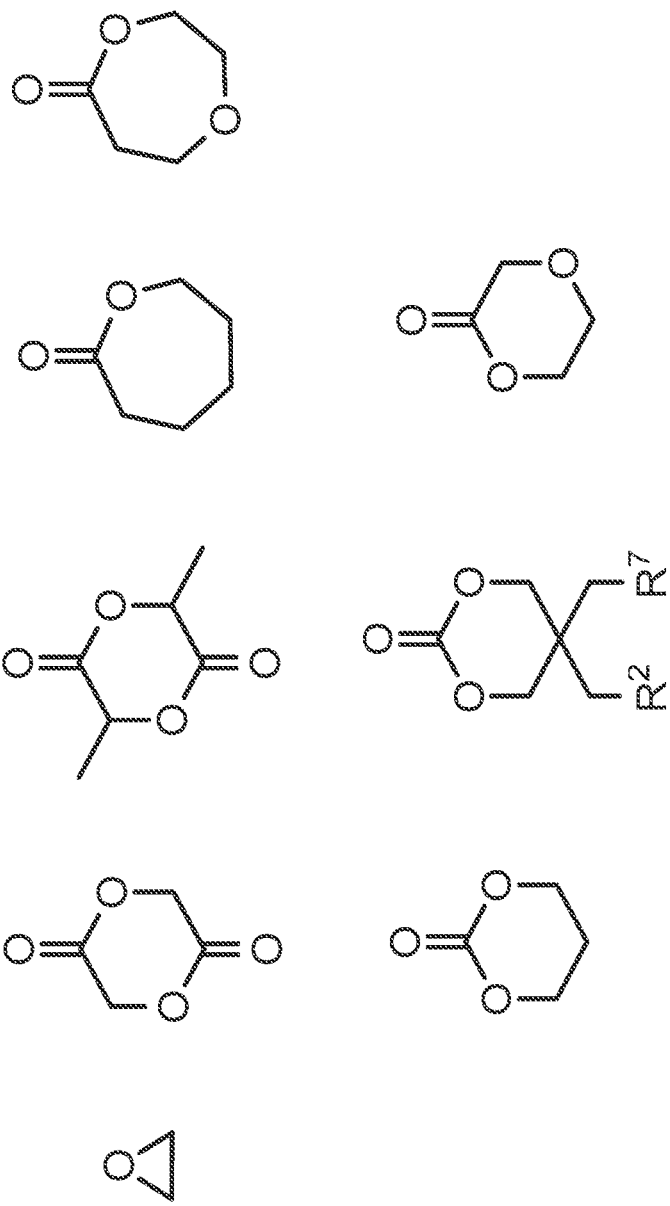
FIG. 4 shows exemplary ring opening polymerization (ROP) substrates.

Polyacetals as macroinitiators for the preparation of block copolymers by ring opening polymerization (ROP) (Albertsson, A.-C. Recent developments in ring opening polymerization of lactones for biomedical applications. *Biomacromolecules* 2003, 4, 1466-1486). ROP is advantageous for making a variety of block copolymers with a PA mid-block and a host of end blocks. Representative exemplary substrates for ROP are shown in FIG. 4.

The glass transition (Tg) behavior can be determined by DSC. Knowledge of the Tg is advantageous as it influences the degradation rate, which controls the therapeutic agent release rate in therapeutic agent delivery applications. The degradation behavior can be characterized as a function of pH by GPC measurements of MW changes. Each cleavage event in the backbone of one chain creates two new chains, effectively cutting the number average molecular weight in half. For a homopolymer, the number of scission events at time t, x(t), is related to the number average molecular weight before scission, $M_n^0$ and the number average weight at time t, $M_n(t)$, by $$x = \frac{2M_n^0}{M_n(t)} - 2 \qquad \text{Eq. 1}$$

Degradation rates can be correlated with the Tg and structural variables that describe the monomers hydrophobicity. For the latter purpose, log P values for the monomers can be using an HPLC method (Leo, A. et al., Partition coefficients and their uses. Chem. Rev. 1971, 71, 525-616; Valko, K. Application of High-Performance Liquid Chromatography Based Measurements of Lipophilicity to Model Biological Distribution. *J. Chromatogr. A* 2004, 1037, 299-310). Correlation of log P with degradation rates and Tg allows tuning of degradation and therapeutic agent release rates of PAs in therapeutic agent delivery applications.

Gels and Block Copolymers. PA homopolymers can also be incorporated into structured materials, e.g., therapeutic agent delivery vehicles. In particular, PAs can be incorporated into dual responsive (i.e., temperature and pH) therapeutic agent delivery vehicles such as micelles and hydrogels. The potential mechanism of therapeutic agent delivery for these two vehicles is similar. Delivery by direct injection can be used to treat a variety of medical conditions including, e.g., malignant tumors and stomach ulcers (Verna, E. C.; Dhar, V. Endoscopic Ultrasound-Guided Fine Needle Injection for Cancer Therapy: The Evolving Role of Therapeutic Endoscopic Ultrasound. *Therap. Adv. Gastroenterol.* 2008, 1, 103-109; Yan, B. M.; Van Dam, J. Endoscopic Ultrasound-Guided Intratumoural Therapy for Pancreatic Cancer. *Can. J. Gastroenterol.* 2008, 22, 405-410; Matthes, K. et al., EUS-Guided Injection of Paclitaxel (OncoGel) Provides Therapeutic Drug Concentrations in the Porcine Pancreas (with Video). *Gastrointest. Endosc.* 2007, 65, 448-453; Sun, S. et al., Endoscopic Ultrasound-Guided Interstitial Chemo-Therapy in the Pancreas: Results in a Canine Model. Endoscopy 2007, 39, 530-534). Once injected, the therapeutic agent delivery vehicles experience a temperature rise sufficient to cause them to fall out of solution and form insoluble aggregates. The acidic environment within the gut or a tumor causes the PA portion(s) of the vehicle to degrade, thereby releasing encapsulated or bound therapeutic agents. Because both therapeutic agent delivery vehicles are nanoscale, they can pass through the syringe used for direct tumor injection.

In some embodiments, the therapeutic agent delivery vehicle is administered to a subject in need thereof. For example, administration may occur to a subject having a tumor cell. In some embodiments, the subject is a rodent, dog, monkey or human. In some embodiments, the subject is a rodent. In some embodiments, the subject is a human.

In some embodiments of formula (I), the tumor cell is a pancreatic cancer cell. In some embodiments of formula (II), the tumor cell is a pancreatic cancer cell. In some embodiments of formula (III), the tumor cell is a pancreatic cancer cell. In some embodiments of formula (IV), the tumor cell is a pancreatic cancer cell. In some embodiments of formula (V), the tumor cell is a pancreatic cancer cell. In some embodiments of formula (VI), the tumor cell is a pancreatic cancer cell.

It will be recognized that one or more features of any embodiments disclosed herein may be combined and/or rearranged within the scope of the invention to produce further embodiments that are also within the scope of the invention. Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Example 1: Synthesis of Polyacetal for Kinetic Studies 1,4-butanediol divinyl ether and ethylene glycol, in a molar feed ratio of 1.027/1, are allowed to react in the presence of pyridinium p-toluenesulfonate in anhydrous dichloromethane. The initial bilayer is gone within 25-30 minutes. After about 2 to 3 hours, the reaction is complete. After a desired time, the solvent (DCM or THF) was removed by high vacuum pump (for 30 min). The resultant was extracted with ethyl acetate (EtOAc, 40 mL), washed three times with dilute aqueous solution of potassium carbonate (each time the aqueous part is saturated by adding excess sodium chloride, NaCl). The organic part was dried over anhydrous sodium sulfate ($Na_2SO_4$), and passed through a short basic-$Al_2O_3$ column. The polymer was isolated after removing the solvent first by rotary and then by high vacuum pump at room temperature for 48 hrs. In case of preparing end-functional polyacetals, the isolated polymer was washed with n-hexane to remove any unreacted monovinyl ether compound and then dried under vacuum.

Example 2: Synthesis of Polyacetal P0a 1,4-butanediol divinyl ether and ethylene glycol and, in a molar feed ratio of 1.034/1, are allowed to react in the presence of pyridinium p-toluenesulfonate in anhydrous dichloromethane for 2 to 3 hours to yield polyacetal P0a.

Example 3: Synthesis of Polyacetal P0b 1,4-butanediol divinyl ether and ethylene glycol and, in a molar feed ratio of 1/1.083, are allowed to react in the presence of pyridinium p-toluenesulfonate in anhydrous dichloromethane for 2 to 3 hours to yield polyacetals P0b.

Example 4: Synthesis of Polyacetal P0c

Ethylene glycol and 1,4-butanediol divinyl ether, in a molar feed ratio of 1.18/1, are allowed to react in the presence of pyridinium p-toluenesulfonate in anhydrous dichloromethane for 2 to 3 hours to yield polyacetal P0c.

Example 5: Synthesis of Polyacetal P1a 1,4-butanediol divinyl ether and diethylene glycol, in a molar feed ratio of 1.04/1, are allowed to react in the presence of pyridinium p-toluenesulfonate in anhydrous dichloromethane for 2 to 3 hours to yield polyacetal P1a.

Example 6: Synthesis of Polyacetal P2a 1,4-butanediol divinyl ether and triethylene glycol, in a molar feed ratio of 1.04/1, are allowed to react in the presence of pyridinium p-toluenesulfonate in anhydrous dichloromethane for 2 to 3 hours to yield polyacetal P2a.

Example 7: Synthesis of Polyacetal P3a 1,4-butanediol divinyl ether and tetraethylene glycol, in a molar feed ratio of 1/1.04, are allowed to react in the presence of pyridinium p-toluenesulfonate in anhydrous dichloromethane for 2 to 3 hours to yield polyacetal P3a.

Example 8: Synthesis of Polyacetal P0.5a 1,4-butanediol divinyl ether, ethylene glycol, and diethylene glycol, in a molar feed ratio of 1.04/0.5/0.5, are allowed to react in the presence of pyridinium p-toluenesulfonate in anhydrous dichloromethane for 2 to 3 hours to yield polyacetal P0.5a.

Example 9: Synthesis of Polyacetal P1.5a 1,4-butanediol divinyl ether, diethylene glycol, and triethylene glycol, in a molar feed ratio of 1.04/0.5/0.5, are allowed to react in the presence of pyridinium p-toluenesulfonate in anhydrous dichloromethane for 2 to 3 hours to yield polyacetal P1.5a.

Example 10: Synthesis of Polyacetal P2.5a 1,4-butanediol divinyl ether, triethylene glycol, and tetraethylene glycol, in a molar feed ratio of 1.04/0.5/0.5, are allowed to react in the presence of pyridinium p-toluenesulfonate in anhydrous dichloromethane for 2 to 3 hours to yield polyacetal P2.5a.

Example 11: Synthesis of Polyacetal P0-2Va

Di(ethylene glycol) divinyl ether and ethylene glycol, in a molar feed ratio of 1.05/1, are allowed to react in the presence of pyridinium p-toluenesulfonate in anhydrous dichloromethane for 2 to 3 hours to yield polyacetal P0-2Va.

Example 12: Synthesis of Polyacetal P0-3Va

Tri(ethylene glycol) divinyl ether and ethylene glycol, in a molar feed ratio of 1.05/1, are allowed to react in the presence of pyridinium p-toluenesulfonate in anhydrous dichloromethane for 2 to 3 hours to yield polyacetal P0-3Va.

Example 13: Synthesis of Polyacetal P1-2Va

Di(ethylene glycol) divinyl ether and diethylene glycol, in a molar feed ratio of 1.05/1, are allowed to react in the presence of pyridinium p-toluenesulfonate in anhydrous dichloromethane for 2 to 3 hours to yield polyacetal P1-2Va.

Example 14: Synthesis of Polyacetal P1-3Va

Tri(ethylene glycol) divinyl ether and diethylene glycol, in a molar feed ratio of 1.05/1, are allowed to react in the presence of pyridinium p-toluenesulfonate in anhydrous dichloromethane for 2 to 3 hours to yield polyacetal P1-3Va.

Example 15: Synthesis of Polyacetal P2-2Va

Di(ethylene glycol) divinyl ether and triethylene glycol, in a molar feed ratio of 1.05/1, are allowed to react in the presence of pyridinium p-toluenesulfonate in anhydrous dichloromethane for 2 to 3 hours to yield polyacetal P2-2Va.

Example 16: Synthesis of Polyacetal P2-3Va

Tri(ethylene glycol) divinyl ether and triethylene glycol, in a molar feed ratio of 1.05/1, are allowed to react in the presence of pyridinium p-toluenesulfonate in anhydrous dichloromethane for 2 to 3 hours to yield polyacetal P2-3Va.

Example 17: Synthesis of Polyacetal P3-2Va

Di(ethylene glycol) divinyl ether and tetraethylene glycol, in a molar feed ratio of 1.05/1, are allowed to react in the presence of pyridinium p-toluenesulfonate in anhydrous dichloromethane for 2 to 3 hours to yield polyacetal P3-2Va.

Example 18: Synthesis of Polyacetal P3-3Va

Tri(ethylene glycol) divinyl ether and tetraethylene glycol, in a molar feed ratio of 1.05/1, are allowed to react in the presence of pyridinium p-toluenesulfonate in anhydrous dichloromethane for 2 to 3 hours to yield polyacetal P3-3Va.

Example 19: Synthesis of Polyacetal P2b 1,4-butanediol divinyl ether and triethylene glycol, in a molar feed ratio of 1.09/1, are allowed to react in the presence of pyridinium p-toluenesulfonate in anhydrous dichloromethane for 2 to 3 hours to yield polyacetal P2b.

Example 20: Synthesis of Polyacetal P2c 1,4-butanediol divinyl ether and triethylene glycol, in a molar feed ratio of 1.19/1, are allowed to react in the presence of pyridinium p-toluenesulfonate in anhydrous dichloromethane for 2 to 3 hours to yield polyacetal P2c.

Example 21: Synthesis of Polyacetal P2d 1,4-butanediol divinyl ether and triethylene glycol, in a molar feed ratio of 1.49/1, are allowed to react in the presence of pyridinium p-toluenesulfonate in anhydrous dichloromethane for 2 to 3 hours to yield polyacetal P2d.

Example 22: Synthesis of Polyacetal P'2a 1,4-butanediol divinyl ether and triethylene glycol, in a molar feed ratio of 1/1.06, are allowed to react in the presence of pyridinium p-toluenesulfonate in anhydrous dichloromethane for 2 to 3 hours to yield polyacetal P'2a.

Example 23: Synthesis of Polyacetal P'2b 1,4-butanediol divinyl ether and triethylene glycol, in a molar feed ratio of 1/1.11, are allowed to react in the presence of pyridinium p-toluenesulfonate in anhydrous dichloromethane for 2 to 3 hours to yield polyacetal P'2b.

Example 24: Synthesis of Polyacetal P'2c 1,4-butanediol divinyl ether and triethylene glycol, in a molar feed ratio of 1/1.21, are allowed to react in the presence of pyridinium p-toluenesulfonate in anhydrous dichloromethane for 2 to 3 hours to yield polyacetal P'2c.

Example 25: Synthesis of Polyacetal P'2d 1,4-butanediol divinyl ether and triethylene glycol, in a molar feed ratio of 1/1.515, are allowed to react in the presence of pyridinium p-toluenesulfonate in anhydrous dichloromethane for 2 to 3 hours to yield polyacetal P'2d.

Example 26: Analysis and Evaluation of Polyacetals

Figure 2B:
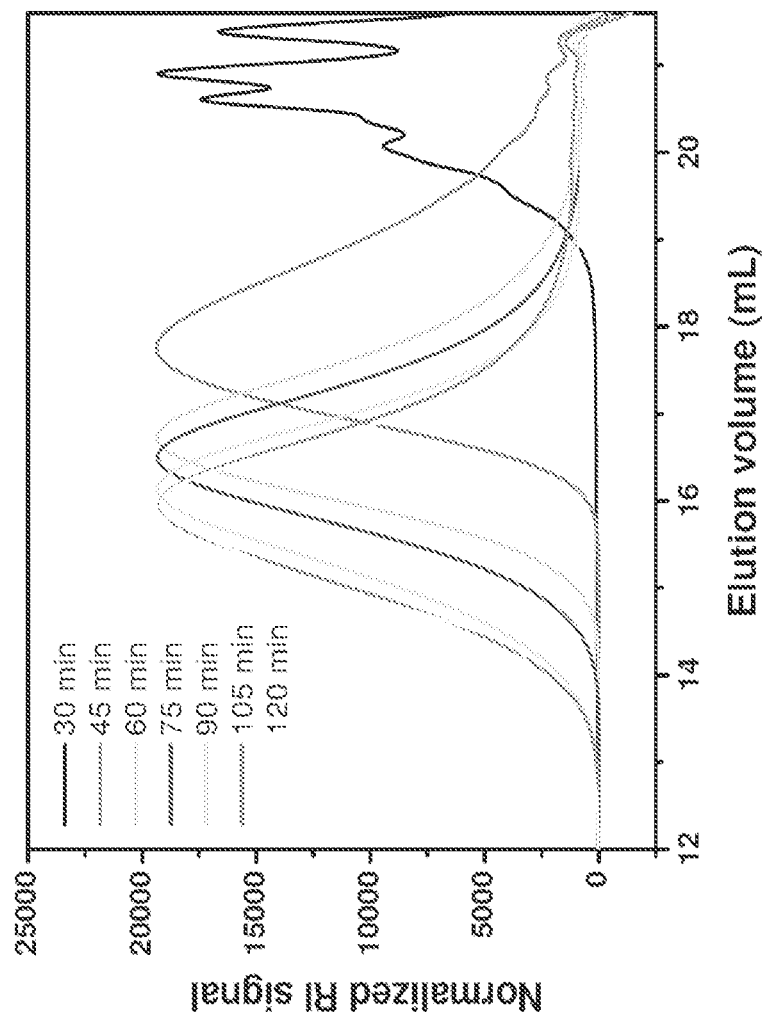
Figure 2C:
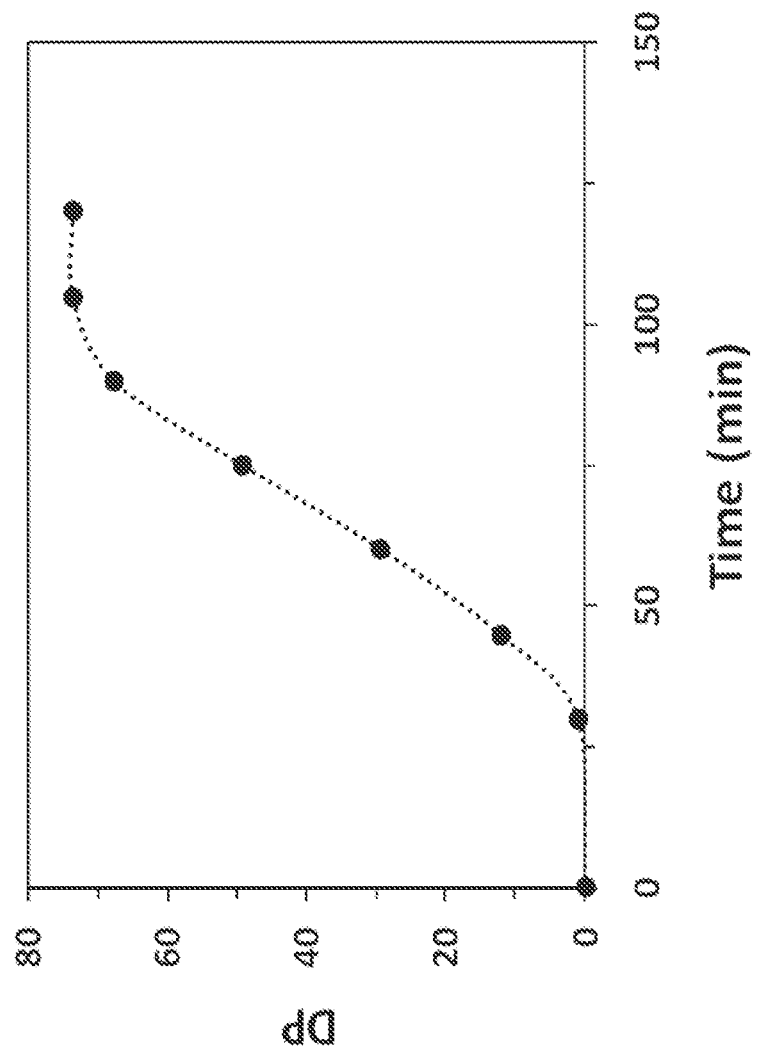

To evaluate the reaction speed, polymerization kinetics were studied for stoichiometric imbalance, $M_{DVE}/M_0 = 1.027/1$ (mol/mol), by using Gel Permeation Chromatography (GPC). The clean sweep in GPC traces (FIG. 2B) indicates the progress of polymerization reaction over time. The initial bilayer ($M_0$ is immiscible with DCM) is gone within 25-30 min indicating the starting point of the polymerization reaction. With the exception of the GPC signal at 30 min (point of clearance), where the overall GPC signal is broad and includes multiple sharp peaks that correspond to dimers and different trimers, the other GPC signals contain only one broad peak with PDI values close to 2, which is characteristic of a step growth polymerization reaction. The polymerization reaction was complete by 2h (FIG. 2C) with 100% conversion. The theoretical molecular weight can be calculated by the following equation assuming 100% conversion (Eq. 2):

Degree of polymerization (DP)(1+r)/(1−r),
where $r=[M_0]/[M_{DVE}]$    (Eq. 2)

The same experiment is repeated using different monomer feed ratios to prepare polyacetals P0a, P0b and $M_D$ (Table 1, entries 1, 2 and 3), respectively.

TABLE 1

Abbreviation of different polyacetals, initial monomers and feed ratio and LCSTs (water, 5 g/L).

| Entry | Polymer | Initial feed ratio (mmol) | LCST (° C.) |
|---|---|---|---|
| 1 | P0a | $M_{DVE}/M_0 = 1.034/1$ | 6.2 |
| 2 | P0b | $M_{DVE}/M_0 = 1.083/1$ | <6.2 |
| 3 | P0c | $M_{DVE}/M_0 = 1.18/1$ | <6.2 |
| 4 | P0.5a | $M_{DVE}/M_0/M_1 = 1.04/0.5/0.5$ | 12.8 |
| 5 | P1a | $M_{DVE}/M_1 = 1.04/1$ | 18.8 |
| 6 | P1.5a | $M_{DVE}/M_1/M_2 = 1.04/0.5/0.5$ | 26.4 |
| 7 | P2a | $M_{DVE}/M_2 = 1.04/1$ | 31.6 |
| 8 | P2b | $M_{DVE}/M_2 = 1.09/1$ | 30.7 |
| 9 | P2c | $M_{DVE}/M_2 = 1.19/1$ | 26 |
| 10 | P2d | $M_{DVE}/M_2 = 1.48/1$ | 17.5 |
| 11 | P2.5a | $M_{DVE}/M_2/M_3 = 1.04/0.5/0.5$ | 37.5 |
| 12 | P3a | $M_{DVE}/M_3 = 1.04/1$ | 42.6 |
| 13 | P0-2Va | $M_{2DVE}/M_0 = 1.05/1$ | 56.3 |
| 14 | P0-3Va | $M_{3DVE}/M_0 = 1.05/1$ | 66.2 |
| 15 | P1-2Va | $M_{2DVE}/M_1 = 1.05/1$ | 66.6 |
| 16 | P1-3Va | $M_{3DVE}/M_1 = 1.05/1$ | 73 |
| 17 | P2-2Va | $M_{2DVE}/M_2 = 1.05/1$ | 72 |
| 18 | P2-3Va | $M_{3DVE}/M_2 = 1.05/1$ | 76.1 |
| 19 | P3-2Va | $M_{2DVE}/M_3 = 1.05/1$ | 75.3 |
| 20 | P3-3Va | $M_{3DVE}/M_3 = 1.05/1$ | 78.6 |
| 21 | P'2a | $M_{DVE}/M_2 = 1/1.06$ | 40 |
| 22 | P'2b | $M_{DVE}/M_2 = 1/1.11$ | 43 |
| 23 | P'2c | $M_{DVE}/M_2 = 1/1.21$ | 50 |
| 24 | P'2d | $M_{DVE}/M_2 = 1/1.515$ | 66 |

Figure 5:
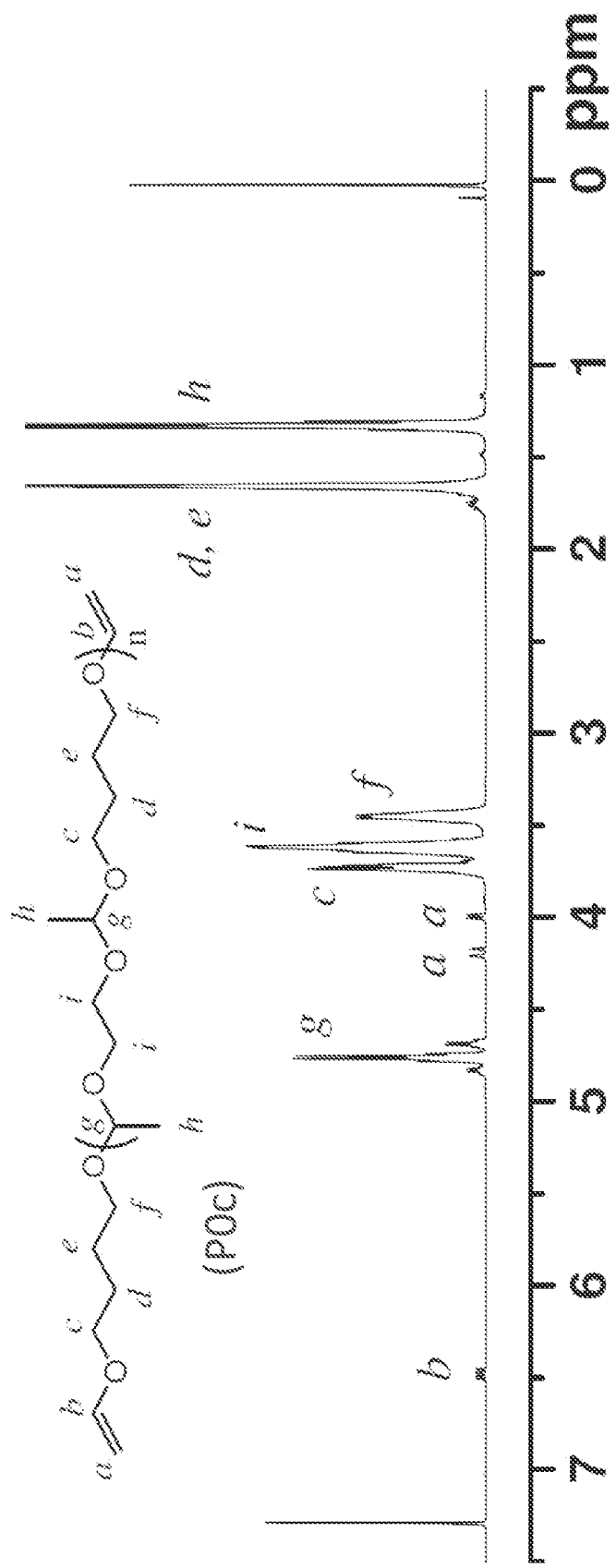
FIG. 5 shows a proton NMR spectrum of polymer P0c in $CDCl_3$.

In order to construct a polymer-therapeutic agent conjugate as a soluble polymeric therapeutic agent carrier, there should advantageously be suitable functional group(s) within the polymer chain. Polyacetals prepared by condensation polymerization have free functional groups at the chain terminals if the monomers are taken in stoichiometric imbalance. A representative example is polyacetal P0c (Table 1, entry 3), which is characterized by $^1$H NMR (FIG. 5) and confirms the presence of free vinyl ether terminal groups. The presence of the terminal free functionalities makes the polyacetals suitable for subsequent therapeutic agent conjugation.

All of the P0-category polyacetals (Table 1, entries 1, 2 and 3) are thermoresponsive, but differ in their LCST. The LCST for P0a (water, ~5 g/L) is 6.2° C. but the LCSTs for P0b and P0c are even less and are difficult to measure. Nonetheless, the thermo-responsiveness arising from P0-category polyacetals, which contain only acetal functionality, suggests that the "acetal" group itself is temperature sensitive.

Figure 6A:
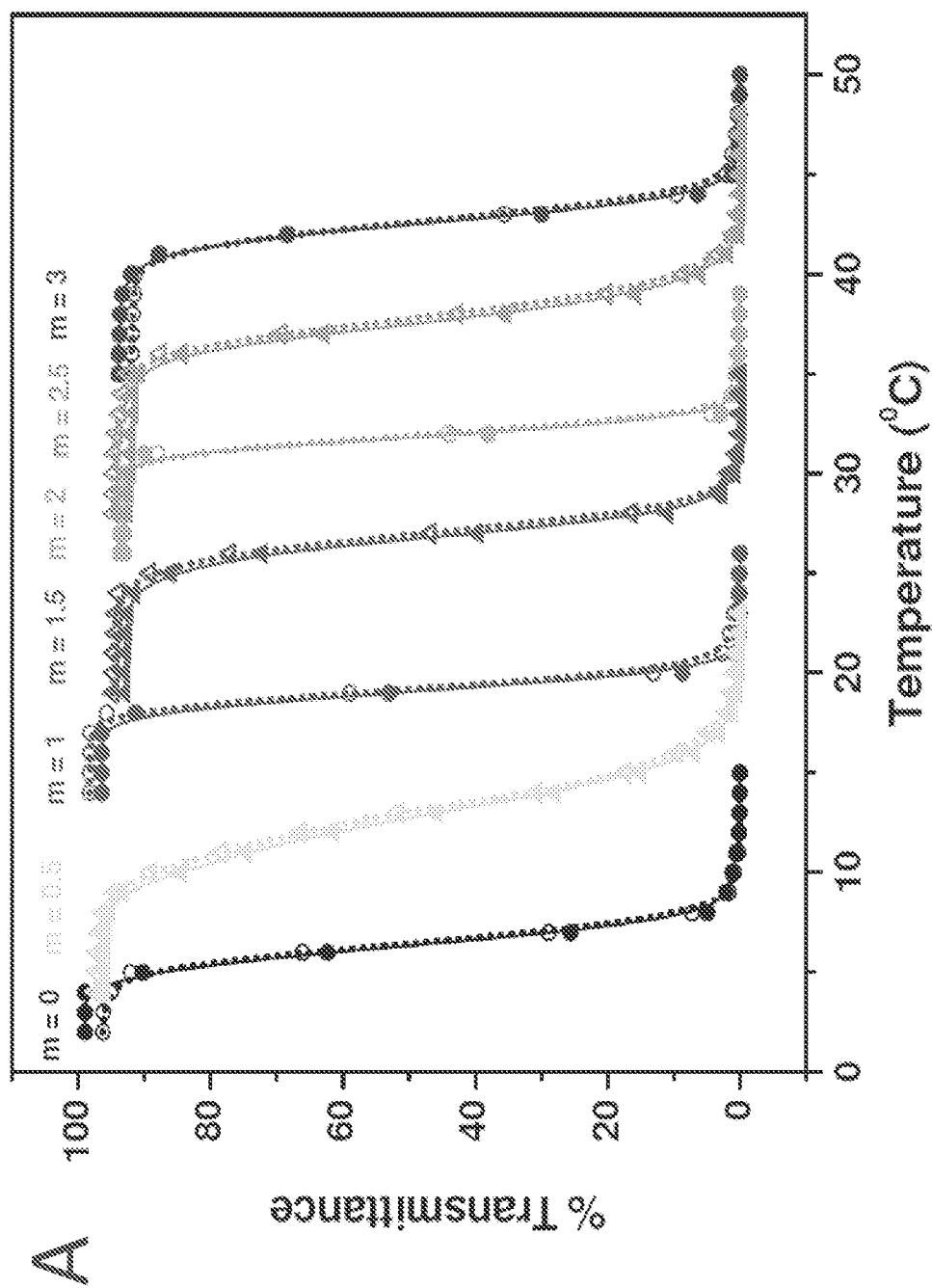
FIGS. 6A-C show (FIG. 6A) plot of the percent transmittance versus temperature for polymers P0a, P0.5a, P1a, P1.5a, P2a, P2.5a, P3a (shown from left to right, with heating shown in solid circle and solid line, cooling shown in empty circle and dotted line)
Figure 6B:
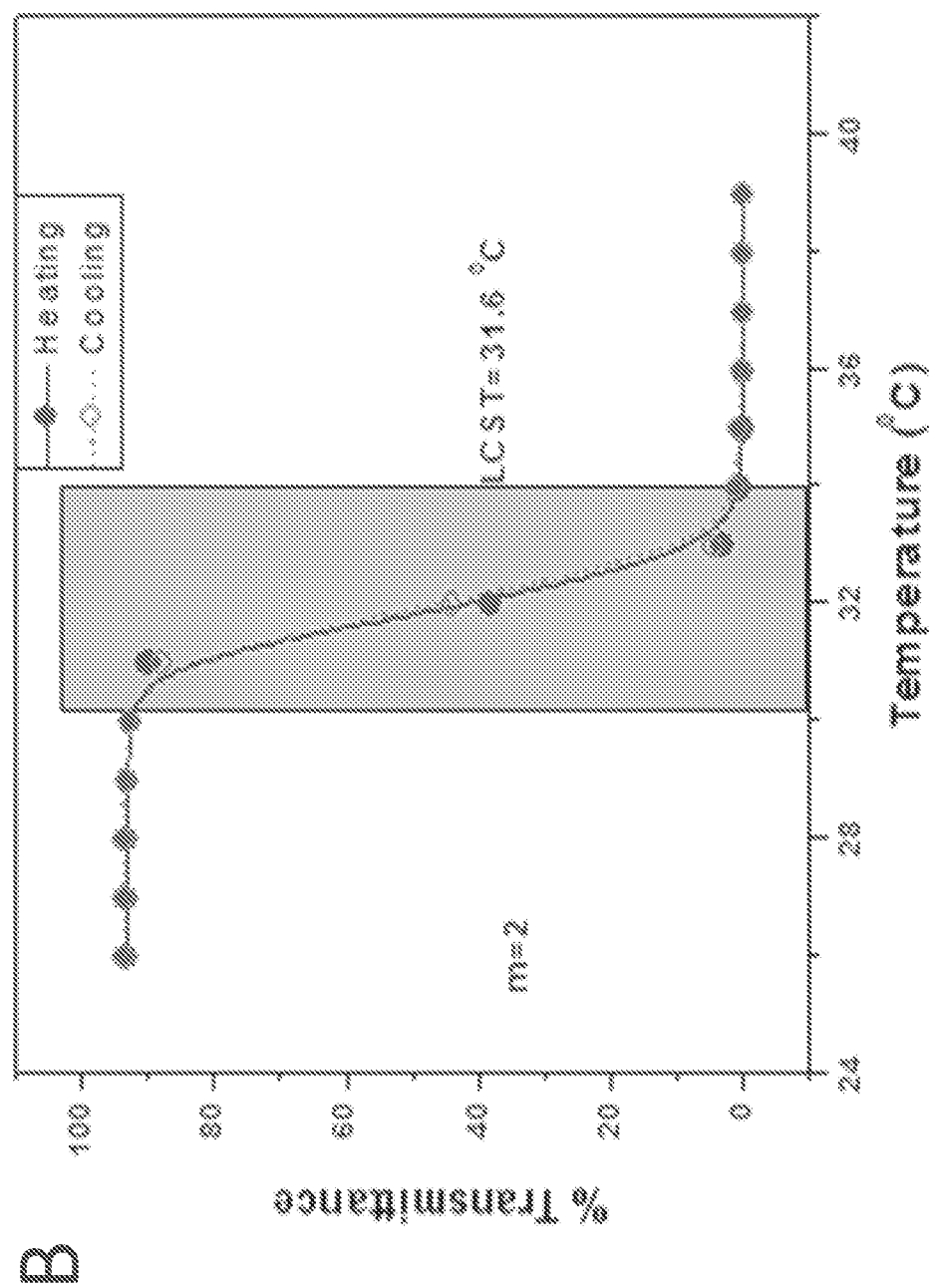
Figure 6C:
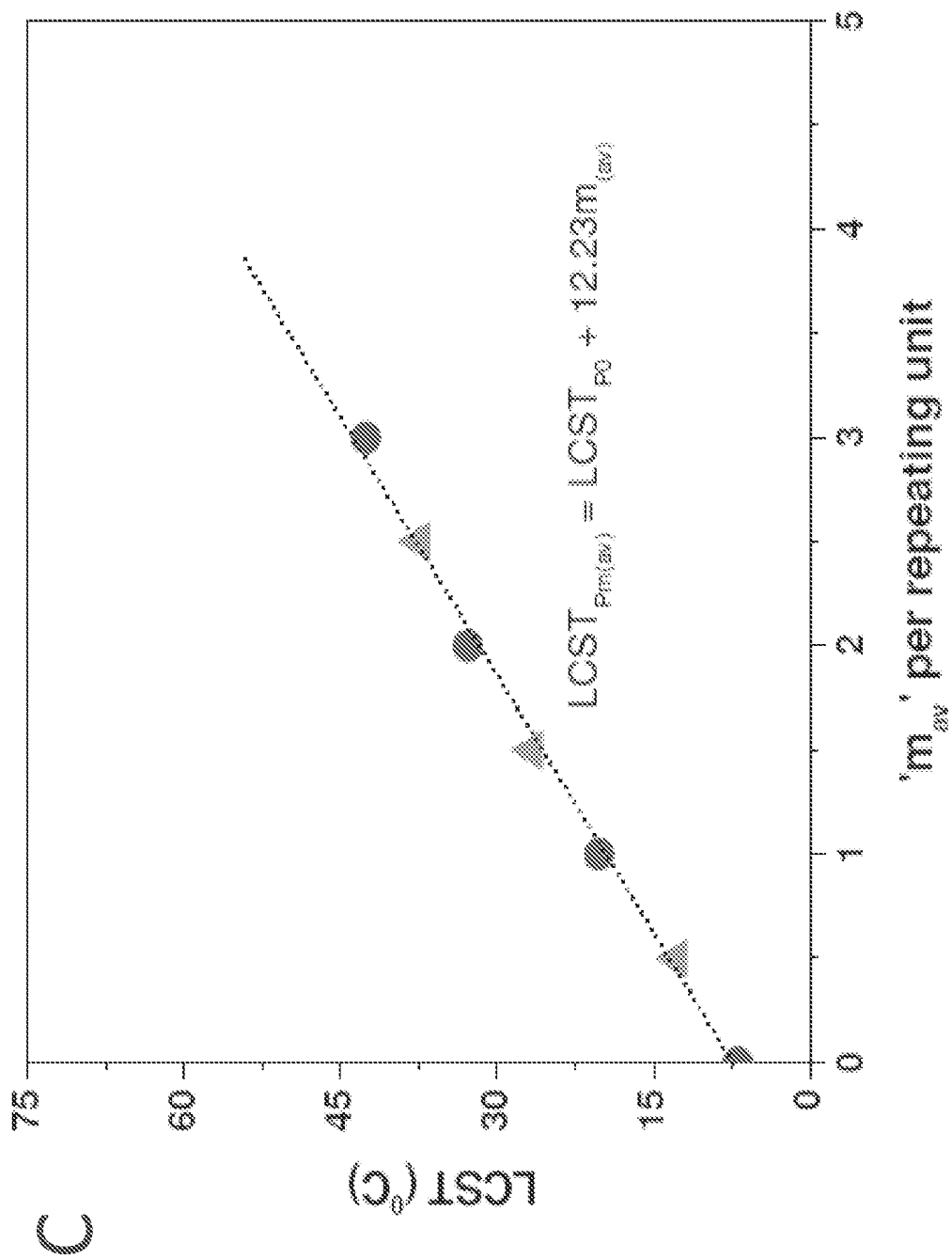

Although polymers with low LCSTs could be applied in thermo-labile protein purification (Hoshino, K.; Taniguchi, M.; Kitao, T.; Morohashi, S.; Sasakura, T. Biotechnol. Bioeng. 1998, 60, 568-579), the low LCSTs prohibit their use in in vivo applications. If the polyacetals are to be used in in in vivo applications, such as hyperthermia treatment, the LCST should range from about body temperature to 42° C. (Meyer, D. E.; Shin, B. C.; Kong, G. A.; Dewhirst, M. W.; Chilkoti, A. J. Control. Rel. 2001, 74, 213-224). To determine whether variation of hydrophilicity within the diol or divinyl ether portion affected the LCST of the resultant polyacetal, different linear diols containing a increasing number of repeating ethylene oxide units (m) were used. Diethylene glycol ($M_1$, m=1), triethylene glycol ($M_2$, m=2) and tetraethylene glycol ($M_3$, m=3) were each condensed with $M_{DVE}$ to prepare P1a, P2a and P3a polyacetals (Table 1, entries 5, 7 and 12), respectively. Such a study offers a simple platform for better understanding the effects of 'm' on the LCSTs of polyacetals (which is important to evaluate the reason behind the absence of any thermosensitivity in the previously reported polyacetals that were prepared from PEG) (Paramonov, S. E.; Bachelder, E. M.; Beaudette, T. T.; Standley, S. M.; Lee, C. C.; Dashe, J.; Frechet, J. M. J. Bioconjugate Chem. 2008, 19, 911-919; Tomlinson, R.; Heller, J.; Brocchini, S.; Duncan, R. Bioconjugate Chem. 2003, 14, 1096-1106; Tomlinson, R.; Klee, M.; Garrett, S.; Heller, J.; Duncan, R.; Brocchini, S. Macromolecules 2002, 35, 473-480; Rickerby, J.; Prabhakar, R.; Ali, M.; Knowles, J.; Brocchini, S. J. Mater. Chem. 2005, 15, 1849-1856; Wang, Y.; Morinaga, H.; Sudo, A.; Endo, T. J. Polym. Sci., Part A: Polym. Chem. 2011, 49, 596-602). The LCST (water, 5 g·L$^{-1}$) values were found to increase systematically with an increasing number of 'm', indicating the dependency of LCST on the hydrophilicity of the respective monomers. The temperature induced phase transitions for all polyacetals were found to be sharp (FIG. 6A) and reversible (a representative example is shown in FIG. 6B), similar to PEGylated polymers (Lutz, J. F.; Hoth, A. Macromolecules 2006, 39, 893-896; Lutz, J. F.; Akdemir, O.; Hoth, A. J. Am. Chem. Soc. 2006, 128, 13046-13047; Lutz, J. F.; Weichenhan, K.; Akdemir, O.; Hoth, A. Macromolecules 2007, 40, 2503-2508; Lutz, J. F. J. Polym. Sci., Part A: Polym. Chem. 2008, 46, 3459-3470). This is in contrast to pNIPAM, where a broad hysteresis was found as a result of an irreversible coil-to-globule transition involving four distinct thermodynamically stable states (Lutz, J. F.; Akdemir, O.; Hoth, A. J. Am. Chem. Soc. 2006, 128, 13046-13047; Wang, X.; Qiu, X.; Wu, C. Macromolecules 1998, 31, 2972-2976). The LCST of P3a (42.6° C.) is close to the temperature that is usually used for local hyperthermia (42° C.) (Meyer, D. E.; Shin, B. C.; Kong, G. A.; Dewhirst, M. W.; Chilkoti, A. J. Control. Rel. 2001, 74, 213-224) whereas the LCST of P2a (31.6° C.) is close to that of pNIPAM (32° C.) (Lutz, J. F.; Akdemir, O.; Hoth, A. J. Am. Chem. Soc. 2006, 128, 13046-13047). Furthermore, the temperature induced phase transitions (heating & cooling) occur within a narrower temperature range (about 5° C.) (marked in FIG. 6B) than that of pNIPAM (about 8° C.) (Lutz, J. F.; Akdemir, O.; Hoth, A. J. Am. Chem. Soc. 2006, 128, 13046-13047). Moreover, a mathematical relationship between the observed LCSTs and 'm' values is found to be a linear function of 'm' with a slope of around 12 (FIG. 6C). LCSTs can be determined, within the studied range, of analogous polyacetals from the following equation (Eq. 3):

$$LCST_{Pm}=LCST_{P0}+12.23m \qquad (Eq. 3)$$

In equation (3), '$LCST_{Pm}$' refers to the LCST of polyacetal, $P_m$, which is prepared from $M_{DVE}$ and a diol having 'm' number of ethylene oxide units. '$LCST_{P0}$' is the LCST of P0-category polyacetals.

A similar correlation was previously observed by Lutz et al. for poly[2-(2'-methoxyethoxy)ethyl methacrylate-co-oligo(ethylene glycol) methacrylate)] [P(MEO2MA-co-OEGMA)] copolymers (Lutz, J. F.; Hoth, A. Macromolecules 2006, 39, 893-896). Based on the above equation, the number of ethylene oxide units (m) in the diol plays a role in determining the LCSTs of the respective polyacetals. Thus, LCST of polyacetals can be tuned by adjusting the 'm' value in the diol portion. To this end, three additional polyacetals, P0.5a, P1.5a and P2.5a (Table 1, entry 4, 6 and 11) were prepared by reacting $M_{DVE}$ with 1:1 (mol/mol) $M_0/M_1$, $M_1/M_2$, and $M_2/M_3$, respectively. By using the mixed diols $M_0/M_1$, $M_1/M_2$, and $M_2/M_3$, the average 'm' value can be controlled in the repeating unit to be 0.5, 1.5 and 2.5, respectively. The thermal profiles (FIG. 6A) of each of the polyacetals P0.5a, P1.5a and P2.5a were found to be in between the thermal profiles of the two separate polyacetals that are individually made from the two corresponding diols. That is, the thermal profile of polyacetal P0.5a is in between that of polyacetals P0a and P1a, the thermal profile of polyacetal P1.5a is in between that of polyacetals P1a and P2a, and the thermal profile of polyacetal P2.5a is in between that of polyacetals P2a and P3a. Moreover, the observed LCST values for P0.5a, P1.5a and P2.5a (12.8, 26.7 and 37.5° C., respectively) almost coincide with the LCST values (13, 25.2, and 37.5° C., respectively) calculated from the above equation (Eq. 3) and fit well with linearity (FIG. 6C). Thus, it is not just the 'm' value of the diol, but rather the average 'm' value in the repeating units that controls the LCST of the polyacetal. Equation (3) is thus modified as follows (Eq. 4):

$$LCST_{Pm(av)}=LCST_{P0}+12.23m_{(av)} \qquad (Eq. 4)$$

In equation (4), '$m_{(av)}$' is the average number of ethylene oxide units in the repeating unit of polyacetal, $Pm_{(av)}$, and '$LCST_{Pm(av)}$' refers to the LCST of $Pm_{(av)}$.

Modification of the equation shows that adjustment of $m_{(av)}$ can be achieved in a number of different ways. For example, $m_{(av)}$ can be modified through the choice of: (i) diols (with fixed divinyl ether), (ii) divinyl ethers (with fixed diol), (iii) mixed diols (with fixed divinyl ether), (iv) mixed divinyl ethers (with fixed diol), or (v) a combination of mixed diols and mixed divinyl ethers. FIG. 6C shows how the LCST varies with the average number of ethylene oxide repeats in the diol, $m_{2,av}$. The circles denote polymers prepared using a single diol, while the triangles denote polymers prepared from a mixture of diols (i.e., $m_2$=1.5 refers to a polymer prepared from a 50:50 mixture of $m_2$=1.0 and $m_2$=2.0 diols). LCST is controlled, with a range that nicely brackets body temperature. A series of polyacetals (Table 1, entries 13-20) were prepared by reacting different diols with di(ethylene glycol) divinyl ether ($M_{2DVE}$) and tri(ethylene glycol) divinyl ether ($M_{3DVE}$). The LCST results indicate that one 'ethylene oxide' unit increases the LCST by about 12° C. The increase in LCST is independent of the source of the ethylene oxide units; that is, LCST is affected regardless of whether the ethylene oxide unit is from the diol or the divinyl ether monomer. Thus, in some embodiments, the LCSTs be varied linearly, and can also be fine-tuned by choosing suitable monomers and adjusting the feed ratio. Such a long range tuning of LCSTs has not been previously reported in the literature for any thermoresponsive polymer.

The modified equation (eq. 4) also indicates that the $LCST_{Pm(av)}$ will be greater than 100° C. if the value of $m_{(av)}$ is 8 or greater. Without being bound by theory, this may be a factor in the lack of any theromoresponsivity in previously reported polycaetals that were mainly prepared from hydrophilic (ethylene glycol based) divinyl ethers and a hydrophilic diol (PEG) (Paramonov, S. E.; Bachelder, E. M.; Beaudette, T. T.; Standley, S. M.; Lee, C. C.; Dashe, J.; Frechet, J. M. J. Bioconjugate Chem. 2008, 19, 911-919; Tomlinson, R.; Heller, J.; Brocchini, S.; Duncan, R. Bioconjugate Chem. 2003, 14, 1096-1106; Tomlinson, R.; Klee, M.; Garrett, S.; Heller, J.; Duncan, R.; Brocchini, S. Macromolecules 2002, 35, 473-480; Rickerby, J.; Prabhakar, R.; Ali, M.; Knowles, J.; Brocchini, S. J. Mater. Chem. 2005, 15, 1849-1856; Wang, Y.; Morinaga, H.; Sudo, A.; Endo, T. J. Polym. Sci., Part A: Polym. Chem. 2011, 49, 596-602). In the instant case, the design of polyacetals with varied LCST or the fine tuning of the LCST for a given polyacetal is provided. For biomedical applications, the fine tuning of a polymer's LCST is particularly advantageous. For hyperthermia-induced therapeutic agent delivery, the LCST of the soluble polymeric therapeutic agent carrier should advantageously be higher than physiological body temperature but less than 42° C. (Meyer, D. E.; Shin, B. C.; Kong, G. A.; Dewhirst, M. W.; Chilkoti, A. *J. Control. Rel.* 2001, 74, 213-224). Thus, a polymer with a LCST in between the LCSTs of P2.5 (37.5° C., close to body temperature) and P3 (42.6° C.) could be designed by adjusting the $M_2/M_3$ molar ratio. Such a polymer can be particularly suitable as a soluble polymeric carrier for thermal-targeted therapeutic agent delivery.

Figure 7A:
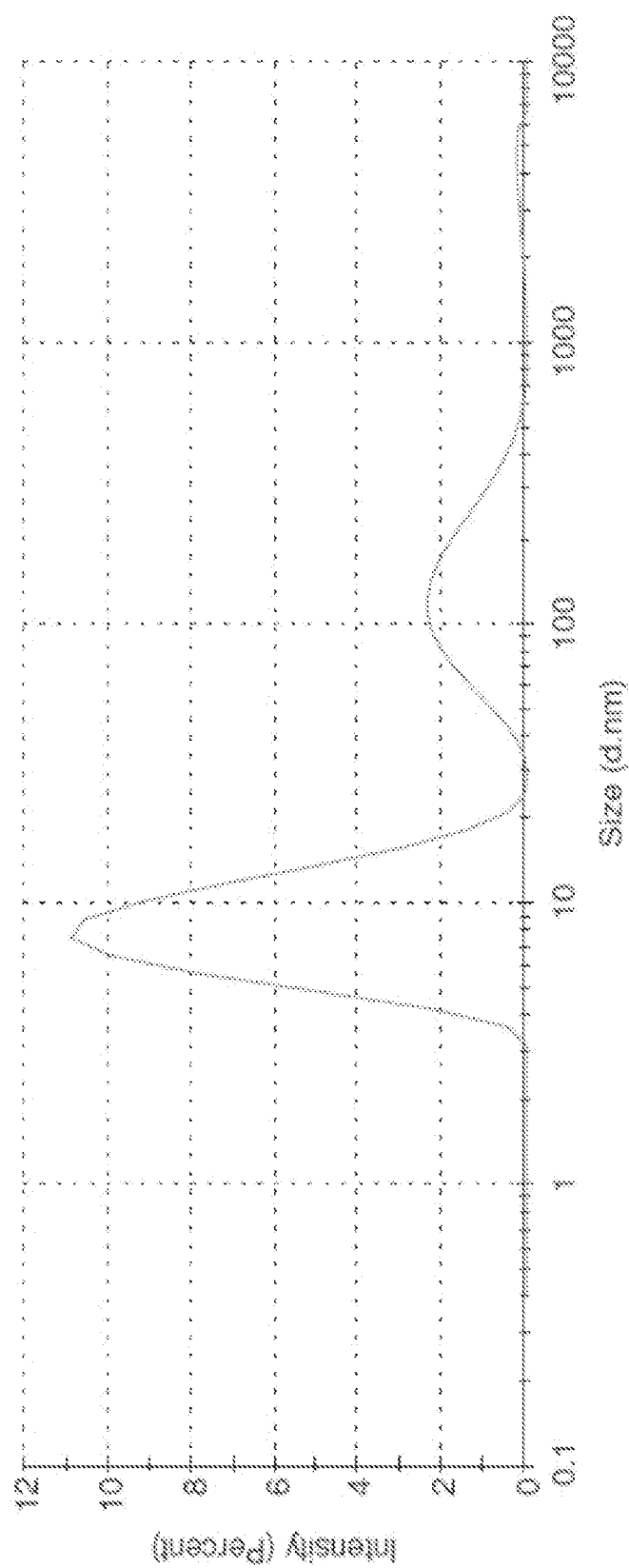
FIGS. 7A-C show (FIG. 7A) particle size distribution of polymer P2a by intensity.
Figure 7B:
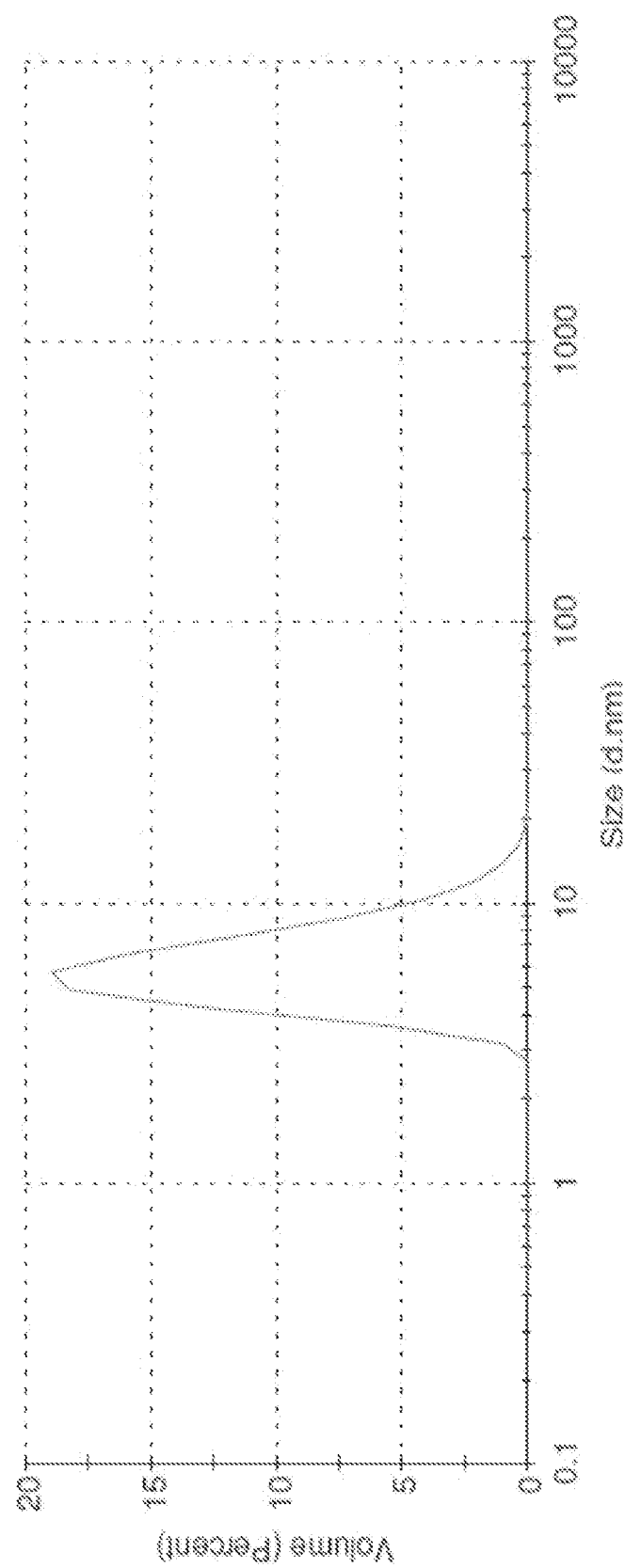
Figure 7C:
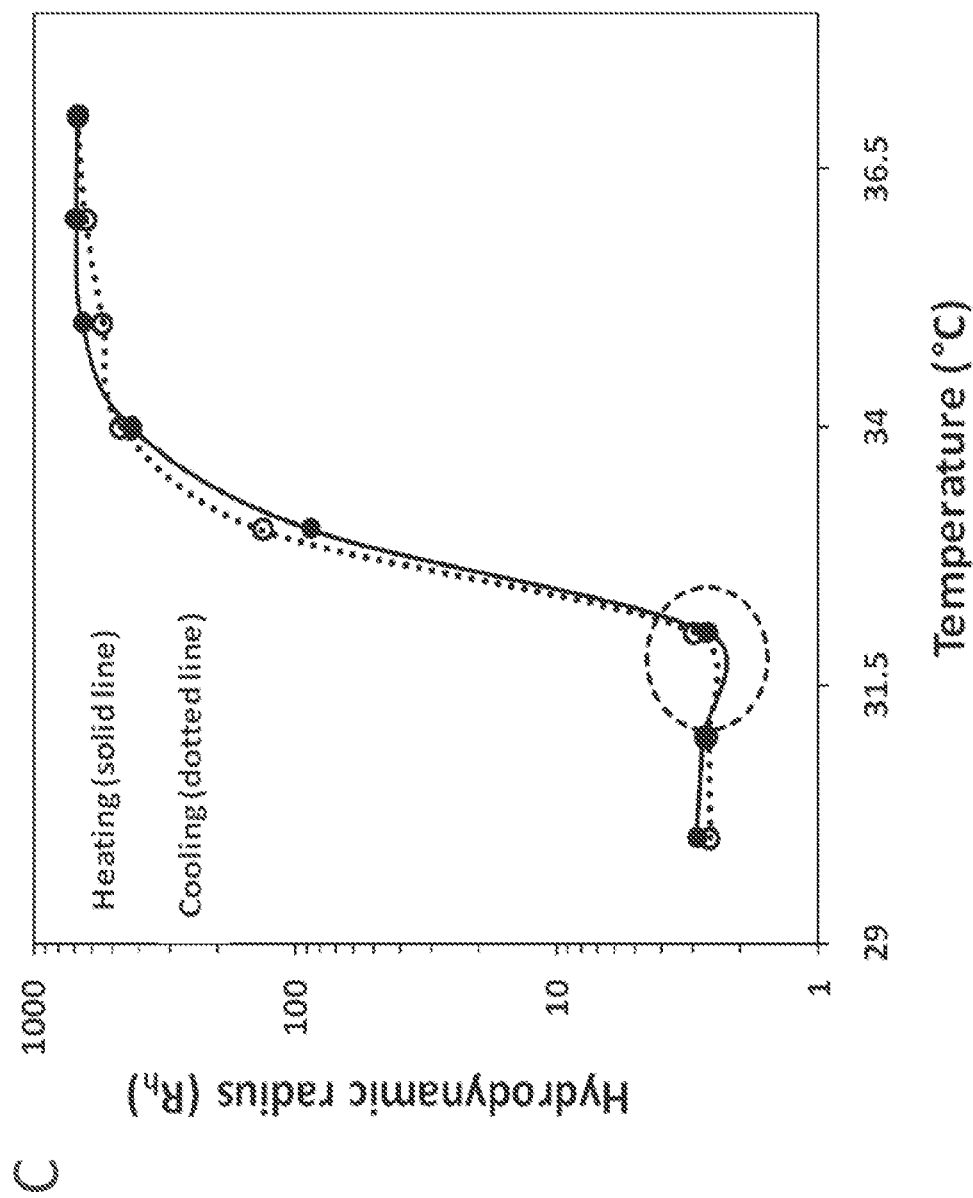

To understand the conformations of polyacetals below and above their LCSTs, as well as the nature of the phase transitions, the thermal behavior of an aqueous solution of polyacetal P2a was monitored by dynamic light scattering (DLS). The P2a polyacetal has an LCST (31.6° C.) that is very close to that of pNIPAM (Lutz, J. F.; Akdemir, O.; Hoth, A. *J. Am. Chem. Soc.* 2006, 128, 13046-13047) and P(MEO2MA-co-OEGMA)] copolymers with 5% OEGMA (Lutz, J. F.; Hoth, A. *Macromolecules* 2006, 39, 893-896; herein incorporated by reference in its entirety). At low temperature (≤32° C.) the solution is optically clear but intensity distribution (FIG. 7A) indicates the coexistence of small and large particles with hydrodynamic radii ($R_h$) of 4.4 and 75 nm, respectively. However, the large objects are present in negligible quantity, as evidenced by the volume distribution (FIG. 7B). The volume distribution shows only one peak, which corresponds to the small particles ($R_h$=3.1 nm). Several attempts were made to remove the large objects but comparable DLS results were obtained each time. A similar phenomenom was observed by Lutz et al. (Lutz, J. F.; Weichenhan, K.; Akdemir, O.; Hoth, A. *Macromolecules* 2007, 40, 2503-2508) for P(MEO2MA-co-OEGMA)] copolymers and pNIPAM and was attributed as the artifacts of the light scattering set-up. Hence, below the LCST, polyacetals adopt mostly a coiled conformation in water. A slight shrinkage of polymer coils is observed shortly before 32° C., followed by an abrupt transition in particle size measured by DLS at 33° C. (FIG. 7C), which is very close to its LCST (31.6° C.), as measured by turbidimetry. Such 'shrinkage' behavior was previously reported for other temperature sensitive polymers and could be evidence for coil dehydration (i.e., coil-to-globule transition) prior to aggregation (Lutz, J. F.; Weichenhan, K.; Akdemir, O.; Hoth, A. *Macromolecules* 2007, 40, 2503-2508; Wang, X.; Qiu, X.; Wu, C. *Macromolecules* 1998, 31, 2972-2976; Lessard, D. G.; Ousalem, M.; Zhu, X. X.; Eisenberg, A.; Carreau, P. J. *J. Polym. Sci., Part B: Polym. Phys.* 2003, 41, 1627-1637. However, after coil dehydration, the particles size increases with temperature and remains almost constant at a temperature≥35° C. with a $R_h$ of approximately 750 nm, which is comparable in size with other thermoresponsive polymers (Lutz, J. F.; Weichenhan, K.; Akdemir, O.; Hoth, A. *Macromolecules* 2007, 40, 2503-2508; Lessard, D. G.; Ousalem, M.; Zhu, X. X.; Eisenberg, A.; Carreau, P. J. *J. Polym. Sci., Part B: Polym. Phys.* 2003, 41, 1627-1637; Aseyev, V.; Hietala, S.; Laukkanen, A.; Nuopponen, M.; Confortini, O.; Du Prez, F. E.; Tenhu, H. Polymer 2005, 46, 7118-7131; Kujawa, P.; Aseyev, V.; Tenhu, H.; Winnik, F. M. *Macromolecules* 2006, 39, 7686-7693) and can be considered stable mesoglobules resulting from the aggregation of collapsed dehydrated chains (Lutz, J. F.; Weichenhan, K.; Akdemir, O.; Hoth, A. *Macromolecules* 2007, 40, 2503-2508; Aseyev, V.; Hietala, S.; Laukkanen, A.; Nuopponen, M.; Confortini, O.; Du Prez, F. E.; Tenhu, H. *Polymer* 2005, 46, 7118-7131; Kujawa, P.; Aseyev, V.; Tenhu, H.; Winnik, F. M. *Macromolecules* 2006, 39, 7686-7693; Schild, H. G. *Prog. Polym. Sci.* 1992, 17, 163-249). Due to the absence of any strong hydrogen bond donors in the molecular structure of the polyacetal (which are present in pNIPAM but not in PEGylated polymers) (Lutz, J. F.; Hoth, A. *Macromolecules* 2006, 39, 893-896; Lutz, J. F.; Akdemir, O.; Hoth, A. *J. Am. Chem. Soc.* 2006, 128, 13046-13047; Lutz, J. F.; Weichenhan, K.; Akdemir, O.; Hoth, A. *Macromolecules* 2007, 40, 2503-2508; Lutz, J. F. *J. Polym. Sci., Part A: Polym. Chem.* 2008, 46, 3459-3470; Wang, X.; Qiu, X.; Wu, C. *Macromolecules* 1998, 31, 2972-2976), the polymer-polymer interactions stabilizing these mesoglobules are probably originated from the weaker vander Waals interactions (Lutz, J. F.; Weichenhan, K.; Akdemir, O.; Hoth, A. *Macromolecules* 2007, 40, 2503-2508) leading to reversible (no hysteresis) phase transition (coil-to-globule transition) in water as indicated from both turbidimetry (FIG. 6B) and light scattering experiments (FIG. 7C).

Figure 8A:
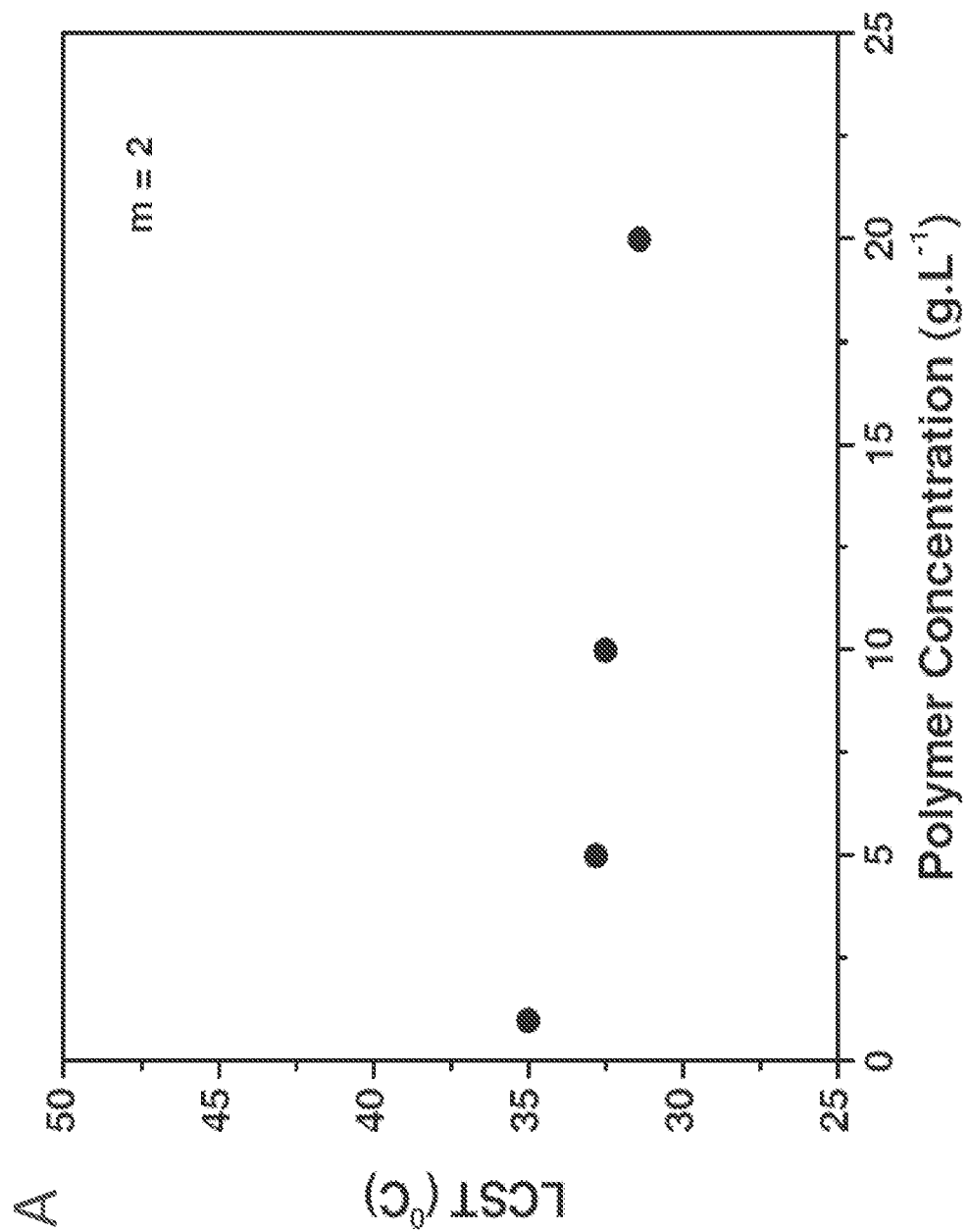
FIGS. 8A-B show (FIG. 8A) variation of LCST of polymer P2a as a function of polymer concentration.
Figure 8B:
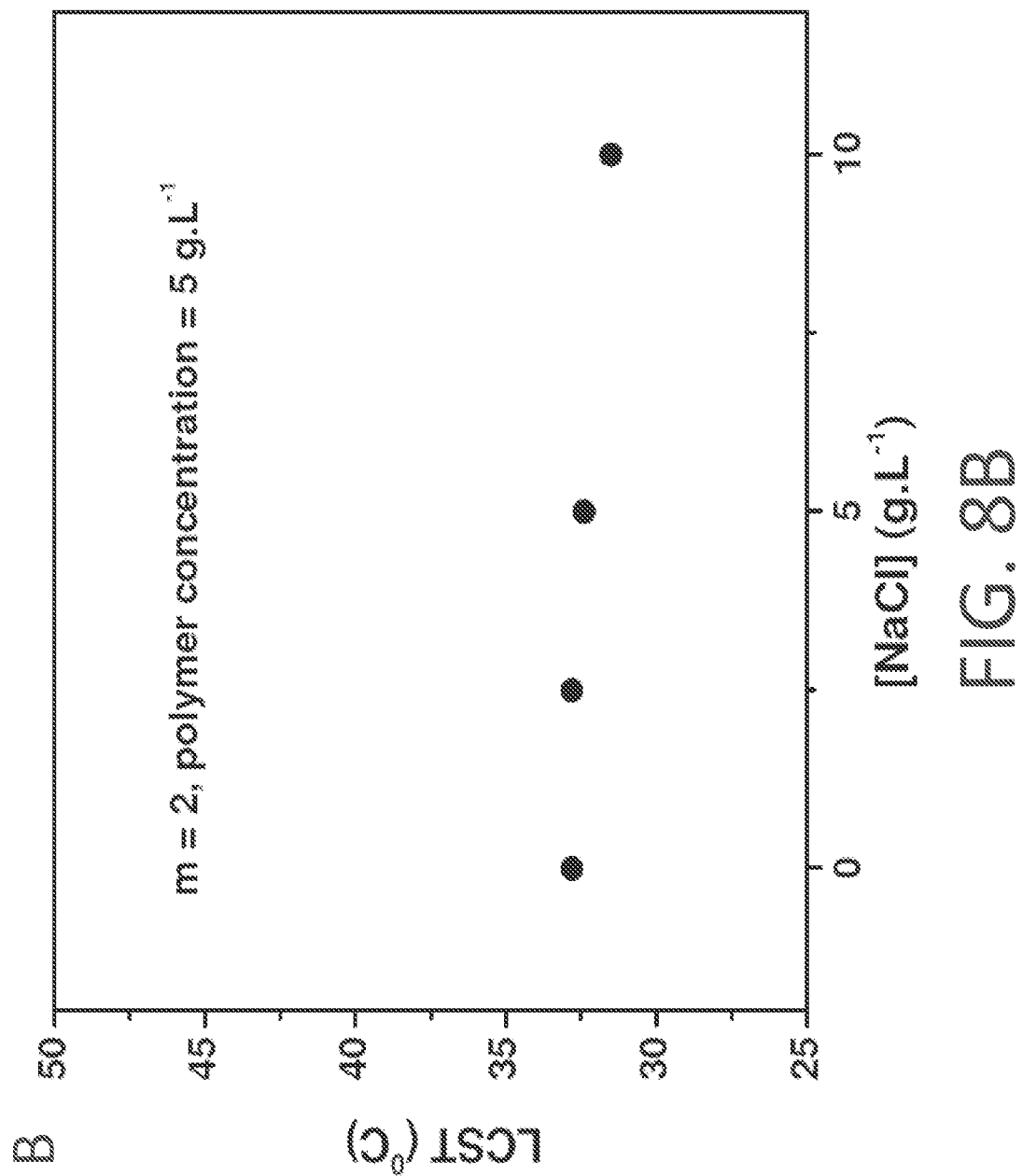

The variation of LCST with polymer concentration, an important issue for biomedical applications, is verified using polyacetal P2a. Within the studied range (1-20 g·L$^{-1}$), the LCST of P2a is almost independent of its concentration in water with a few degree increment at high dilution (FIG. 8A), which was also observed for two thermoresponsive polymers (Lutz, J. F.; Hoth, A. *Macromolecules* 2006, 39, 893-896; Lutz, J. F.; Akdemir, O.; Hoth, A. *J. Am. Chem. Soc.* 2006, 128, 13046-13047). Another important parameter is the influence of salt on the thermal behavior of the polyacetal. The LCST of P2a is measured in the presence of an increasing amount of NaCl. A very negligible effect is found (FIG. 8B), unlike other systems where a typical salting-out effect was observed (Lutz, J. F.; Hoth, A. *Macromolecules* 2006, 39, 893-896; Lutz, J. F.; Akdemir, O.; Hoth, A. *J. Am. Chem. Soc.* 2006, 128, 13046-13047).

Figure 9A:
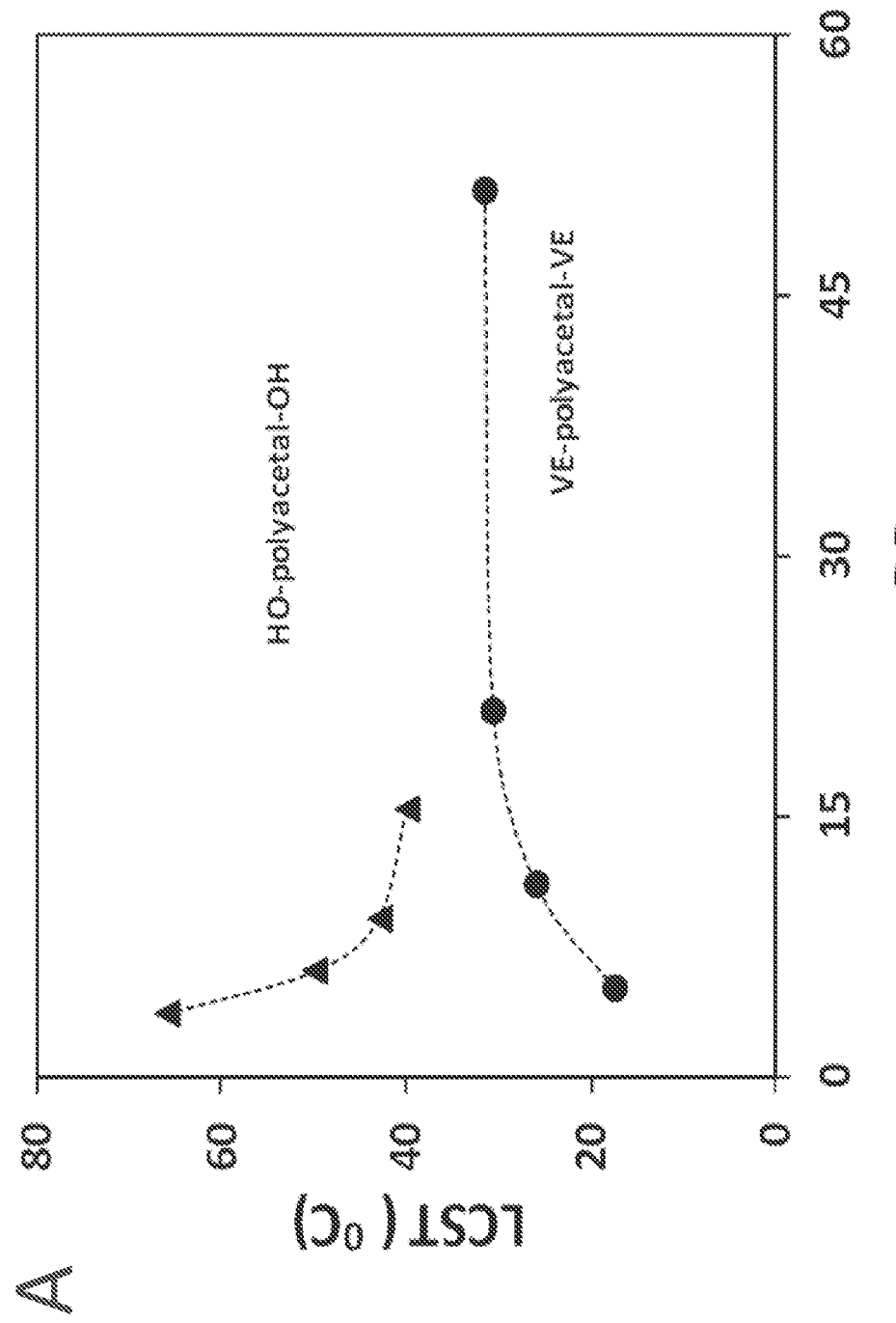
FIGS. 9A-B show the effect of end groups on the LCST of polyacetals.
Figure 9B:
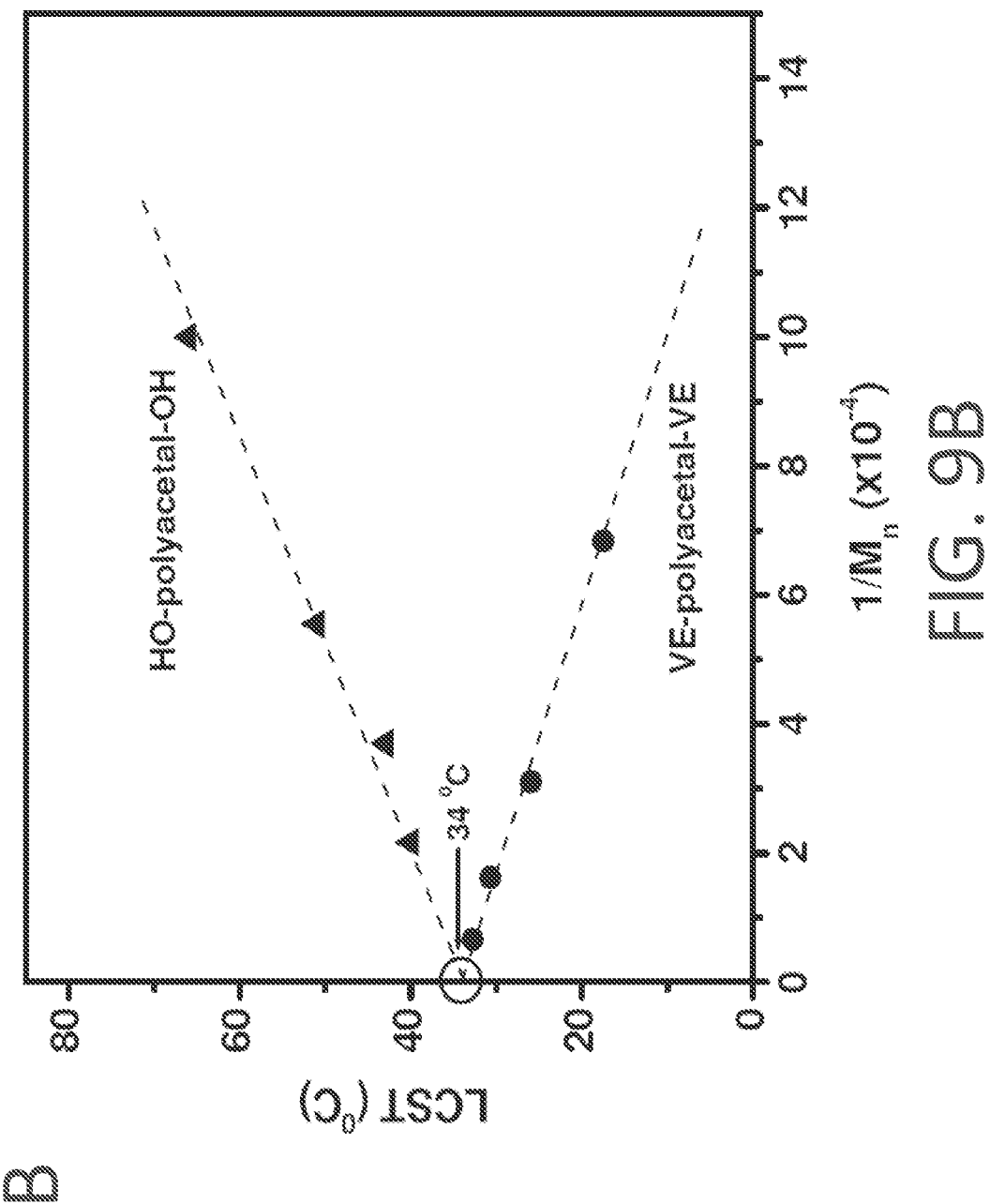

Another parameter is the influence of chain-length on the LCSTs of thermoresponsive polymers, which was found to be inversely dependent (Xia, Y.; Yin, X.; Burke, N. A. D.; Stover, H. D. H. *Macromolecules* 2005, 38, 5937-5943; Schild, H. G.; Tirrell, D. A. *J. Phys. Chem.* 1990, 94, 4352-4356; Patterson, D. *Macromolecules* 1969, 2, 672-677; Furyk, S.; Zhang, Y.; Acosta, D. O.; Cremer, P. S.; Bergbreiter, D. E. *J. Polym. Sci., Part A: Polym. Chem.* 2006, 44, 1492-1501), directly dependent (Tong, Z.; Zeng, F.; Zheng, X. *Macromolecules* 1999, 32, 4488-4490; Zheng, X.; Tong, Z.; Xie, X.; Zeng, F. *Polym. J.* 1998, 30, 284-288), or independent (Fujishige, S.; Kubota, K.; Ando, I. *J. Phys. Chem.* 1989, 93, 3311-3313; Otake, K.; Inomata, H.; Konno, M.; Saito, S. *Macromolecules* 1990, 23, 283-289; Tiktopulo, E. I.; Uversky, V. N.; Lushchik, V. B.; Klenin, S. I.; Bychkova, V. E.; Ptitsyn, O. B. *Macromolecule* 1995, 28, 7519-7524) of the molecular weight. While some of these variations originate from end groups, different polymer concentrations, different techniques of LCST measurement, partially fractionated or unfractionated samples and broad polydispersities, Stover et al. prepared narrow-disperse pNIPAM by ATRP to verify the actual correlation between DPs and LCSTs and obtained an inversely dependent relationship (Xia, Y.; Yin, X.; Burke, N. A. D.; Stover, H. D. H. *Macromolecules* 2005, 38, 5937-5943). A similar explanation was qualitatively advanced by Patterson using Flory-Huggins theory (Patterson, D. *Macromolecules* 1969, 2, 672-677). In the present case, the P2-category polyacetals with different chain-lengths (Table 1, entries 7-10) were prepared. However, the experimental LCSTs were found to increase with increasing chain-length of the polyacetals, and the slope is steeper in the low molecular weight region (FIG. 9A, bottom curve). This direct relationship between LCSTs and molecular weights is abnormal for thermoresponsive polymers. This abnormal behavior is attributed to an 'end group' effect. All of the P2-category polyacetals should have free 'alkyl-vinyl ether' groups at both ends since divinyl ether monomers are used in excess relative to the diols for the polymerization. The hydrophobic end groups disrupt the polymer dissolution by altering the hydrophilic-hydrophobic balance in the polyacetal chains, leading to its phase transition at a lower solution temperature. These hydrophobic end groups have more influence on low molecular weight polymers (or oligomers), leading to a sharp increase of LCSTs in the low DP region and being almost constant for higher DP, indicating the effect of end groups is negligible on the high molecular weight polymers. This type of phenomenon was previously reported for hydrophobically end-modified pNIPAM, which was found to aggregate into (compact or diffuse) micellar structure below its LCST (Furyk, S.; Zhang, Y.; Acosta, D. O.; Cremer, P. S.; Bergbreiter, D. E. *J. Polym. Sci., Part A: Polym. Chem.* 2006, 44, 1492-1501; Chung, J. E.; Yokoyama, M.; Aoyagi, T.; Sakurai, Y.; Okano T. *J. Control. Rel.* 1998, 53, 119-130; Yamazaki, A.; Song, J. M.; Winnik, F. M.; Brash, J. L. *Macromolecules* 1998, 31, 109-115; Chung, J. E.; Yokoyama, M.; Suzuki, K.; Aoyagi, T.; Sakurai, Y.; Okano T. *Colloids Surf, B* 1997, 9. 37-48). However, in the present case, if the abnormal behavior is originated from hydrophobic end groups, polyacetals with hydrophilic end groups should have the reverse order, i.e. the LCSTs should be inversely dependent of molecular weight. To this end, hydroxyl terminated P'2-category polyacetals of different DPs (Table 1, entries 21-24) were prepared by using different monomer feed ratios. The experimental LCSTs were plotted against the DPs in FIG. 9B, top curve. The LCST values were found to be decreasing with increasing molecular weight of polyacetals and the LCST changes vary sharply in the low DP range of hydroxyl terminated polyacetals in the same region. Unlike the hydrophobic end groups, the terminal hydroxyl groups make the polyacetal chain more hydrophilic due to their strong hydrogen bonding with water, leading to the phase transition at higher solution temperatures and also slowing down the phase transition rate. The hydrogen bonding increases the hydrophilicity of low molecular weight (or oligomers) polyacetals and allows the LCSTs to appear at higher temperatures, leading to very sharp changes of LCSTs in the low DP range. The above results suggest that the end groups influence the phase transition of polyacetals and the effect is greater for low molecular weight polymers than for higher molecular weight polymers. Thus, the end group effects are to be neglected if P2 or P'2 have infinite molecular weight (both polyacetals are the same except for the end groups). Consequently, they should have the same LCST value, which could be considered as the LCST for P2 or P'2 polyacetals when having no end groups. LCST value of an infinite molecular weight polyacetal can be calculated by considering the equation (Eq. 5):

$$P = P_\alpha - k/M_n \quad \text{(Eq. 5)}$$

where P is a bulk property, $P_\alpha$ is the bulk property at infinite molecular weight, $M_n$ is the number average molecular weight of the polymer, and k is a constant which depends on the type of end group. Equation (5) typically correlates the end group effect on bulk physical properties of the polymer (Fleischert, C. A.; Koberstein, J. T.; Krukonis, V.; Wetmore, P. A. *Macromolecules* 1993, 26, 4172-4178). In the present case, the LCSTs of P2 and P'2-category polyacetals are scaled with $M_n^{-1}$ (FIG. 9B). The extrapolation to the Y-axis is taken as the LCST of the infinite molecular weight polymer, where the end group effect is considered to be neglected. Since both P2 are P'2 polyacetals are the same except for their end groups, the extrapolations intersect the y-axis at a single point (34° C.), which is the true LCST of the P2 polyacetal. Incorporation of any hydrophilic or hydrophobic end groups leads to an increase or a decrease in the LCST, respectively. FIG. 9B demonstrates that the molecular weight (MW) dependence of the LCST can be attributed to an end group effect. LCSTs scale inversely with MW according to a Fox-Flory type relation and extrapolate to the same infinite MW value for both end groups. The LCST temperatures of PAs can therefore be determined with high precision for essentially any integer or non-integer values of the structural parameters $n_1$, $m_1$ and $m_2$, as well as for any molecular weight. The LCSTs of the PAs are tunable over a temperature range of about 7-80° C. This range encompasses biologically relevant temperatures, including those of normal (37° C.) and malignant tissue, the latter of which is generally characterized by mild hyperthermia, with temperatures 1-2° C. above that of normal tissue. The latter characteristic is particularly advantageous to applications in therapeutic agent delivery vehicles for cancer where TRPs are designed to fall out of solution when they encounter the elevated temperature inside of a tumor.

Example 27

Figure 10A:
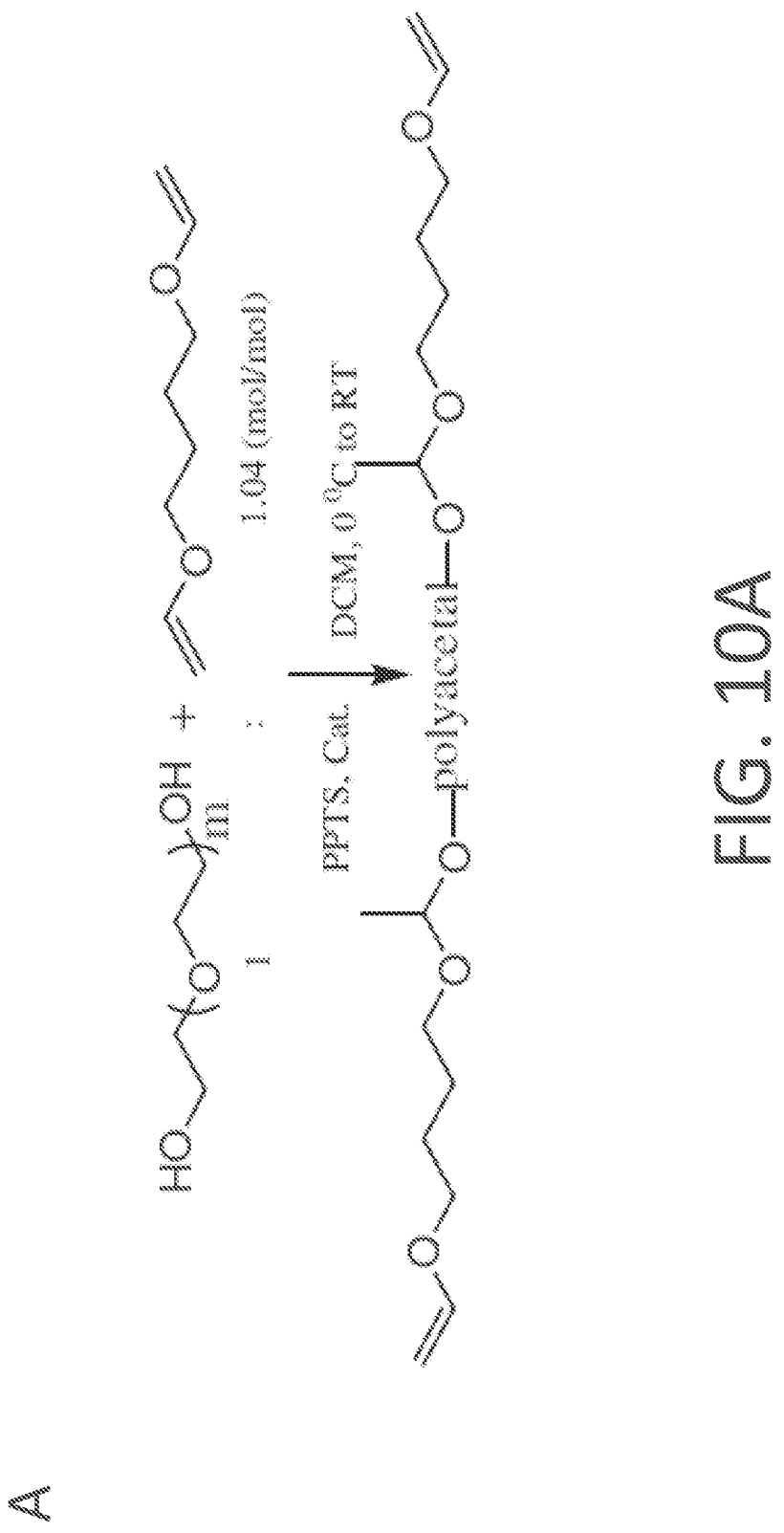
FIGS. 10A-E show the effect of the number of ethylene oxide units on the LCST of polyacetals.
Figures 10B, 10C:
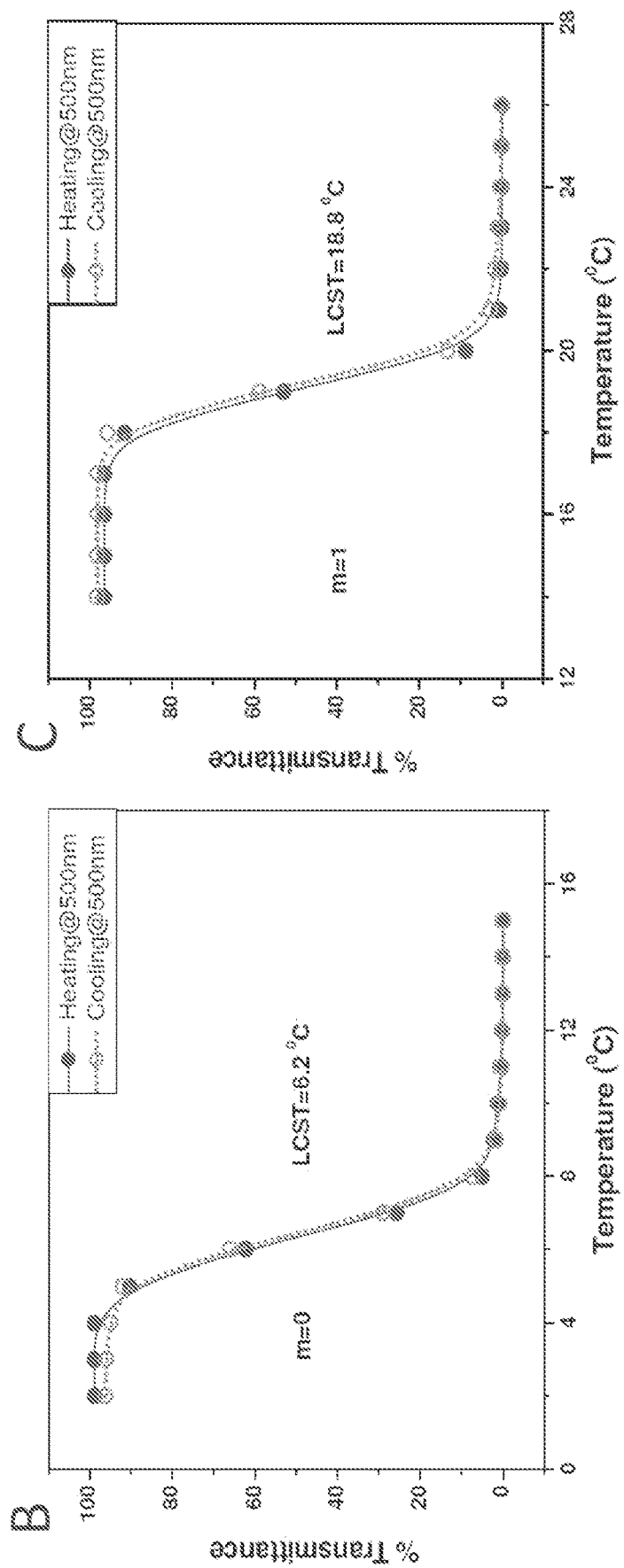
Figure 10E:
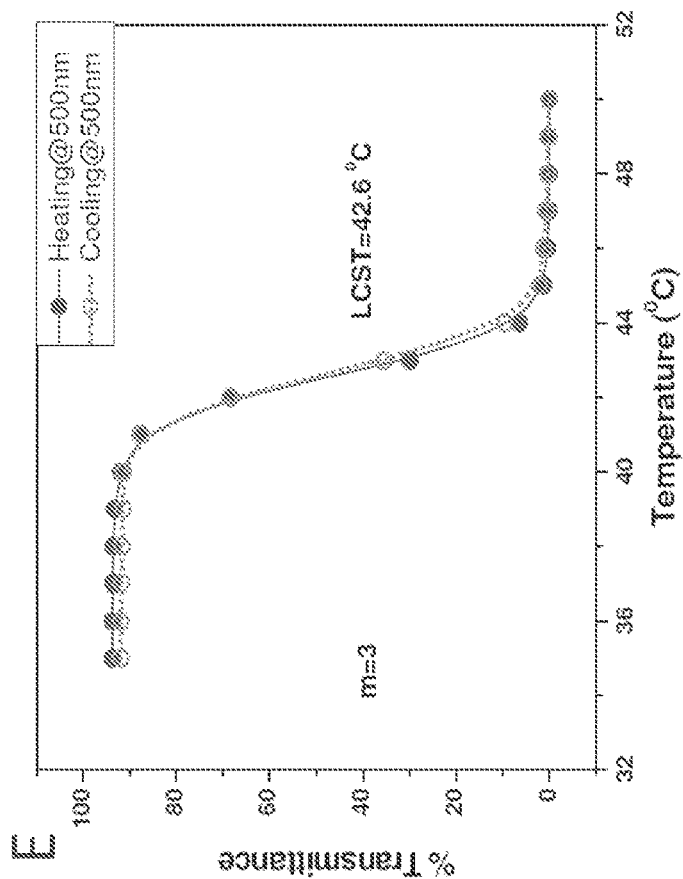
Figure 10D:
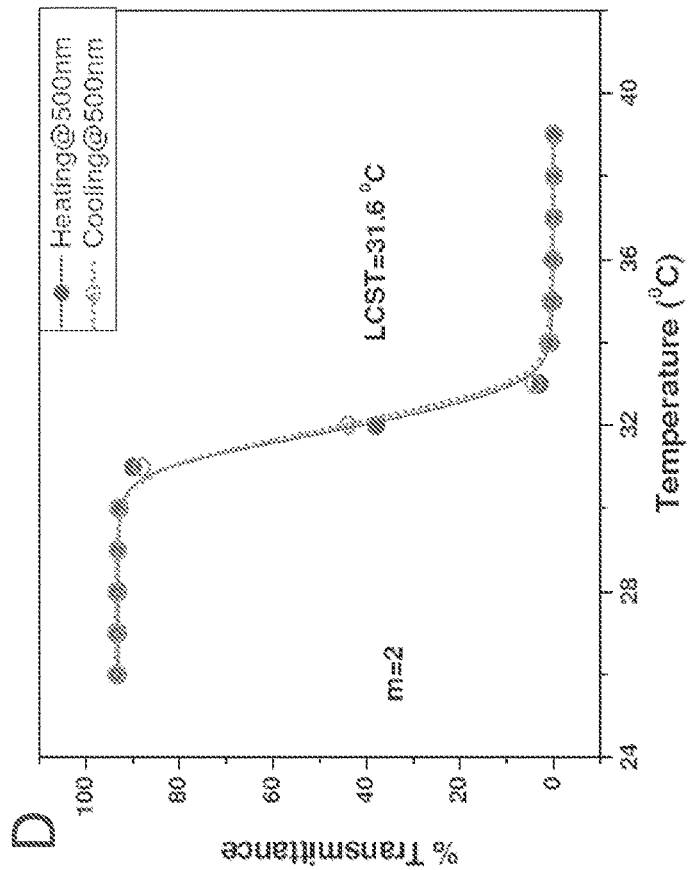

Effect of the number of ethylene oxide units (m) on the LCST of polyacetals. Polyacetals using diols with differing ethylene oxide units were synthesized according to FIG. 10A. Temperature induced phase transitions (heating and cooling) of the resultant polyacetals with m=0 (FIG. 10B), 1 (FIG. 10C), 2 (FIG. 10D), and 3 (FIG. 10E) are shown. The lower critical solution temperature (LCST) of aqueous PA solutions was measured by UV transmittance. There is no hysteresis and the temperature transition is very sharp, occurring over about 4° C.

Example 28

Figure 11A:
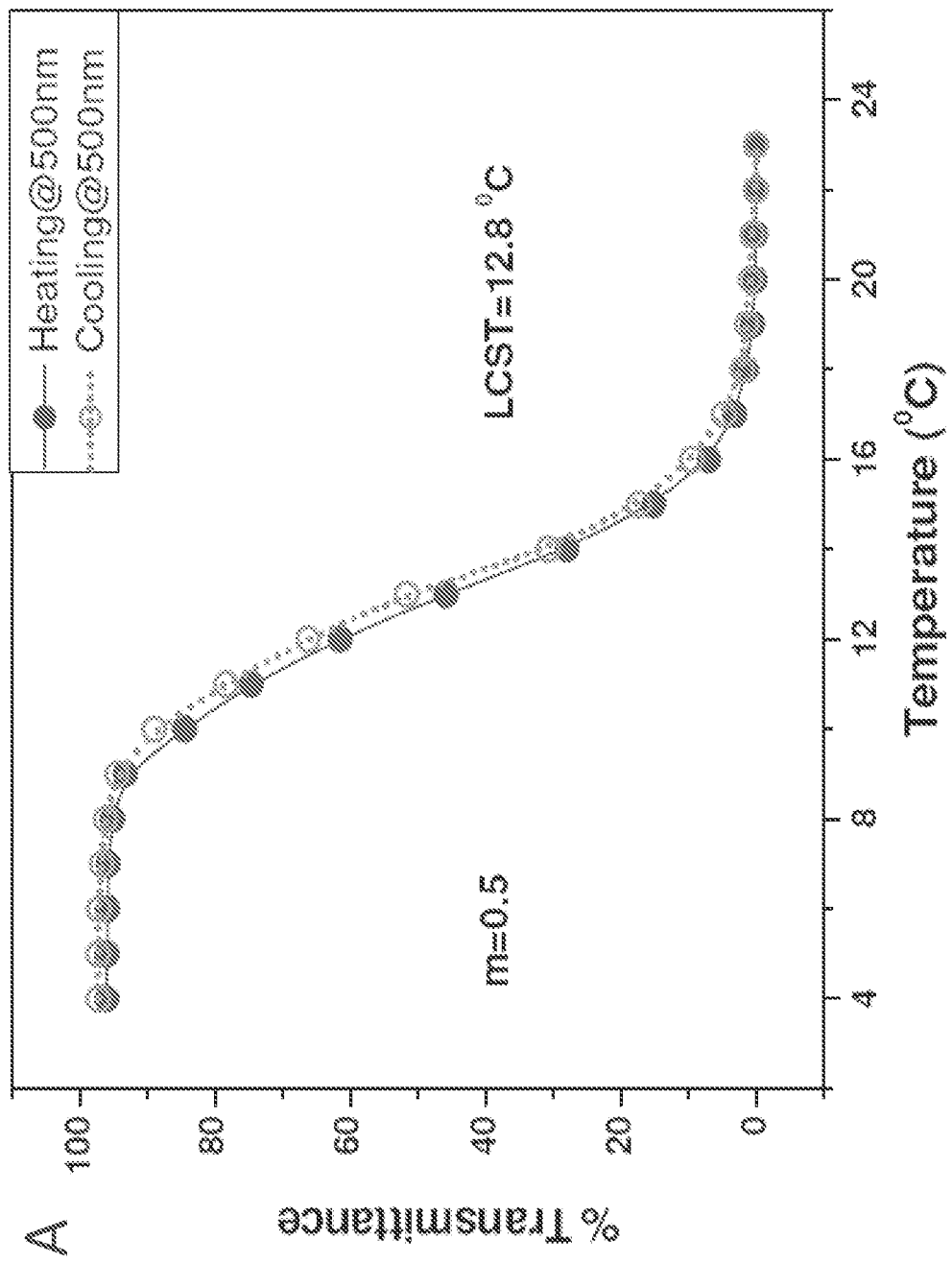
FIGS. 11A-C show the effect of the number of ethylene oxide units in the diol portion of the polyacetals on the LCST of polyacetals.
Figure 11B:
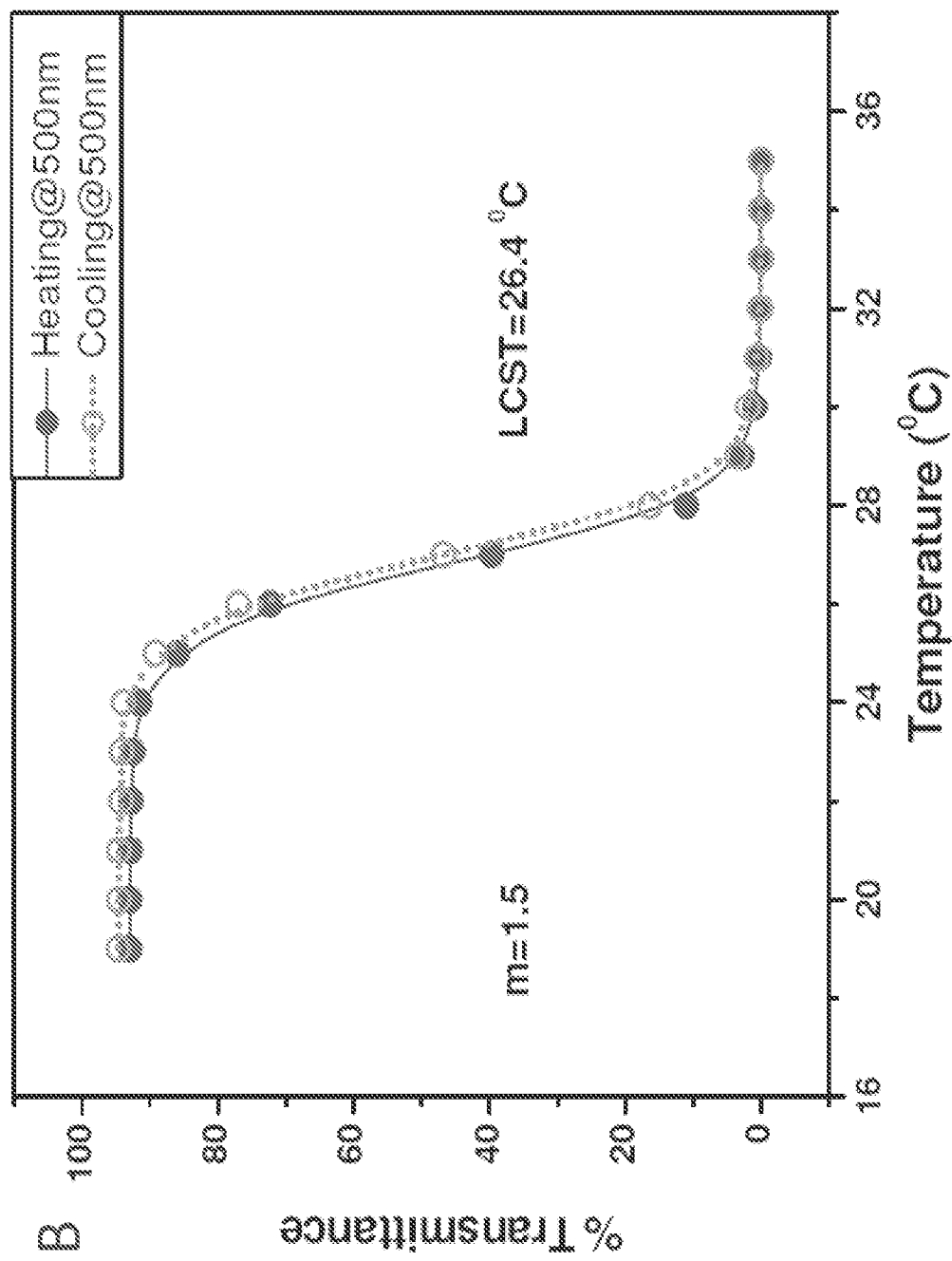
Figure 11C:
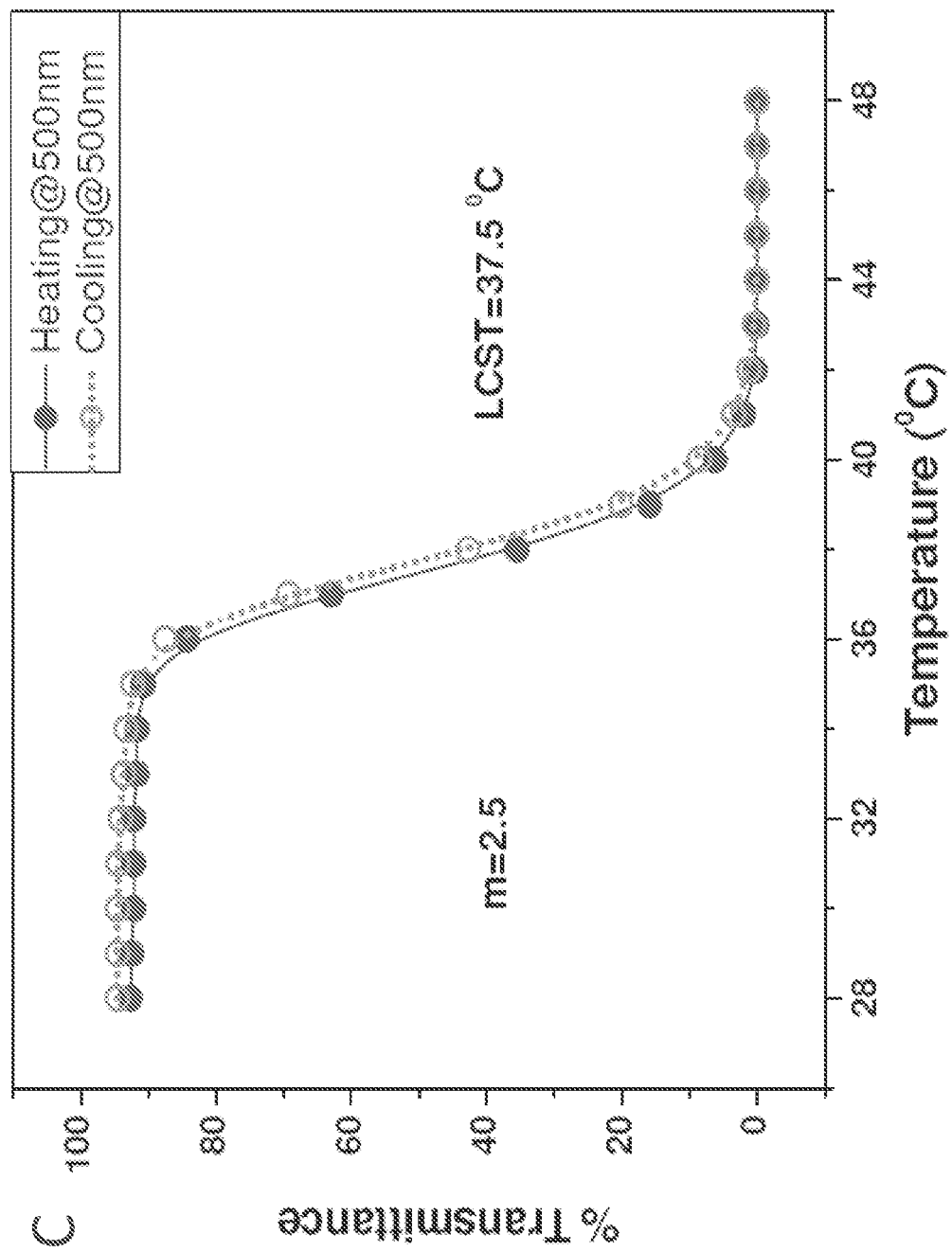

Temperature induced phase transitions (heating and cooling) of polyacetals with different average number of ethylene oxide units (m) in the repeating unit are shown in FIGS. 11A-C. FIG. 11A shows m=0.5, FIG. 11B shows m=1.5, and FIG. 11C shows m=2.5.

Example 29

Figure 12A:
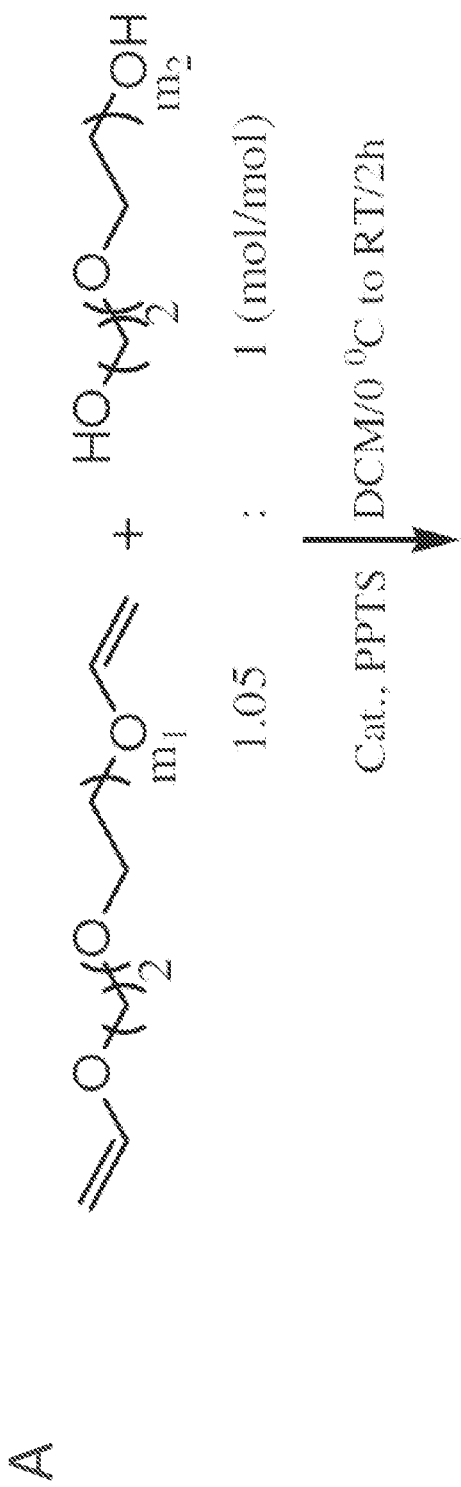
FIGS. 12A-I show the effect of the number of ethylene oxide units in the diol and divinyl ether portions of the polyacetals on the LCST of polyacetals.
Figure 12C:
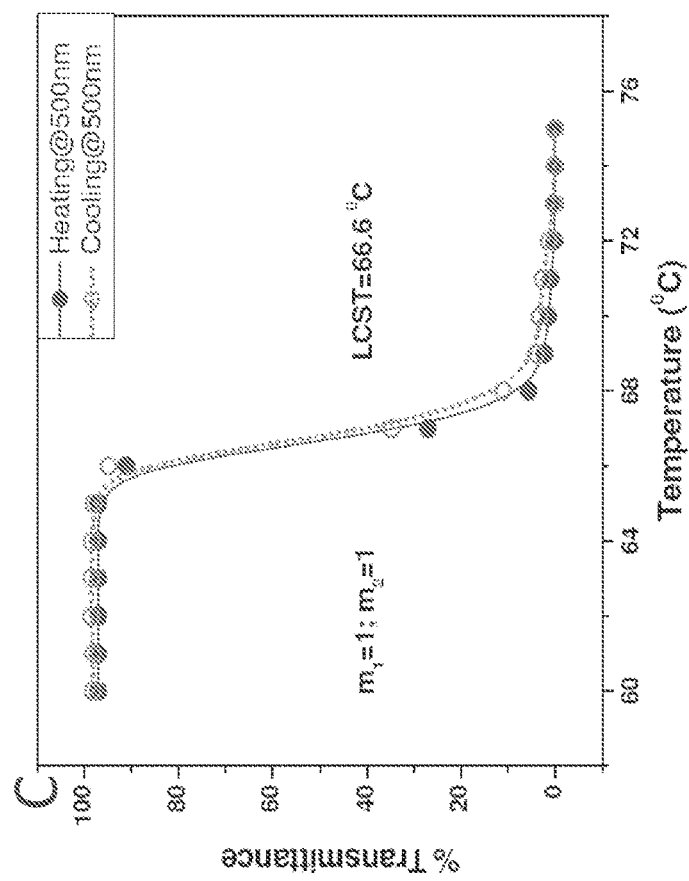
Figure 12B:
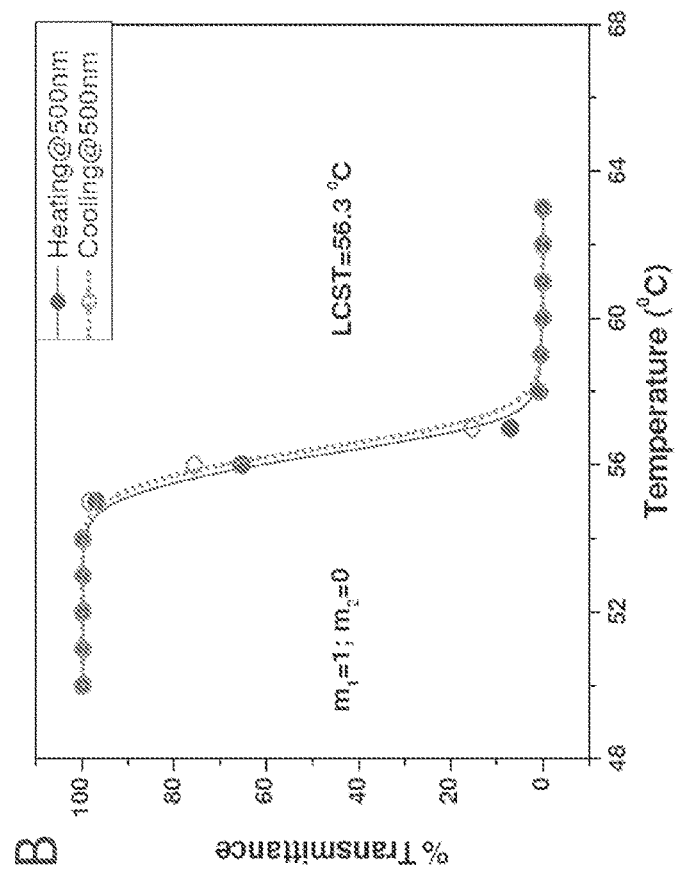
Figure 12E:
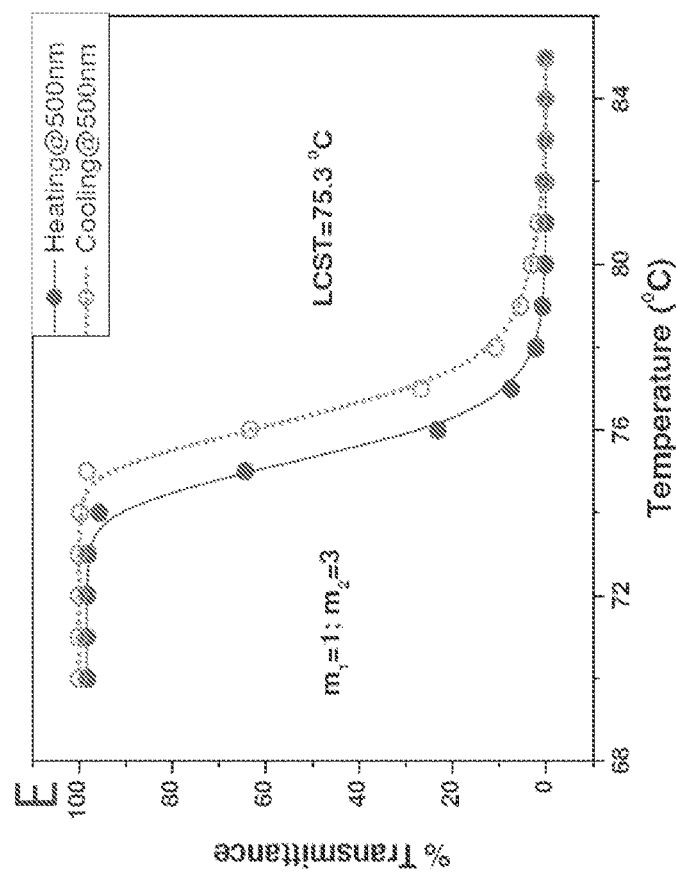
Figure 12D:
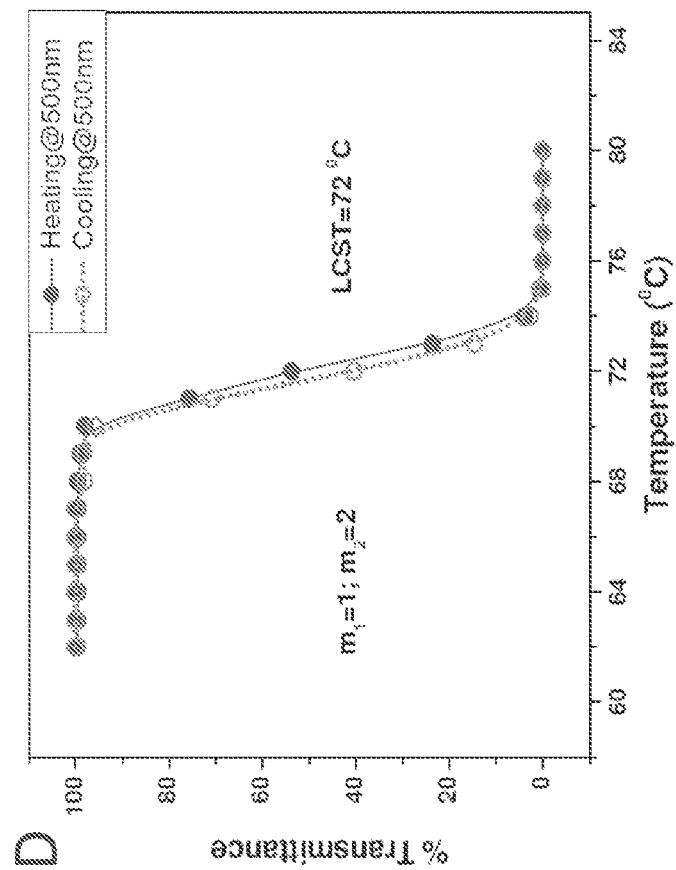
Figures 12F, 12G:
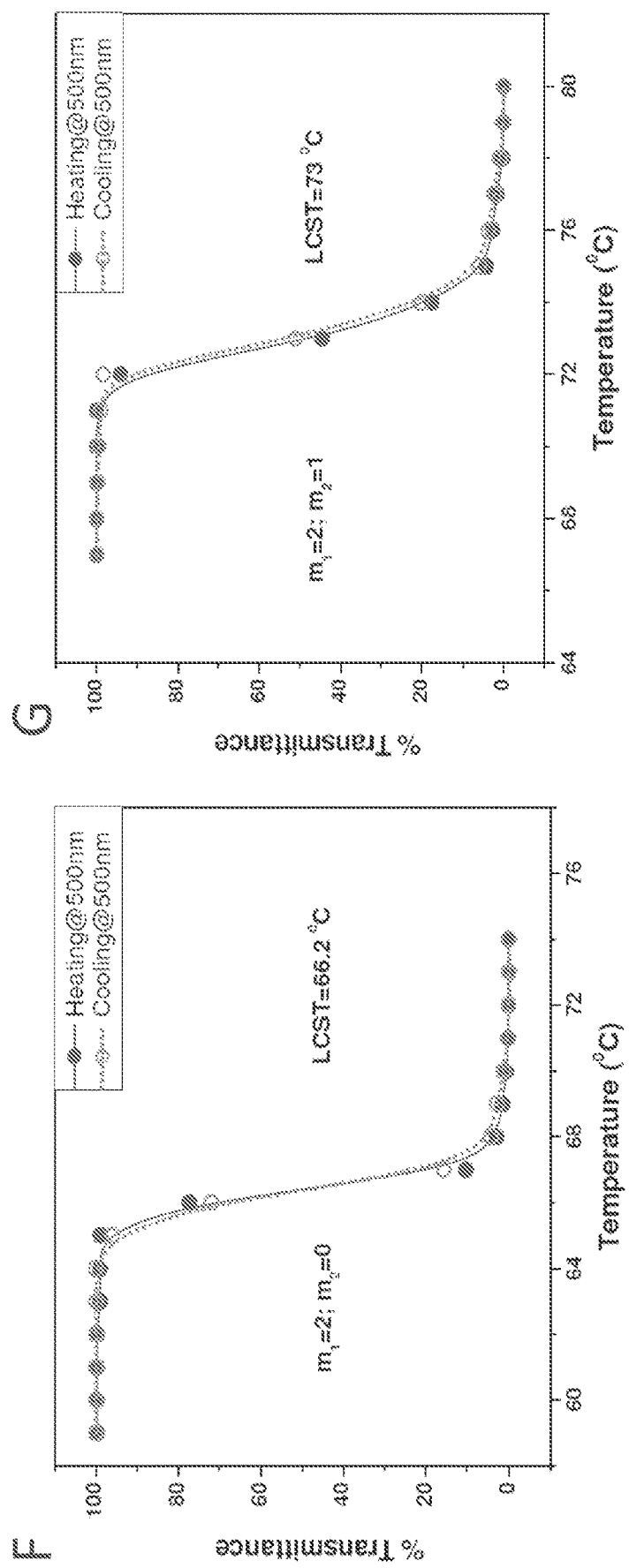
Figures 12H, 12I:
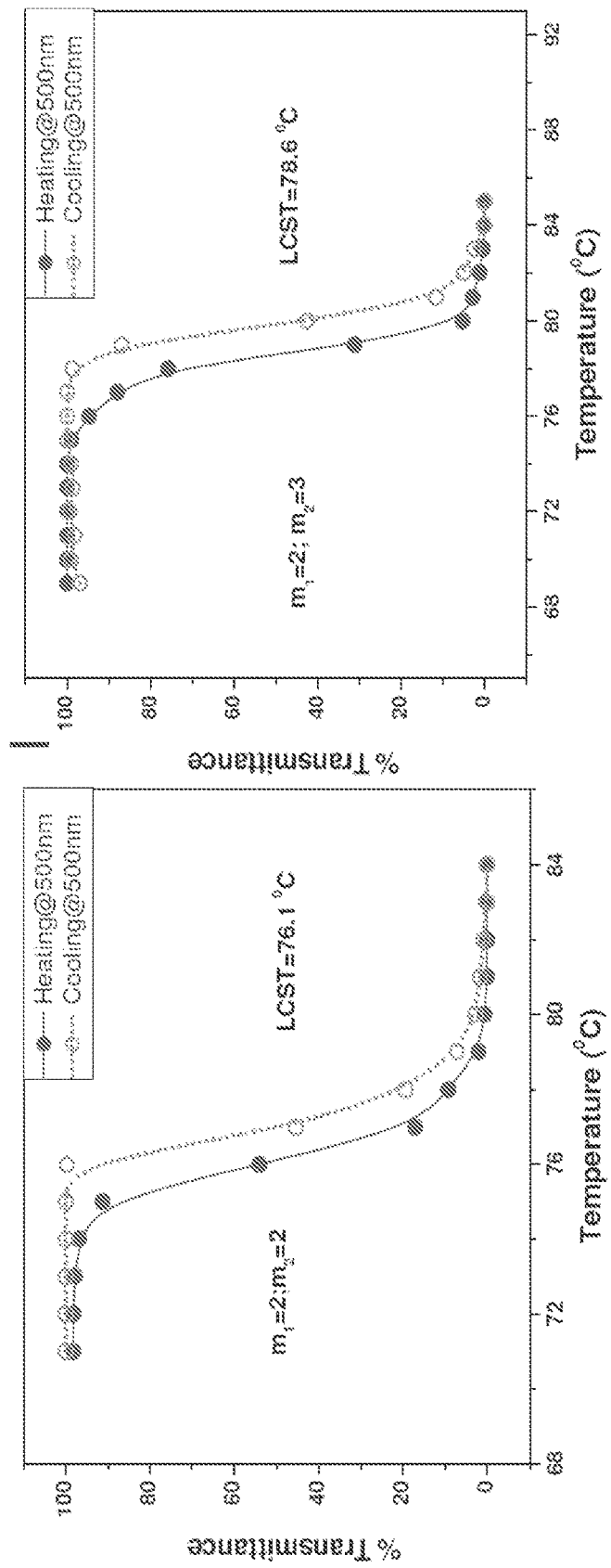

The effect of the number of ethylene oxide units in the diol and divinyl ether portions of the polyacetals on the LCST of polyacetals. (FIG. 12A) Synthetic scheme for polyacetal formation from divinyl ether (di(ethylene glycol) divinyl ether or tri(ethylene glycol) divinyl ether) and linear diol (ethylene glycol, diethylene glycol, triethylene glycol, or tetraethylene glycol), wherein the molar feed ratio of the divinyl ether to the diol is 1.05 to 1. (FIG. 12B) Plot of temperature induced phase transition (heating and cooling) for polyacetal formed from di(ethylene glycol) divinyl ether and ethylene glycol. (FIG. 12C) Plot of temperature induced phase transition (heating and cooling) for polyacetal formed from di(ethylene glycol) divinyl ether and diethylene glycol. (FIG. 12D) Plot of temperature induced phase transition (heating and cooling) for polyacetal formed from di(ethylene glycol) divinyl ether and triethylene glycol. (FIG. 12E) Plot of temperature induced phase transition (heating and cooling) for polyacetal formed from di(ethylene glycol) divinyl ether and tetraethylene glycol. (FIG. 12F) Plot of temperature induced phase transition (heating and cooling) for polyacetal formed from tri(ethylene glycol) divinyl ether and ethylene glycol. (FIG. 12G) Plot of temperature induced phase transition (heating and cooling) for polyacetal formed from tri(ethylene glycol) divinyl ether and diethylene glycol. (FIG. 12H) Plot of temperature induced phase transition (heating and cooling) for polyacetal formed from tri(ethylene glycol) divinyl ether and triethylene glycol. (FIG. 12I) Plot of temperature induced phase transition (heating and cooling) for polyacetal formed from tri(ethylene glycol) divinyl ether and tetraethylene glycol.

Figures 13A, 13B:
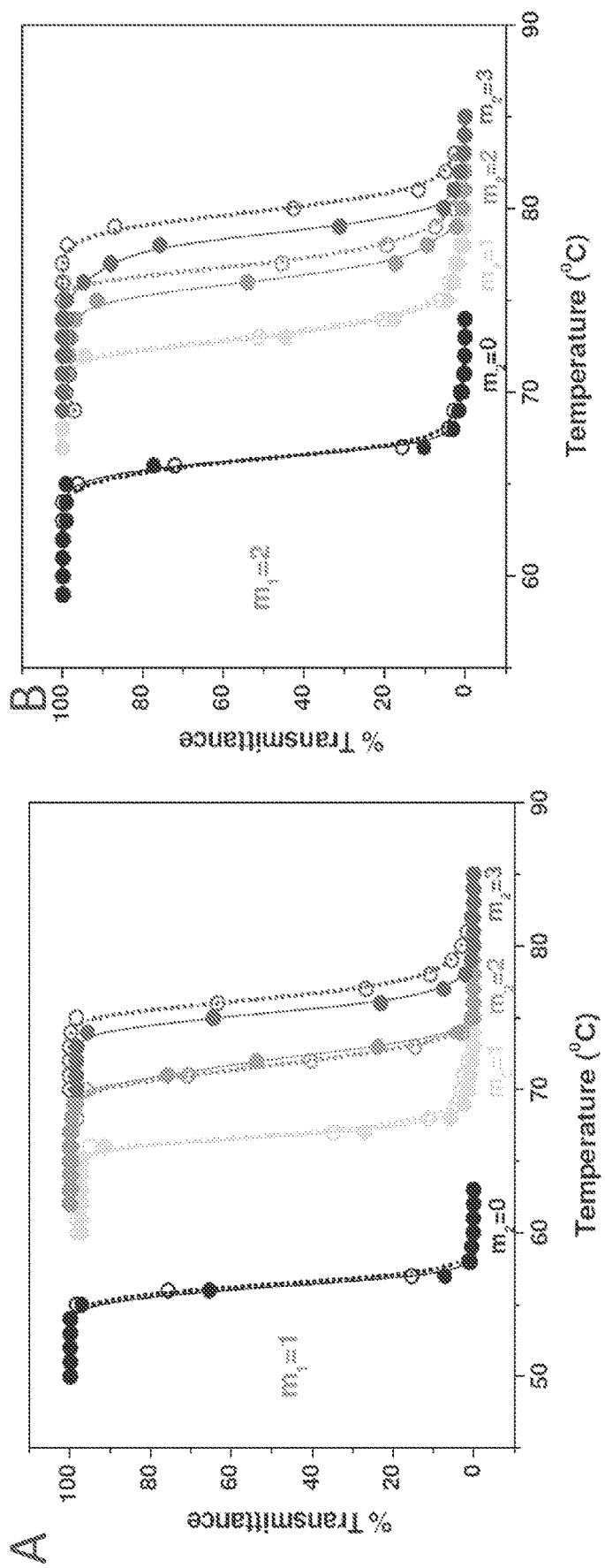
FIGS. 13A-C show (FIG. 13A) the combined plots of % transmittance versus temperature for polyacetals formed from di(ethylene glycol) divinyl ether and diols that vary in the number of ethylene oxide units (heating shown in solid circle and solid line, cooling shown in empty circle and dotted line)
Figure 13C:
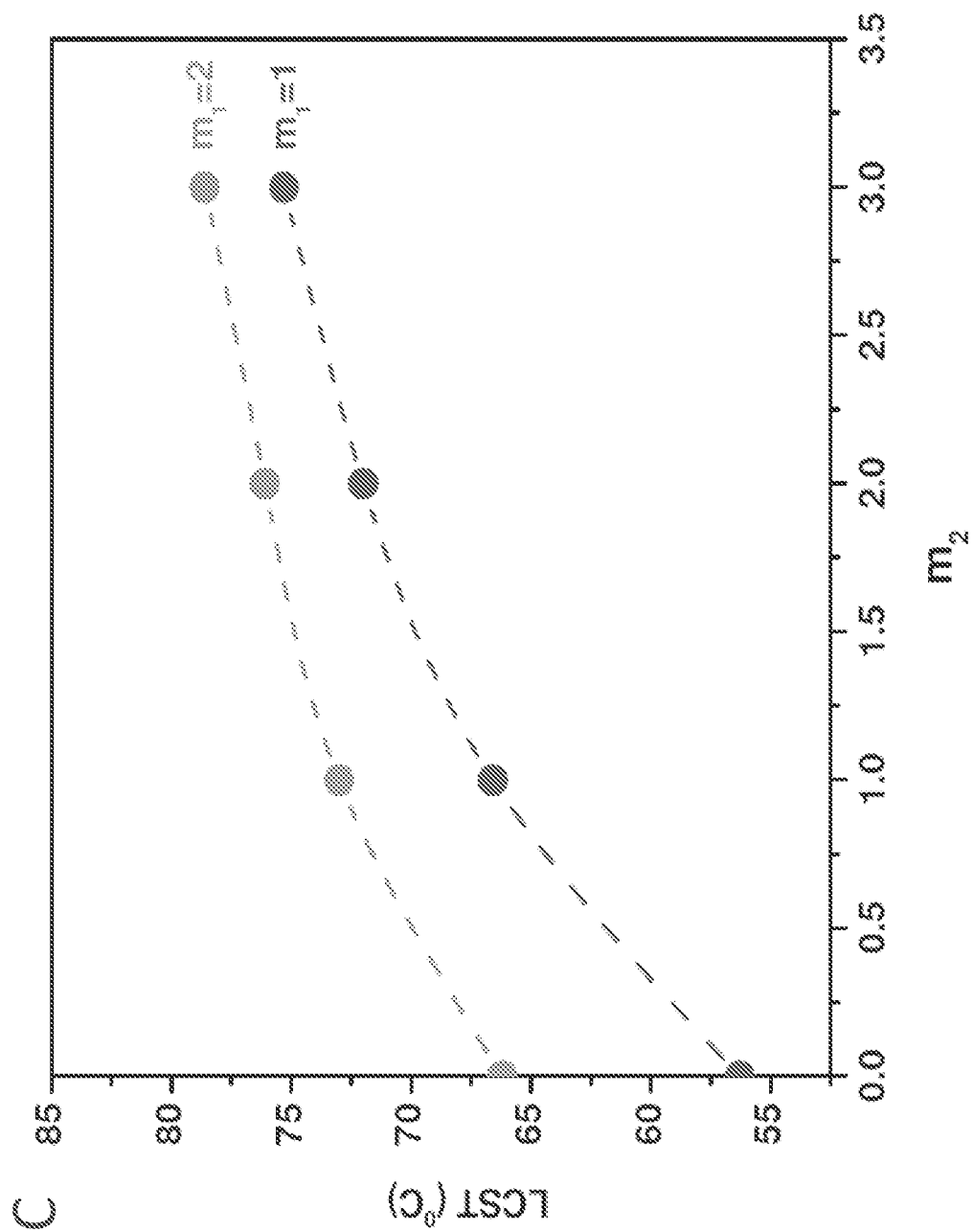

FIGS. 13A-C show (FIG. 13A) the combined plots of % transmittance versus temperature for polyacetals formed from di(ethylene glycol) divinyl ether and diols that vary in the number of ethylene oxide units (heating shown in solid circle and solid line, cooling shown in empty circle and dotted line); (FIG. 13B) the combined plots of % transmittance versus temperature for polyacetals formed from tri(ethylene glycol) divinyl ether and diols that vary in the number of ethylene oxide units (heating shown in solid circle and solid line, cooling shown in empty circle and dotted line); (FIG. 13C) non-linearity in the plot of experimental LCSTs versus $m_2$ (the number of ethylene oxide units in the diol portion of the polyacetal) for polyacetals prepared from di(ethylene glycol) divinyl ether and tri(ethylene glycol) divinyl ether.

Figure 14A:
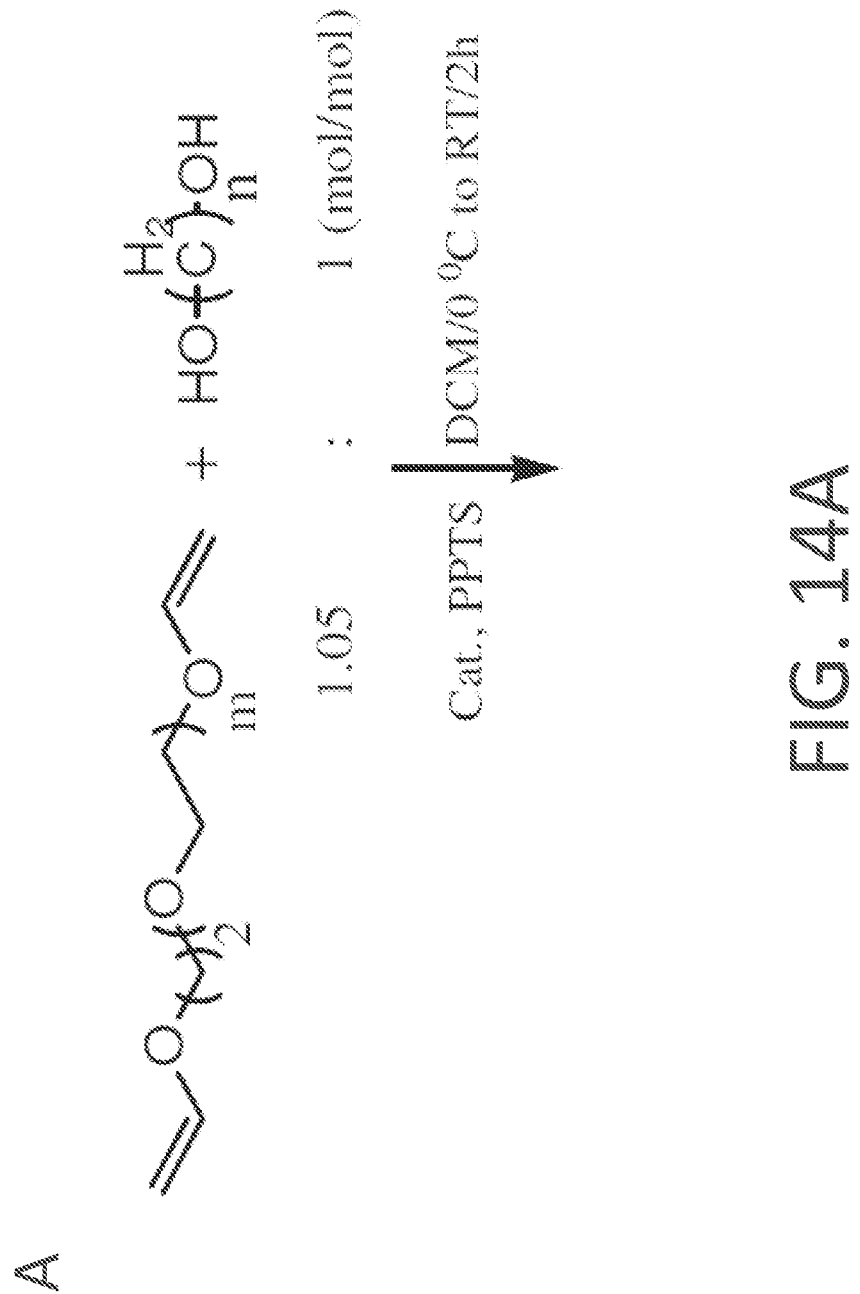
FIGS. 14A-D show the effect of the number of $CH_2$ groups on the LCST of polyacetals.
Figure 14C:
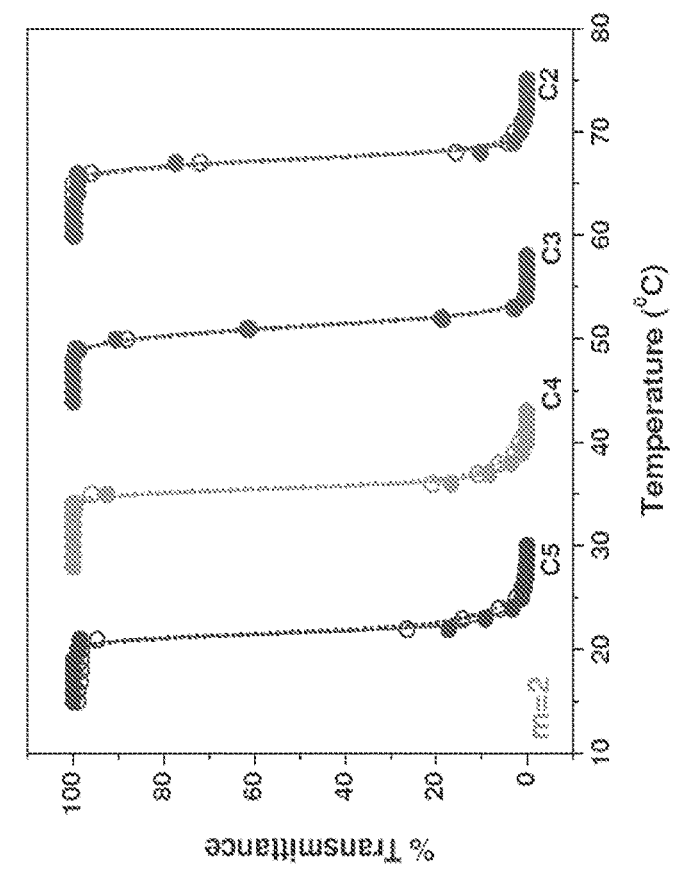
Figure 14B:
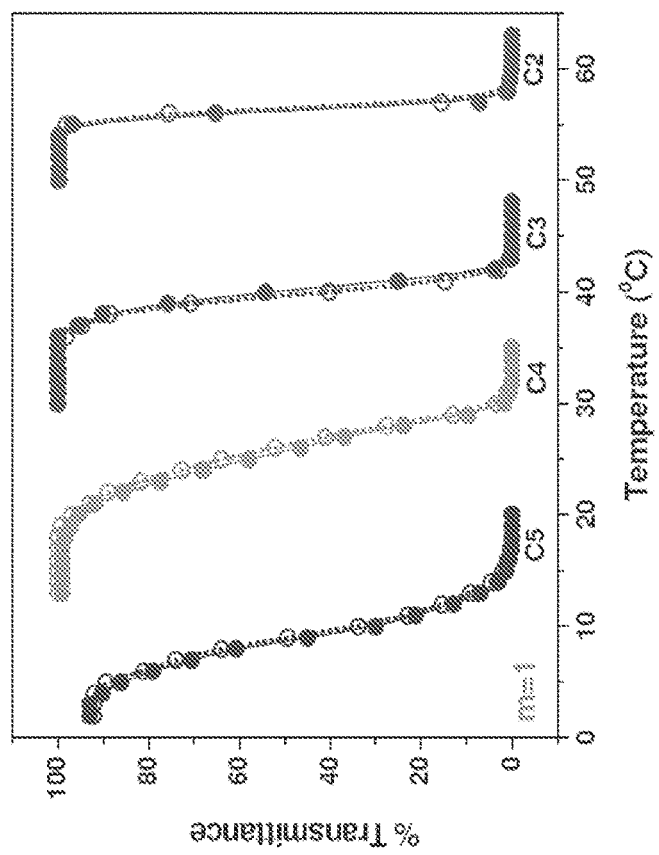
Figure 14D:
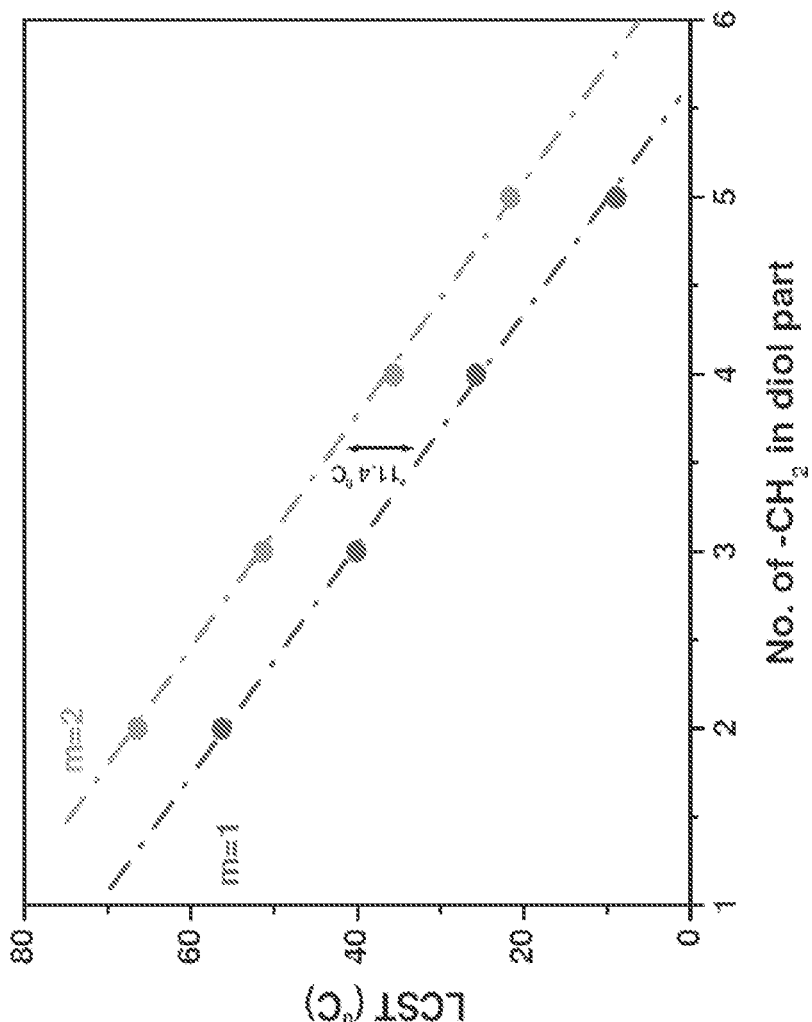
Figures 15A, 15B:
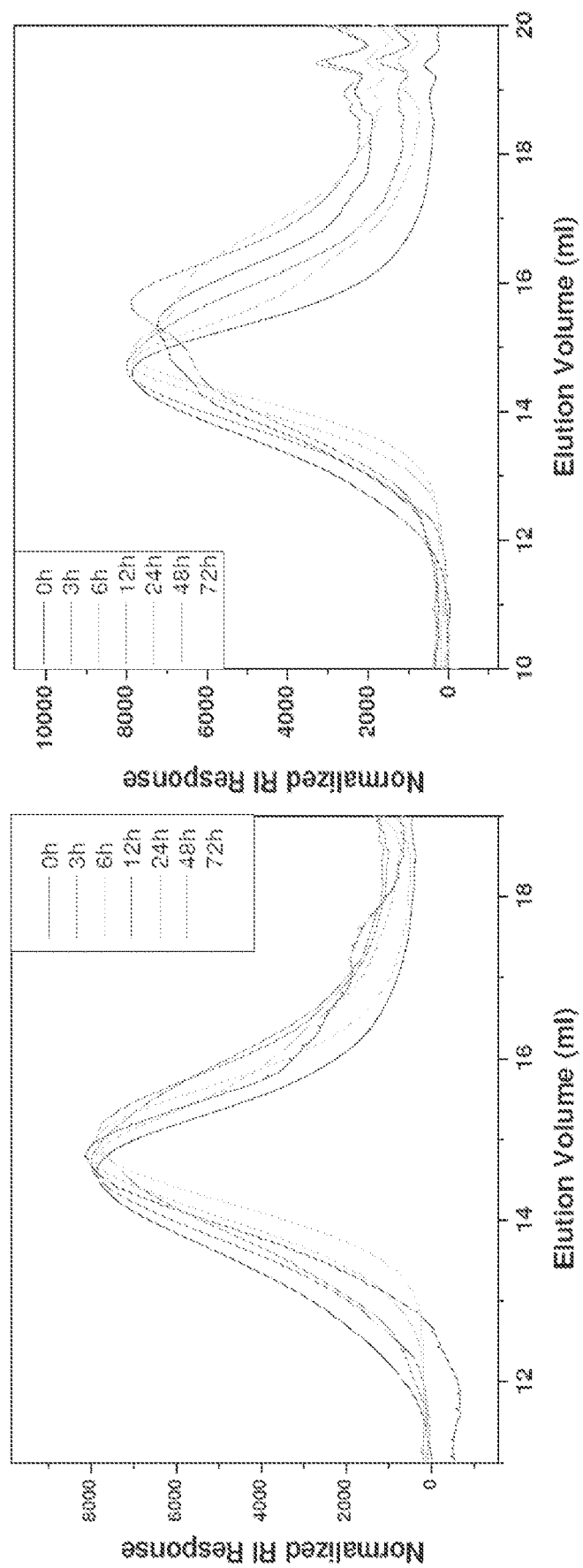
FIGS. 15A-E show degradation studies of the polyacetal P3a at various pH values.
Figure 15D:
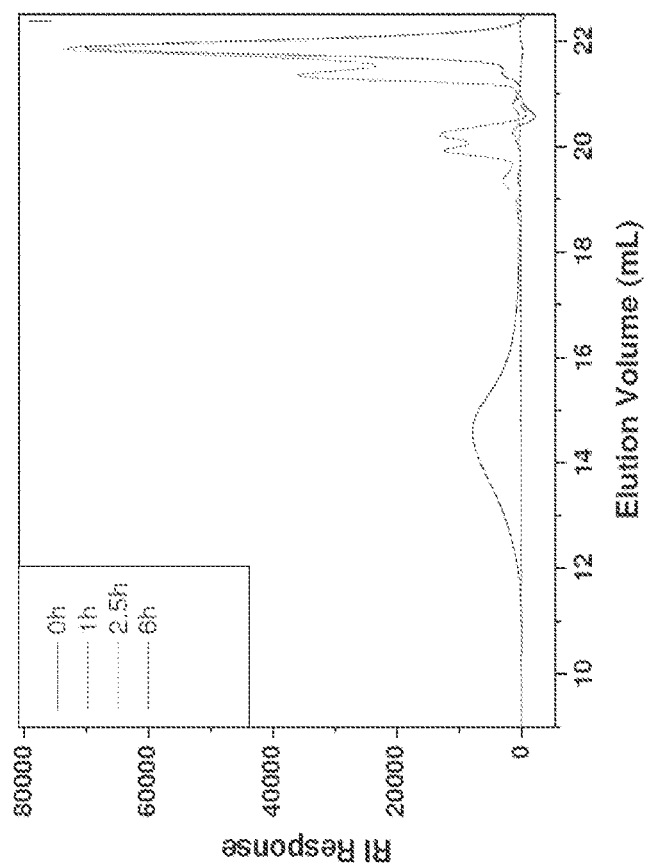
Figure 15C:
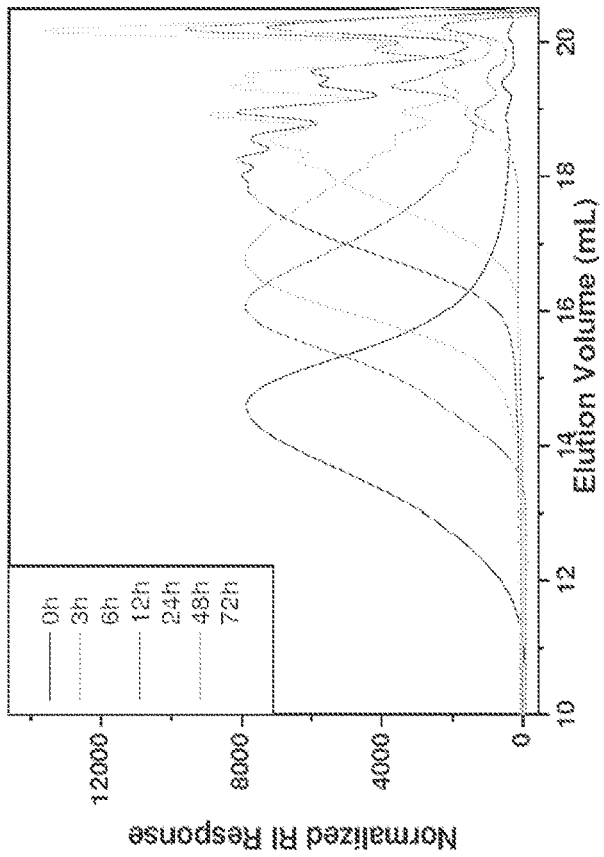
Figure 15E:
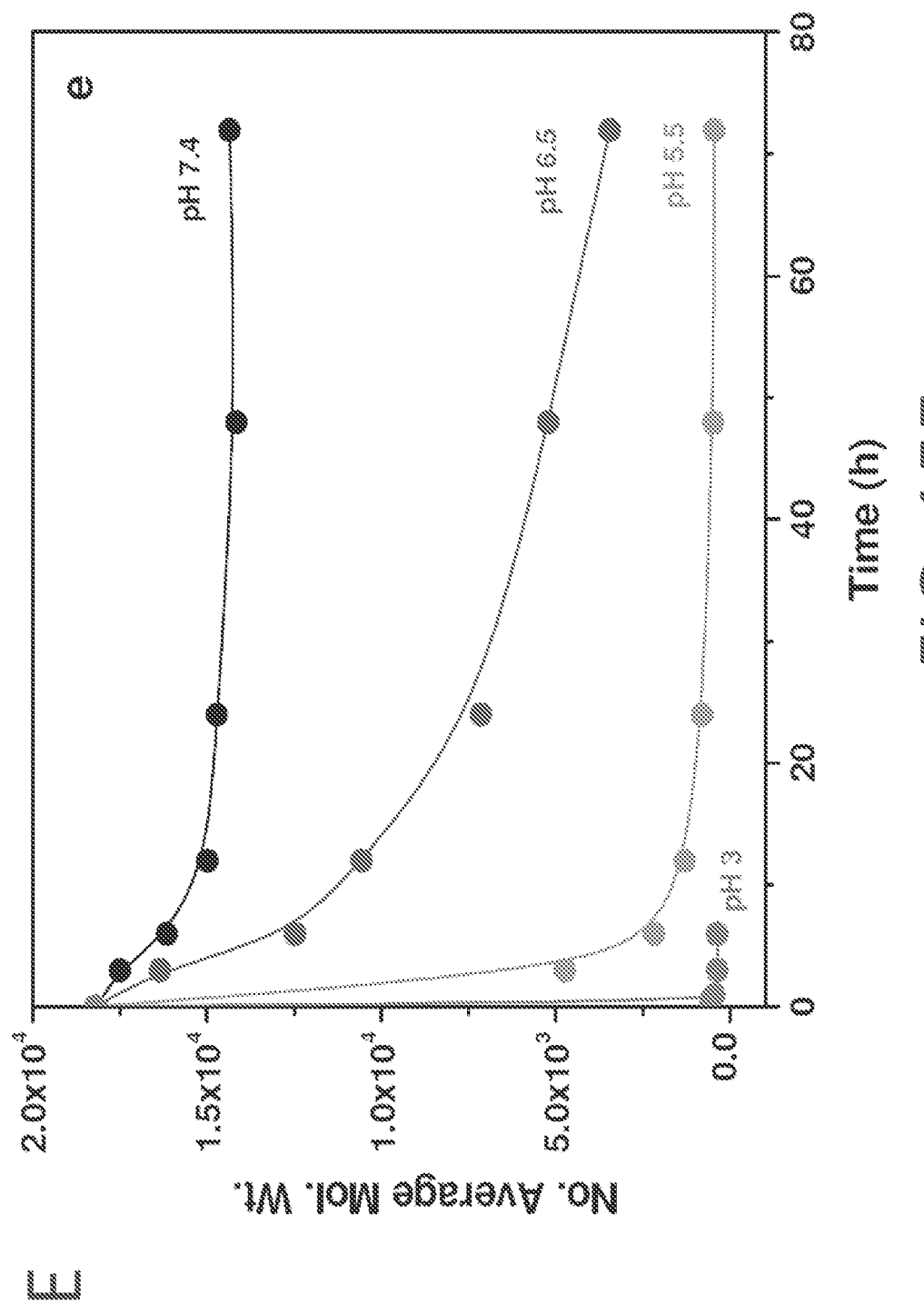

FIGS. 14A-D show the effect of the number of $CH_2$ groups on the LCST of polyacetals. (FIG. 14A) Synthetic scheme for polyacetal formation from divinyl ether (di(ethylene glycol) divinyl ether or tri(ethylene glycol) divinyl ether) and diol (ethylene glycol, 1,3-propanediol, 1,4-butanediol, or 1,5-pentanediol), wherein the molar feed ratio of the divinyl ether to the diol is 1.05 to 1. (FIG. 14B) The combined plots of % transmittance versus temperature for polyacetals formed from di(ethylene glycol) divinyl ether and diols that vary in the number of carbon atoms (heating shown in solid circle and solid line, cooling shown in empty circle and dotted line). (FIG. 14C) The combined plots of % transmittance versus temperature for polyacetals formed from tri(ethylene glycol) divinyl ether and diols that vary in the number of carbon atoms (heating shown in solid circle and solid line, cooling shown in empty circle and dotted line). (FIG. 14D) Plot of the experimental LCSTs versus number of $CH_2$ groups in the diol part of the polyacetal. The LCST is also linearly dependent on the number of hydrophobic methylene groups in the diol monomer (FIG. 14D). Each methylene unit in the diol decreases the LCST by 15.6° C., regardless of the number of ethylene oxide units in the vinyl ether monomer. Each ethylene oxide unit in the vinyl ether monomer adds 11.4° C. to the LCST. To our knowledge, no other TRP offers such structural control over the LCST. The LCST can be dialed to temperatures within the range 7-80° C. by selecting appropriate monomer mixtures.

FIGS. 15A-E show degradation studies of the polyacetal P3a at various pH values. (FIG. 15A) GPC trace for degradation of P3a at pH 7.4. (FIG. 15B) GPC trace for degradation of P3a at pH 6.5. (FIG. 15C) GPC trace for degradation of P3a at pH 5.5. (FIG. 15D) GPC trace for degradation of P3a at pH 3. (FIG. 15E) Plot of no. average molecular weight versus time (h) for the degradation study of P3a at different pH values.

Figure 16A:
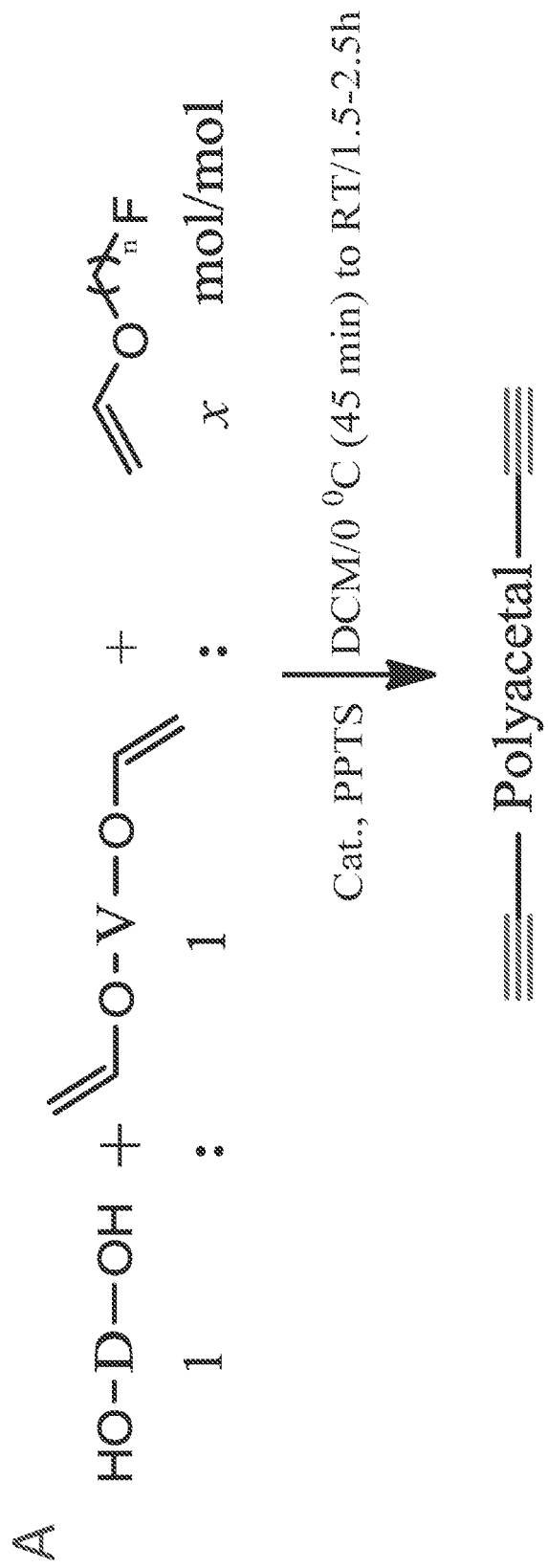
FIGS. 16A-B show (FIG. 16A) the strategy for the preparation of end-clickable polyacetals and (FIG. 16B) characterization of end group of modified polyacetal by proton NMR.
Figure 16B:
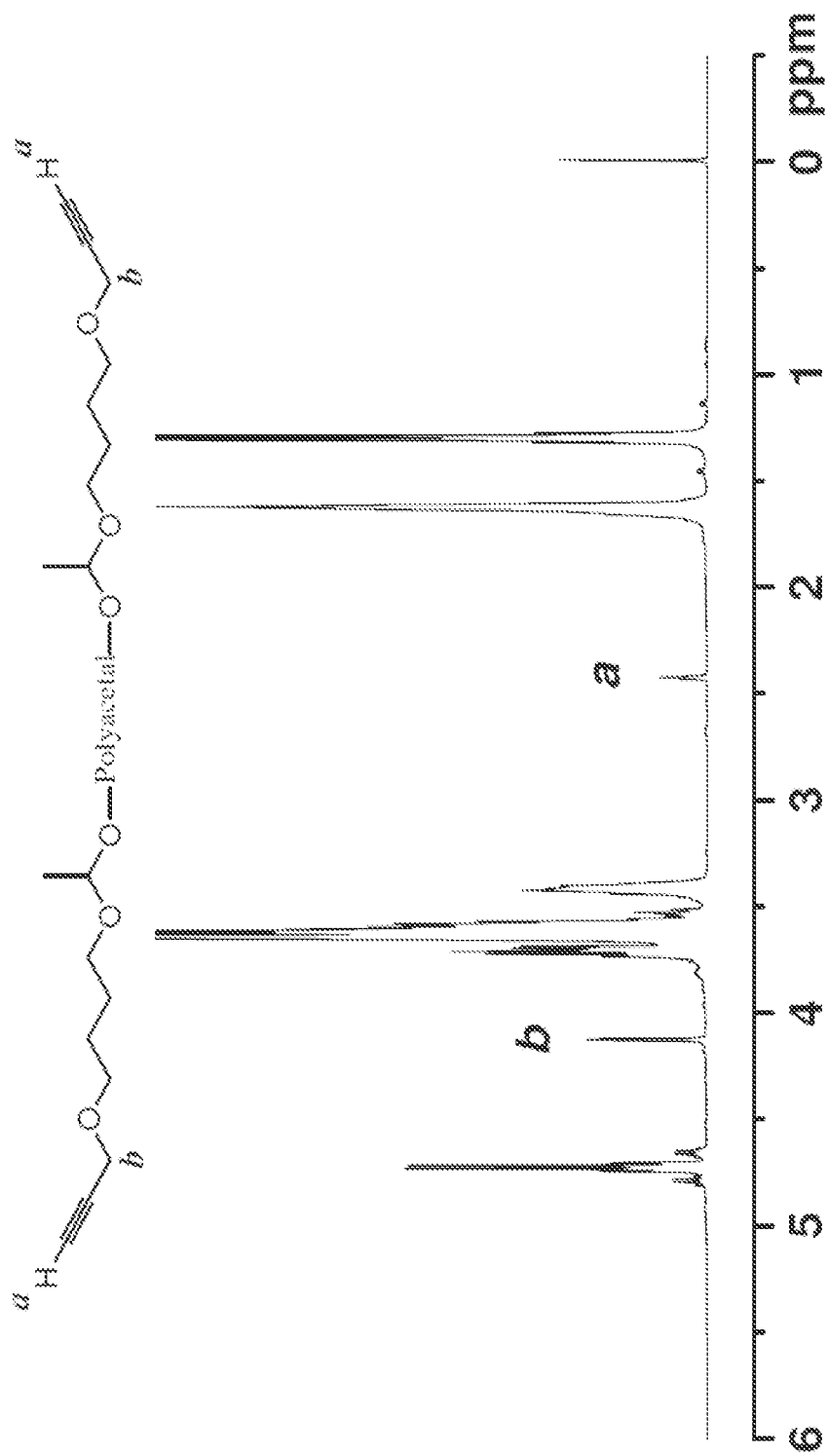

FIGS. 16A-B show (FIG. 16A) the strategy for the preparation of end-clickable polyacetals and (FIG. 16B) characterization of end group of modified polyacetal by proton NMR.

Figure 17A:
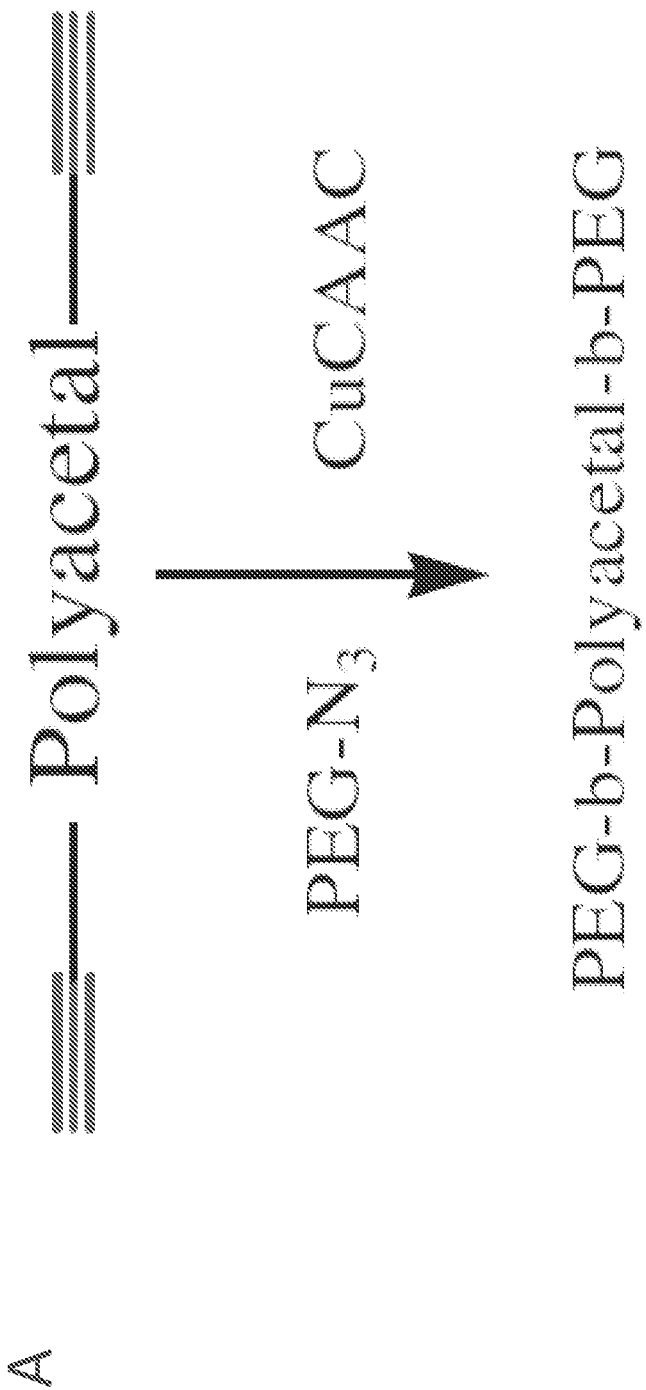
FIGS. 17A-B show (FIG. 17A) preparation of PEG-b-Polyacetal-b-PEG tri-block copolymer by "click" chemistry.
Figure 17B:
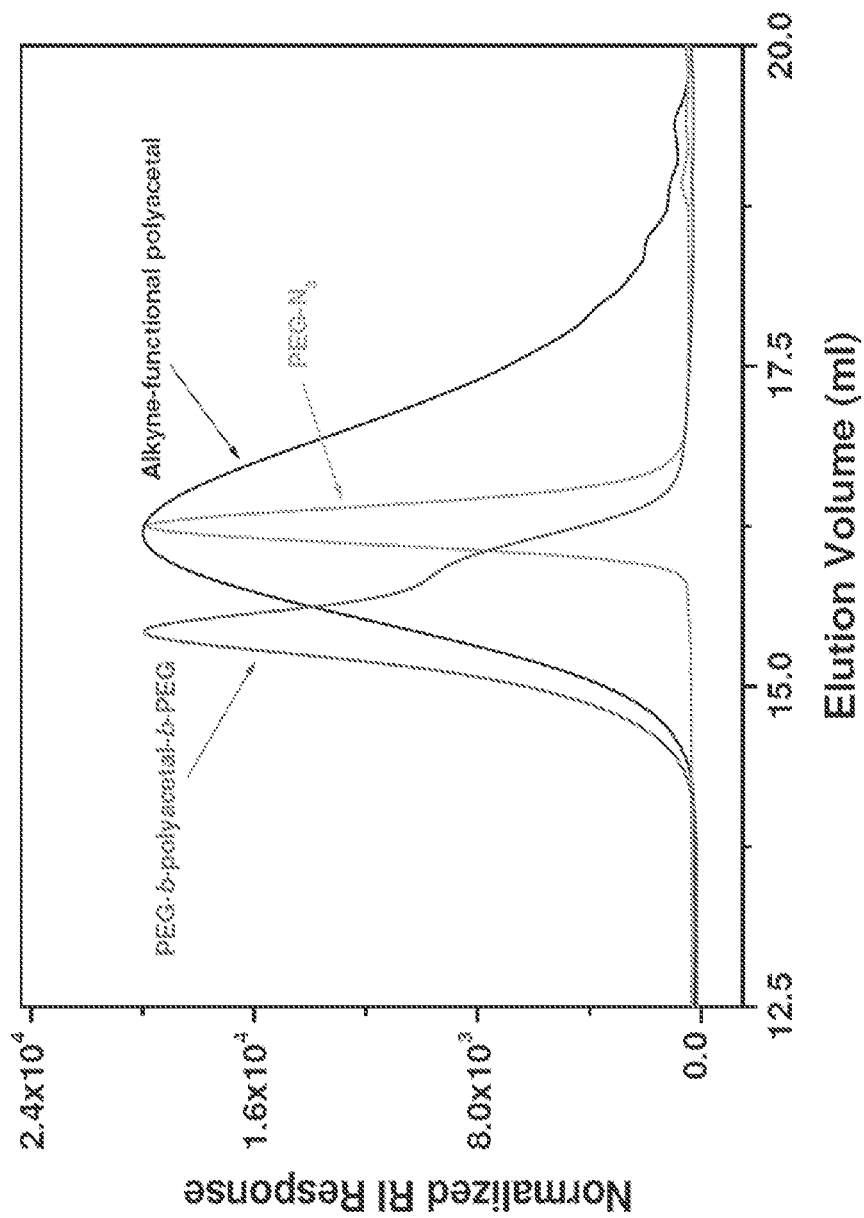

FIGS. 17A-B show (FIG. 17A) preparation of PEG-b-Polyacetal-b-PEG tri-block copolymer by "click" chemistry; (FIG. 17B) GPC traces of end-functional polyacetal, PEG-N3, and PEG-polyacetal-PEG tri-block copolymer.

Figure 18:
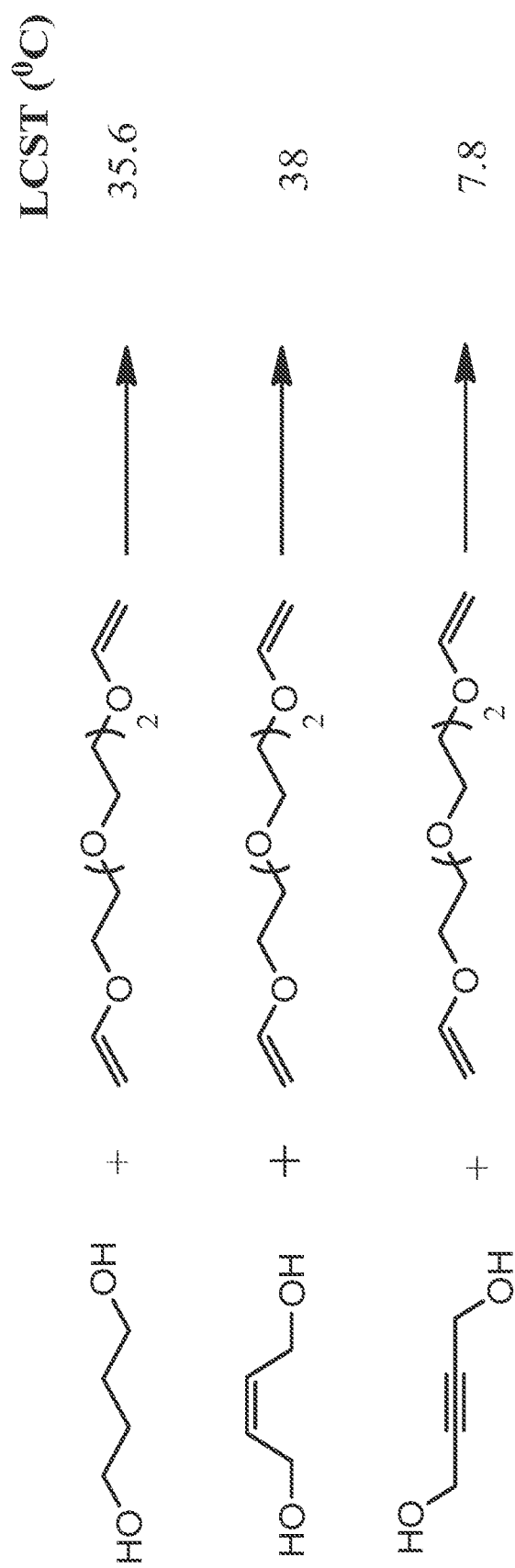
FIG. 18 shows the effect of hybridization on the LCST of polyacetal.

FIG. 18 shows the effect of hybridization on the LCST of polyacetal.

Figure 19:
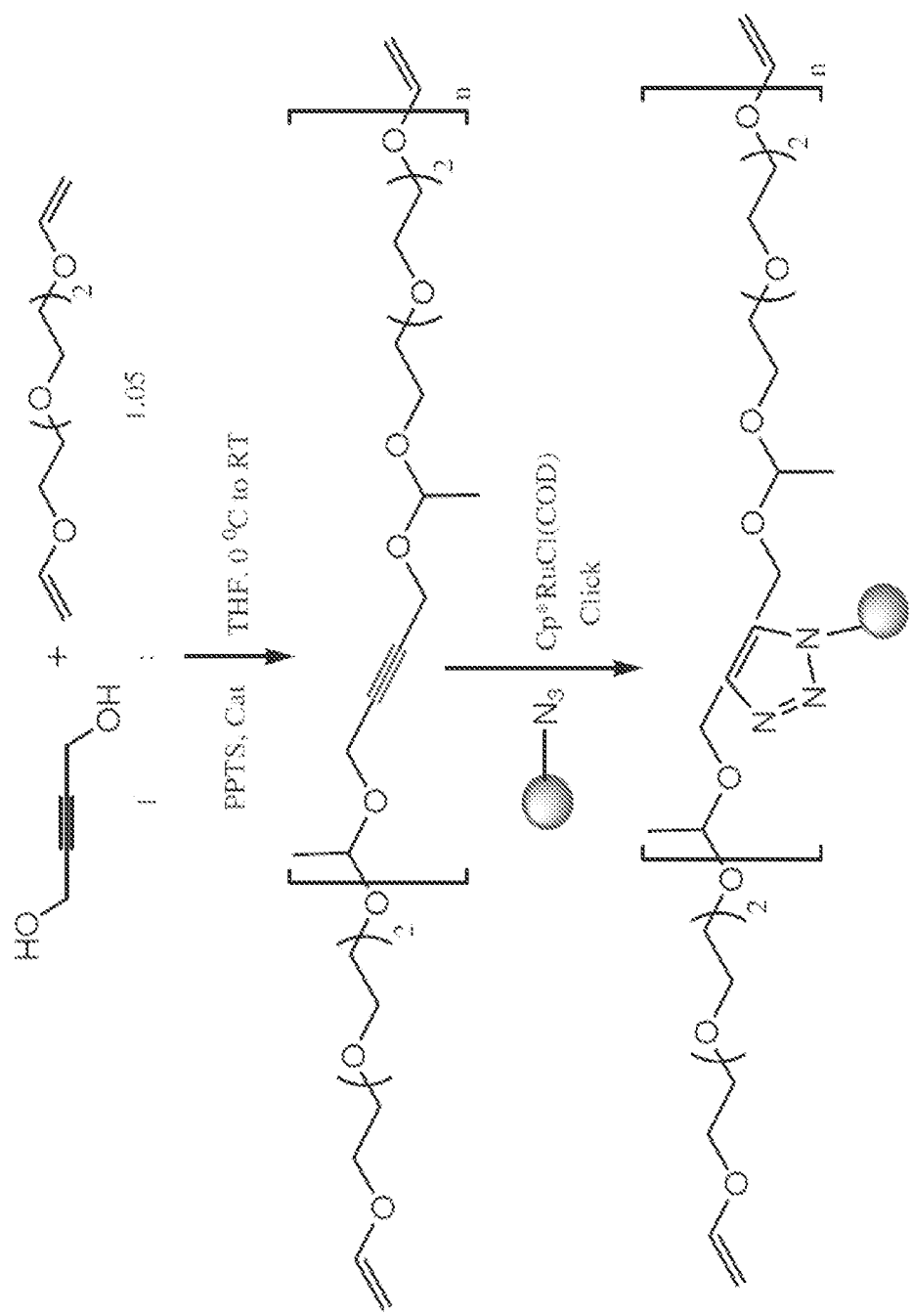
FIG. 19 shows an overview of the preparation of a main-chain clickable polyacetal and their click reactions.

FIG. 19 shows an overview of the preparation of a main-chain clickable polyacetal and their click reactions.

Figure 20A:
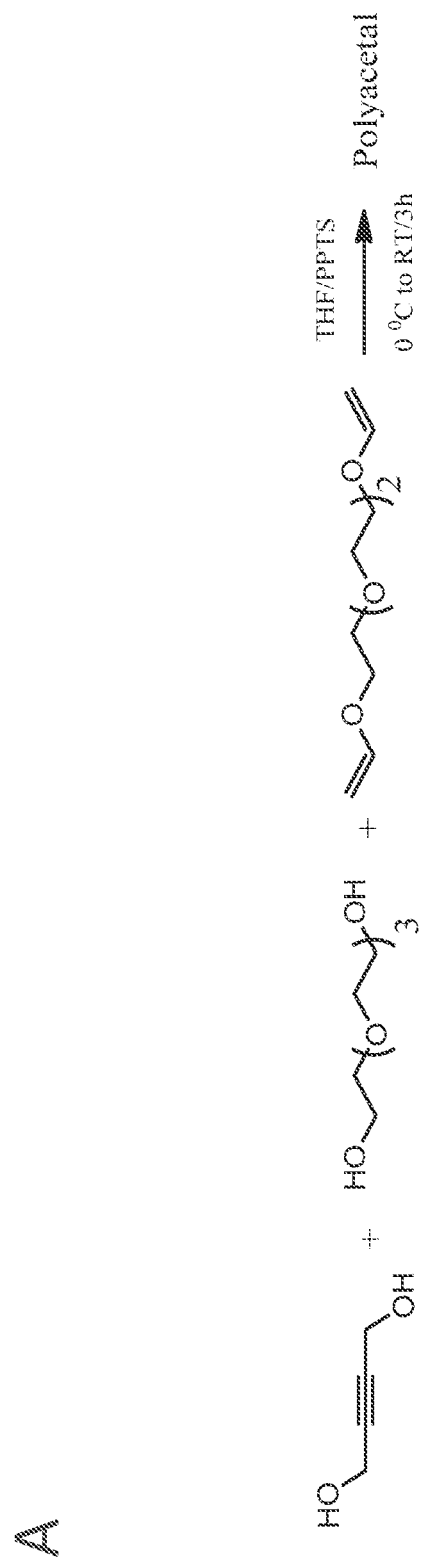
Figure 20B:
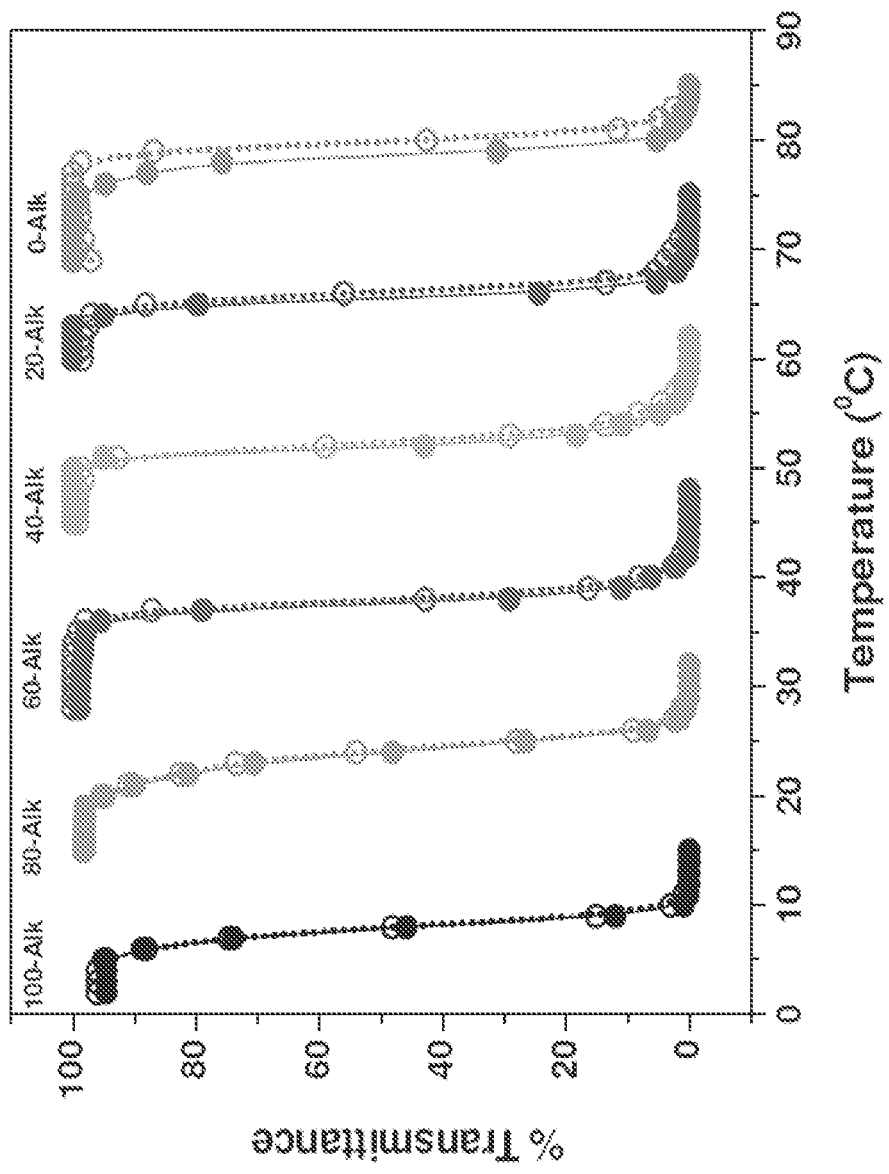
Figure 20C:
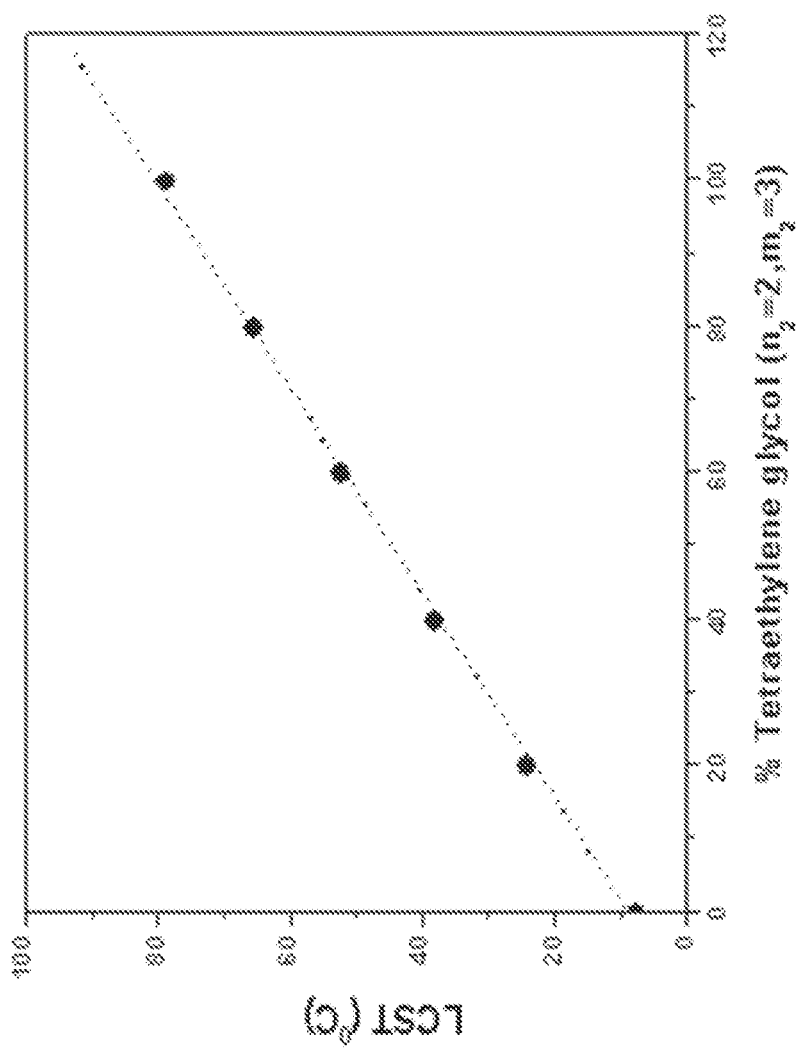
Figure 20D:
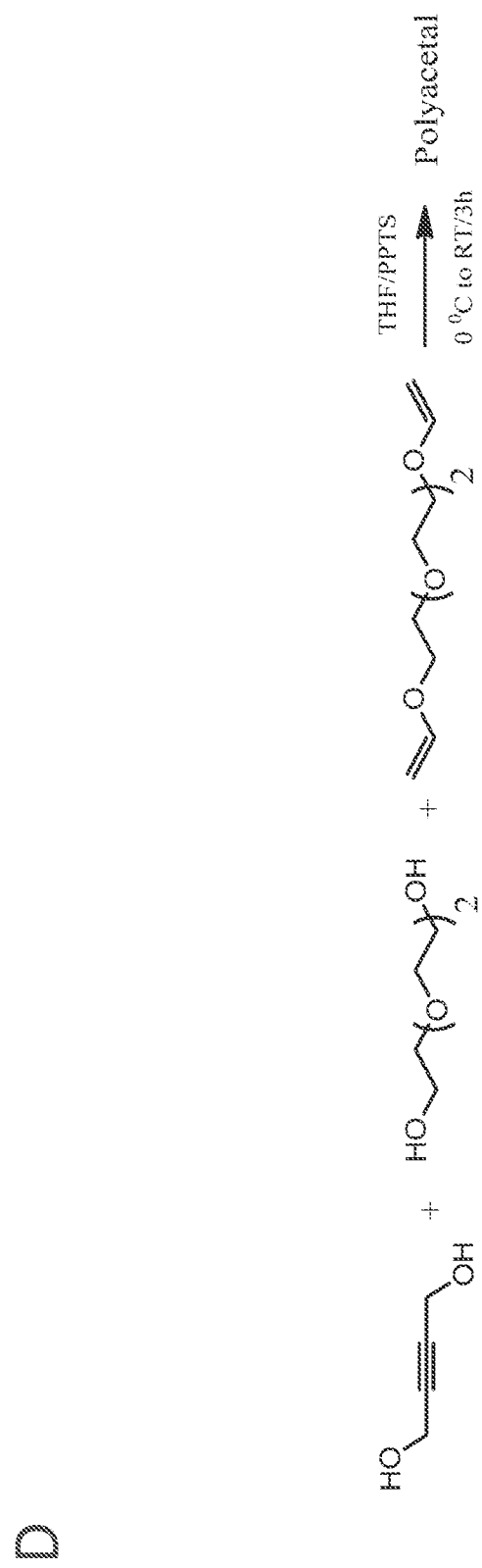
Figure 20E:
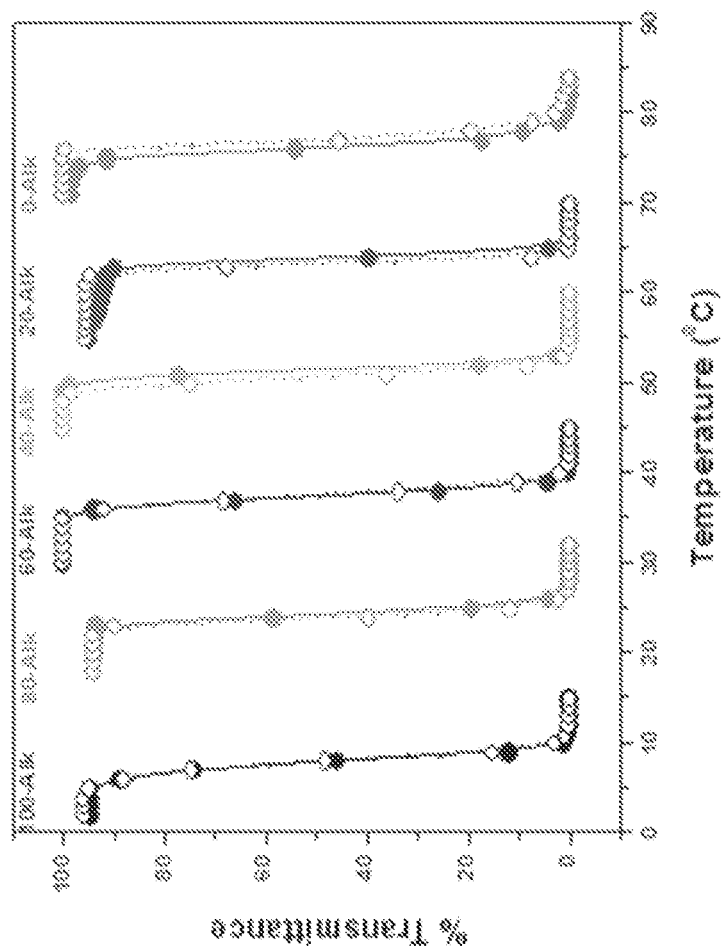
Figure 20F:
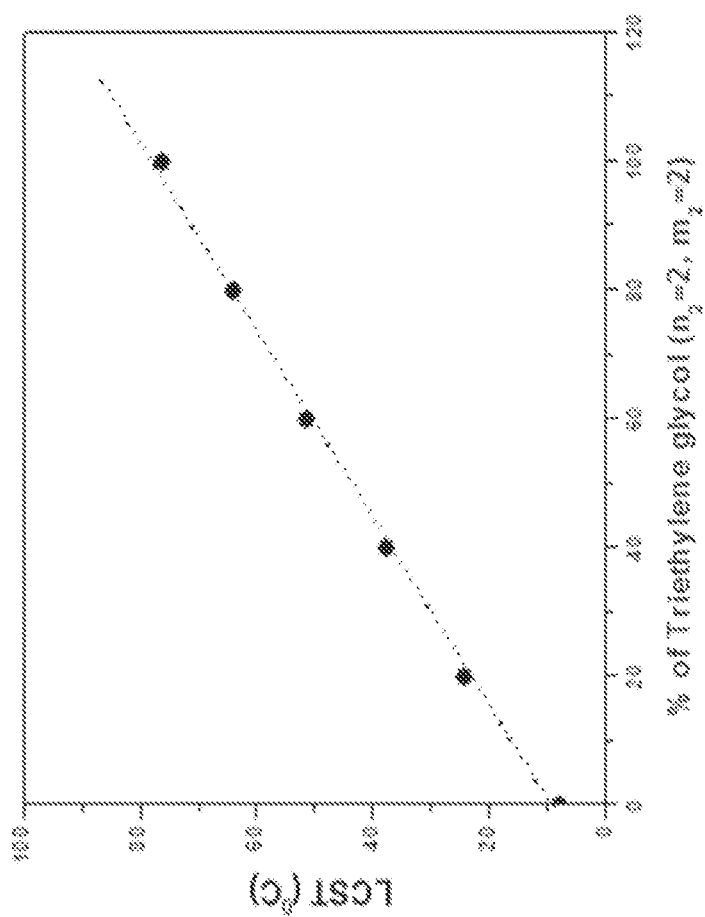
Figure 20G:
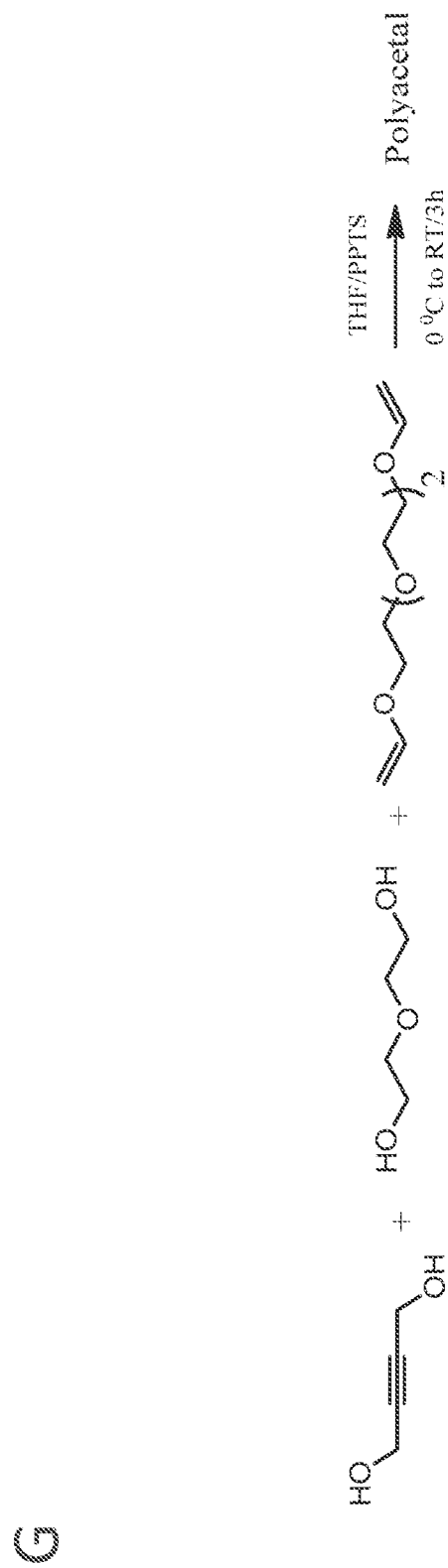
Figure 20H:
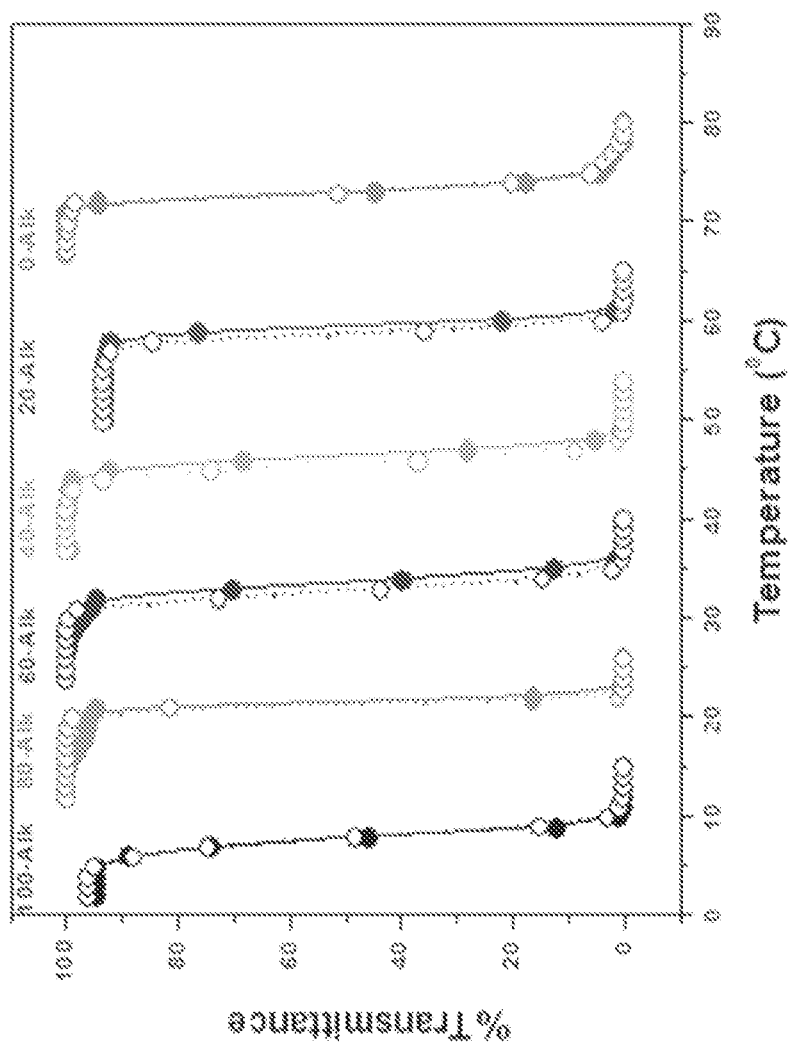
Figure 20I:
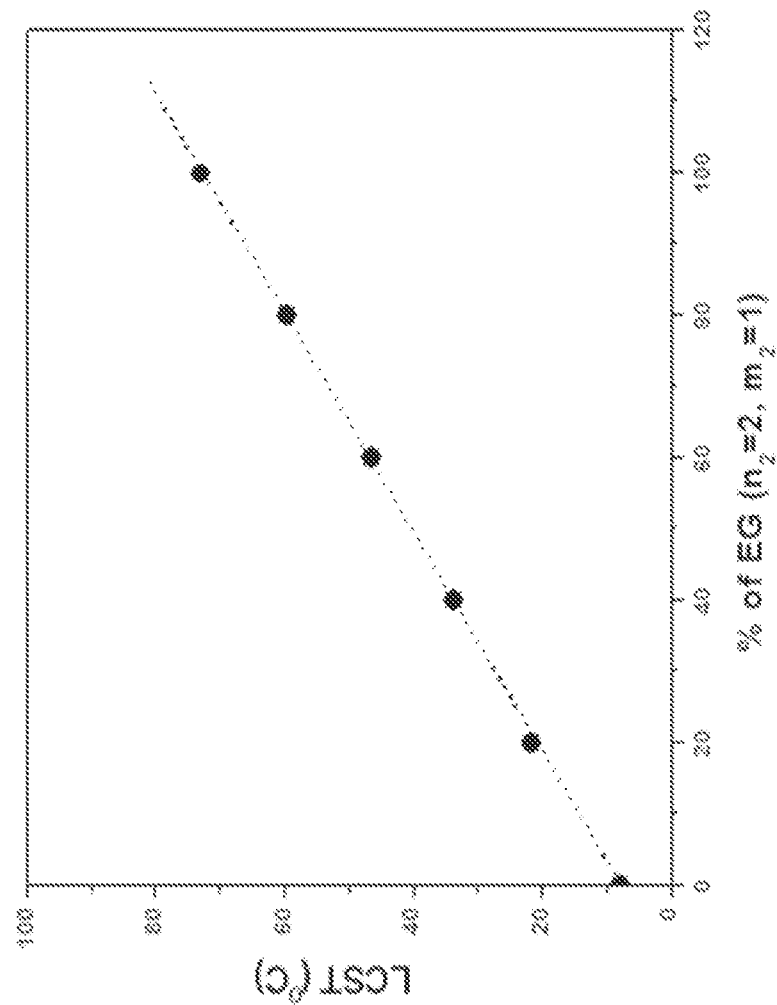
Figure 20J:
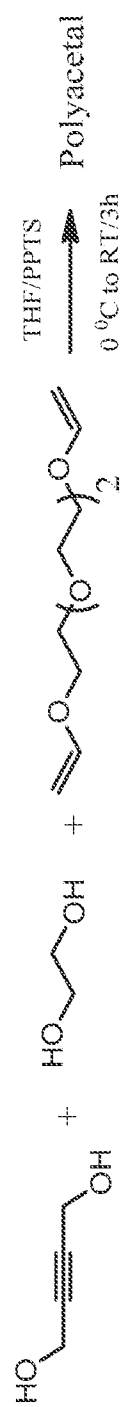
Figure 20K:
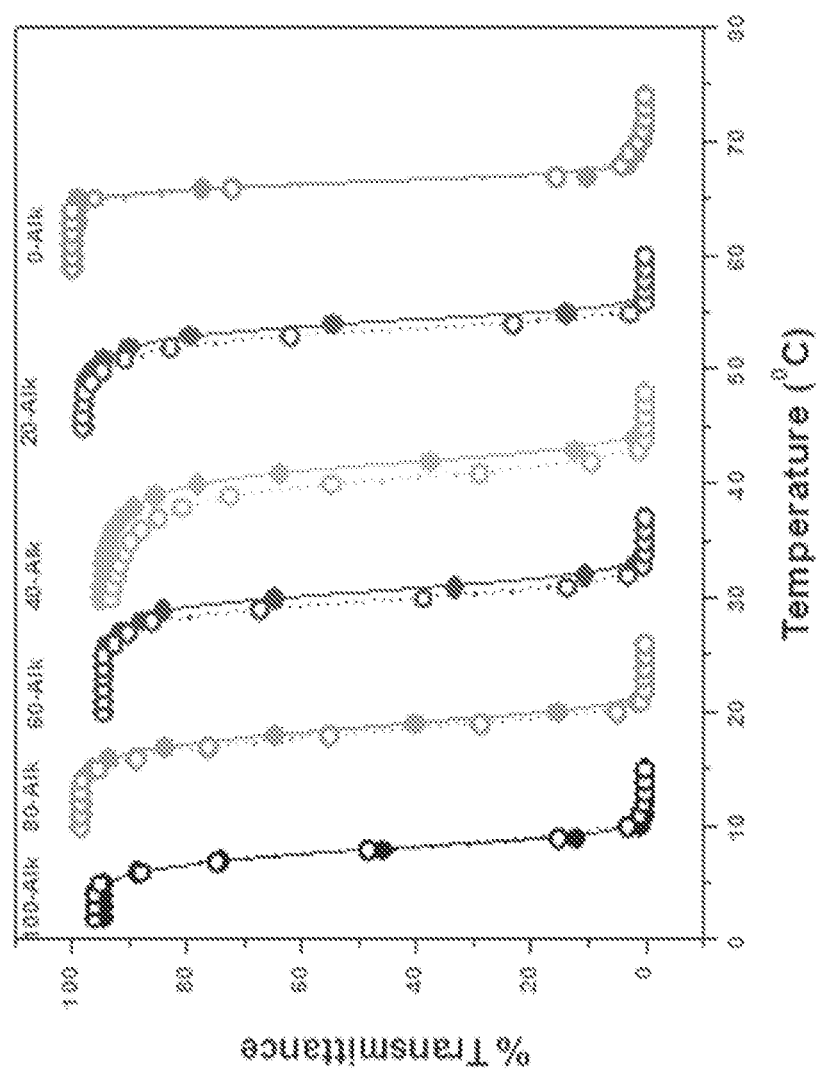
Figure 20L:
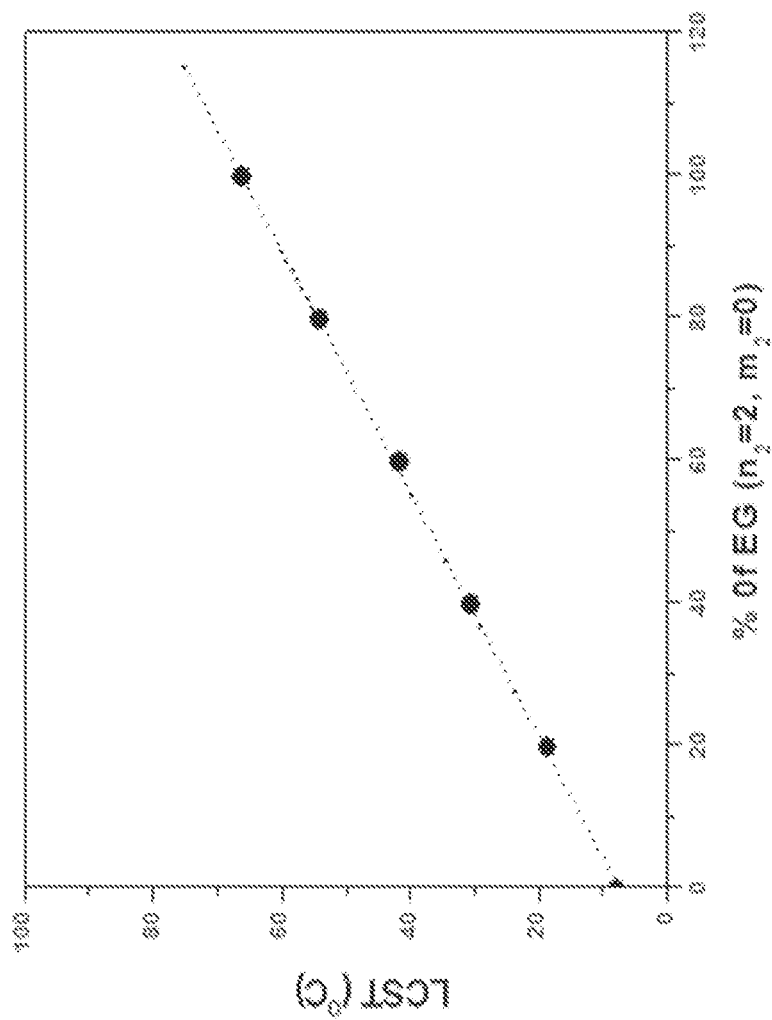

FIGS. 20A-M show the preparation of main-chain clickable polyacetal with higher LCST and related data. (FIG. 20A) Synthetic scheme for polyacetal formation from tri(ethylene glycol) divinyl ether, 1,4-butyne diol, and tetraethylene glycol, wherein the molar feed ratio of the divinyl ether to the diols is 1.05 to 1 and the molar feed ratio of diols is varied. (FIG. 20B) Combined plots of % transmittance versus temperature for polyacetals from FIG. 20A (heating shown in solid circle and solid line, cooling shown in empty circle and dotted line). (FIG. 20C) Plot of the experimental LCSTs versus different percentages of tetraethylene glycol for polyacetals from FIG. 20A. (FIG. 20D) Synthetic scheme for polyacetal formation from tri(ethylene glycol) divinyl ether, 1,4-butyne diol, and triethylene glycol, wherein the molar feed ratio of the divinyl ether to the diols is 1.05 to 1 and the molar feed ratio of diols is varied. (FIG. 20E) Combined plots of % transmittance versus temperature for polyacetals from FIG. 20D (heating shown in solid circle and solid line, cooling shown in empty circle and dotted line). (FIG. 20F) Plot of the experimental LCSTs versus different percentages of triethylene glycol for polyacetals from FIG. 20D. (FIG. 20G) Synthetic scheme for polyacetal formation from tri(ethylene glycol) divinyl ether, 1,4-butyne diol, and diethylene glycol, wherein the molar feed ratio of the divinyl ether to the diols is 1.05 to 1 and the molar feed ratio of diols is varied. (FIG. 20H) Combined plots of % transmittance versus temperature for polyacetals from FIG. 20G (heating shown in solid circle and solid line, cooling shown in empty circle and dotted line). (FIG. 20I) Plot of the experimental LCSTs versus different percentages of diethylene glycol for polyacetals from FIG. 20G. (FIG. 20J) Synthetic scheme for polyacetal formation from tri(ethylene glycol) divinyl ether, 1,4-butyne diol, and ethylene glycol, wherein the molar feed ratio of the divinyl ether to the diols is 1.05 to 1 and the molar feed ratio of diols is varied. (FIG. 20K) Combined plots of % transmittance versus temperature for polyacetals from FIG. 20J (heating shown in solid circle and solid line, cooling shown in empty circle and dotted line). (FIG. 20L) Plot of the experimental LCSTs versus different percentages of ethylene glycol for polyacetals from FIG. 20J. (FIG. 20M) Plot of the experimental LCSTs versus different percentages of diols ($n_2=2$; $m_2=0$ to $n_2=2$; $m_2=3$) for the polyacetals prepared from 1,4-butyne diol and tri-ethylene glycol divinyl ether ($n_1=2$; $m_1=2$) (diol/divinyl ether-1/1.05 (mol/mol)).

Example 30

Figure 21:
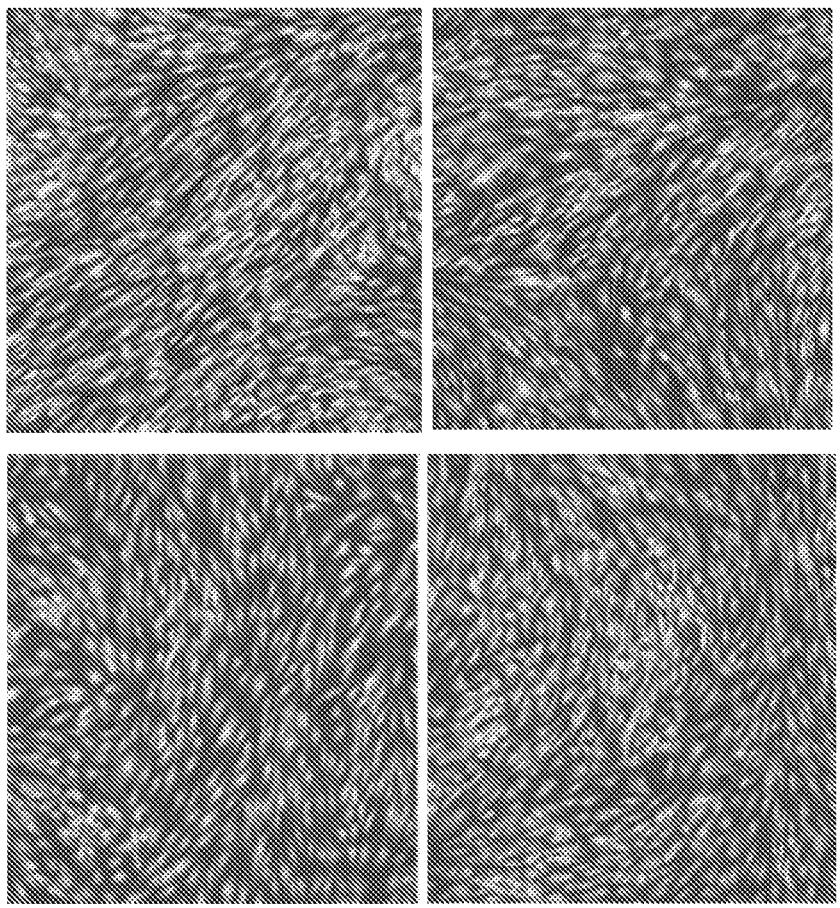
FIG. 21 shows micrographs of cell culture fibroblasts exposed for 72 hours to solutions containing 0, 0.1, 1, and 10 mg/mL (clockwise) of a soluble polyacetal.

Biocompatibility studies. Biocompatibility for polyacetals and pNIPAM using cell cultures (human ACL fibroblasts) indicate that the polyacetals are non-toxic and have biocompatibility equal to or superior than that of pNIPAM. FIG. 21 shows micrographs of fibroblasts exposed for 72 hours to solutions containing (clockwise) 0, 0.1, 1, and 10 mg/$m_1$ of a soluble polyacetal, respectively. Dead cells would show as red in these images. No red cells are observed, indicating that the polyacetals are biocompatible over an extended period of time.

Example 31

Homopolymers and Macromonomers. Alkyne main chain functionality can be incorporated by using an alkyne diol monomer as shown in FIG. 19. Virtually any azide modified moiety, represented by the sphere in the figure, can be grafted onto the main chain by a simple click reaction to form a triazole. The alkyne group was also selected for use because initial results show that these alkyne-functional polyacetals exhibit temperature responsive behavior with appropriate LCSTs.

Example 32

Figure 22:
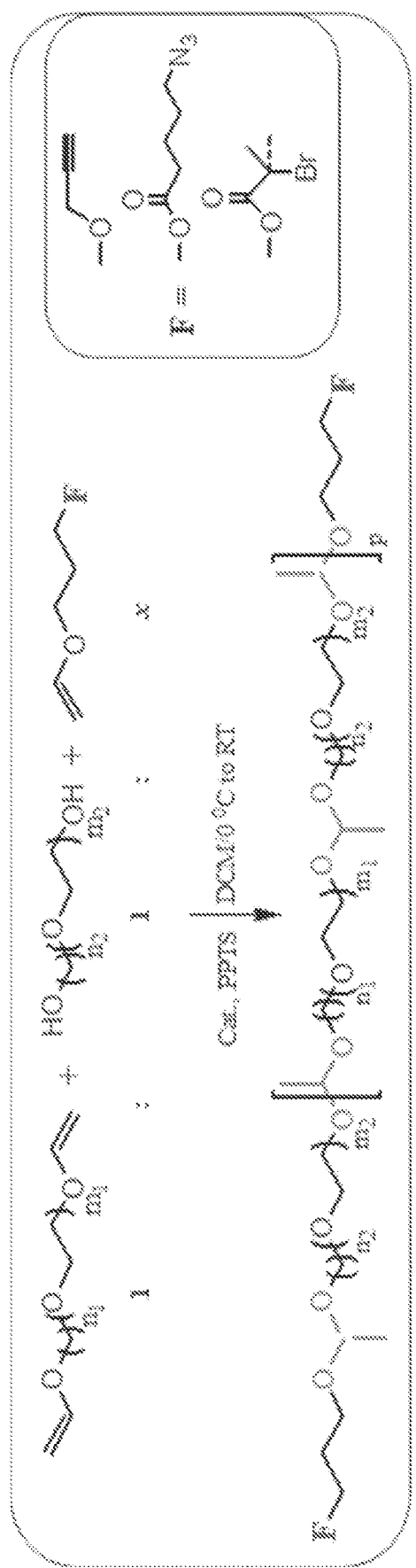
FIG. 22 shows an exemplary scheme for preparation of end-functional polyacetal macromonomers.

End-functional Polyacetal Macromonomers. FIG. 22 shows chain end modification with alkyne and azide functionalities to produce versatile click-functional macromonomers. A first amphiphilic triblock copolymer with a central hydrophobic PA block and terminal poly(ethylene oxide) blocks can be prepared by reacting alkyne terminated PA macromonomer with commercial azide-terminated poly (ethylene oxide) macromonomer. A second triblock can be prepared by reacting hydrophobic alkyne terminated PA midblock with an azide-terminated hydrophilic PA macromonomer. An excess of the hydrophilic PA macromonomer can be used to ensure that the product is primarily a mixture of diblock and triblock polymer with a central hydrophobic block. The two triblocks are dual-responsive amphiphilic triblock copolymers that can be used in pH degradable micellar therapeutic agent delivery.

Example 33

Polyacetals as macroinitiators for the preparation of block copolymers by atom transfer radical polymerization (ATRP) (Matyjaszewski, K.; Xia, J. Fundamentals of Atom Transfer Radical Polymerization. In Handbook of Radical Polymerization, Matyjaszewski, K. T.; Davis, T. P., Eds. Wiley-Interscience: New York, 2002; pp 523-628). Chain ends are modified with tertiary bromine chain ends that are initiators for ATRP as shown in FIG. 22. A block copolymer can be prepared with a hydrophobic PA midblock and PNIPAM end blocks, an interesting multi responsive amphiphilic block copolymer that can be used for micellar therapeutic agent delivery.

Example 34

Polyacetals as macroinitiators for the preparation of block copolymers by ring opening polymerization (ROP) (Albertsson, A.-C. Recent developments in ring opening polymerization of lactones for biomedical applications. *Biomacromolecules* 2003, 4, 1466-1486). ROP requires hydroxyl functional macromonomers, as have already been produced (see FIG. 9B), to prepare alkoxide-functional ROP macroinitiators. A triblock copolymer can be prepared with a hydrophilic PA midblock and degradable, hydrophobic polycaprolactone end blocks, another amphiphilic block copolymer that can be used for micellar therapeutic agent delivery (Hutmacher, D. W. Mechanical properties and cell cultural response of polycaprolactone scaffolds designed and fabricated via fused deposition modeling. Journal of Biomedical Materials Research 2001, 55, 203-216).

Example 35

Figure 23:
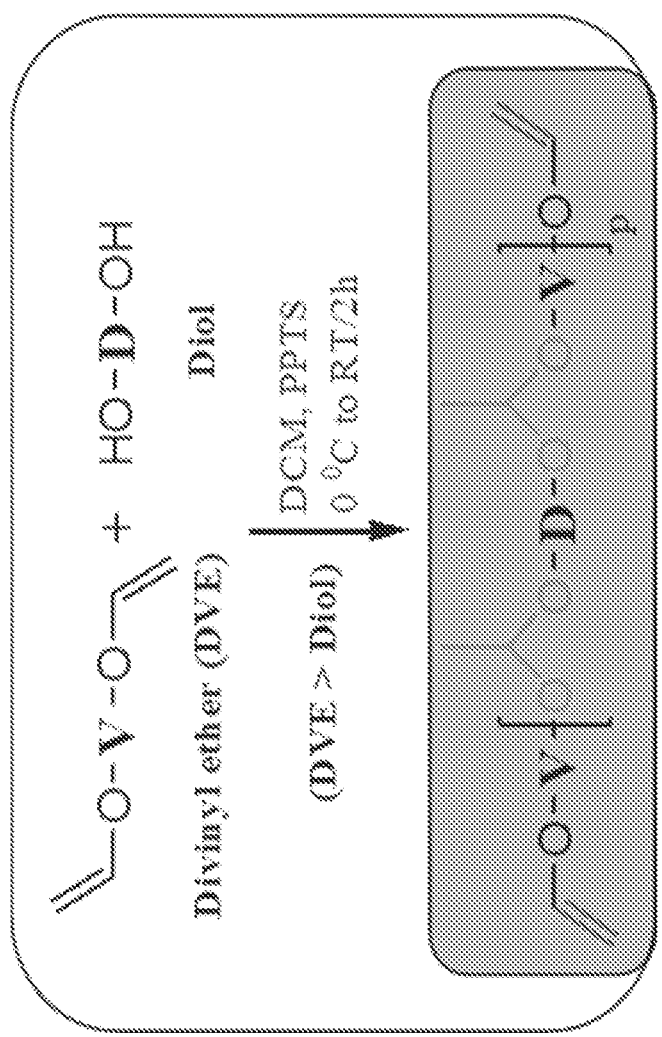
FIG. 23 shows an exemplary scheme for preparation of polyacetals with vinyl termini from divinylethers and diols.
Figure 24:
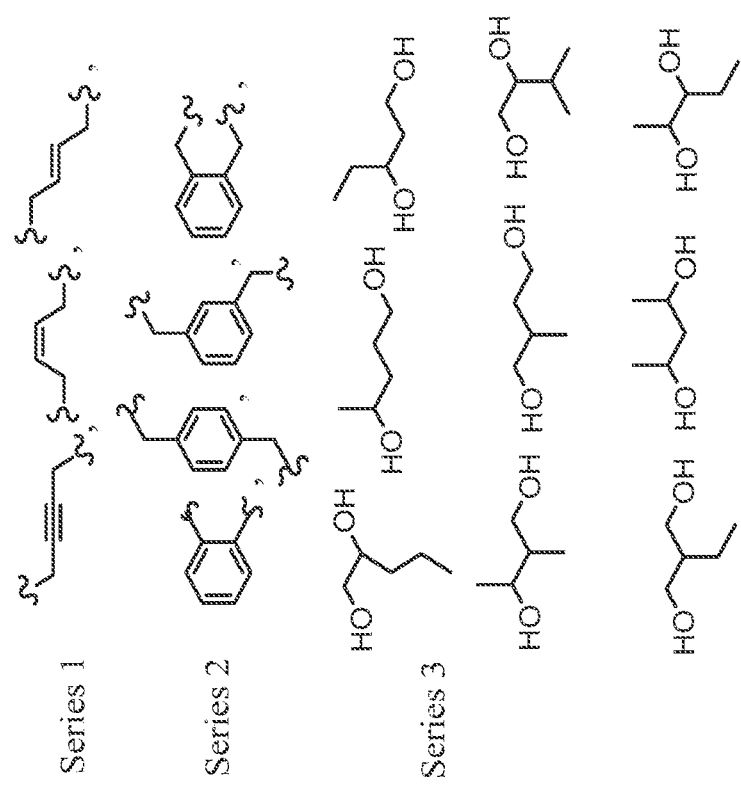
FIG. 24 shows three exemplary series of diols used to make polyacetals.

Polyacetals from several new series of diols to provide additional data on the dependence of the LCST on the monomer structure. The PAs can be prepared from divinyl ether (V) and a diol (D) as shown in FIG. 23. A first series of diols differs in the hybridization of the central carbon atoms, while the second series introduces aromatic groups into the backbone and the third series involves a group of pentane diol isomers, as shown in FIG. 24.

Example 36

Figure 25A:
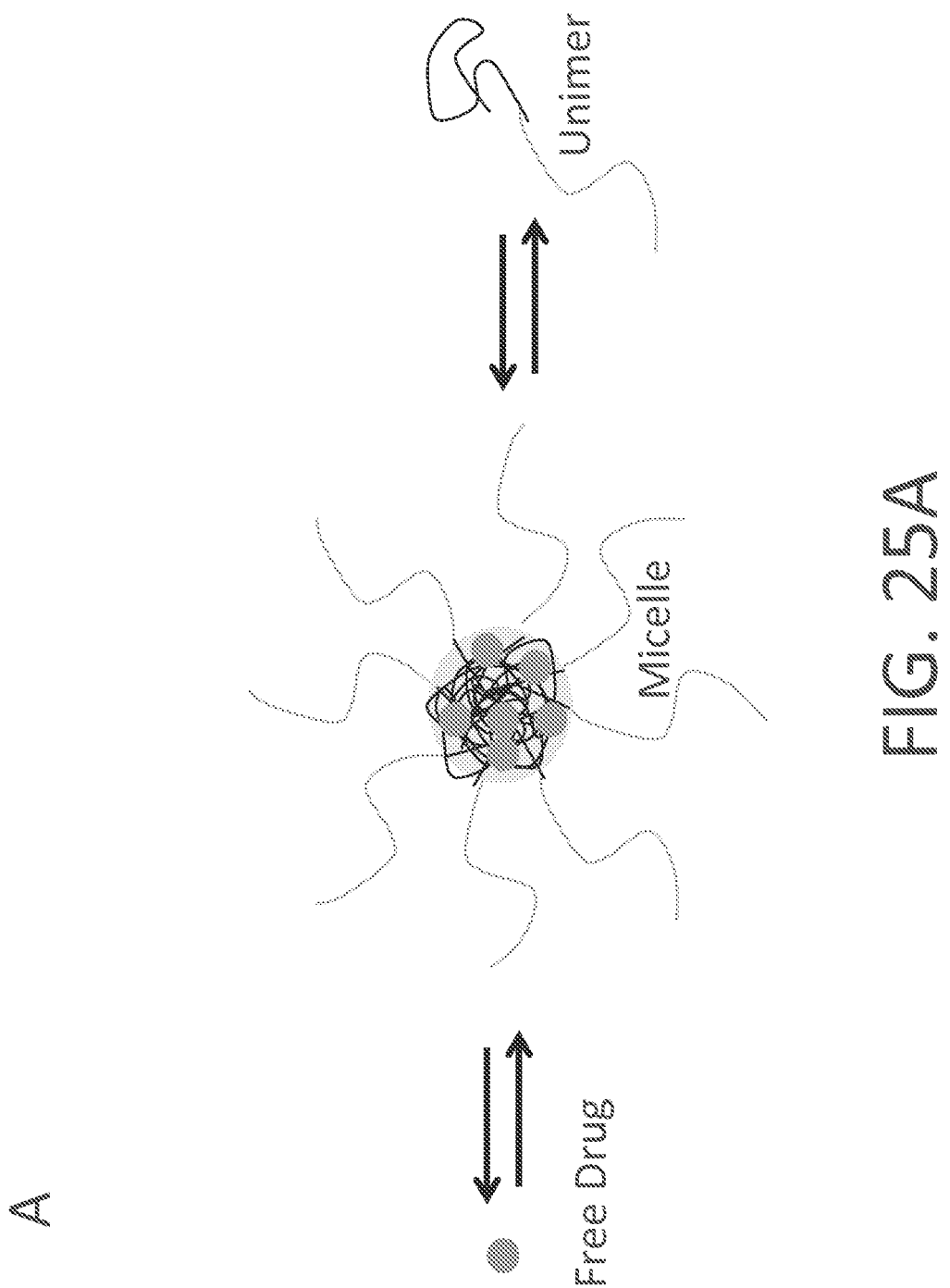
FIGS. 25A-C show an exemplary therapeutic agent delivery mechanism of block copolymer micelles (FIG. 25A) micelles in solution before delivery.
Figure 25B:
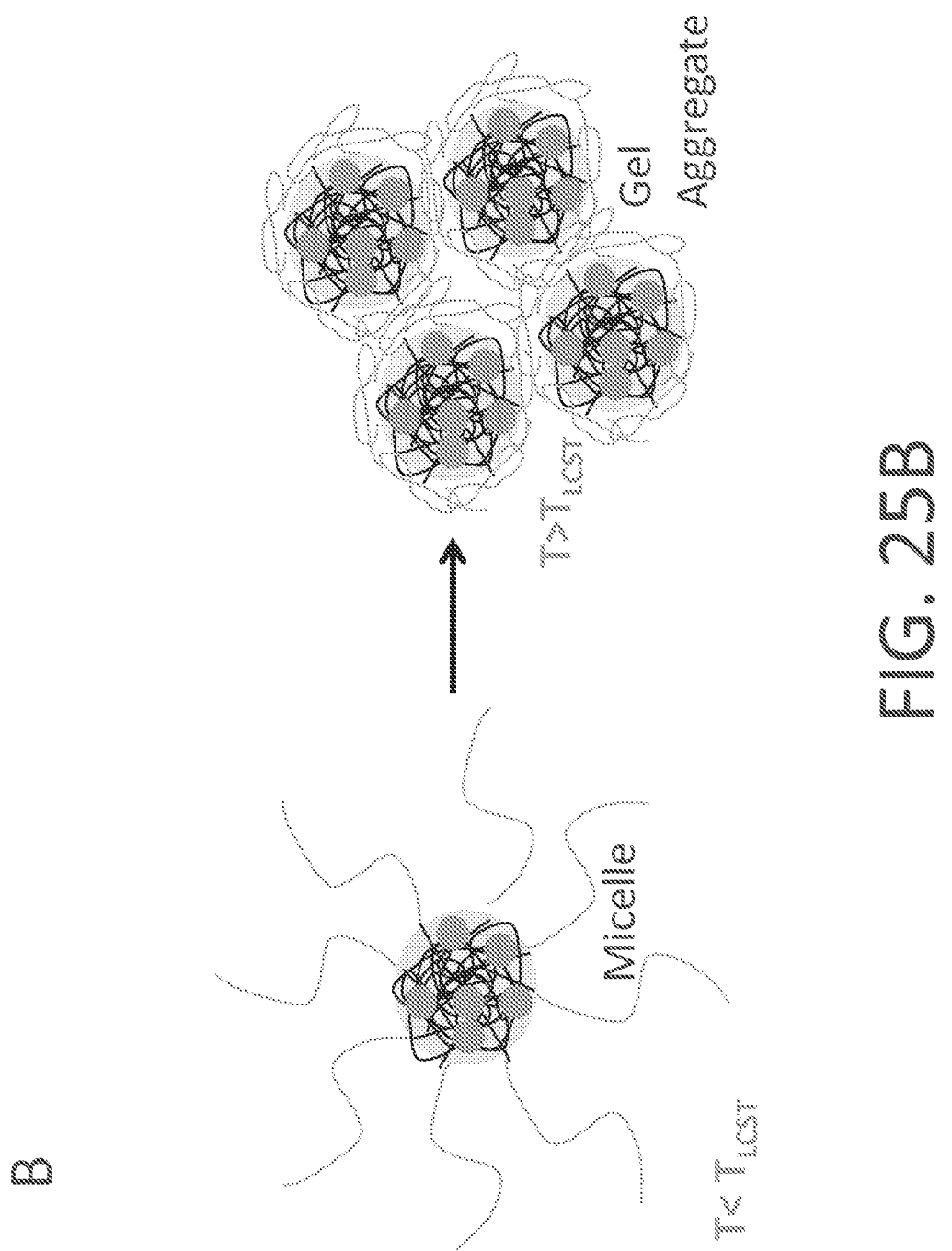
Figure 25C:
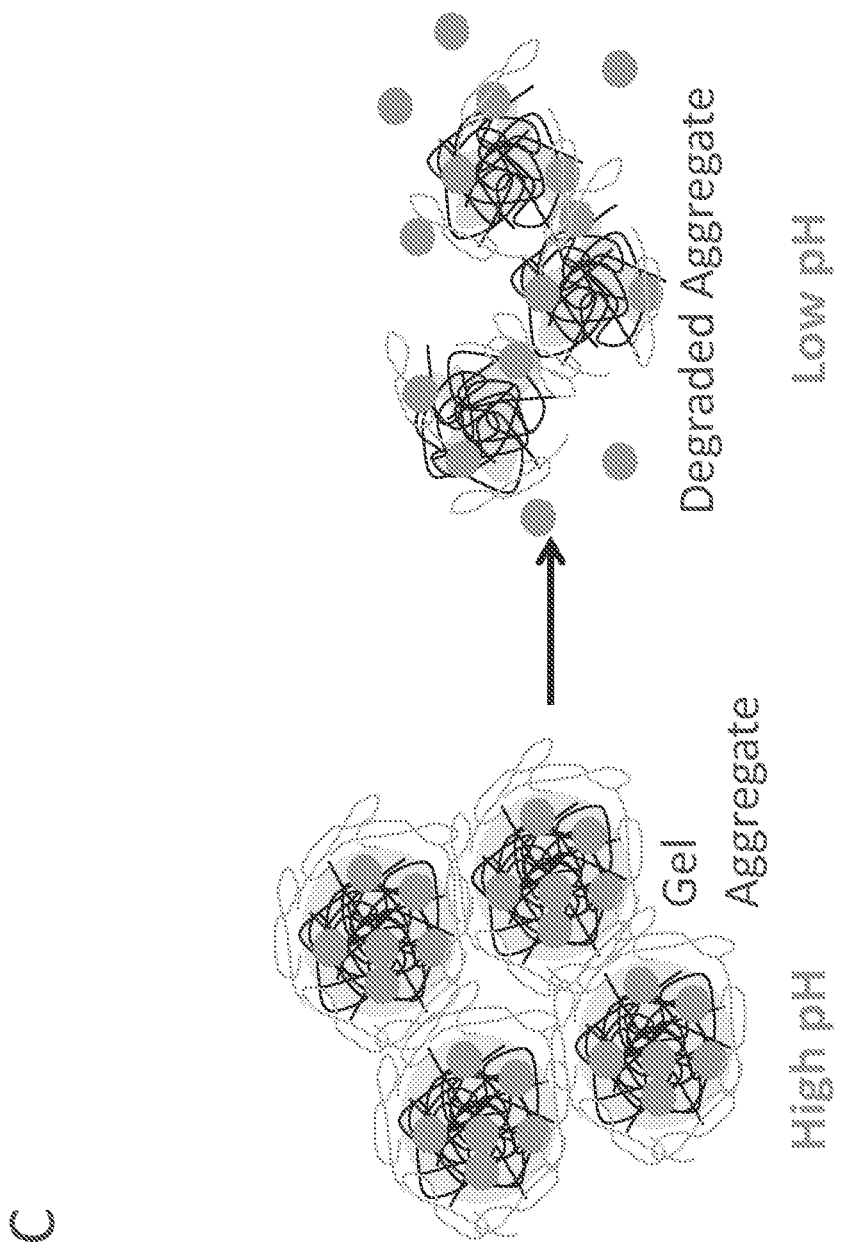

Gels and Block Copolymers. Methods to incorporate PA homopolymers into structured materials can also be developed, such as micelles and hydrogels. The potential mechanism of therapeutic agent delivery for these two vehicles is similar, and is illustrated for micellar therapeutic agent delivery to a tumor in FIG. 25A-C. The micelles are initially well dispersed in aqueous solution of neutral pH (FIG. 25A). The hydrophobic block forms an insoluble micelle core that serves as a reservoir for hydrophobic therapeutic agents and the hydrophilic block forms a corona that disperses the micelle into aqueous media. There is equilibrium between free therapeutic agent and therapeutic agent dissolved within the core of the micelle, and also between free block copolymer dissolved in the aqueous phase (unimer) and block copolymer in the micellar phase. The latter is controlled by the critical micelle concentration (cmc) which marks the concentration at which the micelles first form and which also dictates the unimer concentration in solution. Delivery of active agents using micelles and/or particles is disclosed, e.g., in U.S. Pat. No. 7,951,846, U.S. Patent Publication No. 2009/0011993, *Bioconjugate Chem.* 2008, 19, 911-919, and *RSC Adv.* 2015, 5, 37451.

Once injected, the therapeutic agent delivery vehicles experience a temperature rise sufficient to cause them to fall out of solution and form insoluble aggregates. The acidic environment within the gut or a tumor causes the PA portion(s) of the vehicle to degrade, thereby releasing encapsulated or bound therapeutic agents. Upon injection into a tumor, therapeutic agent laden micelles enter an environment that is about 1-2 degrees warmer than body temperature (~37° C.). At this temperature (FIG. 25B), the hydrophilic PA coronae collapse and the micelles fall out of solution to form an insoluble, immobilized gel of micellar aggregates. The gel experiences a pH ranging from 5-6.5 within the tumor, causing both PA blocks degrade (FIG. 25C); the hydrophilic PA block, rapidly, and the hydrophobic PA block in a controlled manner dictated by its hydrophobicity. Because both therapeutic agent delivery vehicles are nanoscale, they can pass easily through the syringe used for direct tumor injection.

Example 37

Figure 26:
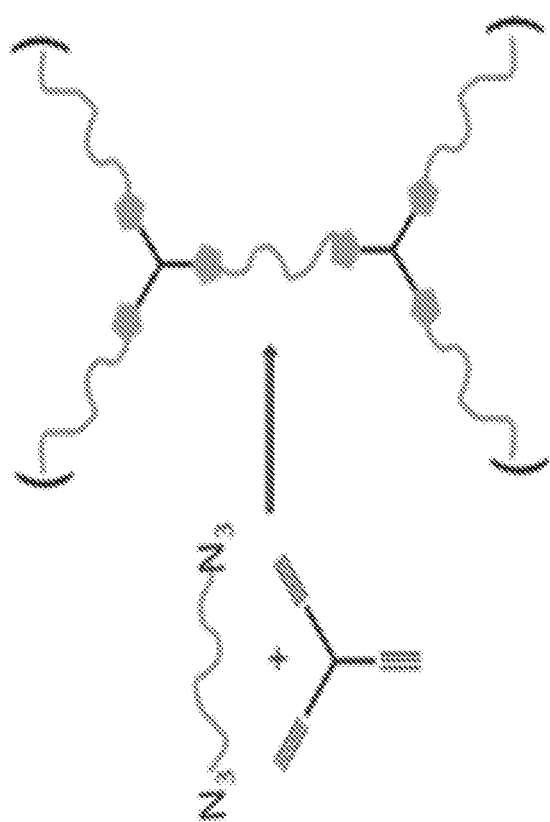
FIG. 26 shows an exemplary formation of end-linked gels by click chemistry using trifunctional cross-linkers and azide-terminated polyacetal macromonomers.

Gels. PA hydrogels can be prepared by synthesizing end-functional macromonomer polyacetals and end-linking with multifunctional crosslinkers. Azide-alkyne click chemistry is particular well suited for this purpose and can be used to prepare end-linked PA gels (Kolb, H. C.; Finn, M. G.; Sharpless, K. B. Click Chemistry: Diverse Chemical Function from a Few Good Reactions. *Angew. Chem. Int. Ed. Engl.* 2001, 40(11), 2004-2021). Tri-isocyanates can also serve as cross-linkers between macomonomer polyacetals to form urethane linkages. Exemplary tri-isocyanates include triphenylmethane-4,4',4"-triisocyanate, 1,3,5-cyclohexane triisocyanate, and 1,3,5-benzene triisocyanate (Krol, P.; Pilch-Pitera, B. *J. Appl. Poly. Sci.* 2008, 107, 1439-1448; U.S. Pat. No. 3,551,469; and Atkinson, S. J.; Ellis, V.-J.; Boyd, S. E.; Brown, C. L. *New J. Chem.* 2007, 31, 155-162). End-functional PAs can be prepared as described in FIG. 22 using an end capping agent to impart functionality (exemplary functionality is denoted as F in FIG. 22). End-linked hydrogels can be prepared by curing diazido-PA macromonomers (where each end of the PA macromonomer is terminated with an azide) with tri- and tetra-functional alkyne crosslinkers such as those reported in, for example, Johnson, J. A.; Lewis, D. R.; Az, D.; Finn, M. G.; Koberstein, J. T.; Turro, N. J. Synthesis of Degradable Model Networks via ATRP and Click Chemistry. *J. Am. Chem. Soc.* 2006, 128, 6564-6565; and Johnson, J. A.; Finn, M. G.; Koberstein, J. T.; Turro, N. J. Construction of Linear Polymers, Dendrimers, Networks, and Other Polymeric Architectures by Copper-Catalyzed Azide-Alkyne Cycloaddition "Click" Chemistry. *Macromol. Rapid Commun.* 2008, 29, 1052-1072; and WO 10/053993. Macroscopic gels can be made by reacting polyacetal macromonomers of fixed MW and varying hydrophilicity with a trifunctional alkyne crosslinker as illustrated in FIG. 26. The pentagons denote triazole linkages that result from the reaction of an alkyne and an azide.

Gel microspheres can also be prepared by emulsion methods (Matalanis, A.; McClements, D. J. Hydrogel Microspheres for Encapsulation of Lipophilic Components: Optimization of Fabrication & Performance. *Food Hydrocoll.* 2013, 31, 15-25). Nanogel particles can be prepared by reactions in inverse microemulsions (Landfester, K. The Generation of Nanoparticles in Miniemulsions. *Adv. Mater.* 2001, 13, 765-768; Landfester, K.; Musyanovych, A. Hydrogels in Miniemulsions. In Chemical Design of Responsive Microgels; Pich, A and Richtering, W, Ed.; *Advances in Polymer Science* 2010; 234, 39-63; Raemdonck, K.; Demeester, J.; De Smedt, S. Advanced Nanogel Engineering for Drug Delivery. *Soft Matter* 2009, 5, 707-715; Landfester, K. Synthesis of Colloidal Particles in Miniemulsions. *Annu. Rev. Mater. Res.* 2006, 36, 231-279).

Swelling ratio of the PAs can be tailored by adjusting the balance between the hydrophobic structural variables, n1 and n2, and the hydrophilic structural variables, m1 and m2. The swelling ratio can be measured for macrogels, and results correlated with the relative hydrophobicity as reflected in the log P values of the monomers and with the LCSTs of the macromonomers. The swelling ratio can be measured according to known procedures (Carroll, G. T.; Triplett, L. D.; Moscatelli, A.; Koberstein, J. T.; Turro, N. J. Photogeneration of Gelatinous Networks from Pre-Existing Polymers. *Journal of Applied Polymer Science,* 2011, 122, 168-174). The degradation rates for macroscopic gels, microgels, and nanogels can be measured as a function of the pH. Degradation rates can be determined by GPC measurements of the molecular weight change and polymer concentrations of the soluble portion of solutions (Carbone, N. D.; Ene, M.; Lancaster, J. R.; Koberstein, J. T. Kinetics and Mechanisms of Radical-Based Branching/Cross-Linking Reactions in Preformed Polymers Induced by Benzophenone and Bis-Benzophenone Photoinitiators. *Macromolecules* 2013, 46, 5434-5444). In the case of macroscopic gels and microgels, the non-degraded particulates can be filtered out prior to GPC analysis. In the case of the nanoparticles, GPC measurements can be performed on the entire solution. Degradation rates can be reported as the number average molecular weight of the degradation products and their concentration as a function of time. The latter measurement requires calibration of the peak area of the refractive index signal against concentration; accomplished by measuring GPC areas for PA solutions of known concentration, a technique used to characterize crosslinking in gels (Carbone, N. D.; Ene, M.; Lancaster, J. R.; Koberstein, J. T. Kinetics and Mechanisms of Radical-Based Branching/Cross-Linking Reactions in Preformed Polymers Induced by Benzophenone and Bis-Benzophenone Photoinitiators. *Macromolecules* 2013, 46, 5434-5444).

Example 38

Block Copolymers for Micellar Therapeutic agent Delivery: Five different types of amphiphilic triblock copolymers that incorporate PA sequences can be synthesized as model vehicles for micellar therapeutic agent delivery. The copolymers are described by the five reactions shown in FIG. 27. Block copolymers utilize the three end-functional PAs described in FIG. 22 as a midblock sequence, thus minimizing the number of PA macromonomers that need to be synthesized. The first block copolymer is prepared by linking alkyne functional hydrophilic PA macromonomer with azide terminated hydrophobic PA macromonomers using azide-alkyne click chemistry (Kolb, H. C. et al., Click Chemistry: Diverse Chemical Function from a Few Good Reactions. *Angew. Chem. Int. Ed. Engl.* 2001, 40(11), 2004-2021). Because both macromonomers are difunctional, an excess of the end-block macromonomer is used and the resultant product can be a mixture of primarily unreacted macromonomer, diblock and triblock copolymers. The second block copolymer is also prepared from two PA macromonomers, but the hydrophobic macromonomer is the mid block and an excess of the hydrophilic end block macromonomer is used. One of each type of block copolymer can be prepared using the same two hydrophilic and hydrophobic macromonomers. The first two amphiphilic block copolymers are temperature responsive and doubly degradable; both sequences are pH-degradable PAs. Because many micelles for therapeutic agent delivery comprise poly(methyl methacrylate) (PMMA) and polyethylene oxide (PEO) blocks, we will also prepare, for comparison sake, block copolymers with central PA blocks coupled to PEO and PMMA end blocks. The first reaction scheme in FIG. 27 is used to couple azide terminated PMMA to alkyne terminated hydrophilic PA midblock, while the second scheme in FIG. 27 is used to couple commercially available azide terminated PEO to alkyne terminated hydrophobic PA midblock.

Figure 27:
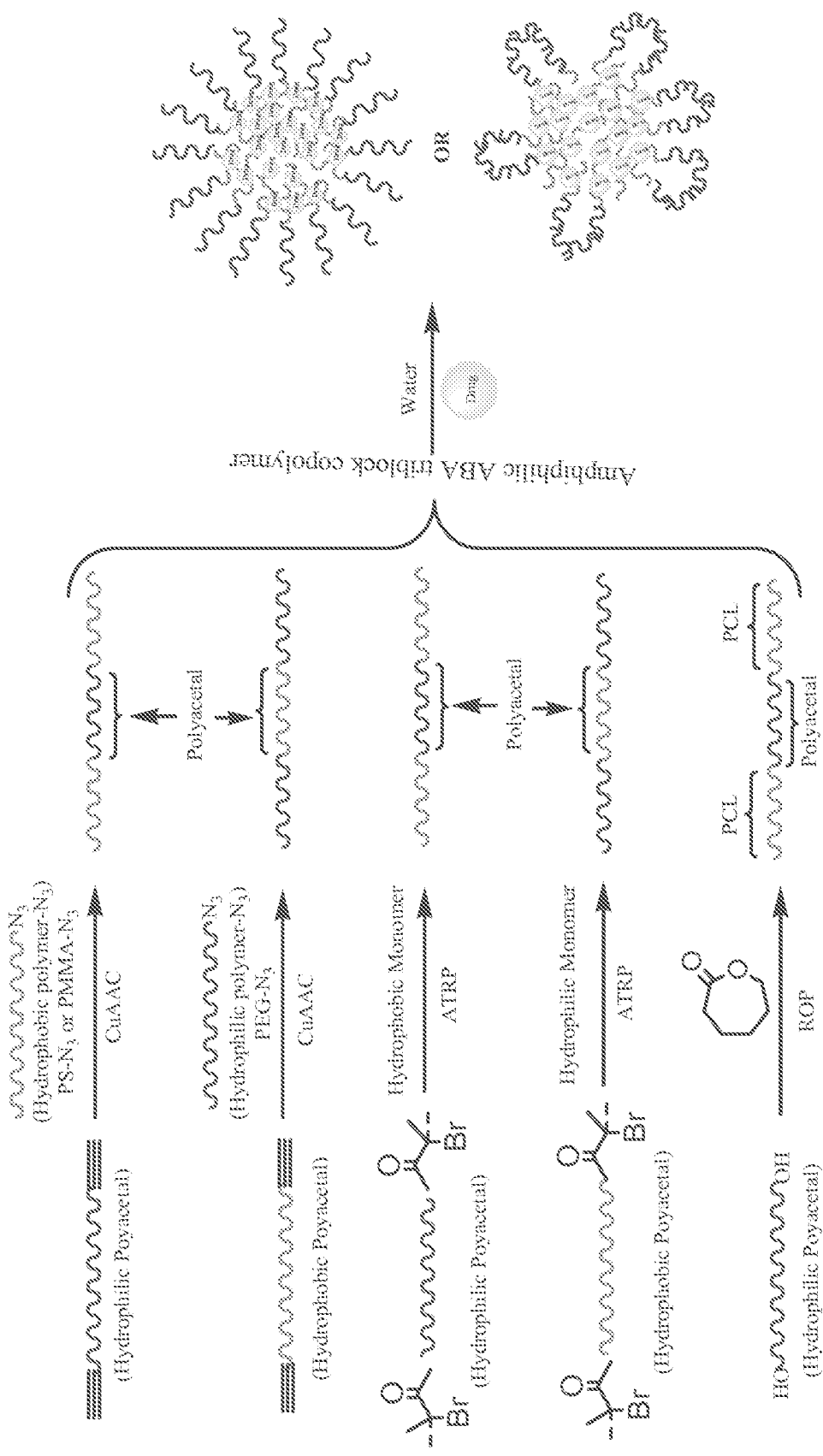
FIG. 27 shows an exemplary scheme for preparation of triblock copolymers via end-linking by azide-alkyne click reactions (top two rows), polyacetal macroinitiators followed by ARTP (third and fourth rows) and hydroxyl-terminated polyacetal macromonomer as an alkoxide initiator for ring opening polymerization of PCL (bottom row).
Figure 28:
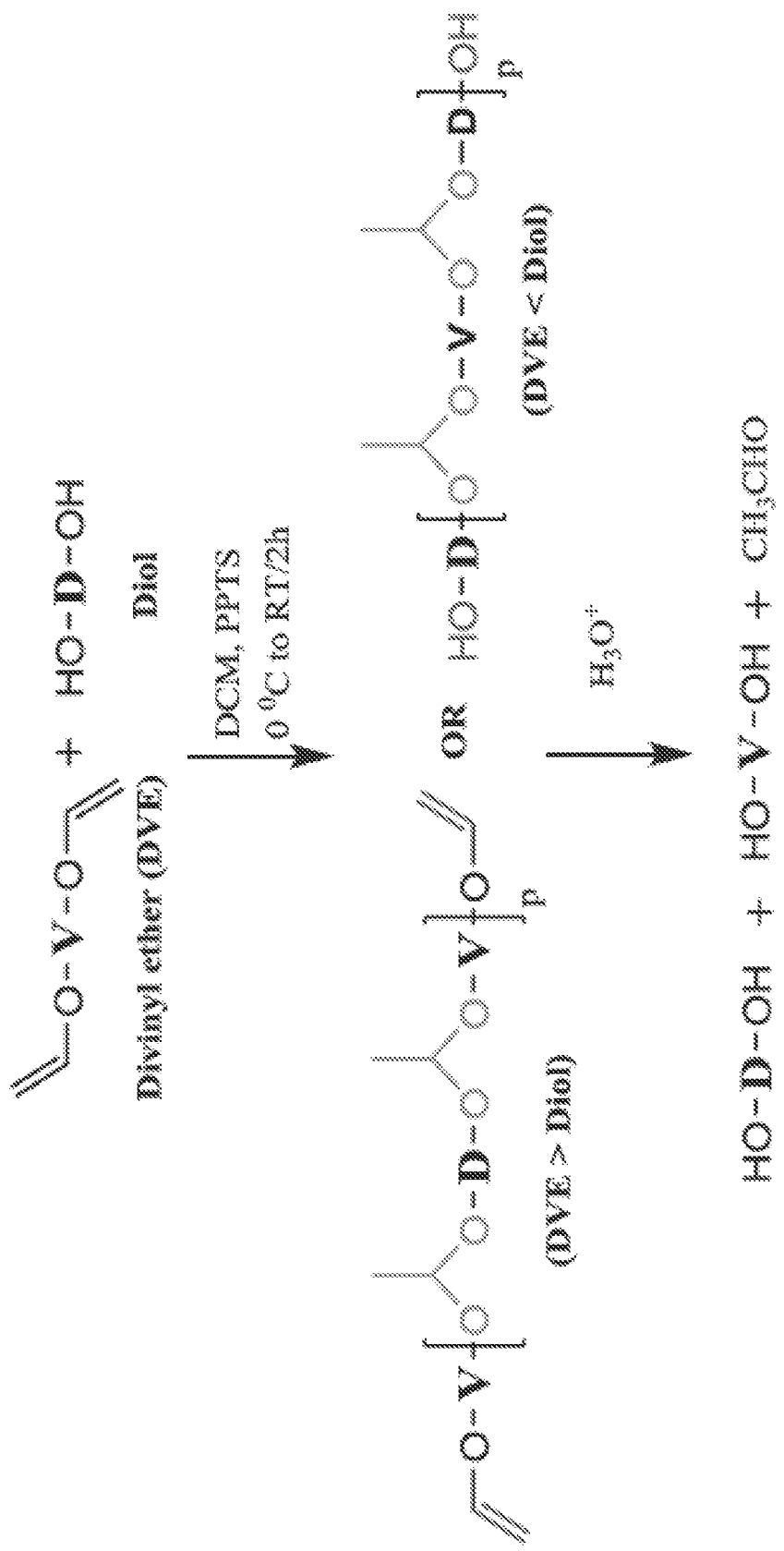
FIG. 28 shows an exemplary scheme for preparation of polyacetals with vinyl termini or polyacetals with alcohol termini from divinylethers and diols. Their degradation under acidic conditions is also shown.

The third and fourth reactions in FIG. 27 produce triblock copolymers by using a PA center block as a difunctional macroinitiator for ATRP. ATRP is a versatile means of synthesizing low polydispersity polymers and block copolymers from a broad variety of monomers. Two different ATRP monomers can be used: temperature responsive NIPAM, and pH-responsive, poly(2-(dimethylamino) ethyl methacrylate), (PDMAEDA) (Agarwal, S. et al., PDMAEMA based gene delivery materials. *Mater. Today* 2012, 15 (9), 388-393; Agut, W. et al., pH and temperature responsive polymeric micelles and polymersomes by self-assembly of poly[2-(dimethylamino)ethyl methacrylate]-b-poly(glutamic acid) double hydrophilic block copolymers. *Langmuir* 2010, 26 (13), 10546-10554). Both monomers are readily polymerized by ATRP and have been used extensively in therapeutic agent delivery applications. When PDMAEDA-based micelles encounter an acidic environment, they protonate and release their therapeutic agent cargo (Car, A. et al., pH-Responsive PDMS-b-PDMAEMA Micelles for Intracellular Anticancer Drug Delivery. *Biomacromolecules* 2014, 15, 3235-3245. dx.doi.org/10.1021/bm500919z). These PA-ATRP block copolymers are all dual responsive, and can exhibit temperature and/or pH response as well as pH degradability.

The fifth reaction in FIG. 27 allows PAs to serve as macroinitiators for ring opening polymerization (ROP) (Albertsson, A.-C. Recent developments in ring opening polymerization of lactones for biomedical applications. *Biomacromolecules* 2003, 4, 1466-1486). The dihydroxy-terminated PA macromonomer can be converted to a dialkoxide in order to initiate the polymerization of polycaprolactone (PCL) endblocks by ROP. PCL is hydrophobic but subject to hydrolytic degradation (Hutmacher, D. W. Mechanical properties and cell cultural response of polycaprolactone scaffolds designed and fabricated via fused deposition modeling. *Journal of Biomedical Materials Research* 2001, 55, 203-216). The PA-PCL block copolymers have temperature responsive hydrophilic block and both blocks are pH degradable.

Several properties of the block copolymers specific to micellar therapeutic agent delivery can be characterized:

1) Critical micelle concentration (cmc): the cmc dictates the amount of free therapeutic agent that is basically lost upon initial injection. The cmc can be correlated to block copolymer MW and composition, the hydrophobicity of the hydrophobic block and the LCST of the hydrophilic block and can be measured by pendant drop surface tensiometry, and by a dye (1,6,-diphenyl-1,3,5-hexatriene) solubilization method that has been employed in studies on therapeutic agent delivery (Anastasiadis, S. H.; Chen, J. K.; Koberstein, J. T.; Siegel, A. F.; Sohn, J. E.; Emerson, J. A. The determination of interfacial-tension by video image-processing of pendant fluid drops. *J. Colloid Interface Sci.* 1987, 119, 55-66; Kim, J.-K.; Garripelli, V. K.; Jeong, U.-H.; Park, J.-S.; Repka, M. A.; Jo, S. Novel pH-Sensitive Polyacetal-Based Block Copolymers for Controlled Drug Delivery. *Int. J. Pharm.* 2010, 401, 79-86).

2) Micellar gel temperature: The gel temperatures at which micelles fall out of solution are determined by DSC and UV transmission as a function of concentration and block copolymer composition (i.e., m1, m2, n1, n2).

3) Degradation rates. The degradation rates of the macromonomers and copolymers can be determined by gel permeation chromatography analysis of MW changes (see FIG. 15) as a function of pH (e.g., phosphate buffers of pH=5.5, 6.5, 7.4), monomer chemical composition, block copolymer concentration and temperature.

4) Therapeutic agent release profiles (Kim, J.-K.; Garripelli, V. K.; Jeong, U.-H.; Park, J.-S.; Repka, M. A.; Jo, S. Novel pH-Sensitive Polyacetal-Based Block Copolymers for Controlled Drug Delivery. *Int. J. Pharm.* 2010, 401, 79-86). Gemcitabine-loaded micelles above the gel temperature are placed in dialysis bags (molecular weight cut-off=1000) with the pH buffers. The bags are suspended in release media, the contents of which are sampled at regular time intervals. The gemcitabine content of the release media is determined by HPLC to characterize the therapeutic agent release rates. The gemcitabine content of the release media at long degradation times provides a measurement of the loading efficiency of each micellar solution (Chu E.; DeVita V. T. Physicians' Cancer Chemotherapy Drug Manual, 2007. Jones & Bartlett).

Figure 29:
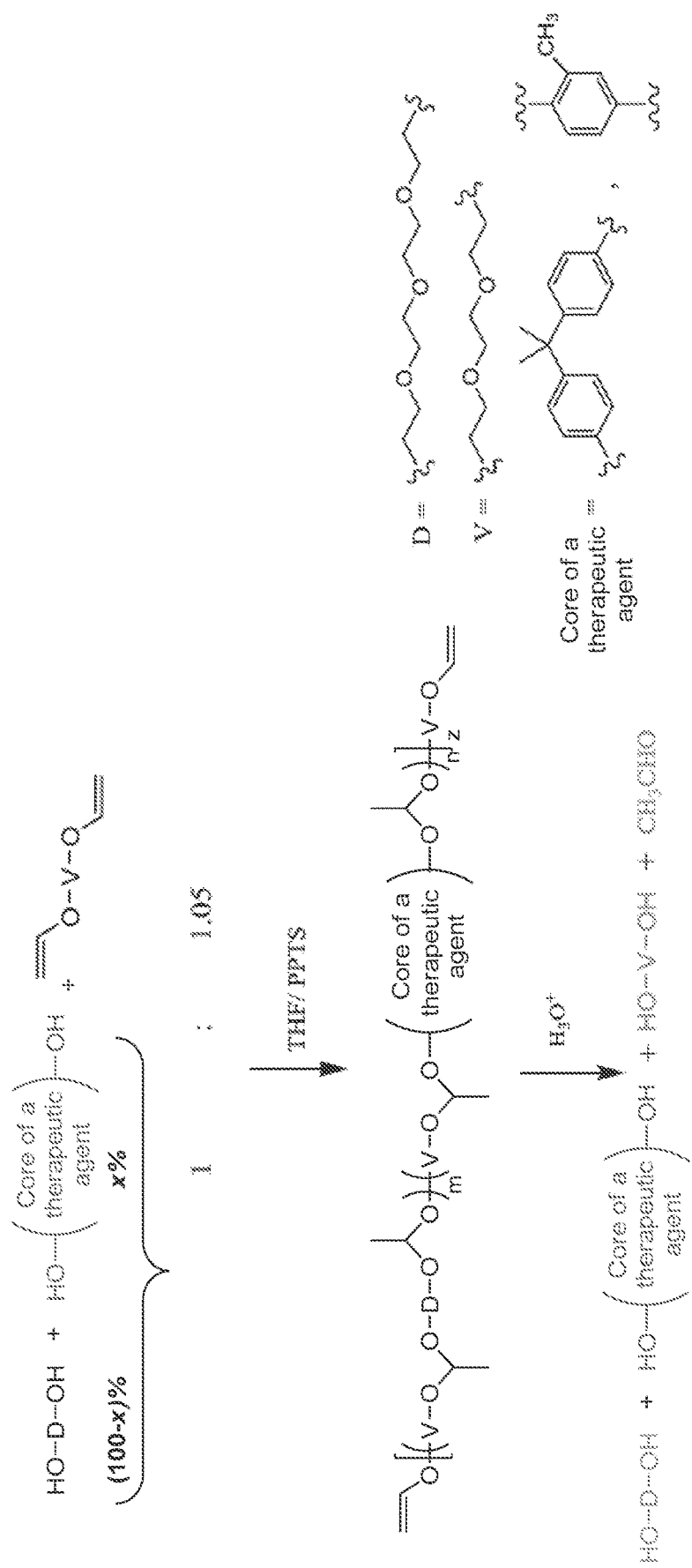
FIG. 29 shows an exemplary scheme for preparation of polyacetal-based polymer therapeutics using mixed diols, one of which is a therapeutic agent comprising a therapeutic agent core and a diol. Their degradation under acidic conditions is also shown.

Example 39: Synthesis of Polyacetal-Based Polymer Therapeutic Agent Conjugates Using Bisphenol A as the Therapeutic Agent As shown in Scheme E and FIG. 29, the polyacetal is formed by treatment of a 1:1.05 (mol/mol) total diol and divinyl ether mixture, using different amounts of two diol monomers, with PPTs in tetrahydrofuran. To prepare the polyacetal-bisphenol A conjugate, a mixture of bisphenol A, tetraethylene glycol, and triethylene glycol divinyl ether, wherein the molar ratio of bisphenol A and tetraethylene glycol to triethylene glycol divinyl ether is 1 to 1.05, are allowed to react in the presence of pyridinium p-toluenesulfonate in anhydrous tetrahydrofuran.

Other hydrophilic diols that can be used with a therapeutic agent for the preparation of polymer therapeutic agent conjugates include, but are not limited to, triethylene glycol and diethylene glycol. Varying the diol provides a strategy for tuning the LCSTs of the polymer therapeutics.

Example 40: Synthesis of Polyacetal-Based Polymer Therapeutic Agent Conjugates Using Methylhydroquinone as the Therapeutic Agent To prepare the polyacetal-methylhydroquinone conjugate, a mixture of methylhydroquinone (MHQ), tetraethylene glycol, and triethylene glycol divinyl ether, wherein the molar ratio of methylhydroquinone and tetraethylene glycol to triethylene glycol divinyl ether is 1 to 1.05, are allowed to react in the presence of pyridinium p-toluenesulfonate in anhydrous tetrahydrofuran.

Example 41: Analysis and Evaluation of Polyacetal-Based Polymer Therapeutic Agent Conjugates The solubility of polyacetal-based polymer therapeutics in water is dependent on the relative amount of therapeutic agent (loading) present within the polymer. Generally, the polymer therapeutics are water soluble up to a certain percent of therapeutic agent present in the polymer, but are water insoluble beyond that percentage.

The temperature induced phase transition of the polymer therapeutics is sharp and occurs over a range of 3-5° C. FIG. 31A shows the temperature induced phase transition for polyacetal-based polymer therapeutics prepared from bisphenol A. FIG. 32A shows the temperature induced phase transition for polyacetal-based polymer therapeutics prepared from MHQ.

FIG. 31B shows the variation of LCST as a function of the percent of bisphenol A in the polyacetal. FIG. 32B shows the variation of LCST as a function of the percent of MHQ in the polyacetal. The data fit well with first order exponential decay, indicating that the LCST of polyacetals can be tuned by adjusting the percentage of therapeutic agent present in the polyacetal.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed:

1. A biodegradable gel comprising a compound of formula (III)

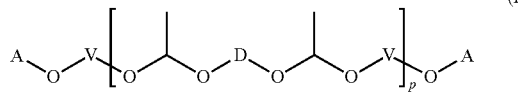

wherein,
A is

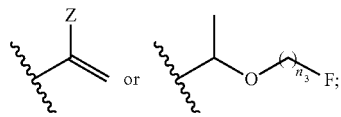

F is

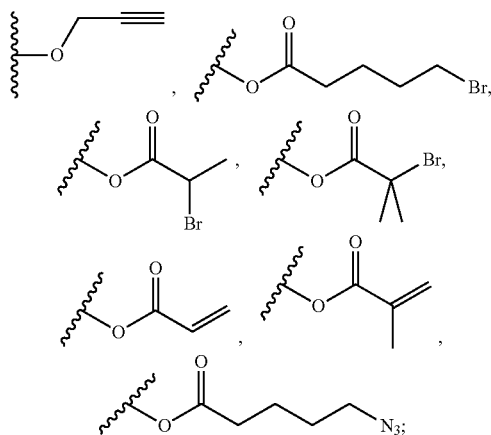

Z is hydrogen, aryl, hetero-aryl, or vinyl;
V is

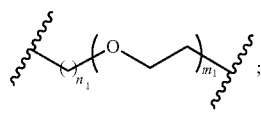

each D is

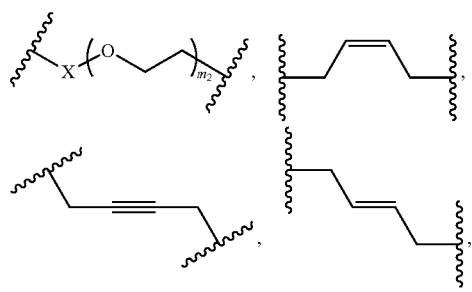

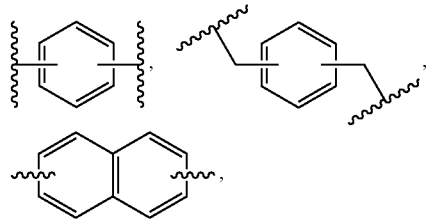

or a diol therapeutic agent covalently attached to the backbone through reactive hydroxyl groups;

each $n_1$ is an integer ranging from 2 to 10;
each $m_1$ is an integer ranging from 0 to 20;
each X is a branched, unbranched, and/or cyclic or acyclic $C_2$-$C_{10}$ alkyl group;
each $m_2$ is an integer ranging from 0 to 20;
$n_3$ is an integer ranging from 2 to 10; and
p is an integer ranging from 3 to 200;
wherein the biodegradable gel optionally comprises the compound of formula (III) crosslinked with a linker at an alkyne or azide terminus of the compound of formula (III), and wherein the biodegradable gel is acid-degradable, thermo-responsive, and water-soluble.

2. The biodegradable gel of claim 1, wherein the value of $[(m_1+m_2)/p]$ is a number ranging from 0 to 8.

3. The biodegradable gel of claim 1, wherein
each $n_1$ is an integer ranging from 2 to 4;
each $m_1$ is an integer ranging from 0 to 2;
each X is a branched, unbranched, and/or cyclic or acyclic $C_2$-$C_5$ alkyl group;
each $m_2$ is an integer ranging from 0 to 3; and
p is an integer ranging from 3 to 100.

4. The biodegradable gel of claim 1, wherein X is $C_2$-$C_5$ unbranched alkyl.

5. The biodegradable gel of claim 1, wherein p is an integer ranging from 3 to 50.

6. The biodegradable gel of claim 1, wherein
A is

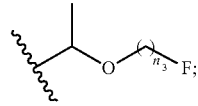

F is

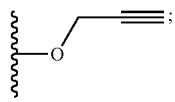 [SMILES: *OCC#C]

each D is

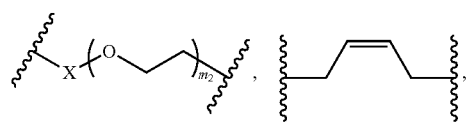

-continued

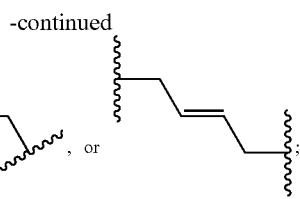

and $n_3$ is 4.

7. A method of delivering a therapeutic agent to a tumor cell, the method comprising the step of,
    contacting the tumor cell with the biodegradable gel of claim 1.

8. The method of claim 7, wherein the biodegradable gel further comprises a second therapeutic agent.

9. The method of claim 8, wherein the second therapeutic agent is gemcitabine.

10. The method of claim 8, wherein the tumor cell is a pancreatic cancer cell.

11. The biodegradable gel of claim 1, wherein the diol therapeutic agent is gemcitabine, bisphenol A, methylhydroquinone, diethylstilbestrol, paclitaxel, doxorubicin, everolimus, pamidronate disodium, nelarabine, azacitidine, bleomycin, bortezomib, capecitabine, cytarabine, daunorubicin hydrochloride, decitabine, docetaxel, epirubicin, etoposide, raloxifene, fulvestrant, fludarabine, goserelin, topotecan, idarubicin, azaepothilone B, lanreotide, leuprolide, mitoxantrone, predinisone, temsirolimus, vinblastine, vincristine, or zoledronic acid.

12. The biodegradable gel of claim 1, wherein the diol therapeutic agent is gemcitabine, bisphenol A, methylhydroquinone, or diethylstilbestrol.

13. The method of claim 8, wherein the second therapeutic agent is a protein, peptide, or carbohydrate.

14. The method of claim 7, wherein the biodegradable gel degrades at a pH ranging from about 5 to about 6.5.

* * * * *